US009951089B2

(12) United States Patent
Austad et al.

(10) Patent No.: US 9,951,089 B2
(45) Date of Patent: Apr. 24, 2018

(54) METHODS OF TREATING A FATTY ACID AMIDE HYDROLASE-MEDIATED CONDITION

(71) Applicant: INFINITY PHARMACEUTICALS, INC., Cambridge, MA (US)

(72) Inventors: Brian C. Austad, Tewksbury, MA (US); Louis Grenier, Newton, MA (US); Michael J. Grogan, Winchester, MA (US); Tao Liu, Ashland, MA (US); Priscilla L. White, Malden, MA (US); Theodore A. Martinot, Jamaica Plain, MA (US); Lin-Chen Yu, Quincy, MA (US)

(73) Assignee: Infinity Pharmaceuticals, Inc., Cambridge, MA (US)

(*) Notice: Subject to any disclaimer, the term of this patent is extended or adjusted under 35 U.S.C. 154(b) by 230 days.

(21) Appl. No.: 14/631,712

(22) Filed: Feb. 25, 2015

(65) Prior Publication Data

US 2015/0239912 A1  Aug. 27, 2015

Related U.S. Application Data

(62) Division of application No. 13/019,262, filed on Feb. 1, 2011, now Pat. No. 9,034,849.

(60) Provisional application No. 61/412,734, filed on Nov. 11, 2010, provisional application No. 61/301,181, filed on Feb. 3, 2010.

(51) Int. Cl.
*A01N 41/06* (2006.01)
*A61K 31/18* (2006.01)
*C07F 5/05* (2006.01)
*C07F 5/02* (2006.01)

(52) U.S. Cl.
CPC ............... *C07F 5/05* (2013.01); *C07F 5/025* (2013.01); *C07B 2200/13* (2013.01)

(58) Field of Classification Search
None
See application file for complete search history.

(56) References Cited

U.S. PATENT DOCUMENTS

| | | |
|---|---|---|
| 4,270,537 A | 6/1981 | Romaine |
| 4,596,556 A | 6/1986 | Morrow et al. |
| 4,790,824 A | 12/1988 | Morrow et al. |
| 4,853,150 A | 8/1989 | Bezborodov et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,089,499 A | 2/1992 | Barker et al. |
| 5,141,496 A | 8/1992 | Dalto et al. |
| 5,190,521 A | 3/1993 | Hubbard et al. |
| 5,198,149 A | 3/1993 | Reiffenrath et al. |
| 5,273,680 A | 12/1993 | Gray et al. |
| 5,312,335 A | 5/1994 | McKinnon et al. |
| 5,328,483 A | 7/1994 | Jacoby |
| 5,328,637 A | 7/1994 | Buchecker et al. |
| 5,334,144 A | 8/1994 | Alchas et al. |
| 5,339,163 A | 8/1994 | Homma et al. |
| 5,340,898 A | 8/1994 | Cavezzan et al. |
| 5,383,851 A | 1/1995 | McKinnon, Jr. et al. |
| 5,417,662 A | 5/1995 | Hjertman et al. |
| 5,417,885 A | 5/1995 | Suzuki et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,541,061 A | 7/1996 | Fodor et al. |
| 5,543,075 A | 8/1996 | Parri et al. |
| 5,550,236 A | 8/1996 | Schlosser et al. |
| 5,569,189 A | 10/1996 | Parsons |
| 5,576,220 A | 11/1996 | Hudson et al. |
| 5,599,302 A | 2/1997 | Lilley et al. |
| 5,616,582 A | 4/1997 | Barker |
| 5,643,893 A | 7/1997 | Benson et al. |
| 5,649,912 A | 7/1997 | Peterson |
| 5,683,623 A | 11/1997 | Chan et al. |
| 5,693,688 A | 12/1997 | Priou |
| 5,704,911 A | 1/1998 | Parsons |
| 5,800,733 A | 9/1998 | Kelly |
| 5,847,149 A | 12/1998 | Fuss et al. |
| 5,849,958 A | 12/1998 | Barnes et al. |
| 5,861,109 A | 1/1999 | Goodby et al. |
| 5,892,131 A | 4/1999 | Barnes et al. |
| 5,893,397 A | 4/1999 | Peterson et al. |
| 5,993,412 A | 11/1999 | Deily et al. |
| 5,998,673 A | 12/1999 | Barnes et al. |
| 6,075,014 A | 6/2000 | Weston et al. |

(Continued)

FOREIGN PATENT DOCUMENTS

CA  2642583 A1  8/2007
DE  4014488 A1  11/1991

(Continued)

OTHER PUBLICATIONS

"For the selling of standards and test methods for new drugs" Pharmaceutical Affairs Bureau Notification No. 568, 2001.
Caujolle et al., "Etude cornparee du pouvoir renforcateur des organoboriques a l'egard des hypnotiques// potentiation of hypnotics by organoboron derivatives," Agressologie 10(1):51-54 (1969). (English translation of Summary provided).
Caujolle et al., "The effect of organoboron derivatives on cardiovascular and ventilatory manifestations of electroshock," Agressologie: Revue Internationale De Physio-Biologie et de Pharmacologie Appliquees aux Effets de l'Agression, 8(5):425-432 (1967). (Eng. Summary provided).

(Continued)

*Primary Examiner* — Jared D Barsky
(74) *Attorney, Agent, or Firm* — TraskBritt

(57) ABSTRACT

The present invention provides fatty acid amide hydrolase inhibitors, solid forms thereof, compositions thereof, and methods of making and using the same.

7 Claims, 35 Drawing Sheets

(56) References Cited

U.S. PATENT DOCUMENTS

| | | |
|---|---|---|
| 6,096,784 A | 8/2000 | Lerner et al. |
| 6,124,005 A | 9/2000 | Kondo et al. |
| 6,143,751 A | 11/2000 | Cheshire et al. |
| 6,174,458 B1 | 1/2001 | Koga et al. |
| 6,177,440 B1 | 1/2001 | Bach et al. |
| 6,197,217 B1 | 3/2001 | Kondo et al. |
| 6,218,445 B1 | 4/2001 | Priou et al. |
| 6,262,319 B1 | 7/2001 | Barnes et al. |
| 6,271,015 B1 | 8/2001 | Gilula et al. |
| 6,309,406 B1 | 10/2001 | Jones et al. |
| 6,326,156 B1 | 12/2001 | Civelli et al. |
| 6,344,474 B1 | 2/2002 | Maruani et al. |
| 6,423,378 B1 | 7/2002 | Cotting et al. |
| 6,600,066 B1 | 7/2003 | Schottek et al. |
| 6,617,125 B2 | 9/2003 | Adler, Jr. |
| 6,753,046 B2 | 6/2004 | Manabe et al. |
| 6,818,260 B2 | 11/2004 | Farrand et al. |
| 6,911,235 B2 | 6/2005 | Frances et al. |
| 6,924,269 B2 | 8/2005 | Miljkovic et al. |
| 6,927,216 B2 | 8/2005 | Cherney et al. |
| 7,037,905 B2 | 5/2006 | Ebdrup et al. |
| 7,037,938 B2 | 5/2006 | Hattori et al. |
| 7,049,304 B2 | 5/2006 | Holmes-Farley et al. |
| 7,074,836 B1 | 7/2006 | Kawada et al. |
| 7,101,915 B1 | 9/2006 | Kawada et al. |
| 7,148,219 B2 | 12/2006 | Lou et al. |
| 7,183,447 B2 | 2/2007 | Pauluth et al. |
| 7,220,783 B2 | 5/2007 | Kawada et al. |
| 7,320,972 B2 | 1/2008 | Martinez et al. |
| 7,351,452 B2 | 4/2008 | Goodby et al. |
| 7,351,728 B2 | 4/2008 | Brooks et al. |
| 7,411,100 B2 | 8/2008 | Pauluth et al. |
| 7,425,281 B2 | 9/2008 | Wand et al. |
| 7,432,375 B2 | 10/2008 | Graczyk et al. |
| 7,521,455 B2 | 4/2009 | Nagase et al. |
| 7,553,496 B2 | 6/2009 | Ambati |
| 7,582,681 B2 | 9/2009 | Schmaus et al. |
| 7,626,020 B2 | 12/2009 | Butlin et al. |
| 7,645,776 B2 | 1/2010 | Ackermann et al. |
| 7,767,277 B2 | 8/2010 | Lietzau et al. |
| 7,776,922 B2 | 8/2010 | Bruggemeier et al. |
| 7,947,663 B2 | 5/2011 | Adams et al. |
| 7,999,137 B2 | 8/2011 | Kunz et al. |
| 8,022,250 B2 | 9/2011 | Raveglia et al. |
| 8,329,675 B2 | 12/2012 | Adams et al. |
| 8,349,814 B2 | 1/2013 | Adams et al. |
| 8,629,125 B2 | 1/2014 | Adams et al. |
| 2002/0164769 A1 | 11/2002 | Curtis et al. |
| 2003/0022886 A1 | 1/2003 | Ishiwata et al. |
| 2003/0096854 A1 | 5/2003 | Lin et al. |
| 2004/0053889 A1 | 3/2004 | Ebdrup et al. |
| 2004/0115475 A1 | 6/2004 | Hashimoto |
| 2004/0204473 A1 | 10/2004 | Lin et al. |
| 2005/0090383 A1 | 4/2005 | Thiele et al. |
| 2005/0182045 A1 | 8/2005 | Nagase et al. |
| 2005/0250825 A1 | 11/2005 | Brooks et al. |
| 2006/0030583 A1 | 2/2006 | Arnold et al. |
| 2006/0058527 A1 | 3/2006 | Kirsch et al. |
| 2006/0135423 A1 | 6/2006 | Ambati |
| 2006/0211698 A1 | 9/2006 | Botyanszki et al. |
| 2006/0234981 A1 | 10/2006 | Baker et al. |
| 2006/0293502 A1 | 12/2006 | Dreyer et al. |
| 2007/0010559 A1 | 1/2007 | Christiansen et al. |
| 2007/0015003 A1 | 1/2007 | Hwang et al. |
| 2007/0082877 A1 | 4/2007 | Dunkel et al. |
| 2007/0125712 A1 | 6/2007 | Little et al. |
| 2007/0129544 A1 | 6/2007 | Ackermann et al. |
| 2008/0132716 A1 | 6/2008 | Lietzau et al. |
| 2008/0171786 A1 | 6/2008 | Bruggemeier et al. |
| 2008/0188371 A1 | 8/2008 | Fischer et al. |
| 2008/0242708 A1 | 10/2008 | Dunkel et al. |
| 2008/0280991 A1 | 11/2008 | Grant et al. |
| 2009/0005321 A1 | 1/2009 | Zimmer et al. |
| 2011/0201574 A1 | 8/2011 | Austad et al. |
| 2015/0239912 A1 | 8/2015 | Austad et al. |

FOREIGN PATENT DOCUMENTS

| | | |
|---|---|---|
| DE | 4220065 A1 | 12/1993 |
| DE | 4445224 A1 | 6/1996 |
| DE | 19710614 A1 | 9/1998 |
| DE | 19909761 A1 | 10/1999 |
| DE | 19858594 A1 | 6/2000 |
| DE | 10009714 A1 | 9/2001 |
| DE | 102005037925 A1 | 2/2007 |
| DE | 102007009944 A1 | 9/2007 |
| EP | 0440082 A2 | 8/1991 |
| EP | 0145441 B1 | 3/1992 |
| EP | 562897 A1 | 9/1993 |
| EP | 614958 A1 | 9/1994 |
| EP | 0739884 A2 | 10/1996 |
| EP | 811593 A1 | 12/1997 |
| EP | 811596 A1 | 12/1997 |
| EP | 952135 B1 | 10/1999 |
| EP | 952149 A2 | 10/1999 |
| EP | 0987238 A1 | 3/2000 |
| EP | 0792883 B1 | 12/2000 |
| EP | 1160233 A2 | 12/2001 |
| EP | 1236726 A1 | 9/2002 |
| EP | 1388538 A1 | 2/2004 |
| EP | 1444981 A1 | 8/2004 |
| FR | 2727416 A1 | 5/1996 |
| FR | 2758329 A1 | 7/1998 |
| GB | 2258232 A | 2/1993 |
| GB | 2280181 A | 1/1995 |
| GB | 2290787 A | 1/1996 |
| GB | 2344817 A | 6/2000 |
| GB | 2410745 A | 8/2005 |
| GB | 2424881 A | 10/2006 |
| JP | 05025158 A | 2/1993 |
| JP | 05331107 A | 12/1993 |
| JP | 07145174 A | 6/1995 |
| JP | 07165717 A | 6/1995 |
| JP | 07206715 A | 8/1995 |
| JP | 08040953 A | 2/1996 |
| JP | 08092137 A | 4/1996 |
| JP | 09030996 A | 2/1997 |
| JP | 09278676 A | 10/1997 |
| JP | 10025261 A | 1/1998 |
| JP | 10059882 A | 3/1998 |
| JP | 10-152491 | 6/1998 |
| JP | 10152491 | 6/1998 |
| JP | 2000001463 A | 1/2000 |
| JP | 200035596 A | 2/2000 |
| JP | 2000336045 A | 12/2000 |
| JP | 2001-39975 | 2/2001 |
| JP | 2002284768 A | 10/2002 |
| JP | 3555325 B2 | 2/2004 |
| JP | 2005162660 A | 6/2005 |
| JP | 2006290786 A | 10/2006 |
| JP | 2007308483 A | 11/2007 |
| PL | 167141 A1 | 7/1995 |
| WO | 199219707 | 11/1992 |
| WO | 199415920 A1 | 7/1994 |
| WO | 199512655 A1 | 5/1995 |
| WO | 199535300 | 12/1995 |
| WO | 199620689 A3 | 7/1996 |
| WO | 199706124 A1 | 2/1997 |
| WO | 199713537 A1 | 4/1997 |
| WO | 199733705 A1 | 9/1997 |
| WO | 199824396 A2 | 6/1998 |
| WO | 199828663 A1 | 7/1998 |
| WO | 199831688 A1 | 7/1998 |
| WO | 199835924 A1 | 8/1998 |
| WO | 199934850 A1 | 7/1999 |
| WO | 200004111 A3 | 1/2000 |
| WO | 200020466 A1 | 4/2000 |
| WO | 200042213 A1 | 7/2000 |
| WO | 200121606 A1 | 3/2001 |
| WO | 2002014381 A2 | 2/2002 |
| WO | 2002057273 A1 | 7/2002 |
| WO | 2002059155 A2 | 8/2002 |
| WO | 2002085916 A1 | 10/2002 |
| WO | 2003059903 A2 | 7/2003 |
| WO | 2003064484 A1 | 8/2003 |

(56) References Cited

FOREIGN PATENT DOCUMENTS

| | | |
|---|---|---|
| WO | 2003105860 A1 | 12/2003 |
| WO | 2004044169 A2 | 5/2004 |
| WO | 2004074232 A1 | 9/2004 |
| WO | 2004080989 A1 | 9/2004 |
| WO | 2004081008 A1 | 9/2004 |
| WO | 2005004799 A2 | 1/2005 |
| WO | 2005013892 A2 | 2/2005 |
| WO | 2005037227 A2 | 4/2005 |
| WO | 2005041904 A2 | 5/2005 |
| WO | 2005051908 A1 | 6/2005 |
| WO | 2005080403 A2 | 9/2005 |
| WO | 2006007384 A2 | 1/2006 |
| WO | 2006024389 A2 | 3/2006 |
| WO | 2006050053 A2 | 5/2006 |
| WO | 2006050054 A2 | 5/2006 |
| WO | 2006050236 A2 | 5/2006 |
| WO | 2006053250 A2 | 5/2006 |
| WO | 2006089067 A2 | 8/2006 |
| WO | 2006091799 A2 | 8/2006 |
| WO | 2006099261 A2 | 9/2006 |
| WO | 2006122186 A2 | 11/2006 |
| WO | 2006124713 A2 | 11/2006 |
| WO | 2006133559 A1 | 12/2006 |
| WO | 2007028104 A2 | 3/2007 |
| WO | 2007031512 A2 | 3/2007 |
| WO | 2007064809 A2 | 6/2007 |
| WO | 2007076875 A2 | 7/2007 |
| WO | 2007078340 A2 | 7/2007 |
| WO | 2007088148 A1 | 8/2007 |
| WO | 2007095638 A2 | 8/2007 |
| WO | 2007104783 A2 | 9/2007 |
| WO | 2007118318 A1 | 10/2007 |
| WO | 2007146965 | 12/2007 |
| WO | 2008002674 A2 | 1/2008 |
| WO | 2008014497 A2 | 1/2008 |
| WO | 2008019743 A1 | 2/2008 |
| WO | 2008020920 A1 | 2/2008 |
| WO | 2008039827 A2 | 4/2008 |
| WO | 2008039829 | 4/2008 |
| WO | 2008047229 A2 | 4/2008 |
| WO | 2008063300 A2 | 5/2008 |
| WO | 2008090780 A1 | 7/2008 |
| WO | 2008105286 A1 | 9/2008 |
| WO | 2008107480 A1 | 9/2008 |
| WO | 2009011904 A1 | 1/2009 |
| WO | 2003045228 A2 | 6/2009 |
| WO | 2009126691 A1 | 10/2009 |
| WO | 2009136646 A1 | 11/2009 |
| WO | 2009138176 A1 | 11/2009 |
| WO | 2010118159 A1 | 10/2010 |
| WO | 2011097233 A1 | 8/2011 |

OTHER PUBLICATIONS

The First Office Action of Chinese Application No. 201180017689.3, dated May 6, 2014, 9 pages.
The Second Office Action of Chinese Application No. 201180017689.3, dated Mar. 26, 2015, 11 pages.
The Third Office Action of Chinese Application No. 201180017689.3, dated Dec. 16, 2016, 8 pages.
Yoko, Kawaguchi, "Drug and crystal polymorphism" Journal of Human Environmental Engineering vol. 4, No. 2, p. 310-317.
Hird et al., "The relationship between molecular structure and mesomorphic properties of 2,2'- and 3,2'-difluoroterphenyls synthesized by palladium-catalysed cross-couplings," Liquid Crystals 18(1):1-11 (1995).
Hiroshi, Ooshima, "Crystallization of Polymorphs and Pseudopolymorphs and Its Control", Pharm Stage, Jan. 15, 2007, vol. 6, No. 10, p. 48-53.
International Preliminary Report on Patentability for PCT/US2011/023352, published as WO2011/097233A1, dated Aug. 7, 2012, 9 pages.
Miller et al., The Flypolipidemic and Anti-Inflammatory Activity of Boronated Aromatic Amino Acids in CF(1) Male Mice, Met. Based Drugs 6(6):337-344 (1999).
SIPO Novelty Search Report dated Apr. 11, 2013 for Appl. No. GCC/P/2007/9295, 5 pages.
Smoum et al., "Noncovalent Inhibition of the Serine Proteases, a-chymotrypsin and Trypsin by Trifluoro(organo) borates," Org. Biomol. Chem. 3(5):941-944 (2005).
Wang et al., "Preparation of Unsymmetrical Biaryls by Pd(II)-Catalyzed Cross-Coupling of Aryl Iodides," Org. Lett. 11:1079-1082 (2009).
McKinney et al., "Structure and Function of Fatty Acid Amide Hydrolase," Ann. Rev. Biochem. 74:411-432 (2005).
McPartland et al., "A shifted repertoire of endocannabinoid genes in the zebrafish (Danio rerio )," Mol. Genet. Genomics 277:555-570 (2007).
Mendelson and Basile, "The Hypnotic Actions of the Fatty Acid Amide, Oleamide," Neuropsychopharmacology 25(5 Suppl):S36-S39 (2001).
Miczek, et al., "Aggression, Anxiety and Vocalizations in Animals: GABAa and 5-HT Anxiolytics," Psvchonharmacologv 121:38-56 (1995).
Miller et al., "Suppression of a Palladium-Mediated Homocoupling in a Suzuki Cross-Coupling Reaction. Development of an Impurity Control Strategy Supporting Synthesis of L Y451395," Org. Proc. Res. Dev. 11 :359-364 (2007).
Minkkila et al., "Discovery of Boronic Acids as Novel and Potent Inhibitors of Fatty Acid Amide Hydrolase," J. Med. Chern. 51:7057-7060 (2008).
Miyaura et al., "Palladium-Catalyzed Cross -Coupling Reactions of Organoboron Compounds," Chem. Rev. 95:2457-2483 (1995).
Morandi et al., "Nanomolar Inhibitors of AmpC β-Lactamase," J. Am. Chern. Soc. 125:685-695 (2003).
Nakamura et al., "Synthesis and Biological Evaluation ofBoronic Acid Containing cis-Stilbenes as Apoptotic Tubulin Polymerization Inhibitors," Chem MedChem 1:729-740 (2006).
Negishi et al., "Formation of Carbon-Carbon and Carbon-Heteroatom Bonds via Organoboranes and Organoborates," Organic Reactions 33:1-78 (1985).
Office Action for JP Appl. No. 2012-552035, dated Jan. 6, 2015.
Pacher et al., "The endocannabinoid system as an emerging target of pharmacotherapy," Pharmacal. Rev. 58 (3):389-462 (2006).
Patricelli et al., "Comparative characterization of a wild type and transmembrane domain-deleted fatty acid amide hydrolase: identification of the transmembrane domain as a site for oligomerization," Biochemistry 37( 43): 15177-15187 (1998).
Philipp et al., "Inhibition of Serine Proteases by Arylboronic Acids," Proc. Nat!. Acad. Sci. U.S.A 68(2):478-480 (1971).
Pillarisetti et al., "Pain and beyond: fatty acide amides and fatty acide amide hydrolase inhibitors in cardiovascular and metabolic diseases," Drug Discov. 1-14 (2009).
Piomelli et al., "Pharmacological Profile ofthe Selective FAAH Inhibitor KDS-4103 (URB597)," CNS Drug Rev. 12 (1):21-38 (2006).
Porsolt et al., "Depression: A New Animal Model Sensitive to Antidepressant Treatments," Nature 266:730-732 (1977).
Prasad et al., "Synthesis ofNovel3-Aryl-N-Methyl-1,2,5,6-Tetrahydropyridine Derivatives by Suzuki coupling: As Acetyl Cholinesterase Inhibitors," 012en Med. CheM. J. 1:4-10 (2007).
Quistad et al., "Fatty Acid Amide Hydrolase Inhibition by Neurotoxic Organophosphous Pesticides," Toxicol. Appl. Pharmacal. 173(1):48-55 (2001).
Ramarao et al., "A Fluorescence-Based Assay for Fatty Acid Amide Hydrolase Compatible with High-Throughput Screening," Anal. Biochem. 343:143-151 (2005).
Rock et al., "An Anti-Fungal Agent Inhibits an Aminoacyl-tRNA Synthetase by Trapping tRNA in the Editing Site," Science 316:1759-1761(2007).
Saghetelian et al., "A FAAH-regulated class of N-acyl taurines that activates TRP ion channels," Biochemistry 45 (30):9007-9015 (2006).
Sakai, N. et al, Toward Biomimetic Ion Channels Formed by Rigid-Rod Molecules: Length-Dependent Ion-Transport Activity of Substituted Oligo(p-Phenylene)s.
Santucci et al., "Some Bromine-containing and Sulfur-containing Aromatic Boronic Acids," JACS 80:193-196 (1958).

(56) References Cited

OTHER PUBLICATIONS

Schlosburg et al., "Targeting Fatty Acide Amide Hydrolase (FAAH) to Treat Pain and Inflammation," The AAOS J. 11(1):39-44 (2009).
Seufer-Wasserthal et al., "Probing the Specificity of the S1 Binding Site of Subtilisin Carlsberg with Boronic Acids," Bioorg. Med. Chem. Lett. 2(1):35-48 (1994).
Shepherd et al., "Behavioural and Pharmacological Characterisation of the Elevated "Zero-Maze" as an Animal Model of Anxiety," Psvchonharmacology 116:56-64 (1994).
Simpelkamp et al., "Boronic Acid Inhibitors as Probes of the Factors Involved in Binding at the Active Sites of Subtilisin Carlsberg and a-Chymotrypsin," Bioorg. Med. Chem. Lett. 2(11): 1391-1394 (1994).
SIPO Examination Report dated Apr. 1, 2013 for Appl. No. GCC/P/2007/9295, 9 pages.
Smoum et al., "A study of the effect on nucleophilic hydrolytic activity of pancreatic elastase, trypsin, chymotrypsin, and leucine aminopeptidase by boronic acids in the presence of arabinogalactan: a subsequent study on the hydrolytic activity of chymotrypsin by boronic acids in the presence of mono-, di-, and trisaccharides," Bioorg. Chem. 31 (6):464-474 (2003).
Snyder et al., "Aryl Boronic Acids. II. Aryl Boronic Anhydrides and Their Amine Complexes," JACS 80:3611 (1958).
Soloway, A.H., "Correlation of drug penetration of brain and chemical structure," Science 128(3338):1572-1574 (1958).
Steru et al., "The Tail Suspension Test: A New Method for Screening Antidepressants in Mice," Psvchonharmacology 85:367-370 (1985).
Suzuki et al., "Design, Synthesis, and Biological Activity of Boronic Acid-Based Histone Deacetylase Inhibitors," J. Med. Chem. 52(9): 2909-2922 (2009).
Tan et al., An Integrated High-Throughput Screening Approach for Purification of Solid Organic Compounds by Trituration and Crystallization in Solvents, vol. 12, No. 1, 2008, pp. 58-65.
Tanaka et al., "Suppression of arthritis by the inhibitors of dipeptidyl peptidase IV," Int. J. Immunopharmacol. (19)1:15-24 (1997).
Tondi et al., "Structure-based design and in-parallel synthesis of inhibitors of AmpC P-lactamase," Chem. Bioi. 8 (6):593-610 (2001).
Uehara et al., "Determination of Trace Amounts of Boron in Steel by Reversed-Phase High-Performance Liquid Chromatography with Azomethine-H as a Precolumn Derivatization Agent," Anal. Sci. 17:1421-1424 (2001).
International Search Report and Written Opinion for PCT/US07/021626 published as WO2008/063300, 16 pages, dated May 6, 2008.
Vandervoorde, "Overview of the Chemical Families of Fatty Acid Amide Hydrolase and Monoacylglycerol Lipase Inhibitors," Curr. Top. Med. Chem. 8(3):247-267 (2008).
Vashchenko et al., "Palladium-catalyzed Suzuki Cross-coupling Reactions in a Microemulsion," Tetrahedron Lett. 49(9): 1445-1449 (2008).
Vippagunta et al., "Crystalline Solids," Adv. Drug Deliv. Rev. 48(1):3-26 (2001).
Walker et al., "Pain modulation by release of the endogenous cannabinoid anandamide," Proc. Natl. Acad. Sci. U.S.A. 96(21):12198-203 (1999).
Wang et al., "High-Throughput Screening for the Discovery of Inhibitors of Fatty Acid Amide Hydrolase Using a Microsome-Based Fluorescent Assay," J. Biomol. Screen. 11:519-527(2006).
Wei et al., "A second fatty acid amide hydrolase with variable distribution among placental mammals," J. Biol. Chem. 281(48):36569-36578 (2006).
Wermuth, C. G. (ed.), "Chapter 13: Molecular Variations Based on Isosteric Replacements", The Practice of Medicinal Chemistry, pp. 204-237, Academic Press Ltd., Copyright (1996).
Weston et al., "Structure-Based Enhancement of Boronic Acid-Based Inhibitors of AmpC P-Lactamase," J. Med. Chem. 41:4577-4586 (1998).
Wilen et al., "Strategies in Optical Resolution," Tetrahedron 33:2725-2736 (1977).
Willner, "Validity, Reliability and Utility of the Chronic Mild Stress Model of Depression: a 10-year Review and Evaluation," Psychopharmacology 134:319-329 (1997).
Winslow et al., "Infant Rat Separation is a Sensitive Test for Novel Anxiolyitics," Prog. Neuro-Psychopharmacol. & Biol. Psvchiat. 15:745-757 (1991).
Adamo et al., "Mechanism of the Palladium-Catalyzed Homocoupling of Arylboronic Acids: Key Involvement of a Palladium Peroxo Complex," JACS 128:6829-6836 (2006).
Asano et al. "Design, Synthesis, and Biological Evaluation of Amnioboronic Acids as Growth-Factor Receptor Inhibitors of EGFR and VEGFR-1 Tyrosine Kinases," ChemBioChem. 5:4S3-490 (2004).
Bellina et al. "Palladium Catalysts for the Suzuki Cross-Coupling Reaction: An Overview of Recent Advances," Syn. 2419-2440 (2004).
Berge et al. "Pharmaceutical Salts," J Pharm Sci. 66(1):1-19 (1977).
Bickerdike et al., "The Influence of 5-Hydroxytryptamine Re-uptake Blockade on CCK Receptor Antagonist Effects in the Rat Elevated Zero-Maze," Eur. J. Pharm. 271:403-411 (1994).
Bracey et al. "Structural Adaptations in Membrane Enzyme That Terminates Endocannabinoid Signaling," Science 29S: 1793-1796 (2002).
Buzzoni et al. "Aza-boronic Acids as Non-β-Lactam Inhibitors of AmpC-β-Lactamase," Bioorganic & Medicinal Chemistry Letters 14:3979-3983 (2004).
Carter et al. "The Inhibition of Rat Liver Chromatin Potease by Congeners of the Phenyboronic Acids," Biochim. Biophvs. Acta (484)1:103-108 (1977).
CAS File Registry, Registry for [ 4[2-(2,6-difluoro-4-propylphenyl)ethyl]-2,6-difluorophenyl]-boronic acid, published Mar. 3, 2003 in Japanese Patent Application No. JP 10059882.
CAS File Registry, Registry No. 874288-40-I, published Feb. 15, 2006.
CAS File Registry, Registry No. 874289-19-7, published Feb. 15, 2006.
CAS File Registry, Registry No. 874290-59-2, published Feb. 15, 2006.
CAS No. 1823, CAS Abstract of EP0952135 (1999).
CAS No. 1901, AN 1983:17023 CAPLUS (1983).
CAS Registry No. 870777-24-5, Dec. 29, 2005.
CAS Registry No. 871125-99-4, Jan. 4, 2006.
Caujolle et al. "Arylboronic Acid Metabolism in the Rat," Sciences Naturelles 270(11):1529-1531, (1970). (English translation of Abstract provided).
Communication pursuant to Article 94(3) EPC from European Patent Office for Application No. 11007264.2, dated Apr. 8, 2015.
Cravatt et al., "Functional disassociation of the central and peripheral fatty acid amide signaling systems," Proc. Natl. Acad. Sci. U.S.A 101(29):10821-10826 (2004).
Deutsch et al., "Design of On-Target FAAH Inhibitors," Chern. Bioi. 12(11):1157-115S (2005).
Dong et al., "The synthesis and transition temperatures of some fluorinated terphenyls with chiral and alkenyl terminal chains," Ferroelectrics (180):245-257 (1996).
Drake et al., "Characterizing high-affinity antigen/antibody complexes by kinetic- and equilibrium-based methods," Anal. Biochem. 328(1):35-43 (2004).
Ebdrup et al., "Structure-activity relationship for aryl and heteroaryl boronic acid inhibitors of hormonesensitive lipase," Bioorg. Med. Chern. 13(6):2305-2312 (2005).
European Search Report dated Nov. 16, 2011, for EU Application No. 11007264.2.
Gavezzotti, "Are Crystal Structures Predictable?" Ace. Chem. Res. 27:309-314 (1994). (From 892 U.S. Appl. No. 11/870,130).
Giang and Cravatt, "Molecular characterization of human and mouse fatty acid amide hydrolases," Proc. Natl. Acad. Sci. U.S.A 94(6):2238-2242 (1997).
Gray et al., "The synthesis and transition-temperatures of some 4,4"- dialkyl-1,1'-4',1 "-terphenyl and 4,4"-alkoxyalkyl-1, 1'- 4', 1

(56) References Cited

OTHER PUBLICATIONS

"-terphenyl with 2,3-difluoro or 2',3'-difluoro substituents and of their biphenyl analogs," J. Chem. Soc.—Perkin Trans. 2 2041-2053 (1989).
Hillard et al., "Characterization of the kinetics and distribution of N-arachidonylethanolamine (anandamide) hydrolysis by rat brain," Biochim. Bioohvs. Acta. 1257(3):249-256 (1995).
Hirano et al., "Bioluminescent Properties of Fluorinated Semi-synthetic Aequorins," Tetrahedron Letters, 39:5541-5544 (1998).
Hirayama, N. et al., "Yuki kagoubutsu kessyo sakusei handbook", 2008. pp. 17-23, pp. 37-40, pp. 45-51, pp. 57-65.
Hird et al., "Cyclohexenyl triflates and arylboronic acids in palladium-catalysed cross-couplings. Synthesis and transition temperatures of some fluoro-substituted biphenylylcyclohexenes," J. Mater. Chern. (5):2239-2245 (1995).
Huang et al., "Identification of a new class of molecules, the arachidonyl amino acids, and characterization of one member that inhibits pain," J. Bioi. Chern. 276(46):42639-42644 2001).
Innocenti et al., "Carbonic Anhydrase Inhibitors. Inhibition of Fungal β-Carbonic Anhydrases from Candida Albicans and Cryptococcus Neoformans with Boronic Acids," Bioorganic & Medicinal Chemistry Letters 1-4 (2009).
Insel et al., "Rat Pup Ultrasonic Calls: Possible Mediation by the Benzodiazepine Receptor Complex," Pharmacal. Biochem. Behav. 24:1263-1267 (1986).
International Search Report and Written Opinion for PCT/US2011/023352, published as WO2011/097233A1, dated Jun. 15, 2011.
Jauhiainen et al., "Aromatic Boronic Acids as Probes of the Catalytic Site of Human Plasma Lecithin—Cholesterol Acyltransferase," Biochem. Biophys. Acta. 918:175-188 (1987).
Jiang et al., "Use of in Situ Isopropoxide Protection in the Metal-Halogen Exchange of Arylboronates," J. Org. Chem. 72:6618-6620 (2007).
Karbarz et al., "Biochemical and Biological Properties of 4-(3-phenyl-[1,2,4]thiadiazol-5-yl)-piperazine-1-carboxylic acid phenylamide, a Mechanism-Based Inhibitor of Fatty Acid Amide Hydrolase," Anesthesia & Analgesia 108, 316-329 (2009).
Kathuria et al., "Modulation of anxiety through blockade of anandamide hydrolysis," Nat. Med. 9(1):76-81 (2003).
Kedia et al., "Reaction Progress Analysis: Powerful Tool for Understanding Suzuki-Miyura Reaction and Control ofPolychlorobiphenyl Impurity," Org. Proc. Res. Dev. 13:420-428 (2009).
Koehler et al., "2-Phenylethaneboronic Acid, a Possible Transition-State Analog for Chymotrypsin," Biochemistry 10:2477 (1971).
Kojima, Takashi, Effective Solid Form Selection for the Pharmaceutical Development, Journal of Pharmaceutical Science and Technology, Japan, Sep. 1, 2008, vol. 68, No. 5, pp. 344-349.
Kong et al., "Structure-Based Discovery of a Boronic Acid Biosostere of Combretastatin A-4," Chem. Bioi. 12 (9):1007-1014 (2005).
Labar et al., "Fatty Acid Amide Hydrolase: From Characterization to Therapeutics," Chem. Biodivers. 4(8): 1882-1902 (2007).
Lambert and Fowler, "The endocannabinoid system: Drug targets, lead compounds, and potential therapeutic applications," J. Med. Chem. 48(16):5059-5087 (2005).
Li et al., "An Improved Protocol for the Preparation of 3-Pyridyl- and Some Arylboronic Acids," J. Org. Chem. 67:5394-5397 (2002).
Lienhard et al., "2 Phenylethaneboronic Acid, A Possible Transition-State Analog for Chymotrypsin," Biochemistry 10(13):2477-2483 (1971).

Lynch et al., "Effects ofNeuropeptide Yon Ingestion of Flavored Solutions in Nondeprived Rats," Phvsiol. Behav. 54:877-880 (1993).
Martin et al., "Inhibition of the RTEM-1 β-Lactamase by Boronic Acids," Bioorg. Med. Chem. Lett. 4:1229-1234 (1994).
Maurelli et al, "Two novel classes of neuroactive fatty acid amides are substrates for mouse neuroblastoma 'anandamide amidohydrolase'," FEBS Lett. 377(1):82-86 (1995).
Glendinning et al., "The synthesis and mesomorphic properties of 4,4"-dialkyl-2,2',3- and 2,2',3'-C25 trifluoro-1,1':4',1"-terphenyls for high dielectric biaxiality ferroelectric liquid crystal mixtures," J. Chem. Soc. Perkin Trans. 2 27-34 (2000).
Helble, Joseph, "Determination of Boronic Acids Derivatized with Azomethine and HPLC Separation with Visible Wavelength Detection." American Association of Pharmaceutical Scientists National Convention, Los Angeles, Nov. 9, 2009.
Winum et al., "Carbonic anhydrase inhibitors. Synthesis and inhibition of cytosolic/tumor-associated carbonic anhydrase isozymes I, II, and IX with boron-containing sulfonamides, sulfamides, and sulfamates: toward agents for boron neutron capture therapy of hypoxic tumors," Bioorg. Med. Chem. Lett. 15(13):3302-3306 (2005).
Yan Jun et al., "Determination of Boron with Chromotropic Acid by High-performance Liquid Chromatography," Analyst 113:1631-1634 (1988).
Yang et al., "Boronic Acid Compounds as Potential Pharmaceutical Agents," Med. Res. Rev. 23(3): 346-368 (2003).
Yu, "Amorphous pharmaceutical solids: preparation, characterization and stabilization," Adv. Drug. Deliv. Rev. 48:27-42 (2001).
Zhang et al., "Studies on antitumor drugs. II. Synthesis of diarylborinic .alpha.-amino acid anhydrides and diarylborinic aminoethyl esters," XP002663674, Retrieved from STN Database Accession No. 1983:17023.
Zheng et al., "Microwave-assisted synthesis of ethynylarylboronates for the construction of boronic acidbased fluorescent sensors for carbohydrates," Tetrahodron Letters, 47:2331-2335 (2006).
Zhong et al., "Suzuki coupling of aryl organics on diamond," Chern. Mater. 20(9):313 7-3144 (2008).
Brittain, H. G. (Ed.), "Polymorphism in pharmaceutical solids" CRC Press, 2009.
Detoisien, T. et al., "A rapid method for screening crystallization conditions and phases of an active pharmaceutical ingredient" Organic Process Research & Development. 2009, vol. 13, No. 6, pp. 1338-1342.
Hilfiker, R. (Ed.), "Polymorphism: in the pharmaceutical industry" John Wiley & Sons, 2006.
Argentina Substantive Examination Report for Argentina Patent Application No. P110100368 dated Apr. 28, 2017—No document available.
Australian Patent Examination Report No. 1 for Australian Patent Application No. 2011213072 dated Oct. 13, 2015, 3 pages.
Canadian Patent Examination and Search Report for Canadian Patent Application No. 2,788,587 dated Feb. 14, 2017, 3 pages.
Israel Office Action for Israel Patent Application No. 221281 dated Sep. 15, 2014, No document available.
Japanese Office Action for Japanese Patent Application No. 2016-012894, dated Dec. 28, 2016; English Translation, 5 pages.
Australian Patent Examination Report No. 2 for Australian Patent Application No. 2011213072 dated Jan. 14, 2016, 4 pages.
Israel Second Office Action for Israel Patent Application No. 221281 dated Jan. 7, 2015, No document available.
Tian, J. et al., "A new strategy of transforming pharmaceutical crystal forms" Journal of the American Chemical Society. 2011, vol. 133, No. 5, pp. 1399-1404.

SEQUENCE LISTING

<160> NUMBER OF SEQ ID NOS: 1

<210> SEQ ID NO 1
<211> LENGTH: 579
<212> TYPE: PRT
<213> ORGANISM: Homo sapiens

<400> SEQUENCE: 1

```
Met Val Gln Tyr Glu Leu Trp Ala Ala Leu Pro Gly Ala Ser Gly Val
1               5                   10                  15

Ala Leu Ala Cys Cys Phe Val Ala Ala Val Ala Leu Arg Trp Ser
                20                  25                  30

Gly Arg Arg Thr Ala Arg Gly Ala Val Val Arg Ala Arg Gln Arg Gln
                35                  40                  45

Arg Ala Gly Leu Glu Asn Met Asp Arg Ala Ala Gln Arg Phe Arg Leu
        50                  55                  60

Gln Asn Pro Asp Leu Asp Ser Glu Ala Leu Leu Ala Leu Pro Leu Pro
65                  70                  75                  80

Gln Leu Val Gln Lys Leu His Ser Arg Glu Leu Ala Pro Glu Ala Val
                85                  90                  95

Leu Phe Thr Tyr Val Gly Lys Ala Trp Glu Val Asn Lys Gly Thr Asn
                100                 105                 110

Cys Val Thr Ser Tyr Leu Ala Asp Cys Glu Thr Gln Leu Ser Gln Ala
                115                 120                 125

Pro Arg Gln Gly Leu Leu Tyr Gly Val Pro Val Ser Leu Lys Glu Cys
        130                 135                 140

Phe Thr Tyr Lys Gly Gln Asp Ser Thr Leu Gly Leu Ser Leu Asn Glu
145                 150                 155                 160

Gly Val Pro Ala Glu Cys Asp Ser Val Val His Val Leu Lys Leu
                165                 170                 175

Gln Gly Ala Val Pro Phe Val His Thr Asn Val Pro Gln Ser Met Phe
                180                 185                 190

Ser Tyr Asp Cys Ser Asn Pro Leu Phe Gly Gln Thr Val Asn Pro Trp
        195                 200                 205

Lys Ser Ser Lys Ser Pro Gly Gly Ser Ser Gly Gly Glu Gly Ala Leu
        210                 215                 220

Ile Gly Ser Gly Gly Ser Pro Leu Gly Leu Gly Thr Asp Ile Gly Gly
225                 230                 235                 240

Ser Ile Arg Phe Pro Ser Ser Phe Cys Gly Ile Cys Gly Leu Lys Pro
                245                 250                 255

Thr Gly Asn Arg Leu Ser Lys Ser Gly Leu Lys Gly Cys Val Tyr Gly
                260                 265                 270

Gln Glu Ala Val Arg Leu Ser Val Gly Pro Met Ala Arg Asp Val Glu
        275                 280                 285

Ser Leu Ala Leu Cys Leu Arg Ala Leu Leu Cys Glu Asp Met Phe Arg
        290                 295                 300

Leu Asp Pro Thr Val Pro Pro Leu Pro Phe Arg Glu Glu Val Tyr Thr
```

-continued

```
305                 310                 315                 320
Ser Ser Gln Pro Leu Arg Val Gly Tyr Tyr Glu Thr Asp Asn Tyr Thr
            325                 330                 335

Met Pro Ser Pro Ala Met Arg Arg Ala Val Leu Glu Thr Lys Gln Ser
            340                 345                 350

Leu Glu Ala Ala Gly His Thr Leu Val Pro Phe Leu Pro Ser Asn Ile
            355                 360                 365

Pro His Ala Leu Glu Thr Leu Ser Thr Gly Gly Leu Phe Ser Asp Gly
            370                 375                 380

Gly His Thr Phe Leu Gln Asn Phe Lys Gly Asp Phe Val Asp Pro Cys
385                 390                 395                 400

Leu Gly Asp Leu Val Ser Ile Leu Lys Leu Pro Gln Trp Leu Lys Gly
            405                 410                 415

Leu Leu Ala Phe Leu Val Lys Pro Leu Leu Pro Arg Leu Ser Ala Phe
            420                 425                 430

Leu Ser Asn Met Lys Ser Arg Ser Ala Gly Lys Leu Trp Glu Leu Gln
            435                 440                 445

His Glu Ile Glu Val Tyr Arg Lys Thr Val Ile Ala Gln Trp Arg Ala
    450                 455                 460

Leu Asp Leu Asp Val Val Leu Thr Pro Met Leu Ala Pro Ala Leu Asp
465                 470                 475                 480

Leu Asn Ala Pro Gly Arg Ala Thr Gly Ala Val Ser Tyr Thr Met Leu
            485                 490                 495

Tyr Asn Cys Leu Asp Phe Pro Ala Gly Val Val Pro Val Thr Thr Val
            500                 505                 510

Thr Ala Glu Asp Glu Ala Gln Met Glu His Tyr Arg Gly Tyr Phe Gly
            515                 520                 525

Asp Ile Trp Asp Lys Met Leu Gln Lys Gly Met Lys Lys Ser Val Gly
            530                 535                 540

Leu Pro Val Ala Val Gln Cys Val Ala Leu Pro Trp Gln Glu Glu Leu
545                 550                 555                 560

Cys Leu Arg Phe Met Arg Glu Val Glu Arg Leu Met Thr Pro Glu Lys
                565                 570                 575

Gln Ser Ser
```

METHODS OF TREATING A FATTY ACID AMIDE HYDROLASE-MEDIATED CONDITION

CROSS-REFERENCE TO RELATED APPLICATIONS

This application is a divisional of U.S. patent application Ser. No. 13/019,262, filed Feb. 1, 2011, now U.S. Pat. No. 9,034,849, issued May 19, 2015, which application claims priority to U.S. Provisional Application No. 61/301,181, filed Feb. 3, 2010, and U.S. Provisional Application No. 61/412,734, filed Nov. 11, 2010, the disclosure of each of which is hereby incorporated herein in its entirety by this reference.

STATEMENT ACCORDING TO 37 C.F.R. § 1.821(c) or (e)—SEQUENCE LISTING SUBMITTED AS PDF FILE WITH A REQUEST TO TRANSFER CRF FROM PARENT APPLICATION

Pursuant to 37 C.F.R. § 1.821(c) or (e), a file containing a PDF version of the Sequence Listing has been submitted concomitant with this application, the contents of which are hereby incorporated by reference. The transmittal documents of this application include a Request to Transfer CRF from the parent application.

BACKGROUND OF THE INVENTION

Fatty acid amide hydrolase (FAAH), also referred to as oleamide hydrolase and anandamide amidohydrolase, is an integral membrane protein responsible for the hydrolysis of several important endogenous neuromodulating fatty acid amides (FAAs), including anandamide, oleoylethanolamide and palmitoylethanolamide, and is intimately involved in their regulation. Because these FAAs interact with cannabinoid and vanilliod receptors, they are often referred to as "endocannabinoids" or "endovanilliods." Initial interest in this area focused on developing FAAH inhibitors to augment the actions of FAAs and reduce pain. Further investigation found FAAH inhibitors, through interactions of the FAAs with unique extracellular and intracellular receptors, can be used to treat a variety of conditions that include, but are not limited to, inflammation, metabolic disorders (e.g., obesity-related conditions and wasting conditions such as cachexias and anorexia), disorders of the central nervous system (e.g., disorders associated with neurotoxicity and/or neurotrauma, stroke, multiple sclerosis, spinal cord injury, movement disorders such as basal ganglia disorders, amylotrophic lateral sclerosis, Alzheimer's disease, epilepsy, mental disorders such as anxiety, depression, learning disorders and Schizophrenia, sleep disorders such as insomnia, nausea and/or emesis, and drug addiction), cardiac disorders (e.g., hypertension, circulatory shock, myocardial reperfusion injury and atherosclerosis) and glaucoma (Pacher et al., "The Endocannabinoid System as an Emerging Target of Pharmacotherapy," *Pharmacological Reviews* (2006) 58:389-462; Pillarisetti et al., "Pain and Beyond: Fatty Acid Amides and Fatty Acid Amide Hydrolase Inhibitors in Cardiovascular and Metabolic Diseases," *Drug Discovery Today* (2009) 597:1-14).

SUMMARY OF THE INVENTION

Compound 1 is a potent FAAH inhibitor and is, therefore, useful for treating conditions mediated by FAAH.

Provided herein are, among other things, crystalline Compound 1, pharmaceutically acceptable salts, hydrates or solvates thereof and/or anhydrides thereof, improved methods of making Compound 1, pharmaceutical compositions comprising Compound 1 and/or anhydrides thereof, and methods of using the same in the treatment of FAAH-mediated conditions. Such embodiments and others are described herein.

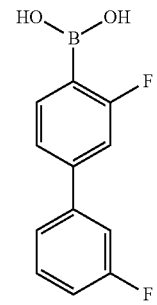

1

For example, in one aspect, provided is crystalline Compound 1, or a pharmaceutically acceptable salt, hydrate or solvate thereof.

In certain embodiments, crystalline Compound 1 is substantially free of any one of the following compounds:

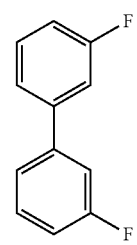

IMP-1

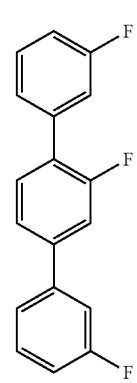

IMP-2

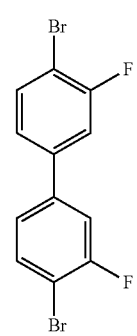

IMP-3

-continued

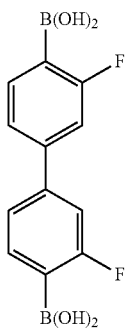

IMP-4

In certain embodiments, crystalline Compound 1 is substantially free of amorphous Compound 1.

In certain embodiments, crystalline Compound 1 is substantially free of other crystalline forms of Compound 1.

In certain embodiments, crystalline Compound 1 is substantially free of one or more anhydrides of Compound 1.

In certain embodiments, one or more anhydrides are selected from Compound 2:

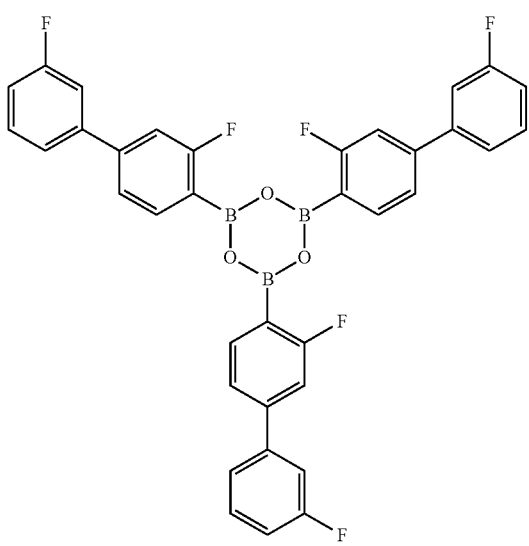

2 or a pharmaceutically acceptable salt, hydrate or solvate thereof.

In certain embodiments, crystalline Compound 1 is pure and isolated.

In certain embodiments, crystalline Compound 1 is crystalline Form A having at least one of the following characteristics:
(i) one or more transition temperatures selected from about 128±5° C. and about 244±2° C. as determined by differential scanning calorimetry (DSC);
(ii) one or more peaks in an X-ray powder diffraction (XRPD) pattern selected from 9.68±0.10, 17.26±0.10, 21.60±0.10, 24.68±0.10, 25.48±0.10, 27.73±0.10 and 29.08±0.10 θ-2θ (degrees);
(iii) an X-ray powder diffraction (XRPD) pattern substantially similar to that depicted in FIG. 1, 19 (row A), 22, or 23; and/or
(iv) a differential scanning calorimetry (DSC) scan substantially similar to that depicted in FIG. 2.

In another aspect, also provided is an anhydride of Compound 1, also referred to herein as Compound 2:

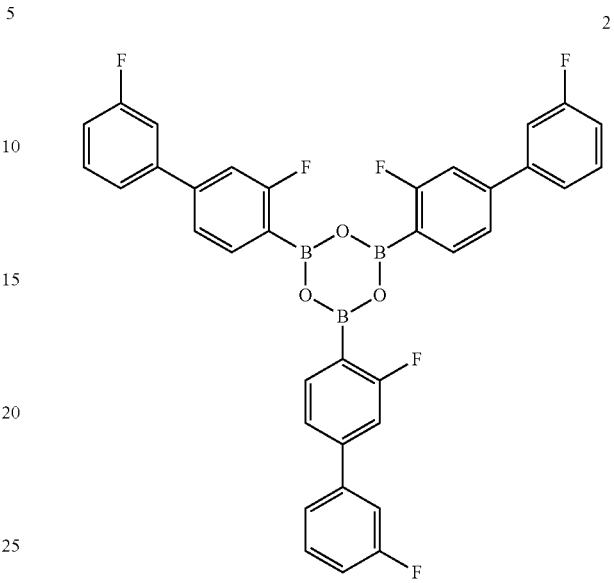

2 or a pharmaceutically acceptable salt, hydrate or solvate thereof.

In certain embodiments, Compound 2 is provided as crystalline Compound 2, or a pharmaceutically acceptable salt, hydrate or solvate thereof.

In certain embodiments, crystalline Compound 2 is substantially free of any one of the following compounds:

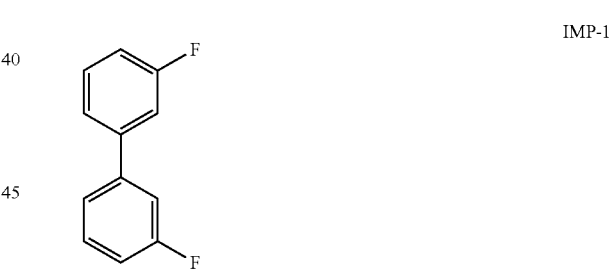

IMP-1

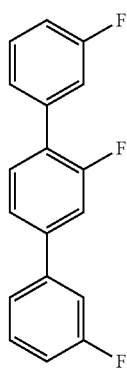

IMP-2

-continued

IMP-3

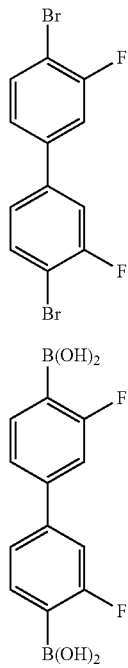

IMP-4

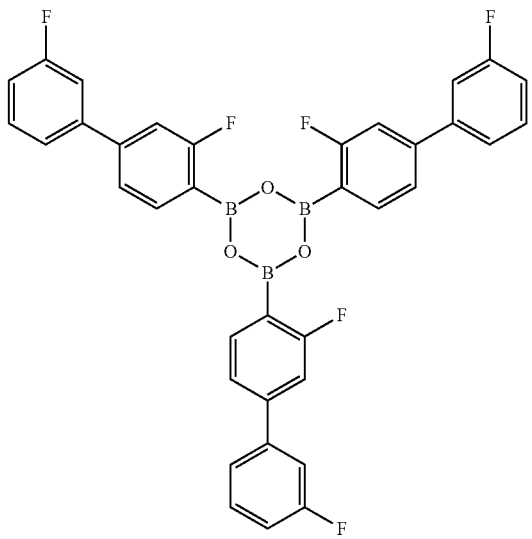

In certain embodiments, crystalline Compound 2 is substantially free of amorphous Compound 2.

In certain embodiments, crystalline Compound 2 is substantially free of other crystalline forms of Compound 2.

In certain embodiments, crystalline Compound 2 is substantially free of Compound 1 or other anhydrides thereof.

In certain embodiments, crystalline Compound 2 is pure and isolated.

In certain embodiments, crystalline Compound 2 is crystalline Form I having at least one of the following characteristics:
(i) one or more transition temperatures selected from about 112±5° C. and about 241±2° C. as determined by differential scanning calorimetry (DSC);
(ii) one or more peaks in an X-ray powder diffraction (XRPD) pattern selected from 6.32±0.10, 12.69±0.10, 17.69±0.10, and 26.77±0.10;
(iii) an X-ray powder diffraction (XRPD) pattern substantially similar to that depicted in FIG. 8, 28, or 29; and/or
(iv) a diffraction scanning calorimetry (DSC) scan substantially similar to that depicted in FIG. 18.

In another aspect, provided is a pharmaceutical composition comprising crystalline Compound 1:

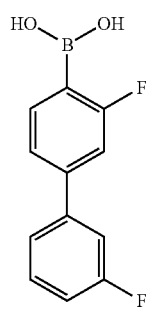

or a pharmaceutically acceptable salt, hydrate or solvate thereof, and a pharmaceutically acceptable excipient.

In certain embodiments, the pharmaceutical composition further comprises crystalline Compound 2:

or a pharmaceutically acceptable salt, hydrate or solvate thereof.

In yet another aspect, provided is a method of preparing Compound 1:

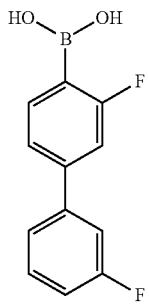

or a pharmaceutically acceptable salt, hydrate or solvate thereof comprising the steps of:
(a) coupling a compound of formula E-1:

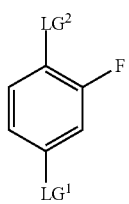

wherein:
LG$^1$ and LG$^2$ are independently selected from a halogen or sulfonate;

with a compound of formula E-2:

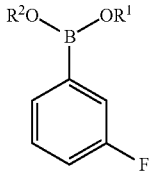

wherein each $R^1$ and $R^2$ is independently selected from hydrogen or an $C_{1-6}$ alkyl, $C_{2-6}$ alkenyl, $C_{2-6}$ alkynyl, $C_{6-12}$ aryl or $C_{6-12}$ heteroaryl group, or $R^1$ and $R^2$ are joined to form a 5-8 membered ring;

in order to provide a compound of formula E-3:

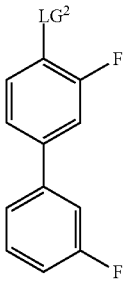

wherein:

$LG^2$ is selected from a halogen or sulfonate; and (b) reacting E-3 with a boronation reagent and a metal reagent in order to provide Compound 1.

In certain embodiments, the method further comprises crystallizing Compound 1 of step (b) to provide crystalline Compound 1.

In certain embodiments, the crystallizing step comprises crystallizing Compound 1 from a polar solution comprising water, a polar apolar solvent or a mixture thereof.

In certain embodiments, the crystallizing step comprises crystallizing Compound 1 from a mixture of water and acetone.

In certain embodiments, the crystalline Compound 1 is further washed with a non-polar solution.

In certain embodiments, the non-polar solution comprises hexanes, heptanes or a mixture thereof.

In certain embodiments, E-1 is E-1 b:

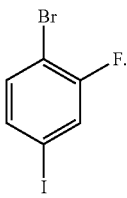

In certain embodiments, E-2 is E-2a:

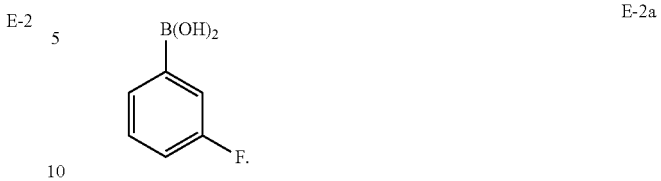

In certain embodiments, E-3 is E-3a:

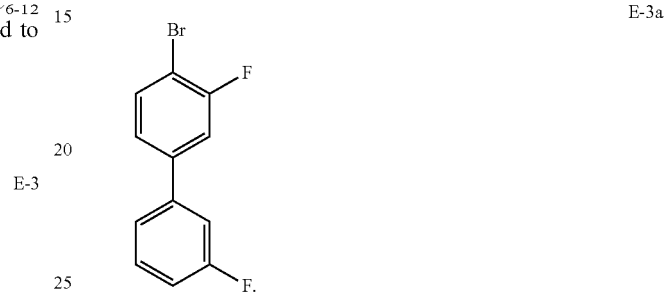

In certain embodiments, the coupling step comprises a palladium catalyst. In certain embodiments, the palladium catalyst is selected from $Pd(PPh_3)_4$, $Pd(OAc)_2$, $Pd_2(dba)_3$, $Pd(dppf)_2Cl_2$, and $PdCl_2(PPh_3)_2$.

In certain embodiments, the coupling step comprises a base. In certain embodiments, the base is selected from triethylamine, diisopropylethylamine, potassium carbonate, sodium carbonate, cesium carbonate, potassium bicarbonate, sodium bicarbonate, cesium bicarbonate, potassium acetate, sodium acetate, potassium phosphate, lithium hydroxide, sodium hydroxide and magnesium hydroxide.

In certain embodiments, the boronation reagent is a boronate ester. In certain embodiments, the boronate ester is selected from trimethyl borate, triethyl borate, triallyl borate, triisopropyl borate, Tributyl borate, Tri-tert-butyl borate, Tripentyl borate, Trihexyl borate, Tritolyl borate, Tribenzyl borate, Triphenyl borate, Trimethylene borate, Triethanolamine borate, Trimethallyl borate, 2-Methoxy-4,4,5,5-tetramethyl-1,3,2-dioxaborolane, 2-Methoxy-4,4,6-trimethyl-1,3,2-dioxaborinane, 2-Isopropoxy-4,4,5,5-tetramethyl-1,3,2-dioxaborolane, 2-Isopropoxy-4,4,6-trimethyl-1,3,2-dioxaborinane, 2-(2-dimethylaminoethoxy)-4-methyl-1,3,2-dioxaborinane, 2-butoxy-4,4,6-trimethyl-1,3,2-dioxaborinane, tris(2,2,2-trifluoroethyl) borate, tris(1-isopropyl-2-methylpropyl) borate, and 2,2'-(2-methyl-2,4-pentanediyldioxy)bis (4,4,6-trimethyl-1,3,2-dioxaborinane).

In certain embodiments, the metal reagent is an alkyl lithium reagent. In certain embodiments, the alkyl lithium reagent is n-butyllithium or hexyllithium. In certain embodiments, the metal reagent is an alkylmagnesium halide. In some embodiments, the alkylmagnesium halide is methylmagnesium bromide.

In certain embodiments, the method step (b) further comprises the steps of dehydrating Compound 1 in order to provide an anhydride of Compound 1 followed by hydrolysis of the anhydride of Compound 1 in order to provide Compound 1. In certain embodiments, the dehydration step is performed in situ (i.e., Compound 1 is not isolated). In certain embodiments, the hydrolysis step is performed by addition of water to the anhydride of Compound 1.

In certain embodiments, the anhydride of Compound 1 is Compound 2:

Compound 2

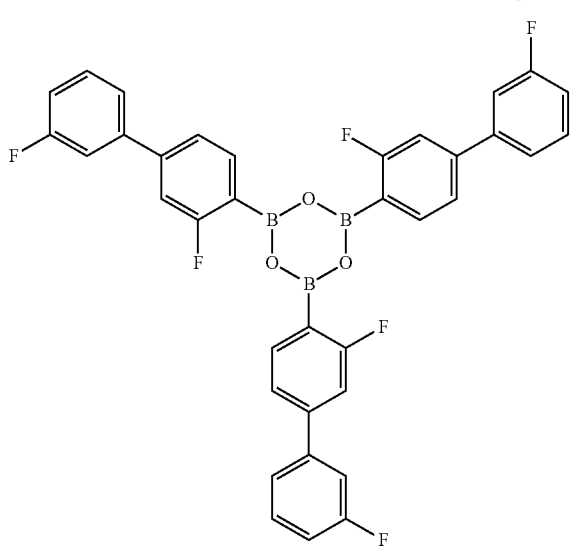

or a pharmaceutically acceptable salt, hydrate or solvate thereof.

In certain embodiments, this method provides pure and isolated crystalline Compound 1. In certain embodiments, these additional steps (i.e., dehydration followed by hydrolysis) provide pure and isolated crystalline Compound 1.

In yet another aspect, provided is a method of treating an FAAH-mediated condition comprising administering to a subject in need thereof a therapeutically effective amount of crystalline Compound 1, as defined herein.

In certain embodiments, the FAAH-mediated condition is selected from a painful condition, an inflammatory condition, an immune disorder, a disorder of the central nervous system, a metabolic disorder, a cardiac disorder and glaucoma.

In certain embodiments, the FAAH-mediated condition is a painful condition selected from neuropathic pain, central pain, deafferentation pain, chronic pain, post-operative pain, pre-operative pain, nociceptive pain, acute pain, non-inflammatory pain, inflammatory pain, pain associated with cancer, wound pain, burn pain, pain associated with medical procedures, pain resulting from pruritus, painful bladder syndrome, pain associated with premenstrual dysphoric disorder, pain associated with premenstrual syndrome, pain associated with chronic fatigue syndrome, pain associated with pre-term labor, pain associated with withdrawal symptoms from drug addiction, joint pain, arthritic pain, lumbosacral pain, musculo-skeletal pain, headache, migraine, muscle ache, lower back pain, neck pain, toothache dental/maxillofacial pain and visceral pain.

In certain embodiments, the FAAH-mediated condition is an inflammatory condition or an immune disorder.

In certain embodiments, the inflammatory condition or immune disorder is a gastrointestinal disorder.

In certain embodiments, the inflammatory condition or immune disorder is a skin condition.

In certain embodiments, the FAAH-mediated condition is a disorder of the central nervous system selected from neurotoxicity and/or neurotrauma, stroke, multiple sclerosis, spinal cord injury, epilepsy, a mental disorder, a sleep condition, a movement disorder, nausea and/or emesis, amyotrophic lateral sclerosis, Alzheimer's disease and drug addiction.

In certain embodiments, the FAAH-mediated condition is a metabolic disorder selected from a wasting condition or an obesity-related condition or complication thereof.

In certain embodiments, the FAAH-mediated condition is a cardiac disorder selected from hypertension, circulatory shock, myocardial reperfusion injury and atherosclerosis.

In certain embodiments, the FAAH-mediated condition is glaucoma.

In yet another aspect, provided is a compound of the formula:

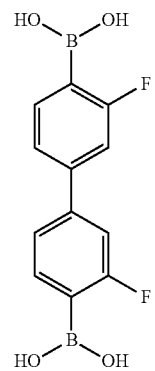 [SMILES: OB(O)c1ccc(-c2ccc(B(O)O)c(F)c2)cc1F]

or a pharmaceutically acceptable salt, solvate or hydrate thereof.

SEQUENCE IDENTIFICATION NUMBERS

Figure 1:
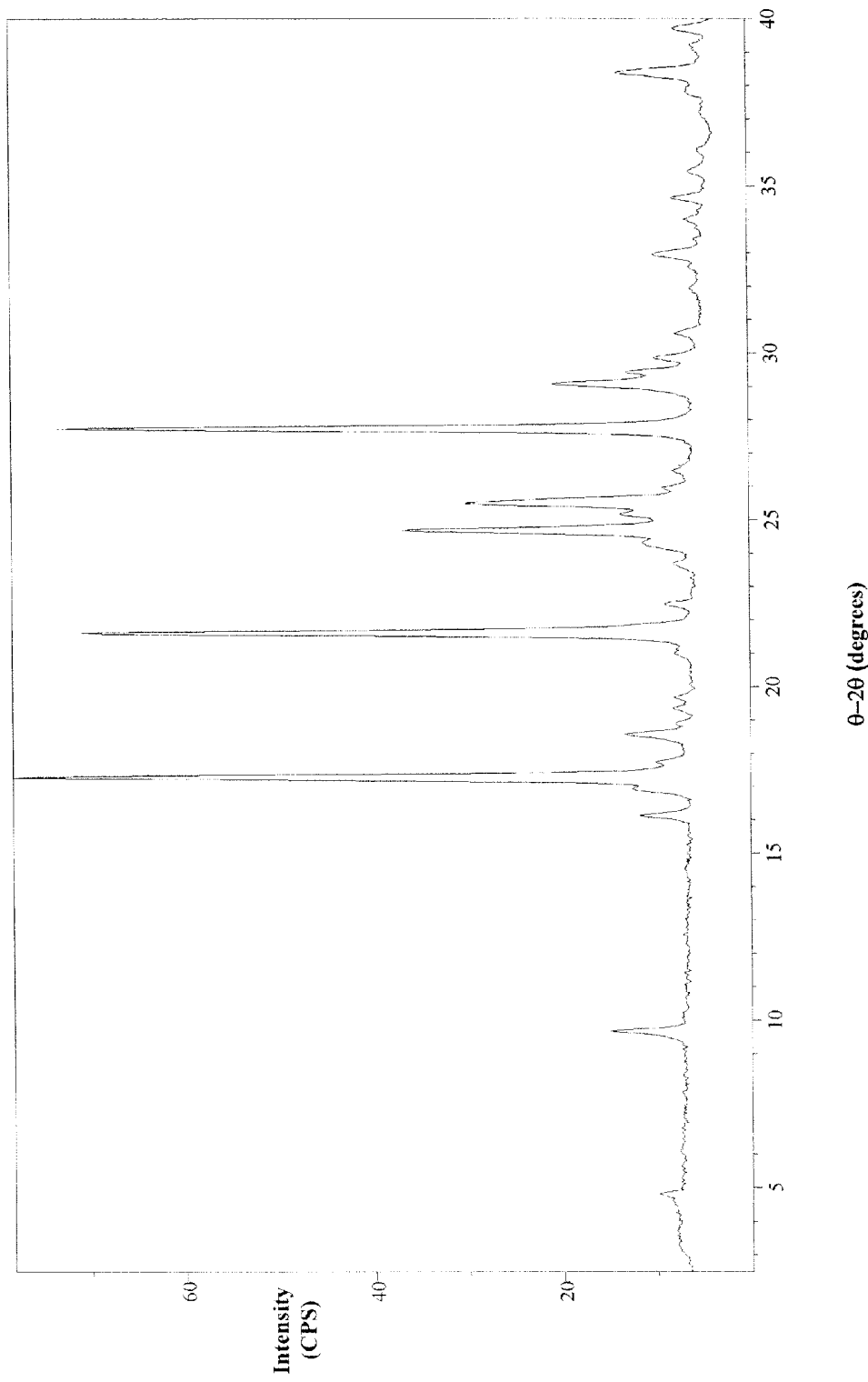
FIG. 1 shows an X-ray Diffraction Pattern of Form A of Compound 1.

SEQ ID NO:1: *Homo sapiens* FAAH amino acid sequence

MVQYELWAALPGASGVALACCFVAAAVALRWSGRRTARGAVVRARQRQR

AGLENMDRAAQRFRLQNPDLDSEALLALPLPQLVQKLHSRELAPEAVLF

TYVGKAWEVNKGTNCVTSYLADCETQLSQAPRQGLLYGVPVSLKECFTY

KGQDSTLGLSLNEGVPAECDSVVVHVLKLQGAVPFVHTNVPQSMFSYDC

SNPLFGQTVNPWKSSKSPGGSSGGEGALIGSGGSPLGLGTDIGGSIRFP

SSFCGICGLKPTGNRLSKSGLKGCVYGQEAVRLSVGPMARDVESLALCL

RALLCEDMFRLDPTVPPLPFREEVYTSSQPLRVGYYETDNYTMPSPAMR

RAVLETKQSLEAAGHTLVPFLPSNIPHALETLSTGGLFSDGGHTFLQNF

KGDFVDPCLGDLVSILKLPQWLKGLLAFLVKPLLPRLSAFLSNMKSRSA

GKLWELQHEIEVYRKTVIAQWRALDLDVVLTPMLAPALDLNAPGRATGA

VSYTMLYNCLDFPAGVVPVTTVTAEDEAQMEHYRGYFGDIWDKMLQKGM

KKSVGLPVAVQCVALPWQEELCLRFMREVERLMTPEKQSS.

DEFINITIONS

Chemical Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The term "alkyl," as used herein, refers to saturated, straight- or branched-chain optionally substituted hydrocarbon radicals derived from an aliphatic moiety containing between one and six carbon atoms (e.g., $C_{1-6}$ alkyl) by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain optionally substituted aliphatic moiety having at least one carbon-carbon double bond by the removal of a single hydrogen atom. In certain embodiments, the alkenyl group employed in the invention contains 2-6 carbon atoms (e.g., $C_{2-6}$ alkenyl). In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain optionally substituted aliphatic moiety having at least one carbon-carbon triple bond by the removal of a single hydrogen atom. In certain embodiments, the alkynyl group employed in the invention contains 2-6 carbon atoms (e.g., $C_{2-6}$ alkynyl). In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

The term "aryl," used alone or as part of a larger moiety as in "aralkyl," "aralkoxy," or "aryloxyalkyl," refers to monocyclic and bicyclic optionally substituted ring systems having a total of five to twelve ring members, wherein at least one ring in the system is aromatic and wherein each ring in the system contains three to seven ring members. In some embodiments, "aryl" refers to monocyclic and bicyclic optionally substituted ring systems having a total of six to twelve ring members (e.g., $C_{6-12}$ aryl), wherein at least one ring in the system is aromatic and wherein each ring in the system contains three to seven ring members. The term "aryl" may be used interchangeably with the term "aryl ring." In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenantriidinyl, or tetrahydronaphthyl, and the like.

The terms "heteroaryl" used alone or as part of a larger moiety, e.g., "heteroaralkyl" or "heteroaralkoxy," refer to optionally substituted groups having 5 to 10 ring atoms, preferably 5, 6, or 9 ring atoms; having 6, 10, or 14 π electrons shared in a cyclic array; and having, in addition to carbon atoms, from one to five heteroatoms. In some embodiments, the term "heteroaryl" refers to optionally substituted groups as defined above having 6 to 10 ring atoms (e.g., $C_{6-12}$ heteroaryl). The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$, which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)O$-N(R^\circ)_2$; or $-(C_{1-4}$ straight or branched)alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, —(CH$_2$)$_{0-2}$OR˙, —(CH$_2$)$_{0-2}$CH(OR˙)$_2$; —O(haloR˙), —CN, —N$_3$, —(CH$_2$)$_{0-2}$C(O)R˙, —(CH$_2$)$_{0-2}$C(O)OH, —(CH$_2$)$_{0-2}$C(O)OR˙, —(CH$_2$)$_{0-2}$SR˙, —(CH$_2$)$_{0-2}$SH, —(CH$_2$)$_{0-2}$NH$_2$, —(CH$_2$)$_{0-2}$NHR˙, —(CH$_2$)$_{0-2}$NR˙$_2$, —NO$_2$, —SiR˙$_3$, —C(O)SR˙, —(C$_{1-4}$ straight or branched alkylene)C(O)OR˙, or —SSR˙, wherein each R˙ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic, which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic, which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic, which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of R† are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "boronic acid" refers to any chemical compound comprising a —B(OH)$_2$ moiety. Arylboronic acid compounds readily form anhydrides by dehydration of the boronic acid moiety (see, for example, Snyder et al., *J. Am. Chem. Soc.* (1958) 80:3611). An "anhydride" of a boronic acid includes, but is not limited to, dimers, trimers and oligomers of the boronic acid and mixtures thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66:1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

A compound is referred to as "isolated" (e.g., "isolated Compound 1" or "isolated Compound 2") if the compound is free from the reaction mixture from which it was synthesized. Isolation of a compound can be performed by any method known to one skilled in the art, including chromatography (e.g., high pressure liquid chromatography (HPLC)), trituration, precipitation, crystallization, distillation, and/or extraction, or any sequential combination thereof. Compounds may be isolated as solids. At sufficiently high temperature, the solid may melt, and thus the compound may also be isolated in its liquid phase.

As used herein "amorphous" refers to a solid form of a compound wherein there is no long-range order of the positions of the atoms. The amorphous nature of a solid can be confirmed, for example, by examination of the X-ray powder diffraction pattern. If the XRPD does not show any sharp intensity peaks, and/or has one or more "halos" (broad bumps) in the XRPD then the compound is amorphous.

As used herein, "crystalline" refers to a solid form of a compound wherein there exists long-range atomic order in the positions of the atoms. The crystalline nature of a solid can be confirmed, for example, by examination of the X-ray powder diffraction pattern. If the XRPD shows sharp intensity peaks in the XRPD then the compound is crystalline.

As used herein, "polymorph" refers to a crystalline compound having more than one crystal structure, e.g., resulting from differences in molecular packing and/or molecular conformation of the compound in the solid state. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation. One exemplary way of characterizing a polymorph is via its unique X-ray powder diffraction (XRPD) pattern.

The term "solvate" refers to a crystalline compound wherein a stoichiometric or non-stoichiometric amount of solvent, or mixture of solvents, is incorporated into the crystal structure.

The term "hydrate" refers to a crystalline compound where a stoichiometric or non-stoichiometric amount of water is incorporated into the crystal structure.

As used herein, "chemically stable" refers to a compound that exhibits total organic impurities of less than about 10%, less than about 5%, less than about 4%, less than about 3%, less than about 2%, less than about 1%, less than about 0.5%, less than about 0.25%, or less than about 0.1%, when subjected to a particular condition including, for example, a stressing condition for a period of time. As used herein, "physically stable" refers to crystalline forms, or a mixture of crystalline and/or amorphous forms, that do not undergo crystal form change when subjected to a particular condition including, for example, a stressing condition for a period of time, with or without dessicant. In some embodiments, the stressing condition is relative humidity, storing at a temperature between 1-10, 10-20, 20-30, 30-40, 40-50, 50-60, 60-70, 70-80, 80-90, or 90-100° C. In certain embodiments, the period of time is at least 1, at least 2, at least 3, at least 4, at least 5, at least 10, or at least 20 weeks.

As used herein, the terms "about" and "approximately" when used in combination with a numeric value or range of values used to characterize a particular crystal form, amorphous form, or mixture thereof of a compound mean the value or range of values may deviate to an extent deemed reasonable to one of ordinary skill in the art while describing the particular crystal form, amorphous form, or mixture thereof.

DETAILED DESCRIPTION OF THE INVENTION

Compound 1, also referred to as 3,3'-difluorobiphenyl-4-ylboronic acid, is particularly useful for treating conditions mediated by FAAH. Compound 1 is provided in the class of molecules described in US2009/0099131 and WO2008/63300, the entirety of each of which is incorporated herein by reference.

Methods for Preparing Compound 1

The present invention provides various improved methods to prepare Compound 1 and anhydrides provided therefrom.

For example, in one aspect, provided is a method of preparing Compound 1 comprising a biaryl cross-coupling step (S–1), followed by a metallation/boronation step (S-2), as depicted in Scheme 1, wherein the variable $LG^1$ and $LG^2$ are leaving groups and the group —$BOR^1OR^2$ corresponds to a boronic acid (i.e., —$B(OH)_2$) or a protected form thereof.

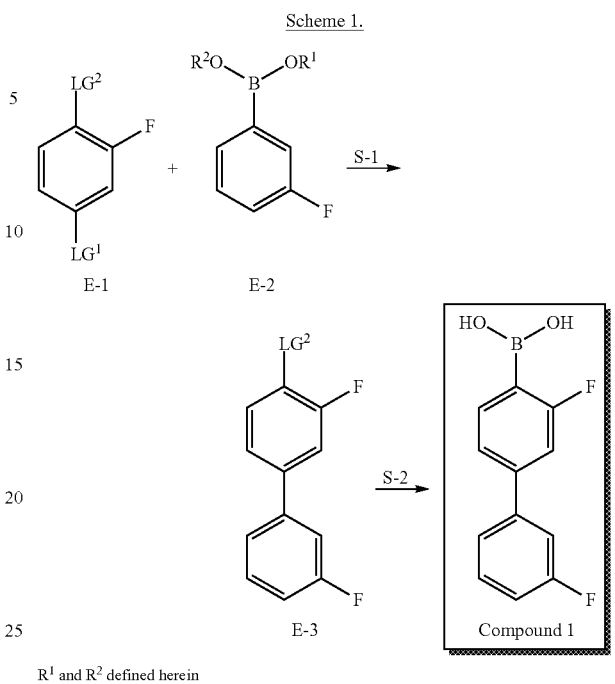

$R^1$ and $R^2$ defined herein (i) Step S-1. Biaryl Cross-Coupling Reaction

The coupling reaction between E-1 and E-2 occurs, generally, via displacement of $LG^1$ of compound E-1, wherein both $LG^1$ and $LG^2$ are leaving groups. A "leaving group" is a group that is subject to nucleophilic displacement, i.e., a chemical group that is readily displaced by an incoming chemical moiety (e.g., a cross-coupling catalyst capable of oxidative addition). Leaving groups are well known in the art, e.g., see, *Advanced Organic Chemistry*, Jerry March, 5th Ed., pp. 351-357, John Wiley and Sons, N.Y. Exemplary leaving groups include, but are not limited to, halogens (e.g., chloro, iodo, bromo, fluoro) and sulfonates (e.g., methanesulfonyloxy (mesyloxy), toluenesulfonyloxy, trifluoromethanesulfonyloxy).

In certain embodiments, $LG^1$ and $LG^2$ are independently selected from halogen and sulfonate. In certain embodiments, $LG^1$ and $LG^2$ are independently selected from halogen. In certain embodiments, $LG^1$ and $LG^2$ are independently selected from —Br or —I. In certain embodiments, $LG^1$ is —Br. In certain embodiments, $LG^1$ is —I. In certain embodiments, $LG^2$ is —Br. In certain embodiments, $LG^2$ is —I. In certain embodiments, $LG^1$ is —Br and $LG^2$ is —Br (e.g., 1,4-dibromo-2-fluorobenzene, "E-1a"). In certain embodiments, $LG^1$ is —I and $LG^2$ is —Br (e.g., 1-bromo-2-fluoro-4-iodobenzene, "E-1b"). As described generally above, compound E-2 corresponds to a boronic acid (wherein $R^1$ and $R^2$ are hydrogen), a protected form thereof, or boronate ester. In some embodiments, $R^1$ and $R^2$ are independently selected from hydrogen or an $C_{1-6}$ alkyl, $C_{2-6}$ alkenyl, $C_{2-6}$ alkynyl, $C_{6-12}$ aryl or $C_{6-12}$ heteroaryl group, or $R^1$ and $R^2$ are joined to form a 5-8 membered ring, provided that $R^1$ and $R^2$ are not both hydrogen. In certain embodiments, E-2 is a boronic acid wherein $R^1$ and $R^2$ are hydrogen (e.g., 3-fluorophenylboronic acid, "E-2a." In some embodiments, E2 is a boronate ester. Exemplary boronate esters include, without limitation, ethyl esters, mannitol esters, picolinates, and pinacol esters.

In some embodiments, the biaryl cross-coupling reaction of step S-1 takes place in the presence of one or more catalysts (e.g., organic or inorganic catalysts). In some embodiments, the catalyst is an organic catalyst. In some embodiments, the catalyst is an inorganic catalyst. In some embodiments, the inorganic catalyst is a Group 10 transition metal catalyst (e.g., nickel catalyst, palladium catalyst, platinum catalyst). In some embodiments, the inorganic catalyst is an organometallic catalyst (e.g., comprising an inorganic metal and at least one organic ligand). In some embodiments, the inorganic metal is a Group 10 transition metal (e.g., nickel, palladium, platinum).

In certain embodiments, the inorganic catalyst is a palladium catalyst. In certain embodiments, the inorganic catalyst is a palladium catalyst and the reaction is a Suzuki coupling. In certain embodiments, the palladium catalyst comprises one or more types of ligands. Exemplary ligands include phosphine ligands (e.g., $PPh_3$, $P(tBu)_3$, diphenylphosphorylferrocene (dppf), diisopropylphosphorylferrocene (dipf)), halogens (e.g., fluorine, chlorine, bromine, iodine), carboxylates (e.g., acetates), organic compounds capable of ligating to a metal to form a complex (e.g., dibenzylideneacetone (dba), 1,3- or 1,5-cyclooctadiene (COD)), and donor solvents (e.g., THF, diethylether, etc.). Exemplary palladium catalysts include, but are not limited to, $Pd(PPh_3)_4$, $Pd(OAc)_2$, $Pd_2(dba)_3$, $Pd(dppf)_2Cl_2$, and $PdCl_2(PPh_3)_2$. In certain embodiments, the catalyst is $PdCl_2(PPh_3)_2$.

In some embodiments, the catalyst loading of step S-1 is from about 0.01 mol % to about 10 mol % of catalyst relative to substrate (i.e., relative to compound E-1). In certain embodiments, the catalyst loading is about 0.1 mol % to about 5 mol %. In certain embodiments, the catalyst loading is about 0.1 mol % to about 4 mol %. In certain embodiments, the catalyst loading is about 0.1 mol % to about 3 mol %. In certain embodiments, the catalyst loading is about 0.1 mol % to about 2 mol %. In certain embodiments, the catalyst loading is about 0.1 mol % to about 1 mol %. In certain embodiments, the catalyst loading is about 0.1% to about 0.5 mol %. In certain embodiments, the catalyst loading is about 0.2 to about 0.5 mol %.

In certain embodiments, the catalyst loading is less than about 5 mol %, less than about 4 mol %, less than about 3 mol %, less than about 2 mol %, less than about 1 mol %, less than about 0.9 mol %, less than about 0.8 mol %, less than about 0.7 mol %, less than about 0.6 mol %, less than about 0.5 mol %, less than about 0.4 mol %, less than about 0.3 mol %, less than about 0.2 mol %, or less than about 0.1 mol %. In certain embodiments, the catalyst is used in an amount of less than about 3.0 mol %.

In some embodiments, the step S-1 occurs in the presence of one or more bases, e.g., organic or inorganic bases. Exemplary organic bases include, but are not limited to, tertiary amines (e.g., triethylamine, diisopropylethylamine). Exemplary inorganic bases include, but are not limited to, carbonates (e.g., potassium carbonate, sodium carbonate, cesium carbonate), bicarbonates (e.g., potassium bicarbonate, sodium bicarbonate, cesium bicarbonate), acetates (e.g., potassium acetate, sodium acetate), phosphates (e.g., potassium phosphate), hydroxides (e.g., lithium hydroxide, sodium hydroxide, magnesium hydroxide). In certain embodiments, the base is an inorganic base. In certain embodiments, the base is sodium bicarbonate ($NaHCO_3$). In certain embodiments, the base is sodium carbonate ($Na_2CO_3$).

In some embodiments, the base of step S-1 is provided in about 1 to about 6 equivalents or in about 2 to about 4 equivalents of base relative to substrate. In certain embodiments, the base of step S-1 is provided in less than about 6 equivalents, less than about 5 equivalents or, less than about 4 equivalents of base relative to substrate. In certain embodiments, about 3 equivalents of base is employed.

In some embodiments, the step S-1 occurs in the presence of one or more solvents. Exemplary solvents include, but are not limited to, organic solvents, water and/or mixtures thereof. Exemplary organic solvents include, but are not limited to, alcohol solvents (e.g., methanol, ethanol, 1-propanol, isopropanol, 1,2-propanediol, n-butanol, t-butanol, t-amyl alcohol), ethers (e.g., tetrahydrofuran, 2-methyltetrahydrofuran, diethylether, 1,4-dioxane, 1,2-dimethoxyethane, methyl t-butyl ether, diethoxy methane), aromatic solvents (e.g., benzene, toluene, xylenes), acetonitrile, dimethylsulfoxide, dimethylformamide, N-methylpyrrolidinone, halogenated solvents (e.g., dichloromethane, chloroform, dichloroethane), esters (e.g., methyl acetate, ethyl acetate, 2-propyl acetate), ketones (e.g., methyl isobutyl ketone, acetone), and hydrocarbons (e.g., hexanes, n-heptane, cyclohexane).

In some embodiments, the solvent is a mixture of an organic solvent and water. In some embodiments, the solvent is a mixture of an alcohol solvent and water. In certain embodiments, the solvent mixture is a mixture of 1-propyl alcohol (1-PrOH) and water. Exemplary percentages of organic solvent in water for these mixtures include, but are not limited to, about 10% to about 90% organic solvent in water, about 20% to about 90% organic solvent in water, about 25% to about 90% organic solvent in water, about 30% to about 80% organic solvent in water, about 40% to about 80% organic solvent in water, or about 50% to about 80% organic solvent in water (e.g., 1-PrOH in water). Exemplary ratios of organic solvent to water for these mixtures include, but are not limited to, 10:1, 9:1, 8:1, 7:1, 6:1, 5:1, 4:1, 3:1, 2:1, and 1:1 of organic solvent to water (e.g., 1-PrOH to $H_2O$). In certain embodiments, the ratio of 1-PrOH:$H_2O$ is about 4:1 (i.e., about 75% 1-PrOH in water). In certain embodiments, the ratio of 1-PrOH:$H_2O$ is about 8:3 (i.e., about 62.5% 1-PrOH in water).

In some embodiments, the step S-1 requires an amount of solvent such that the concentration of the reaction is about 0.01 M to about 10 M. In some embodiments, the concentration of the reaction is about 0.1 M to about 5 M. In some embodiments, the concentration of the reaction is about 0.1 M to about 2.5 M. In some embodiments, the concentration of the reaction is about 0.1 M to about 1.5 M. In some embodiments, the concentration of the reaction is about 0.5 M to about 1.5 M.

In some embodiments, the step S-1 requires an amount of solvent ranging from about 8 volumes of solvent to about 12 volumes of solvent. In some embodiments, the step S-1 requires an amount of solvent ranging from about 8 volumes of solvent to about 11 volumes of solvent. In some embodiments, the step S-1 requires an amount of solvent ranging from about 9 volumes of solvent to about 11 volumes of solvent. In some embodiments, the step S-1 requires an amount of solvent ranging from about 9.5 volumes of solvent to about 11 volumes of solvent. In some embodiments, the step S-1 requires an amount of solvent ranging from about 10 volumes of solvent to about 11 volumes of solvent. In some embodiments, the step S-1 requires an amount of solvent of about 10.0, 10.1, 10.2, 10.3, 10.4, 10.5, 10.6, 10.7, 10.8, 10.9, or 11.0 volumes of solvent. In some embodiments, the step S-1 requires an amount of solvent of about 10.7 volumes of solvent. In some embodiments, the step S-1 requires an amount of solvent of about 10.0 volumes of solvent.

In some embodiments, the step S-1 requires a temperature from about 50° C. to about 100° C. In certain embodiments, the reaction temperature is from about 70° C. to about 90° C. In some embodiments, the reaction temperature is from about 75° C. to about 90° C. In some embodiments, the reaction temperature is from about 75° C. to about 85° C. In some embodiments, the reaction temperature is about 83° C.

Reaction times for the step S-1 range from about 10 to about 30 hours. In some embodiments, the reaction time ranges from about 12 to about 24 hours. In certain embodiments, the reaction time ranges from about 14 to about 20 hours.

The product of step S-1 may be processed to remove impurities prior to performing step S-2. In some embodiments, processing comprises treatment with a suitable solid support in order to reduce the amount of residual catalyst present. In certain embodiments, treatment with a suitable solid support comprises silica gel treatment. In certain embodiments, silica gel treatment may be performed as a batch fed operation or as an in-line filtration operation. In certain embodiments, silica gel treatment is performed as an in-line filtration operation prior to step S-2.

(ii) Step S-2. Metallation-Boronation Reaction

As depicted above Scheme 1, E-3 is used to generate Compound 1 via metallation/boronation. As used herein, the metallation/boronation reaction of step S-2 requires a boronation reagent and a metal reagent capable of undergoing exchange with $LG^2$ of E-3. Such metal reagent is capable of metallating (e.g., with lithium or magnesium) E3. In certain embodiments, $LG^2$ of E-3 is bromo (i.e., 4-bromo-3,3'-difluorobiphenyl, "E-3a").

In certain embodiments, the metal reagent of S-2 is an alkyl lithium reagent. In certain embodiments, the alkyl lithium reagent is n-butyllithium or hexyllithium. In certain embodiments, the alkyl lithium reagent is hexyllithium.

In certain embodiments, the metal reagent of S-2 is magnesium metal or an alkylmagnesium halide (e.g., methylmagnesium bromide).

In certain embodiments, the boronation reagent of S-2 is a borate ester reagent, e.g., $B(OR^3)_3$ wherein each $R^3$ is independently a $C_{1-6}$ alkyl, $C_{2-6}$ alkenyl, $C_{2-6}$ alkynyl, $C_{6-12}$ aryl or $C_{6-12}$ heteroaryl group, or two $R^3$ groups are joined to form a 5-8 membered ring. In certain embodiments, the boronation reagent is $B(OR^3)_3$ wherein each $R^3$ is independently methyl, ethyl, propyl, isopropyl, butyl, cyclohexyl. Exemplary borate ester reagents include, but are not limited to, trimethyl borate, triethyl borate, triallyl borate, triisopropyl borate, Tributyl borate, Tri-tert-butyl borate, Tripentyl borate, Trihexyl borate, Tritolyl borate, Tribenzyl borate, Triphenyl borate, Trimethylene borate, Triethanolamine borate, Trimethallyl borate, 2-Methoxy-4,4,5,5-tetramethyl-1,3,2-dioxaborolane, 2-Methoxy-4,4,6-trimethyl-1,3,2-dioxaborinane, 2-Isopropoxy-4,4,5,5-tetramethyl-1,3,2-dioxaborolane, 2-Isopropoxy-4,4,6-trimethyl-1,3,2-dioxaborinane, 2-(2-dimethylaminoethoxy)-4-methyl-1,3,2-dioxaborinane, 2-butoxy-4,4,6-trimethyl-1,3,2-dioxaborinane, tris(2,2,2-trifluoroethyl) borate, tris(1-isopropyl-2-methylpropyl) borate, and 2,2'-(2-methyl-2,4-pentanediyldioxy) bis(4,4,6-trimethyl-1,3,2-dioxaborinane). In certain embodiments, the borate ester reagent is $B(OiPr)_3$ (triisopropyl borate).

In certain embodiments, the alkyl lithium reagent of S-2 is hexyllithium and the boronation reagent of S-2 is $B(OiPr)_3$.

In certain embodiments, the boronation reagent is provided in about 1 equivalent to about 1.5 equivalents to E-3. In certain embodiments, the boronation reagent is provided in about 1 equivalent to about 1.4 equivalents, in about 1 equivalent to about 1.3 equivalents, in about 1 equivalent to about 1.2 equivalents, or in about 1 equivalent to about 1.1 equivalents, relative to E-3. In certain embodiments, the boronation reagent is provided in about 1 equivalent to about 1.3 equivalents relative to E-3.

In certain embodiments, the metal reagent is provided in about 1 equivalent to about 1.5 equivalents to E-3. In certain embodiments, the metal reagent is provided in about in about 1 equivalent to about 1.4 equivalents, in about 1 equivalent to about 1.3 equivalents, in about 1 equivalent to about 1.2 equivalents, or in about 1 equivalent to about 1.1 equivalents, relative to E-3. In certain embodiments, the metal reagent is provided in about 1 equivalent to about 1.2 equivalents relative to E-3.

In certain embodiments, the metal reagent is titrated prior to use. Titration methods are well known to those of skill in the chemical arts. In some embodiments, in order to avoid any excess addition, the reaction is undercharged with an initial portion of metal reagent, the extent of conversion is determined (using, e.g., HPLC analysis), and an additional portion of metal reagent is added as needed to drive the reaction to completion.

In some embodiments, the metallation/boronation step S-2 occurs in the presence of one or more organic solvents. Exemplary organic solvents include, but are not limited to, aromatic solvents (e.g., benzene, toluene, xylenes), ethers (e.g., tetrahydrofuran, 2-methyltetrahydrofuran, 1,2-dimethoxyethane, 1,4-dioxane, methyl t-butyl ether, diethoxy methane) and hydrocarbons (e.g., hexanes, n-heptane, cyclohexane). In certain embodiments, the solvent is selected from an ether, a hydrocarbon or a mixture thereof. In certain embodiments, the solvent is a combination of 2-methyltetrahydrofuran and a hydrocarbon. In certain embodiments, the solvent is a combination of 2-methyltetrahydrofuran and n-heptane. In certain embodiments, the solvent combination of an ether (e.g., 2-methyltetrahydrofuran) and a hydrocarbon (e.g., n-heptane) is provided in a ratio of 2:1 ether to hydrocarbon.

In some embodiments, the temperature of the reaction of step S-2 ranges from about −78° C. to about 0° C. during the metal reagent addition. In some embodiments, the temperature ranges from about −78° C. to about −10° C. In some embodiments, the temperature ranges from about −78° C. to about −20° C. In some embodiments, the temperature ranges from about −78° C. to about −30° C. In some embodiments, the temperature ranges from about −60° C. to about −30° C. In some embodiments, the temperature ranges from about −50° C. to about −30° C. In some embodiments, the temperature is about −78° C., about −65° C., about −60° C., about −55° C., about −50° C., about −45° C., about −40° C., about −35° C., or about −30° C. In certain embodiments, the temperature is about −35° C.

In some embodiments, the metal reagent of S-2 is added slowly over time to minimize the occurrence of by-products. One of skill in the art would recognize that the rate of addition may change depending on the scale on which the reaction is performed. In certain embodiments, the metal reagent is added over a period of no less than about 60 minutes. In some embodiments, the required amount of metal reagent is added over a period of about 60, 80, or 120 minutes. In certain embodiments, the metal reagent is added over a period of no less than about 120 minutes. In some embodiments, the metal reagent is added over a period of time ranging from about 60 minutes to about 120 minutes.

Upon completion of the reaction, step S-2 is quenched with water. In certain embodiments, wherein the boronating reagent is a borate ester reagent, the quench involved is an acidic quench (using, e.g., 1 M HCl) in order to hydrolyze the boronic ester formed in situ to the boronic acid, Compound 1. In certain embodiments, the aqueous layer is then separated and discarded and the organic layer is concentrated to provide Compound 1. However, in certain embodiments, Compound 1 is provided after the quench of step S-2 using additional steps and methods as described below and herein (e.g., provided after steps S-3 and S-4).

(iii) Crystallization of Compound 1

In certain embodiments, specific crystalline or amorphous forms, or mixtures thereof, of Compound 1 or a derivative thereof, can be made using the methods described herein, as well as other methods known to those of ordinary skill in the art. In certain embodiments, such methods provide Compound 1 as the "Form A" crystal form, which, in some embodiments, exhibits the characteristics and properties described herein. In certain embodiments, such methods provide Compound 1 as the "Material B" crystal form, which, in some embodiments, exhibits the characteristics and properties described herein. In certain embodiments, such methods provide a mixture of Form A and Material B.

Crystalline forms may be prepared by the methods described herein or by techniques known in the art, including heating, cooling, freeze drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces such as, e.g., in nanopores or capillaries, recrystallization on surfaces or templates such as, e.g., on polymers, recrystallization in the presence of additives, such as, e.g., co-crystal countermolecules, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation and precipitation from a supercritical fluid. The particle size of the resulting crystalline forms, which can vary, (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing or sonication.

In certain embodiments, the method provides an additional step of crystallizing Compound 1 from a non-polar or polar solution.

In certain embodiments, Compound 1 is crystallized from a non-polar solution. Exemplary non-polar solutions include a hydrocarbon solvents (e.g., hexanes, heptanes), aromatic solvents (e.g., benzene, toluene, xylenes), or mixtures thereof. For example, in certain embodiments, step S-2 is quenched with water, treated with a non-polar solution and the reaction mixture distilled under vacuum to provide crystalline Compound 1. In certain embodiments, the temperature of the distillation is below about 45° C.

In certain embodiments, Compound 1 is crystallized from a polar solution (e.g., water, a polar aprotic organic solvent, or a mixture thereof). In certain embodiments, Compound 1 is crystallized from a mixture of water and a polar aprotic organic solvent. In certain embodiments, the mixture of polar aprotic organic solvent in water is from about 5% to about 95% polar aprotic organic solvent in water, from about 10% to about 90% polar aprotic organic solvent in water, from about 15% to about 85% polar aprotic organic solvent in water, from about 20% to about 80% polar aprotic organic solvent in water, from about 25% to about 75% polar aprotic organic solvent in water, from about 30% to about 70% polar aprotic organic solvent in water, from about 35% to about 65% polar aprotic organic solvent in water, or from about 40% to about 70% polar aprotic organic solvent in water.

Exemplary polar aprotic organic solvents include, but are not limited to, acetone, and acetonitrile or a mixture thereof. In certain embodiments, the polar aprotic organic solvent is acetone.

For example, in certain embodiments, Compound 1 isolated from the reaction mixture of step S-2 is crystallized from a polar solution of acetone and water. In certain embodiments, the polar solution is from about 5% to about 95% acetone in water, from about 10% to about 90% acetone in water, from about 15% to about 85% acetone in water, from about 20% to about 80% acetone in water, from about 25% to about 75% acetone in water, from about 30% to about 70% acetone in water, from about 35% to about 65% acetone in water, or from about 40% to about 70% acetone in water.

In certain embodiments, the crystallization step involves dissolving Compound 1 in a first solvent (e.g., acetone) and heating to a desired temperature (e.g., reflux) while an appropriate amount of a second solvent (e.g., water) is added such that the solution, upon cooling to ambient temperature, forms recrystallized Compound 1. In certain embodiments, alternating portions of the first and second solvents (e.g., acetone and water) are added to the refluxing solution in iterations prior to cooling of the solution. In some embodiments, the cooling of the solution occurs for a specified amount of time (e.g., greater than about 8 hours) and/or at a specified temperature (e.g., from about 20° C. to about 30° C., or about 25° C. plus or minus 5° C.). In some embodiments, crystalline Compound 1 is isolated via filtration and dried using any method known in the chemical arts to afford Compound 1 substantially free from water as assessed using methods known in the art to measure water content (e.g., Karl Fischer titration). In certain embodiments, the Compound 1 crystallized from a polar solution is further washed with a non-polar solution. In certain embodiments, the non-polar solution comprises a hydrocarbon solvent, e.g., hexanes or heptanes or a mixture thereof. In some embodiments, crystalline Compound 1 provided by this method has an X-ray powder diffraction pattern substantially similar to that depicted in FIG. 1, Form A.

In some embodiments, the formation of the Form A crystal form of Compound 1 is accomplished by crystallization in a solvent selected from acetone, acetonitrile, chloroform, dichloromethane, diethyl ether, dimethylformamide, p-dioxane, ethyl acetate, heptane, tetrahydrofuran, isopropyl ether, methyl ethyl ketone, 2-methyl tetrahydrofuran, methyl iso-butyl ketone, tert-butyl methyl ether, nitromethane, toluene, or water. In certain embodiments, crystallization of Form A is performed in a mixture of one or more of said solvents. In some embodiments, crystallization is performed in the following mixture of solvents: 1:1 heptane/chloroform, 2:1 heptane/THF, 1:1 acetone/water, 1:1 acetonitrile water, 1:1 dimethylformamide/water; 1:1 p-dioxane/water, or 1:1 THF/water.

In some embodiments, provided herein are methods for forming a crystal form of Compound 1 comprising (a) dissolving Compound 1 in a 50:50 mixture of acetone and water at a temperature of about 51° C.; (b) filtering the resulting solution; (c) allowing the solution to cool to ambient temperature; and (d) allowing the solution to stand at ambient temperature for at least 1 day. In some embodiments, the filtering of step (b) is accomplished via hot filtering. In a particular embodiment, the filtering of step (b) is accomplished via hot filtering into a warm container. In certain embodiments, the temperature of about 51° C. of step (a) is obtained by heating the solution in a container on a hot plate. In further embodiments, in step (c), the solution is cooled to ambient temperature by turning the hot plate off and allowing the solution to stand on the hot plate as the hot plate cools. In certain embodiments, the methods provide a Form A crystal form of Compound 1.

In certain embodiments, provided herein are methods for forming a crystal form of Compound 1 comprising crystallization from acetone. In one embodiment, the methods comprise slow evaporation. In some embodiments, the methods comprise crash precipitation with heptane. In certain embodiments, the methods provide a Form A crystal form of Compound 1.

In certain embodiments, provided herein are methods for forming a crystal form of Compound 1 comprising crystallization from acetonitrile. In some embodiments, the methods comprise slow evaporation. In some embodiments, the methods comprise heating to 51° C., slow cooling from a temperature of about 51° C. to about room temperature and, in some embodiments, allowing the solution to stand at room temperature for about 1 day. In some embodiments, the methods comprise vapor diffusion with water over, in some embodiments, about 8 days. In certain embodiments, the methods provide a Form A crystal form of Compound 1.

In certain embodiments, provided herein are methods for forming a crystal form of Compound 1 comprising crystallization from chloroform. In some embodiments, the methods comprise slow evaporation. In some embodiments, the methods comprise heating to 51° C., slow cooling from a temperature of about 51° C. to about room temperature and, in further embodiments, allowing the solution to stand at room temperature for about 1 day and, in even further embodiments, subsequently cooling to about 0° C. In further embodiments, the solution is kept at about 0° C. for about 11 days. In some embodiments, the methods comprise vapor diffusion with heptane over, in some embodiments, about 13 days. In certain embodiments, the methods provide a Form A crystal form of Compound 1.

In certain embodiments, provided herein are methods for forming a crystal form of Compound 1 comprising crystallization from dichloromethane. In some embodiments, the methods comprise slow evaporation. In some embodiments, the methods comprise crash precipitation with heptane. In certain embodiments, the methods provide a Form A crystal form of Compound 1.

In certain embodiments, provided herein are methods for forming a crystal form of Compound 1 comprising crystallization from diethyl ether. In some embodiments, the methods comprise slow evaporation. In certain embodiments, the methods provide a Form A crystal form of Compound 1.

In certain embodiments, provided herein are methods for forming a crystal form of Compound 1 comprising crystallization from dimethylformamide. In some embodiments, the methods comprise fast evaporation. In certain embodiments, the methods provide a Form A crystal form of Compound 1.

In certain embodiments, provided herein are methods for forming a crystal form of Compound 1 comprising crystallization from p-dioxane. In some embodiments, the methods comprise slow evaporation. In certain embodiments, the methods provide a Form A crystal form of Compound 1.

In certain embodiments, provided herein are methods for forming a crystal form of Compound 1 comprising crystallization from ethyl acetate. In some embodiments, the methods comprise slow evaporation. In some embodiments, the methods comprise crash precipitation from heptane. In certain embodiments, the methods provide a Form A crystal form of Compound 1.

In certain embodiments, provided herein are methods for forming a crystal form of Compound 1 comprising crystallization from heptane. In some embodiments, the methods comprise slurrying at room temperature for, in some embodiments, about 14 days. In certain embodiments, the methods provide a Form A crystal form of Compound 1.

In certain embodiments, provided herein are methods for forming a crystal form of Compound 1 comprising crystallization from 2:1 heptane/chloroform. In some embodiments, the methods comprise slow evaporation. In certain embodiments, the methods provide a Form A crystal form of Compound 1.

In certain embodiments, provided herein are methods for forming a crystal form of Compound 1 comprising crystallization from 2:1 heptane/THF. In some embodiments, the methods comprise slow evaporation. In certain embodiments, the methods provide a Form A crystal form of Compound 1.

In certain embodiments, provided herein are methods for forming a crystal form of Compound 1 comprising crystallization from isopropyl ether. In some embodiments, the methods comprise slow evaporation. In some embodiments, the methods comprise slurrying at room temperature for, in some embodiments, about 14 days. In some embodiments, the methods comprise heating to 51° C., slow cooling from a temperature of about 51° C. to about room temperature and, in further embodiments, allowing the solution to stand at room temperature for about 1 day. In some embodiments, the methods comprise crash precipitation with heptane. In certain embodiments, the methods provide a Form A crystal form of Compound 1.

In certain embodiments, provided herein are methods for forming a crystal form of Compound 1 comprising crystallization from methyl ethyl ketone. In some embodiments, the methods comprise slow evaporation. In some embodiments, the methods comprise crash precipitation with heptane. In certain embodiments, the methods provide a Form A crystal form of Compound 1.

In certain embodiments, provided herein are methods for forming a crystal form of Compound 1 comprising crystallization from 2-methyl THF. In some embodiments, the methods comprise slow evaporation. In certain embodiments, the methods provide a Form A crystal form of Compound 1.

In certain embodiments, provided herein are methods for forming a crystal form of Compound 1 comprising crystallization from methyl iso-butyl ketone. In some embodiments, the methods comprise slow evaporation. In certain embodiments, the methods provide a Form A crystal form of Compound 1.

In certain embodiments, provided herein are methods for forming a crystal form of Compound 1 comprising crystallization from tert-butyl methyl ether. In some embodiments, the methods comprise slow evaporation. In some embodiments, the methods comprise crash precipitation with heptane. In certain embodiments, the methods provide a Form A crystal form of Compound 1.

In certain embodiments, provided herein are methods for forming a crystal form of Compound 1 comprising crystallization from nitromethane. In some embodiments, the methods comprise slow evaporation. In some embodiments, the methods comprise slurrying at room temperature for, in some embodiments, about 14 days. In some embodiments, the methods comprise heating to 51° C., slow cooling from a temperature of about 51° C. to about room temperature and, in further embodiments, allowing the solution to stand at room temperature for about 1 day and, in even further embodiments, subsequently cooling to about 0° C. In a further embodiment, the solution is kept at about 0° C. for about 11 days. In certain embodiments, the methods provide a Form A crystal form of Compound 1.

In certain embodiments, provided herein are methods for forming a crystal form of Compound 1 comprising crystallization from toluene. In some embodiments, the methods comprise fast evaporation. In some embodiments, the methods comprise slurrying at room temperature for, in some embodiments, about 14 days. In some embodiments, the methods comprise heating to 51° C., slow cooling from a temperature of about 51° C. to about room temperature and, in further embodiments, allowing the solution to stand at room temperature for about 1 day. In certain embodiments, the methods provide a Form A crystal form of Compound 1.

In certain embodiments, provided herein are methods for forming a crystal form of Compound 1 comprising crystallization from water. In some embodiments, the methods comprise slurrying at room temperature for, in some embodiments, about 14 days. In certain embodiments, the methods provide a Form A crystal form of Compound 1.

In certain embodiments, provided herein are methods for forming a crystal form of Compound 1 comprising crystallization from 50:50 acetone/water. In some embodiments, the methods comprise partial slow evaporation. In some embodiments, the methods comprise slurrying at room temperature for, in some embodiments, about 14 days. In some embodiments, the methods comprise heating to 51° C., slow cooling from a temperature of about 51° C. to about room temperature and, in further embodiments, allowing the solution to stand at room temperature for about 1 day. In certain embodiments, the methods provide a Form A crystal form of Compound 1.

In certain embodiments, provided herein are methods for forming a crystal form of Compound 1 comprising crystallization from 50:50 acetonitrile/water. In some embodiments, the methods comprise partial slow evaporation. In some embodiments, the methods comprise slurrying at room temperature for, in some embodiments, about 14 days. In some embodiments, the methods comprise heating to 51° C., slow cooling from a temperature of about 51° C. to about room temperature and, in further embodiments, allowing the solution to stand at room temperature for about 1 day. In certain embodiments, the methods provide a Form A crystal form of Compound 1.

In certain embodiments, provided herein are methods for forming a crystal form of Compound 1 comprising crystallization from 50:50 dimethylformamide/water. In some embodiments, the methods comprise fast evaporation. In some embodiments, the methods comprise slurrying at room temperature for, in some embodiments, about 14 days. In some embodiments, the methods comprise heating to 51° C., slow cooling from a temperature of about 51° C. to about room temperature and, in further embodiments, allowing the solution to stand at room temperature for about 1 day. In certain embodiments, the methods provide a Form A crystal form of Compound 1.

In certain embodiments, provided herein are methods for forming a crystal form of Compound 1 comprising crystallization from 50:50 p-dioxane/water. In some embodiments, the methods comprise slow evaporation. In some embodiments, the methods comprise heating to 51° C., slow cooling from a temperature of about 51° C. to about room temperature and, in further embodiments, allowing the solution to stand at room temperature for about 1 day and, in even further embodiments, subsequently cooling to about 0° C. In further embodiments, the solution is kept at about 0° C. for about 11 days. In certain embodiments, the methods provide a Form A crystal form of Compound 1.

In certain embodiments, provided herein are methods for forming a crystal form of Compound 1 comprising crystallization from THF. In some embodiments, the methods comprise slow evaporation. In some embodiments, the methods comprise vapor diffusion. In some embodiments, the methods comprise vapor diffusion with heptane or water. In some embodiments, the methods comprise vapor diffusion for 1, 2, 3, 4, 5, 6, 7, or 8 days. In certain embodiments, the methods provide Form A crystal form of Compound 1. In certain embodiments, the methods provide Material B crystal form of Compound 1. In certain embodiments, the methods provide a mixture of Form A and Material B crystal forms.

In certain embodiments, provided herein are methods for forming a Form A crystal form of Compound 1 by storing a Material B crystal form at a temperature of from 15-50° C., 20-35° C., or about 25° C.

In some embodiments, the crystallization step provides crystalline Compound 1 having greater than about 90% purity (e.g., as determined by HPLC). In some embodiments, the crystallization step provides crystalline Compound 1 having greater than about 95% purity. In some embodiments, the crystallization step provides crystalline Compound 1 having greater than about 98% purity. In some embodiments, the crystallization step provides crystalline Compound 1 having greater than about 99% purity. In some embodiments, the crystallization step provides crystalline Compound 1 having greater than about 99.1%, about 99.2%, about 99.3%, about 99.4%, about 99.5%, about 99.6%, about 99.7%, about 99.8%, or 99.9% purity. In certain embodiments, the crystallization step provides crystalline Compound 1 have greater than about 90% purity to about 100% purity as determined by HPLC. In certain embodiments, the present invention provides Compound 1 characterized in that it has less than about 400 ppm acetone present as a residual solvent. In certain embodiments, the present invention provides Compound 1 characterized in that it has less than about 300 ppm acetone present as a residual solvent. In certain embodiments, the present invention provides Compound 1 characterized in that it has no acetone present to about 400 ppm acetone present as a residual solvent. In certain embodiments, the present invention provides Compound 1 characterized in that it has from about 200 ppm to about 400 ppm acetone present as a residual solvent. In certain embodiments, the present invention provides Compound 1 characterized in that it has from about 250 ppm to about 350 ppm acetone present as a residual solvent.

Figure 7:
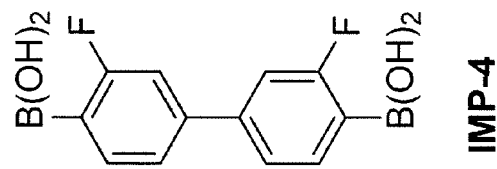
FIG. 7 depicts impurities generated during the synthesis of Compound 1.
Figure 7:
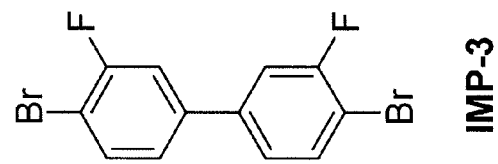
Figure 7:
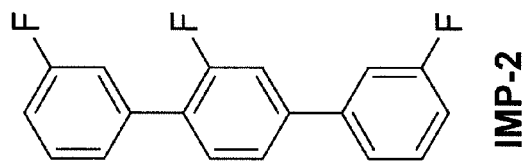
Figure 7:
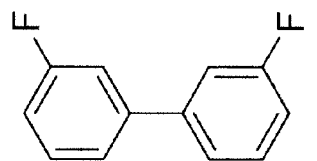

It has been found, for example, that either crystallization of Compound 1 from a non-polar solution (e.g., hexanes, n-heptane) or by washing crystalline Compound 1 with a non-polar solution provides Compound 1 substantially free of one or more non-polar impurities selected from IMP-1 and IMP-2 and IMP-3 (FIG. 7).

In certain embodiments, crystalline Compound 1 is provided substantially free of non-polar impurity IMP-1 (FIG. 7). As used herein "substantially free of IMP-1" refers to crystalline Compound 1 having less than about 0.1% a/a of the IMP-1 as determined by HPLC. In certain embodiments, Compound 1 has less than about 0.09% a/a, less than about 0.08% a/a, less than about 0.07% a/a, less than about 0.06% a/a, less than about 0.05% a/a, less than about 0.04% a/a, less than about 0.03% a/a, less than about 0.02% a/a, or less than about 0.01% a/a of IMP-1 as determined by HPLC. In certain embodiments, Compound 1 has less than about 0.1% a/a to about 0.01% a/a of IMP-1 as determined by HPLC.

In certain embodiments, crystalline Compound 1 is provided substantially free of non-polar impurity IMP-2 (FIG. 7). As used herein "substantially free of IMP-2" refers to crystalline Compound 1 having less than about 0.1% a/a of the IMP-2 as determined by HPLC. In certain embodiments, Compound 1 has less than about 0.09% a/a, less than about 0.08% a/a, less than about 0.07% a/a, less than about 0.06% a/a, less than about 0.05% a/a, less than about 0.04% a/a, less than about 0.03% a/a, less than about 0.02% a/a, or less than about 0.01% a/a of IMP-2 as determined by HPLC. In certain embodiments, Compound 1 has less than about 0.1% a/a to about 0.01% a/a of IMP-2 as determined by HPLC.

In certain embodiments, crystalline Compound 1 is provided substantially free of non-polar impurity IMP-3 (FIG. 7). As used herein "substantially free of IMP-3" refers to crystalline Compound 1 having less than about 0.1% a/a of the IMP-3 as determined by HPLC. In certain embodiments, Compound 1 has less than about 0.09% a/a, less than about 0.08% a/a, less than about 0.07% a/a, less than about 0.06% a/a, less than about 0.05% a/a, less than about 0.04% a/a, less than about 0.03% a/a, less than about 0.02% a/a, or less than about 0.01% a/a of IMP-3 as determined by HPLC. In certain embodiments, Compound 1 has less than about 0.1% a/a to about 0.01% a/a of IMP-3 as determined by HPLC.

It has also been found that crystallization from a polar solution (e.g., a mixture of a polar aprotic organic solvent and water) provides Compound 1 substantially free of polar impurity IMP-4 (FIG. 7).

As used herein "substantially free of IMP-4" refers to crystalline Compound 1 having less than about 0.1% a/a of the IMP-4 as determined by HPLC. In certain embodiments, Compound 1 has less than about 0.09% a/a, less than about 0.08% a/a, less than about 0.07% a/a, less than about 0.06% a/a, less than about 0.05% a/a, less than about 0.04% a/a, less than about 0.03% a/a, less than about 0.02% a/a, or less than about 0.01% a/a of IMP-4 as determined by HPLC. In certain embodiments, Compound 1 has less than about 0.1% a/a to about 0.01% a/a of IMP-4 as determined by HPLC.

In certain embodiments, the crystalline Compound 1 is further recrystallized from a polar solution (e.g., a mixture of water and a polar aprotic organic solvent). In certain embodiments, crystalline Compound 1 is further recrystallized from a mixture of acetone and water.

(iv) Intermediate Anhydride Formation

In certain embodiments, the above step S-2 method further comprises, after an aqueous quench and separation of the aqueous and organic layer: (i) azeotroping the organic layer to provide Compound 1 anhydride (e.g., formed via dehydration of Compound 1), followed by (ii) hydrolysis of the anhydride intermediate via treatment with water to provide Compound 1 (Scheme 2).

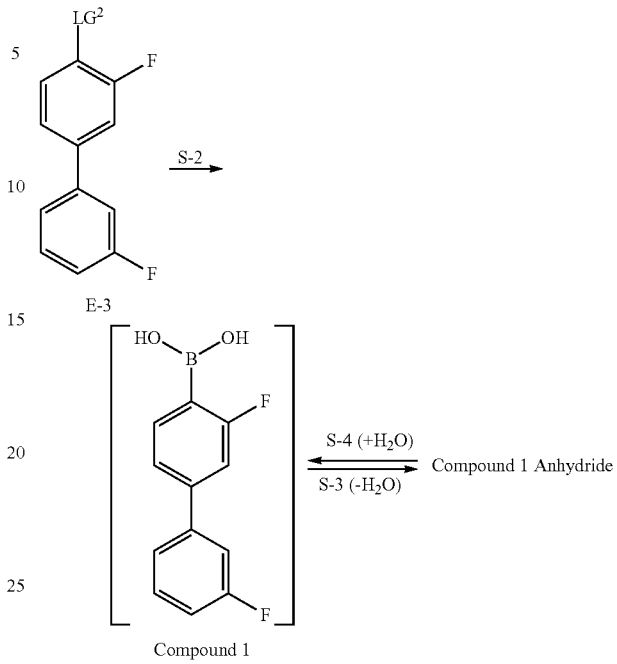

Scheme 2.

Step S-3. Azeotropic Distillation

In certain embodiments, the azeotroping step is a solvent exchange step (e.g., optionally first distilling the organic phase of the reaction mixture, followed by treatment of the concentrate with an azeotroping solvent, followed by additional distillation). In some embodiments, the solvent exchange step may optionally and additionally comprise steps of: (1) replenishing the organic phase with the azeotroping solvent and (2) distilling off a portion of the resulting organic phase. Solvent exchange steps (1) and (2) can be repeated as needed. In certain embodiments, the azeotroping solvent facilitates removal of water and/or other organic solvents provided in the reaction mixture to provide an anhydride of Compound 1 (also referred to herein as "Compound 1 anhydride"). In certain embodiments, the azeotroping solvent is a non-polar solution (e.g., hexanes, n-heptane). In certain embodiments, the Compound 1 anhydride is filtered from the reaction to afford a crystalline solid. In some embodiments, crystalline Compound 1 anhydride provided by this method has an X-ray powder diffraction pattern substantially similar to that depicted in FIG. 8, Form I.

One of ordinary skill in the art will appreciate that the "Compound 1 anhydride" can exist as a dimer, trimer, tetramer, oligomer, or mixtures thereof and can comprise linear or cyclic anhydrides. Such anhydride forms are contemplated and include, but are not limited to, those depicted in Scheme 3. In certain embodiments, the "Compound 1 anhydride" is the cyclic trimer depicted in Scheme 3, also referred to herein as "Compound 2."

Scheme 3.

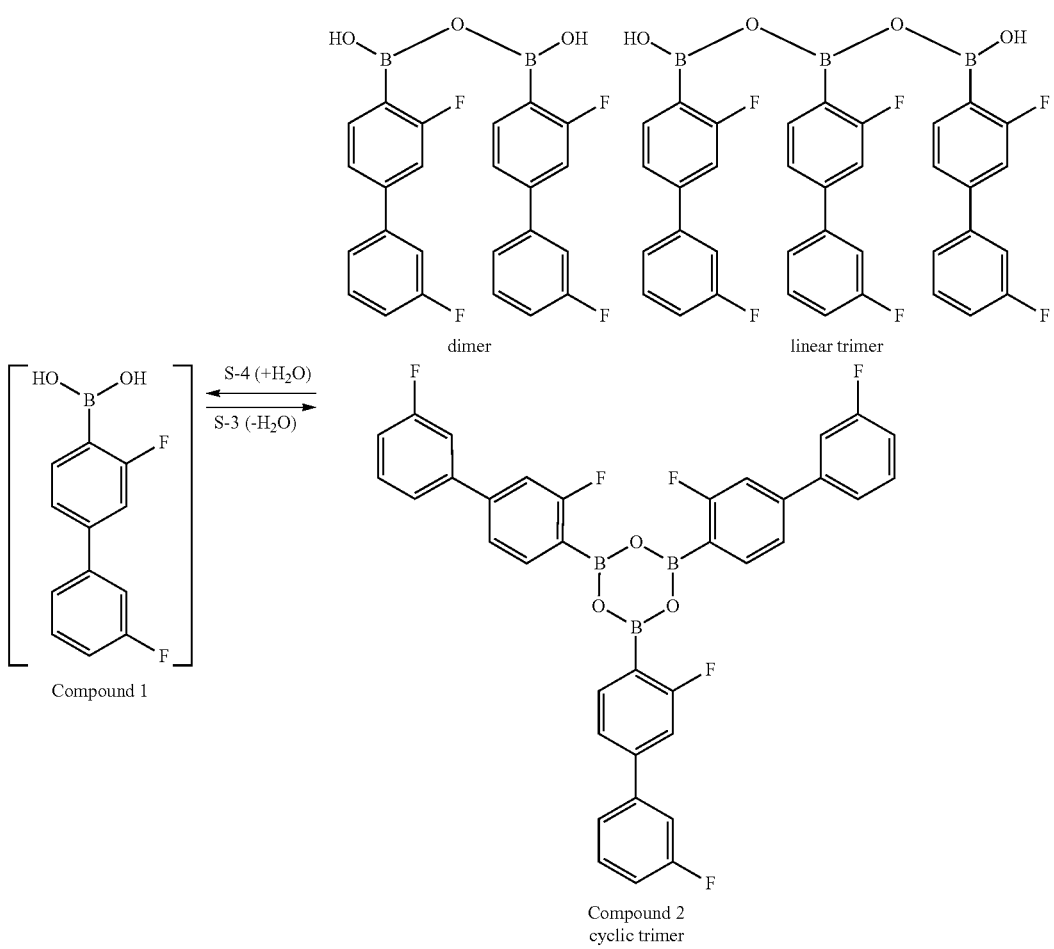

Step S-4. Hydrolysis of the Anhydride

The "Compound 1 anhydride" is provided by dehydration of Compound 1 from step S-3 and is hydrolyzed back to Compound 1 upon exposure to water (i.e., step S-4). Thus, in some embodiments, the step S-3 to provide the Compound 1 anhydride is followed by hydrolysis of the Compound 1 anhydride by treatment with water to provide crystalline Compound 1 (step S-4).

For example, in certain embodiments, the hydrolysis step involves heating (e.g., refluxing) Compound 1 anhydride in a mixture of water and a polar aprotic organic solvent (e.g., acetone, acetonitrile, or a mixture thereof) to provide crystalline Compound 1 (e.g., for example, such that Compound 1 precipitates from the mixture). In certain embodiments, the polar aprotic organic solvent is acetone, acetonitrile or a mixture thereof. In certain embodiments, the polar aprotic organic solvent is acetone.

In certain embodiments, the mixture of polar aprotic organic solvent in water is from about 5% to about 95% polar aprotic organic solvent in water, from about 10% to about 90% polar aprotic organic solvent in water, from about 15% to about 85% polar aprotic organic solvent in water, from about 20% to about 80% polar aprotic organic solvent in water, from about 25% to about 75% polar aprotic organic solvent in water, from about 30% to about 70% polar aprotic organic solvent in water, from about 35% to about 65% polar aprotic organic solvent in water, or from about 40% to about 70% polar aprotic organic solvent in water.

In certain embodiments, portions of the polar solution and water are added to the refluxing solution in iterations prior to cooling of the solution. In some embodiments, the cooling of the solution occurs for a specified amount of time (e.g., greater than about 8 hours) and/or at a specified temperature (e.g., about 25° C.). In some embodiments, Compound 1 is isolated via filtration and dried using any method known in the chemical arts.

In certain embodiments, Compound 1 provided by the above hydrolysis step is crystalline Compound 1, as described herein. In some embodiments, crystalline Compound 1 provided by this method has an X-ray powder diffraction pattern substantially similar to that depicted in FIG. 1, Form A.

In some embodiments, crystalline Compound 1 provided by the above hydrolysis step has greater than about 90% purity (e.g., as determined by HPLC). In some embodiments, crystalline Compound 1 provided by the above hydrolysis step has greater than about 95% purity. In some embodiments, crystalline Compound 1 provided by the above hydrolysis step has greater than about 98% purity. In some embodiments, crystalline Compound 1 provided by the above hydrolysis step has greater than about 99% purity. In some embodiments, crystalline Compound 1 provided by the above hydrolysis step has greater than about 99.1%, about 99.2%, about 99.3%, about 99.4%, about 99.5%, about 99.6%, about 99.7%, about 99.8%, or about 99.9% purity. In certain embodiments, crystalline Compound 1 provided by the above hydrolysis step has greater than about 90% purity to about 100% purity as determined by HPLC.

In certain embodiments, the present invention provides crystalline Compound 1 from the above hydrolysis step having less than about 400 ppm acetone present as a residual solvent. In certain embodiments, the present invention provides crystalline Compound 1 from the above hydrolysis step having less than about 300 ppm acetone present as a residual solvent. In certain embodiments, the present invention provides crystalline Compound 1 from the above hydrolysis step having no acetone present to about 400 ppm acetone present as a residual solvent. In certain embodiments, the present invention provides crystalline Compound 1 from the above hydrolysis step having from about 200 ppm to about 400 ppm acetone present as a residual solvent. In certain embodiments, the present invention provides crystalline Compound 1 from the above hydrolysis step having from about 250 ppm to about 350 ppm acetone present as a residual solvent.

It has been found that washing crystalline Compound 1 with a non-polar solution after the above hydrolysis step provides Compound 1 substantially free of one or more non-polar impurities selected from IMP-1 and IMP-2 and IMP-3 (FIG. 7).

In certain embodiments, crystalline Compound 1 from the above hydrolysis step is provided substantially free of non-polar impurity IMP-1 (FIG. 7). As used herein "substantially free of IMP-1" refers to crystalline Compound 1 having less than about 0.1% a/a of the IMP-1 as determined by HPLC. In certain embodiments, Compound 1 has less than about 0.09% a/a, less than about 0.08% a/a, less than about 0.07% a/a, less than about 0.06% a/a, less than about 0.05% a/a, less than about 0.04% a/a, less than about 0.03% a/a, less than about 0.02% a/a, or less than about 0.01% a/a of IMP-1 as determined by HPLC. In some embodiments, Compound 1 is less than about 0.05% a/a of IMP-1 as determined by HPLC. In certain embodiments, Compound 1 has less than about 0.1% a/a to about 0.01% a/a of IMP-1 as determined by HPLC.

In certain embodiments, crystalline Compound 1 from the above hydrolysis step is provided substantially free of non-polar impurity IMP-2 (FIG. 7). As used herein "substantially free of IMP-2" refers to crystalline Compound 1 having lees than about 0.1% a/a of the IMP-2 as determined by HPLC. In certain embodiments, Compound 1 has less than about 0.09% a/a, less than about 0.08% a/a, less than about 0.07% a/a, less than about 0.06% a/a, less than about 0.05% a/a, less than about 0.04% a/a, less than about 0.03% a/a, less than about 0.02% a/a, or less than about 0.01% a/a of IMP-2 as determined by HPLC. In some embodiments, Compound 1 is less than about 0.05% a/a of IMP-2 as determined by HPLC. In certain embodiments, Compound 1 has less than about 0.1% a/a to about 0.01% a/a of IMP-2 as determined by HPLC.

In certain embodiments, crystalline Compound 1 from the above hydrolysis step is provided substantially free of non-polar impurity IMP-3 (FIG. 7). As used herein "substantially free of IMP-3" refers to crystalline Compound 1 having less than about 0.1% a/a of the IMP-3 as determined by HPLC. In certain embodiments, Compound 1 has less than about 0.09% a/a, less than about 0.08% a/a, less than about 0.07% a/a, less than about 0.06% a/a, less than about 0.05% a/a, less than about 0.04% a/a, less than about 0.03% a/a, less than about 0.02% a/a, or less than about 0.01% a/a of IMP-3 as determined by HPLC. In some embodiments, Compound 1 is less than about 0.05% a/a of IMP-3 as determined by HPLC. In certain embodiments, Compound 1 has less than about 0.1% a/a to about 0.01% a/a of IMP-3 as determined by HPLC.

It has also been found that crystallization from a polar solution (e.g., a mixture of a polar aprotic organic solvent and water) after the above hydrolysis step provides Compound 1 substantially free of polar impurity IMP-4 (FIG. 7). As used herein "substantially free of IMP-4" refers to crystalline Compound 1 having less than about 0.1% a/a of the IMP-4 as determined by HPLC. In certain embodiments, Compound 1 has less than about 0.09% a/a, less than about 0.08% a/a, less than about 0.07% a/a, less than about 0.06% a/a, less than about 0.05% a/a, less than about 0.04% a/a, less than about 0.03% a/a, less than about 0.02% a/a, or less than about 0.01% a/a of IMP-4 as determined by HPLC. In some embodiments, Compound 1 is less than about 0.05% a/a of IMP-4 as determined by HPLC. In certain embodiments, Compound 1 has less than about 0.1% a/a to about 0.01% a/a of IMP-4 as determined by HPLC.

In certain embodiments, the crystalline Compound 1 is further recrystallized from a polar solution (e.g., a mixture of water and a polar aprotic organic solvent). In certain embodiments, crystalline Compound 1 is further recrystallized from a mixture of acetone and water.

(v) Other Embodiments of the Method of Preparation

In certain embodiments, the present invention provides a method of preparing Compound 1:

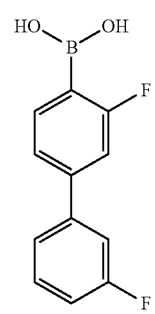

or a pharmaceutically acceptable salt, hydrate or solvate thereof and/or anhydride thereof;

comprising the steps of:

(a) coupling a compound of formula E-1:

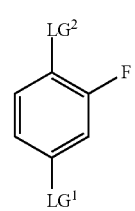

wherein:

$LG^1$ and $LG^2$ are independently selected from a halogen or sulfonate;

with a compound of formula E-2:

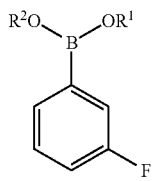

wherein each $R^1$ and $R^2$ is independently selected from hydrogen or an $C_{1-6}$ alkyl, $C_{2-6}$ alkenyl, $C_{2-6}$ alkynyl, $C_{6-12}$ aryl or $C_{6-12}$ heteroaryl group, or $R^1$ and $R^2$ are joined to form a 5-8 membered ring;

in order to provide a compound of formula E-3:

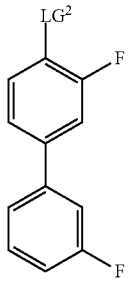

wherein:
$LG^2$ is selected from a halogen or sulfonate;

(b) reacting E-3 with a boronation reagent and a metal reagent in order to provide Compound 1.

In certain embodiments, E-1 is E-1b:

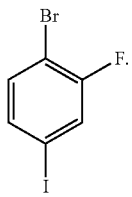

In certain embodiments, E-2 is E-2a:

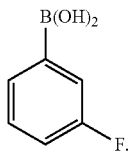

In certain embodiments, E-3 is E-3a:

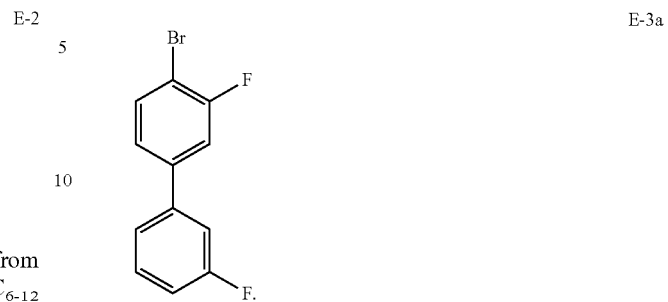

In certain embodiments, the coupling step comprises a palladium catalyst. In certain embodiments, the palladium catalyst is selected from $Pd(PPh_3)_4$, $Pd(OAc)_2$, $Pd_2(dba)_3$, $Pd(dppf)_2Cl_2$, and $PdCl_2(PPh_3)_2$.

In certain embodiments, the coupling step comprises a base. In certain embodiments, the base is selected from triethylamine, diisopropylethylamine, potassium carbonate, sodium carbonate, cesium carbonate, potassium bicarbonate, sodium bicarbonate, cesium bicarbonate, potassium acetate, sodium acetate, potassium phosphate, lithium hydroxide, sodium hydroxide and magnesium hydroxide.

In certain embodiments, the boronation reagent is a boronate ester. In certain embodiments, the boronate ester is selected from trimethyl borate, triethyl borate, triallyl borate, triisopropyl borate, Tributyl borate, Tri-tert-butyl borate, Tripentyl borate, Trihexyl borate, Tritolyl borate, Tribenzyl borate, Triphenyl borate, Trimethylene borate, Triethanolamine borate, Trimethallyl borate, 2-Methoxy-4,4,5,5-tetramethyl-1,3,2-dioxaborolane, 2-Methoxy-4,4,6-trimethyl-1,3,2-dioxaborinane, 2-Isopropoxy-4,4,5,5-tetramethyl-1,3,2-dioxaborolane, 2-Isopropoxy-4,4,6-trimethyl-1,3,2-dioxaborinane, 2-(2-dimethylaminoethoxy)-4-methyl-1,3,2-dioxaborinane, 2-butoxy-4,4,6-trimethyl-1,3,2-dioxaborinane, tris(2,2,2-trifluoroethyl) borate, tris(1-isopropyl-2-methylpropyl) borate, and 2,2'-(2-methyl-2,4-pentanediyldioxy)bis (4,4,6-trimethyl-1,3,2-dioxaborinane).

In certain embodiments, the metal reagent is an alkyl lithium reagent. In certain embodiments, the alkyl lithium reagent is n-butyllithium or hexyllithium.

In certain embodiments, the method further comprises crystallizing Compound 1 of step (b) to provide crystalline Compound 1. Exemplary methods of crystallizing and recrystallizing Compound 1 have been described above and herein.

For example, in certain embodiments, the crystallizing step comprises crystallizing Compound 1 from a polar solution comprising water, a polar apolar solvent or a mixture thereof. In certain embodiments, the crystallizing step comprises crystallizing Compound 1 from a mixture of water and acetone. In certain embodiments, the crystalline Compound 1 is further washed with a non-polar solution. In certain embodiments, the non-polar solution comprises hexanes, heptanes or a mixture thereof. In certain embodiments, the crystalline Compound 1 is further recrystallized from a mixture of water and acetone.

Exemplary crystalline Compound 1 provided by these methods is further described in the following section and in the Examples.

In certain embodiments, the method step (b) further comprises the steps of dehydrating Compound 1 in order to provide an anhydride of Compound 1 followed by hydrolysis of the anhydride of Compound 1 in order to provide Compound 1. In certain embodiments, the dehydration step is performed in situ (i.e., Compound 1 is not isolated). In certain embodiments, the dehydration step is an azeotroping step. In certain embodiments, the azeotroping is performed by solvent exchange of the reaction mixture. In certain embodiments, the hydrolysis step is performed by addition of water to the anhydride of Compound 1. Exemplary methods of dehydration, azeotroping and hydrolyses have also been described above and herein.

In certain embodiments, the anhydride of Compound 1 ("Compound 1 anhydride") is Compound 2:

Compound 2

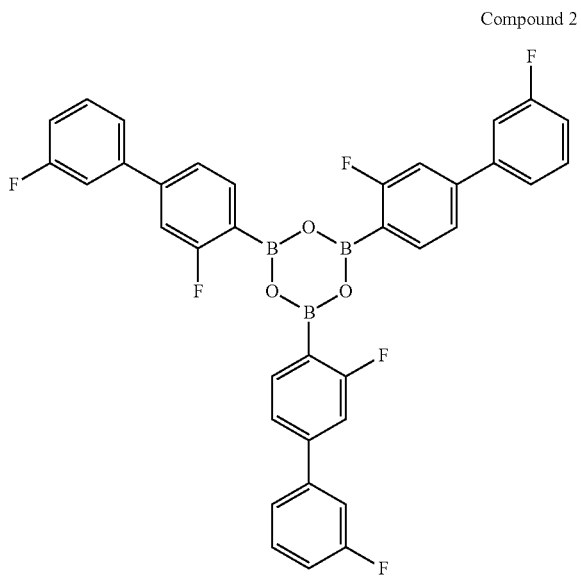 [SMILES: Fc1cccc(-c2ccc(B3OB(c4ccc(-c5cccc(F)c5)cc4F)OB(c4ccc(-c5cccc(F)c5)cc4F)O3)c(F)c2)c1]

or a pharmaceutically acceptable salt, hydrate or solvate thereof.

In certain embodiments, Compound 2 is crystalline. Exemplary crystalline Compound 2 provided by these methods is further described in the following section and in the Examples.

Solid Forms of Compound 1 and Anhydrides Thereof

Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., Adv. Drug. Deliv. Rev., (2001) 48:3-26; L. Yu, Adv. Drug. Deliv. Rev., (2001) 48:27-42). A change in solid form may affect a variety of physical and chemical properties, which may provide benefits or drawbacks in processing, formulation, stability and bioavailability, among other important pharmaceutical characteristics.

Whether crystalline or amorphous, potential solid forms of a pharmaceutical compound may include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., Solid State Chemistry of Drugs, (1999) SSCI, West Lafayette).

Additional diversity among the potential solid forms of a pharmaceutical compound may arise from the possibility of multiple-component solids. Crystalline solids comprising two or more ionic species are termed salts (see, e.g., Handbook of Pharmaceutical Salts: Properties, Selection and Use, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., Solid State Chemistry of Drugs, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, a multiple-component crystal form, a single-component amorphous form and/or a multiple-component amorphous form comprising the compound of formula (I) and a pharmaceutically acceptable diluent, excipient or carrier.

Solid form and related terms refer to a physical form, which is not predominantly in a liquid or a gaseous state. Solid forms may be crystalline, amorphous or mixtures thereof. A "single-component" solid form comprising a particular compound consists essentially of that compound. A "multiple-component" solid form comprising a particular compound comprises that compound and a significant quantity of one or more additional species, such as ions and/or molecules, within the solid form. The solid forms provided herein may be crystalline, amorphous, or an intermediate form. The crystal forms described herein, therefore, may have varying degrees of crystallinity or lattice order. The solid forms described herein are not limited to any particular degree of crystallinity or lattice order, and may be 0-100% crystalline. Methods of determining the degree of crystallinity are known to those of ordinary skill in the, such as those described in R. Suryanarayanan, X-Ray Power Diffractometry, Physical Characterization of Pharmaceutical Salts, H. G. Brittain, Editor, Mercel Dekkter, Murray Hill, N.J., 1995, pp. 187-199, which is incorporated herein by reference in its entirety. In some embodiments, the solid forms described herein are about 0, 5, 10, 15, 20, 25, 30, 35, 40, 45, 50, 55, 60, 65, 70, 75, 80, 85, 90, 95 or 100% crystalline.

Solid forms may exhibit distinct physical characterization data that are unique to a particular solid form, such as the crystal forms described herein. These characterization data may be obtained by various techniques known to those skilled in the art, including, for example, X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms described herein by performing one of these characterization techniques and determining whether the resulting data is "substantially similar" to the reference data provided herein, which is identified as being characteristic of a particular solid form. Characterization data that is "substantially similar" to those of a reference solid form is understood by those skilled in the art to correspond to the same solid form as the reference solid form. In analyzing whether data is "substantially similar," a person of ordinary skill in the art understands that particular characterization data points may vary to a reasonable extent while still describing a given solid form, due to, for example, experimental error and routine sample-to-sample analysis.

Compound 1

It is contemplated that Compound 1 can exist in a variety of solid forms. Such solid forms include crystalline solids, such as polymorphs, solvates and hydrates of crystalline Compound 1, as well as amorphous solids, or mixtures thereof. All such solid forms of Compound 1 are contemplated under the present invention.

In some embodiments, provided herein is crystalline Compound 1:

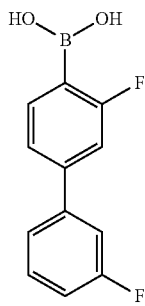

1 or a pharmaceutically acceptable salt, hydrate or solvate thereof.

In some embodiments, crystalline Compound 1 is substantially free of any one of the following compounds:

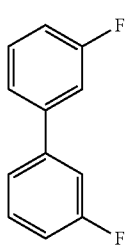

IMP-1

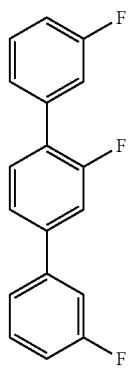

IMP-2

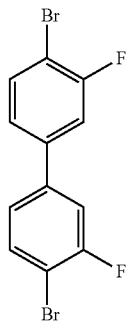

IMP-3

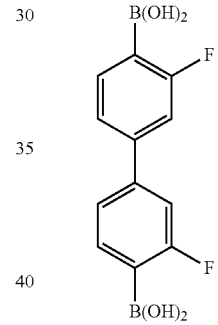

IMP-4

In certain embodiments of the present invention, Compound 1 is provided as a crystalline solid ("crystalline Compound 1"). In certain embodiments, crystalline Compound 1 is a solid form substantially free of amorphous Compound 1. In certain embodiments, crystalline Compound 1 is a solid form substantially free of other crystalline forms (i.e., polymorphs) of Compound 1. In certain embodiments, crystalline Compound 1 is a solid form substantially free of one or more anhydrides of Compound 1 (e.g., a dimer, trimer, or oligomer of Compound 1, e.g., Compound 2). In certain embodiments, Compound 1 is provided as pure and isolated crystalline Compound 1.

As defined herein, "pure and isolated" refers to the isolated crystalline Compound 1 having at least one of the following characteristics:
 (i) a crystalline solid having greater than 90% purity (e.g., as determined by HPLC);
 (ii) a crystalline solid having less than about 400 ppm acetone present as a residual solvent;
 (iii) a crystalline solid substantially free of non-polar impurities IMP-1 and IMP-2 and IMP-3, as defined above and herein;
 (iv) a crystalline solid substantially free of polar impurity IMP-4 as defined above and herein;

(v) a crystalline solid substantially free of amorphous Compound 1;

(vi) a crystalline solid substantially free of one or more anhydrides of Compound 1; and/or (vii) a crystalline solid substantially free of other crystalline forms of Compound 1.

In certain embodiments, "pure and isolated" refers to the isolated crystalline Compound 1 having at least two of the above listed (i) to (vii) characteristics. In certain embodiments, "pure and isolated" refers to the isolated crystalline Compound 1 having at least three of the above listed (i) to (vii) characteristics. In certain embodiments, "pure and isolated" refers to the isolated crystalline Compound 1 having at least four of the above listed (i) to (vii) characteristics. In certain embodiments, "pure and isolated" refers to the isolated crystalline Compound 1 having at least five of the above listed (i) to (vii) characteristics. In certain embodiments, "pure and isolated" refers to the isolated crystalline Compound 1 having at least six of the above listed (i) to (vii) characteristics. In certain embodiments, "pure and isolated" refers to the isolated crystalline Compound 1 having all seven of the above listed (i) to (vii) characteristics.

The phrase "substantially free of amorphous Compound 1" means that about 90% to about 100% by weight, about 95% to about 100% by weight, about 98% to about 100% by weight, or about 99% to about 100% by weight of Compound 1 is crystalline (i.e., not amorphous).

The phrase "substantially free of one or more anhydrides of Compound 1" means that at about 90% to about 100% by weight, about 95% to about 100% by weight, about 98% to about 100% by weight, or about 99% to about 100% by weight of Compound 1 is provided as the monomer (i.e., not an anhydride thereof).

The phrase "substantially free of one or more other crystalline forms of Compound 1" means that at about 90% to about 100% by weight, about 95% to about 100% by weight, about 98% to about 100% by weight, or about 99% to about 100% by weight of Compound 1 is provided in a specific crystalline form, e.g., "Form A," "Form A1," or "Material B."

Form A, Compound 1

Figure 2:
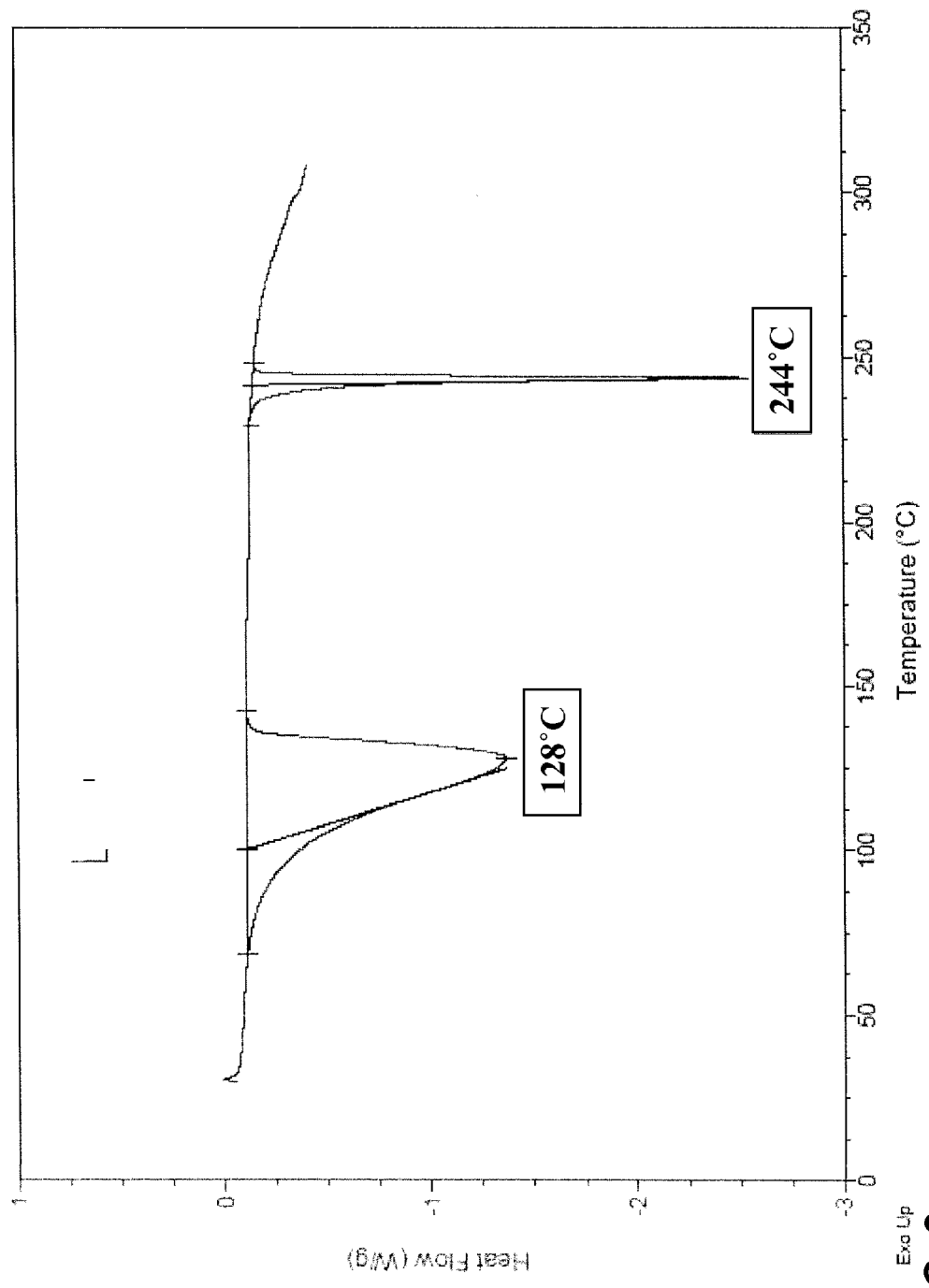
FIG. 2 shows a Differential Scanning calorimetry (DSC) trace of Form A of Compound 1.

"Form A," in certain embodiments, refers to a specific crystalline form of Compound 1 having, in some embodiments, at least one of the following characteristics:

(i) one or more transition temperatures selected from about 128±5° C. and about 244±2° C. as determined by differential scanning calorimetry (DSC);

(ii) one or more peaks in an X-ray powder diffraction (XRPD) pattern selected from 9.68±0.10, 17.26±0.10, 21.60±0.10, 24.68±0.10, 25.48±0.10, 27.73±0.10 and 29.08±0.10 θ-2θ degrees);

(iii) an X-ray powder diffraction (XRPD) pattern substantially similar to that depicted in FIG. 1, 19 (row A), 22, or 23; and/or (iv) a differential scanning calorimetry (DSC) scan substantially similar to that depicted in FIG. 2.

In some embodiments, Form A is isolated. In certain embodiments, "Form A" is characterized by peaks in an XRPD pattern located at 1, 2, 3, 4, 5, 6, or all of the following approximate peak positions: 9.68±0.10, 17.26±0.10, 21.60±0.10, 24.68±0.10, 25.48±0.10, 27.73±0.10 and 29.08±0.10 θ-2θ (degrees). In certain embodiments, "Form A" is characterized by two or more peaks selected from 9.68±0.10, 17.26±0.10, 21.60±0.10, 24.68±0.10, 25.48±0.10, 27.73±0.10 and 29.08±0.10. In certain embodiments, "Form A" is characterized by three or more peaks selected from 9.68±0.10, 17.26±0.10, 21.60±0.10, 24.68±0.10, 25.48±0.10, 27.73±0.10 and 29.08±0.10. In certain embodiments, "Form A" is characterized by four or more peaks selected from 9.68±0.10, 17.26±0.10, 21.60±0.10, 24.68±0.10, 25.48±0.10, 27.73±0.10 and 29.08±0.10. In certain embodiments, "Form A" is characterized by five or more peaks selected from 9.68±0.10, 17.26±0.10, 21.60±0.10, 24.68±0.10, 25.48±0.10, 27.73±0.10 and 29.08±0.10. In certain embodiments, "Form A" is characterized by six or more peaks selected from 9.68±0.10, 17.26±0.10, 21.60±0.10, 24.68±0.10, 25.48±0.10, 27.73±0.10 and 29.08±0.10. In certain embodiments, "Form A" is characterized by all of the following peaks: 9.68±0.10, 17.26±0.10, 21.60±0.10, 24.68±0.10, 25.48±0.10, 27.73±0.10 and 29.08±0.10. In certain embodiments, "Form A" is characterized by the X-ray powder diffraction pattern substantially similar to that depicted in FIG. 1, 19 (row A), 22, or 23.

In certain embodiments, provided herein is a crystalline form of Compound 1 having an XRPD pattern comprising peaks at approximately 17.26, 21.60, and 27.73 degrees 2θ. In further embodiments, the XRPD pattern further comprises peaks at approximately 24.68 and 25.48 degrees 2θ. In even further embodiments, the XRPD pattern further comprises peaks at approximately 9.68 and 29.08 degrees 2θ.

In some embodiments, provided herein is a crystal form having at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, or all of the following approximate XRPD pattern peaks: 4.8, 9.7, 16.1, 16.9, 17.3, 17.8, 18.6, 18.9, 19.3, 19.7, 21.0, 21.6, 22.5, 23.7, 24.3, 24.7, 25.2, 25.5, 26.0, 26.5, 27.7, 29.0, 29.4, and 29.8 degrees 2θ. In some embodiments, the crystal form has at least 8, at least 9, or at least 10 peaks. In some embodiments, the crystal form has at least 10 peaks.

In some embodiments, provided herein is an isolated Form A crystal form of Compound 1. In certain embodiments, the isolated Form A crystal form has an XRPD pattern, which is substantially similar to the pattern of FIG. 1, 19 (row A), 22, or 23. In some embodiments, provided herein is an isolated Form A crystal form of Compound 1, which has an XRPD pattern comprising peaks at approximately 17.3, 21.6, and 27.7 degrees 2θ when analyzed using copper Kα radiation.

In certain embodiments, "Form A" is characterized by one or more transition temperatures selected from about 128±5° C. and about 244±2° C. as determined by differential scanning calorimetry (DSC). In certain embodiments, "Form A" is characterized by a transition temperature of about 244±2° C. as determined by differential scanning calorimetry (DSC). In certain embodiments, "Form A" is characterized by a transition temperature of about 128±5° C. as determined by differential scanning calorimetry (DSC). In certain embodiments, "Form A" is characterized by two transition temperatures selected from about 128±5° C. and about 244±2° C. as determined by differential scanning calorimetry (DSC). In certain embodiments, "Form A" is characterized by a differential scanning calorimetry (DSC) scan substantially similar to that depicted in FIG. 2.

In certain embodiments, "Form A" refers to a specific crystalline form of Compound 1 having at least two of the above listed (i) to (iv) characteristics. In certain embodiments, "Form A" refers to a specific crystalline form of Compound 1 having at least three of the above listed (i) to (iv) characteristics. In certain embodiments, "Form A" refers to a specific crystalline form of Compound 1 having all four of the above listed (i) to (iv) characteristics.

In certain embodiments, Form A may have one or more preferred orientations. Such preferred orientations may be observable in high-resolution XRPD patterns, which may, in some embodiments, exhibit preferred orientation effects evidenced by a small number of high-intensity peaks.

In certain embodiments, the Form A crystal form of Compound 1 has the following approximate monoclinic cell parameters and calculated volume: a=5.45 Å; b=5.16 Å; c=36.12 Å; α=90°; β=90°; γ=90°; V=1016.5 Å$^3$. In some embodiments, the molecular weight of an asymmetric unit of a Form A crystal form of Compound 1 is about 234.0 g/mol with Z=4. In certain embodiments, the calculated density of the unit is about 1.5 g Cm$^{-3}$.

In some embodiments, the Form A crystal form of Compound 1 is chemically stable. In some embodiments, the Form A crystal form of Compound 1 is physically stable.

In some embodiments, the Form A crystal form of Compound 1 is substantially free of other crystalline forms of Compound 1.

In some embodiments, Form A is stable upon stressing at approximately 75%, 80%, 85%, 90%, 95%, 97%, or 99% relative humidity. In certain embodiments, Form A is stable at approximately 75%, 80%, 85%, 90%, 95%, 97%, or 99% relative humidity at about 40° C. In yet another embodiment, Form A is stable at approximately 75%, 80%, 85%, 90%, 95%, 97%, or 99% relative humidity at about 40° C. for about 1 week.

The term "substantially similar," when used herein in the context of comparing X-ray powder diffraction pattern or differential scanning calorimetry scan obtained for a solid form of a compound, e.g., of Compound 1, means that two spectra share defining characteristics sufficient to differentiate them from a spectrum obtained for a different form of that compound. In certain embodiments, the term "substantially similar" means that two spectra are the same, i.e., visibly overlap. In certain embodiments, spectra or characterization data that are substantially similar to those of a reference crystalline form, amorphous form, or mixture thereof, is understood by those of ordinary skill in the art to correspond to the same crystalline form, amorphous form, or mixture thereof as the particular reference. In analyzing whether spectra or characterization data are substantially similar, a person of ordinary skill in the art understands that particular characterization data points may vary to a reasonable extent while still describing a given solid form, due to, for example, experimental error and routine sample-to-sample analysis, or due to preferred orientation effects.

In certain embodiments, the XRPD peaks above (degrees 2θ peaks) are when analyzed using copper Kα radiation.

In some embodiments, Form A is obtained by crystallization from acetone, acetonitrile, chloroform, dichloromethane, diethyl ether, DMF, p-dioxane, ethyl acetate, heptanes, 2:1 heptane:chloroform, 2:1 heptane:THF, isopropyl ether, methyl ethyl ketone, 2-methyltetrahydrofuran, methyl isobutyl ketone, tert-butyl methyl ether, nitromethane, THF, toluene, water, 1:1 acetone:water, 1:1 acetonitrile:water, 1:1 DMF:water, or 1:1 dioxane:water.

In some embodiments, Form A is obtained by slow evaporation from acetone. In some embodiments, Form A is obtained from crash precipitation with heptane from acetone.

In some embodiments, Form A is obtained from slow evaporation form acetonitrile. In some embodiments, Form A is obtained by vapor diffusion with water from acetonitrile. In particular embodiments, vapor diffusion is performed over about 8 days.

In some embodiments, Form A is obtained by slow evaporation from diethyl ether.

In some embodiments, Form is obtained by fast evaporation from DMF. In some embodiments, Form A is obtained by slow evaporation from p-dioxane.

In some embodiments, Form A is obtained from slow evaporation or crash precipitation with heptanes from ethyl acetate.

In some embodiments, Form A is obtained by slurrying in heptane. In particular embodiments, the slurrying is performed at room temperature. In another embodiment, the slurrying is performed at room temperature for about 14 days.

In some embodiments, Form A is obtained by slow evaporation from 2:1 heptane:chloroform.

In some embodiments, Form A is obtained by slow evaporation from 2:1 heptane:THF.

In some embodiments, Form A is obtained by slow evaporation from isopropyl ether.

In some embodiments, Form A is obtained by slow cooling from isopropyl ether. In certain embodiments, the solution of Form A and isopropyl ether is cooled from about 51° C. to room temperature and allowed to stand for 1 day. In some embodiments, Form A is obtained by slow crash precipitation with heptane from isopropyl ether.

In some embodiments, Form A is obtained by slow evaporation from methyl ethyl ketone. In some embodiments, Form A is obtained by crash precipitation with heptane from methyl ethyl ketone.

In some embodiments, Form A is obtained by slow evaporation from 2-methyl THF.

In some embodiments, Form A is obtained by slow evaporation from MTBE. In some embodiments, Form A is obtained by crash precipitation with heptane from MTBE.

In some embodiments, Form A is obtained by slow evaporation from nitromethane.

In some embodiments, Form A is obtained by fast evaporation, slurry, or slow cooling from toluene. In certain embodiments, the slurry is performed at about room temperature over about 14 days. In certain embodiments, the solution of toluene and Compound 1 is cooled from about 51° C. to room temperature and allowed to stand for 1 day.

In some embodiments, Form A is obtained by slurry from water. In certain embodiments, the slurry is performed at room temperature for about 14 days.

In some embodiments, Form A is obtained by slow evaporation, slurry, or slow cooling from 1:1 acetone:water. In certain embodiments, the slurry is performed at about room temperature over about 14 days. In certain embodiments, the solution of Compound 1 and acetone/water is cooled from about 51° C. to room temperature and allowed to stand for 1 day.

In some embodiments, Form A is obtained by slow evaporation, slurry, or slow cooling from 1:1 acetonitrile:water. In certain embodiments, the slurry is performed at about room temperature over about 14 days. In certain embodiments, the solution of Compound 1 and acetone/water is cooled from about 51° C. to room temperature and allowed to stand for 1 day.

In some embodiments, Form A is obtained by fast evaporation, slurry, or slow cooling from 1:1 DMF:water. In certain embodiments, the slurry is performed at about room temperature over about 14 days. In certain embodiments, the solution of Compound 1 and acetone/water is cooled from about 51° C. to room temperature and allowed to stand for 1 day.

In some embodiments, Form A is obtained by slow evaporation, or slurry from 1:1 p-dioxane:water. In certain embodiments, the slurry is performed at about room temperature over about 14 days. In certain embodiments, the solution of Compound 1 and acetone/water is cooled from about 51° C. to room temperature and allowed to stand for 1 day.

Form A1 Compound 1

Figure 31:
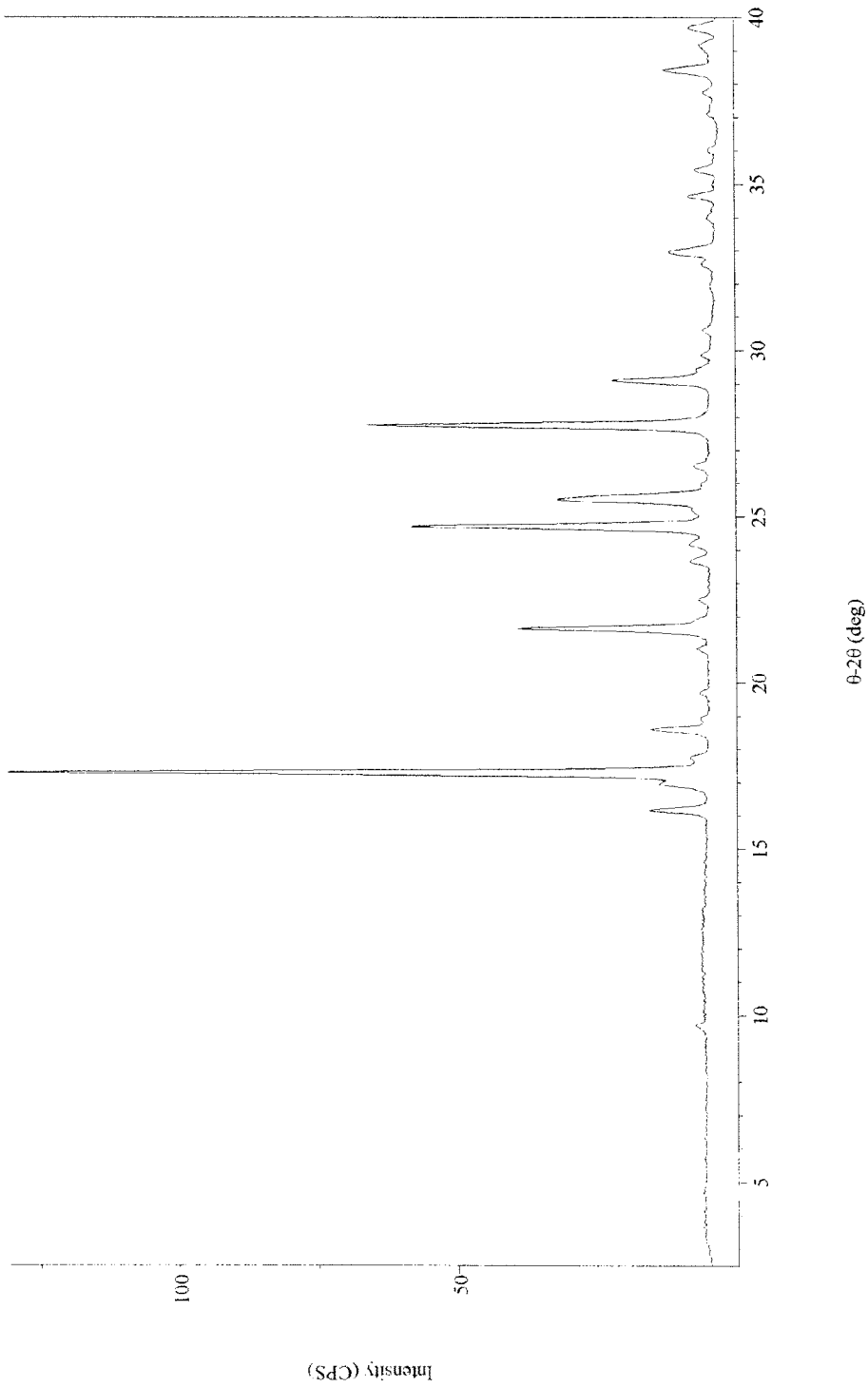
FIG. 31 shows an XRPD pattern of Form A1 of Compound 1.
Figure 32:
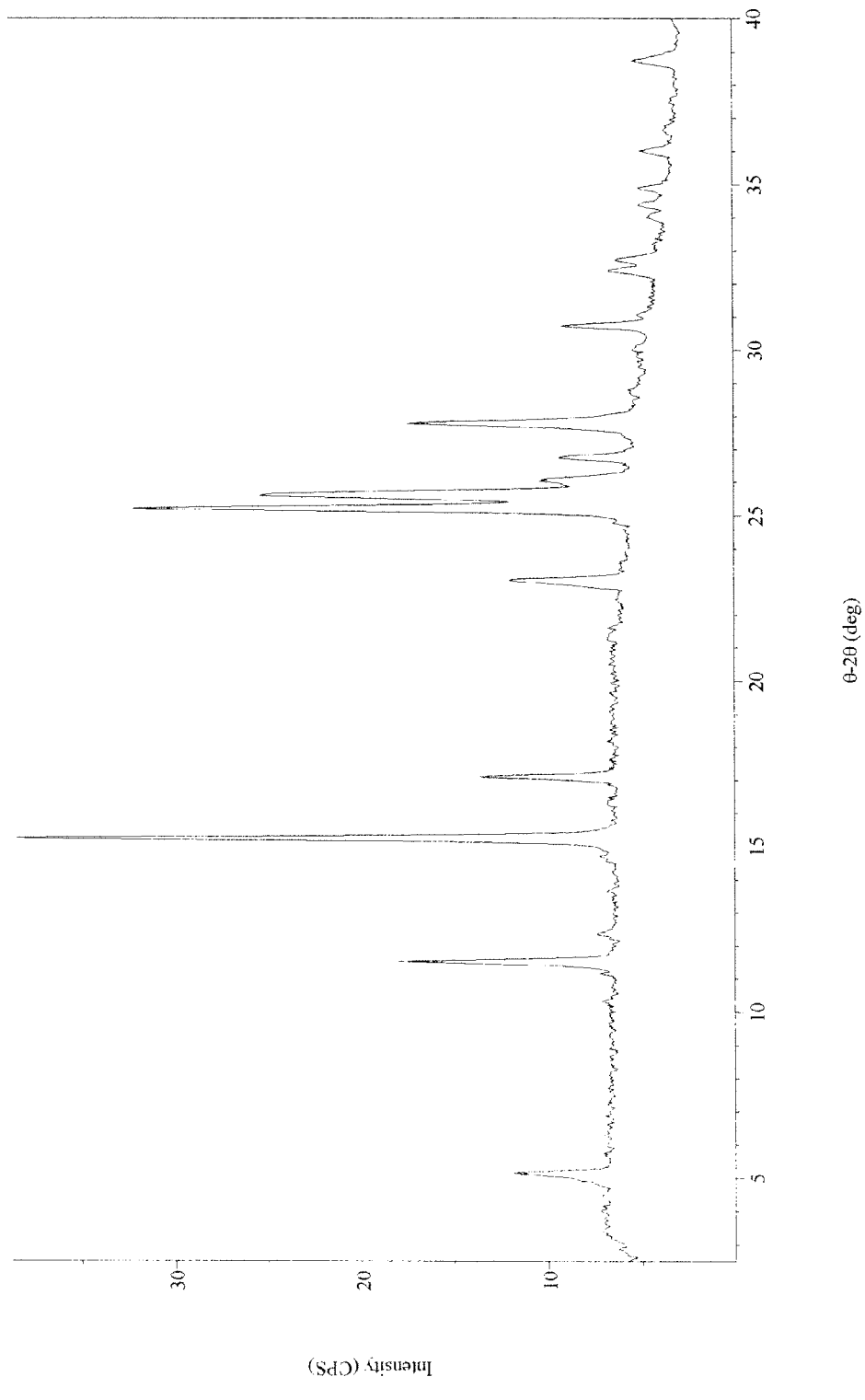
FIG. 32 shows an XRPD pattern of Material B of Compound 1.

In some embodiments, provided herein is a Form A1 crystal form of Compound 1. A representative XRPD pattern of Form A1 is provided in FIG. 31. In some embodiments, provided herein is the Form A1 crystal form of Compound A1, which has an XRPD pattern, which is substantially similar to the pattern exhibited in FIG. 31. In some embodiments, the Form A1 crystal form of Compound 1 is isolated.

In some embodiments, Form A1 is obtained by crystallization of Compound 1 from chloroform, dichloromethane, isopropyl ether, or methyl isobutyl ether. In some embodiments, Form A1 is obtained by slow evaporation from chloroform. In some embodiments, Form A1 is obtained by slow evaporation or crash precipitation with heptane from dichloromethane.

Material B, Compound 1

In some embodiments, provided herein is a Material B crystal form of Compound 1. In some embodiments, the Form B crystal form of Compound 1 is isolated. A representative XRPD pattern of Material B is provided in FIG. 19 (row B), 32, or 35. In some embodiments, provided herein is the Material B crystal frm of Compound 1, which has an XRPD pattern which is substantially similar to the pattern exhibited in FIG. 19 (row B), 32, or 35.

In certain embodiments, Material B is characterized by a DSC thermogram comprising one, two, three, or more thermal events at about 119° C. or higher.

In certain embodiments, Material B undergoes a weight loss of about 10.14% when heated from 25 to 130° C. In certain embodiments, such weight loss is determined by TGA analysis.

Figure 34:
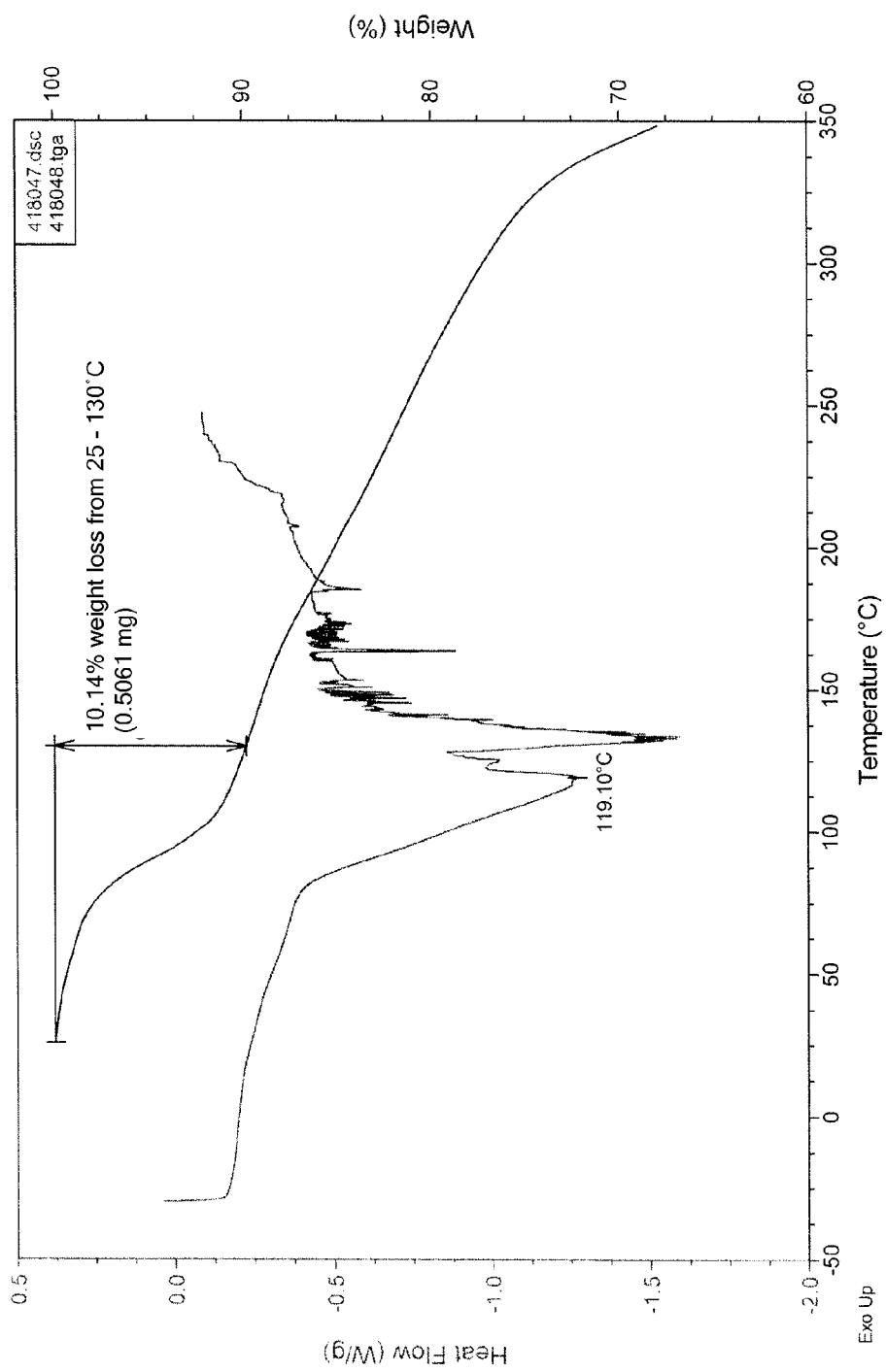
FIG. 34 shows a DSC and TGA overlay of Material B of Compound 1.
Figure 35:
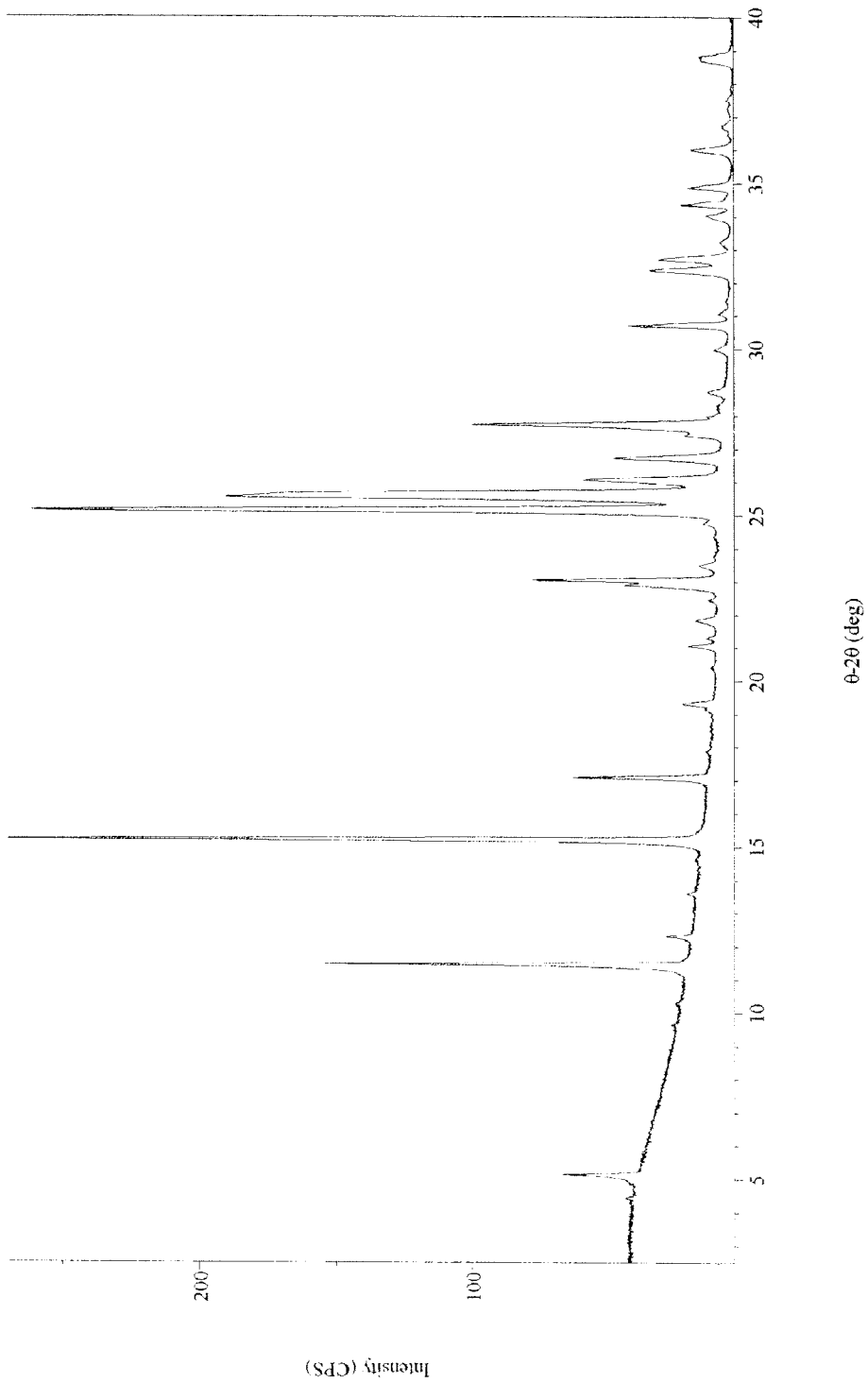
FIG. 35 shows an XRPD pattern of Material B of Compound 1.

In certain embodiments, Material B is characterized by a TGA or DSC thermogram substantially similar to that depicted in FIG. 34.

In some embodiments, provided herein is an isolated Material B crystal form of Compound 1. In certain embodiments, the isolated Material B crystal form of Compound 1 has an XRPD pattern which is substantially similar to the pattern exhibited in FIG. 19 (row B) or 32.

In some embodiments, the Material B crystal form of Compound 1 is chemically stable. In some embodiments, the Material B crystal form of Compound 1 is physically stable.

In some embodiments, the Material B crystal form is substantially free of other crystal forms of Compound 1.

Figure 33:
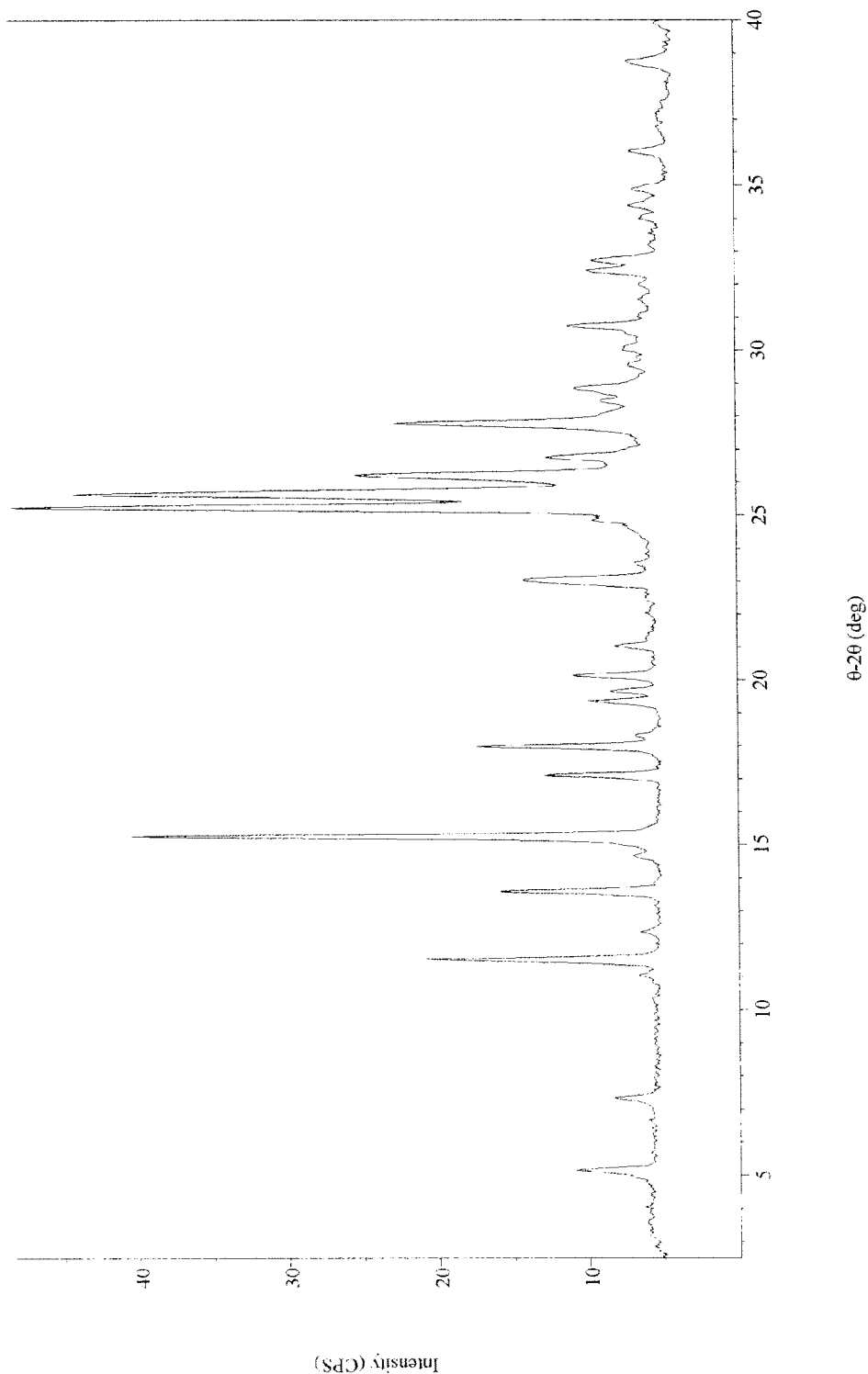
FIG. 33 shows an XRPD pattern of a mixture comprising Material B of Compound 1 and a second component.

In some embodiments, provided herein is a mixture comprising Material B and a second component. An exemplary XRPD pattern of this mixture is provided in FIG. 33.

In some embodiments, Material B is hydrated. In some embodiments, Material B is not solvated or hydrated.

In some embodiments, Material B is obtained by crystallization from THF. In some embodiments, Material B is obtained by slow evaporation of Compound 1 from THF. In particular embodiments, the slow evaporation is performed on a scale of about 30 mg of Compound 1 or less. In some embodiments, Material B is obtained by vapor diffusion with heptane for one day from THF.

In some embodiments, Material B is obtained by subjecting a mixture of Form A and Material B to water and/or heat. In some embodiments, Material B is obtained by subjecting a mixture of Form A and Material B to about 80%, 85%, 90%, 95%, 97%, or 99% relative humidity at elevated temperatures. In certain embodiments, the elevated temperature is about 40° C.

Compound 1 Form A/Material B Mixture

Figure 19:
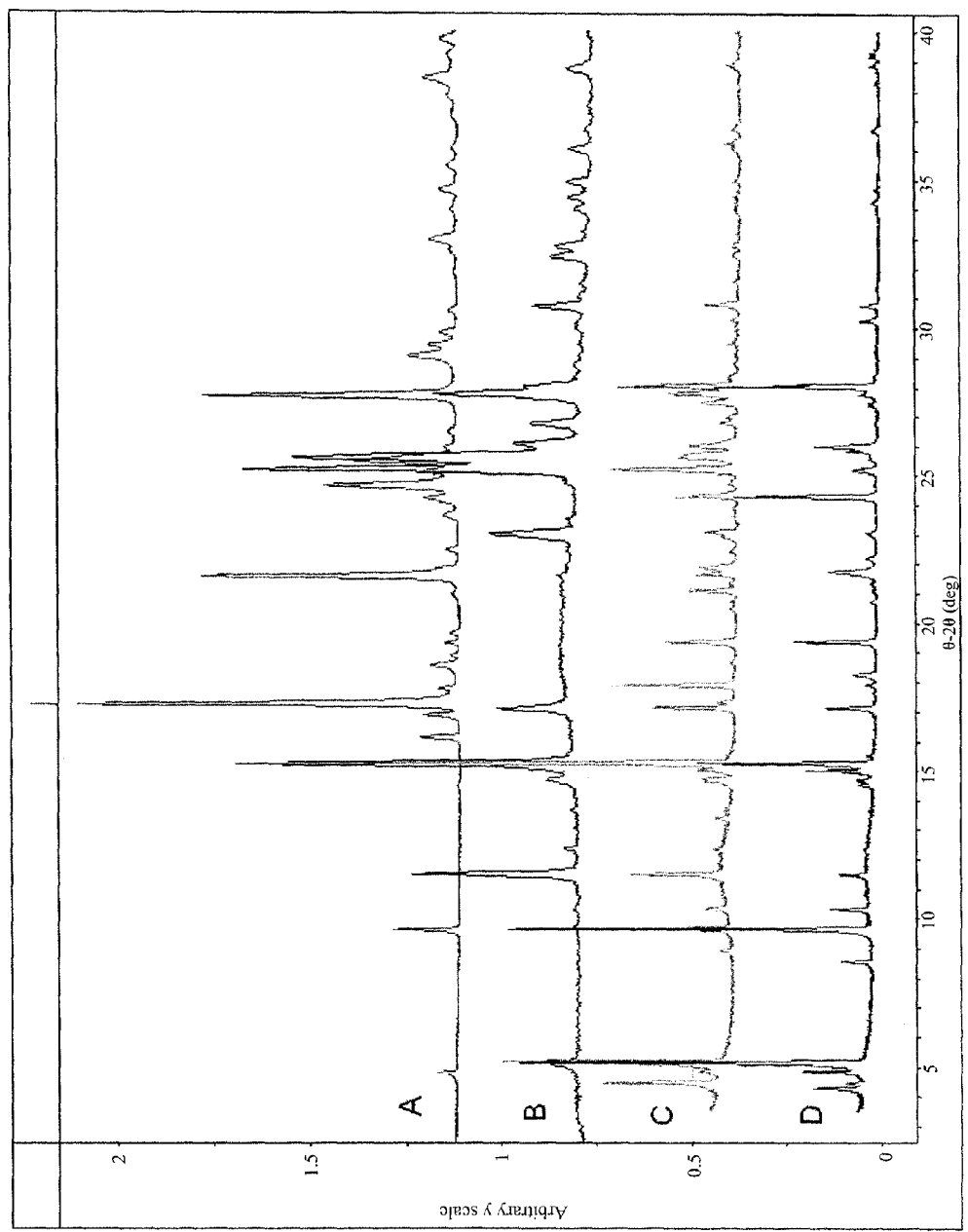
FIG. 19 (rows A-D) shows an XRPD overlay of Form A and Material B of Compound 1. Row A is an exemplary XRPD pattern of Form A crystal form. Row B is an exemplary XRPD pattern of Material B crystal form. Rows C and D show exemplary XRPD patterns for a mixture of Form A and Material B crystal forms.

In some embodiments, provided herein are mixtures of Form A and Material B crystal forms. FIG. 19 (rows C and D) provides exemplary XRPD patterns of such a mixture. In some embodiments, the mixtures are isolated. In some embodiments, provided herein is an isolated mixture of Form A and Material B crystal forms of Compound 1, which has an XRPD pattern that is substantially similar to FIG. 19 (row C or D).

Compound 2

As described above and herein, dehydration of Compound 1 forms anhydrides, e.g., dimers, trimers, and/or oligomer anhydrides of Compound 1. Assays can be used to distinguish the various anhydrides from Compound 1 (the monomer) and from each other. Exemplary such assays include, but are not limited to, elemental analysis, X-ray diffraction, X-ray powder diffraction (XRPD) analysis, $^1$H nuclear magnetic resonance (NMR) analysis, and Karl Fischer oven method evaporative coulometric titration.

In certain embodiments, the present invention provides a Compound 1 anhydride, wherein in the anhydride is a dimer, trimer, and/or oligomer of Compound 1, or a mixture thereof, as a crystalline solid ("crystalline Compound 1 anhydride"). In some embodiments, the present invention provides the crystalline Compound 1 anhydride as a trimer (e.g., a linear or cyclic trimer). In some embodiments, the present invention provides the crystalline Compound 1 anhydride as a cyclic trimer, i.e., Compound 2, as defined herein.

In some embodiments, provided here is crystalline Compound 2:

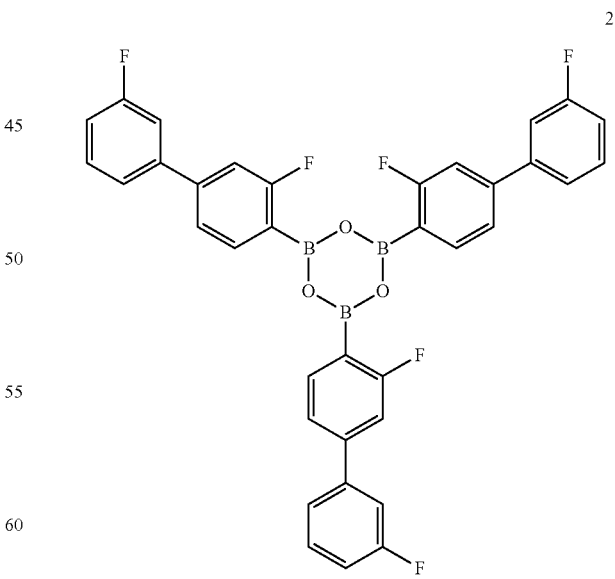

or a pharmaceutically acceptable salt, hydrate or solvate thereof.

In some embodiments, the crystalline Compound 2 is substantially free of any one of the following compounds:

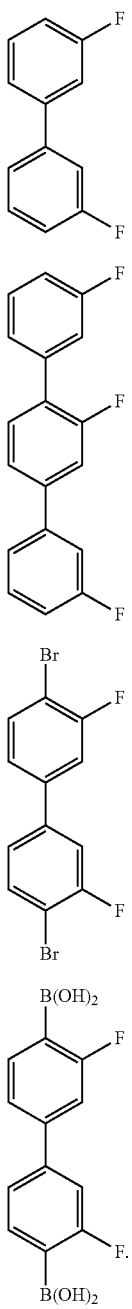
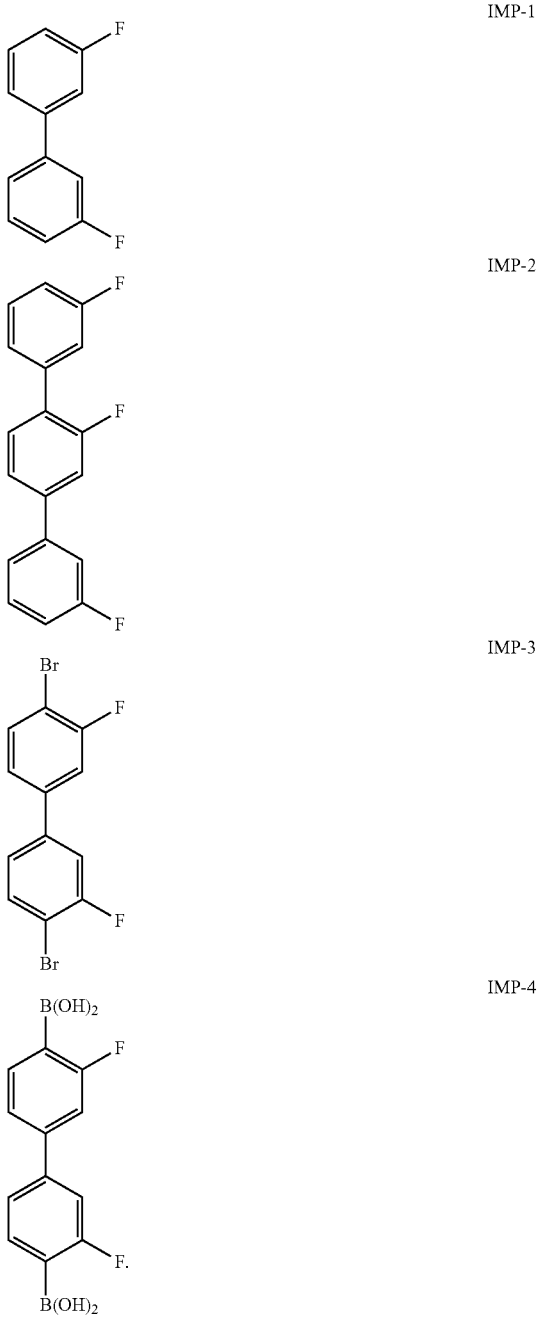

In some embodiments, the crystalline Compound 2 is substantially free of Compound 1 or other anhydrides thereof.

In certain embodiments, crystalline Compound 2 is a solid form substantially free of amorphous Compound 2. In certain embodiments, crystalline Compound 2 is a solid form substantially free of one or more other crystalline forms of Compound 2. In certain embodiments, crystalline Compound 2 is a solid form substantially free of crystalline Compound 1. In certain embodiments, crystalline Compound 2 is a solid form substantially free of other anhydrides of Compound 1 (e.g., dimer, linear trimer, oligomers of Compound 1). In certain embodiments, Compound 2 is provided as pure and isolated crystalline Compound 2.

As defined herein, "pure and isolated" refers to the isolated crystalline Compound 2 having at least one of the following characteristics:
(i) a crystalline solid having greater than 90% purity (e.g., as determined by HPLC);
(ii) a crystalline solid having less than about 400 ppm acetone present as a residual solvent;
(iii) a crystalline solid substantially free of non-polar impurities IMP-1 and IMP-2 and IMP-3, as defined above and herein;
(iv) a crystalline solid substantially free of polar impurity IMP-4 as defined above and herein;
(v) a crystalline solid substantially free of amorphous Compound 2;
(vi) a crystalline solid substantially free of Compound 1 or other anhydrides thereof; and/or
(vii) a crystalline solid substantially free of other crystalline forms of Compound 2.

In certain embodiments, "pure and isolated" refers to the isolated crystalline Compound 2 having at least two of the above listed (i) to (vii) characteristics. In certain embodiments, "pure and isolated" refers to the isolated crystalline Compound 2 having at least three of the above listed (i) to (vii) characteristics. In certain embodiments, "pure and isolated" refers to the isolated crystalline Compound 2 having at least four of the above listed (i) to (vii) characteristics. In certain embodiments, "pure and isolated" refers to the isolated crystalline Compound 2 having at least five of the above listed (i) to (vii) characteristics. In certain embodiments, "pure and isolated" refers to the isolated crystalline Compound 2 having at least six of the above listed (i) to (vii) characteristics. In certain embodiments, "pure and isolated" refers to the isolated crystalline Compound 2 having all seven of the above listed (i) to (vii) characteristics.

The phrase "substantially free of amorphous Compound 2" means that about 90% to about 100% by weight, about 95% to about 100% by weight, about 98% to about 100% by weight, or about 99% to about 100% by weight of Compound 2 is crystalline (i.e., not amorphous).

The phrase "substantially free of Compound 1 or other anhydride thereof" means that at about 90% to about 100% by weight, about 95% to about 100% by weight, about 98% to about 100% by weight, or about 99% to about 100% by weight of Compound 2 is provided as the cyclic trimer (i.e., not as the monomer or dimer, linear trimer or other oligomers of Compound 1).

The phrase "substantially free of one or more other crystalline forms of Compound 2" means that at about 90% to about 100% by weight, about 95% to about 100% by weight, about 98% to about 100% by weight, or about 99% to about 100% by weight of Compound 2 is provided in a specific crystalline form, e.g., "Form I."

Figure 18:
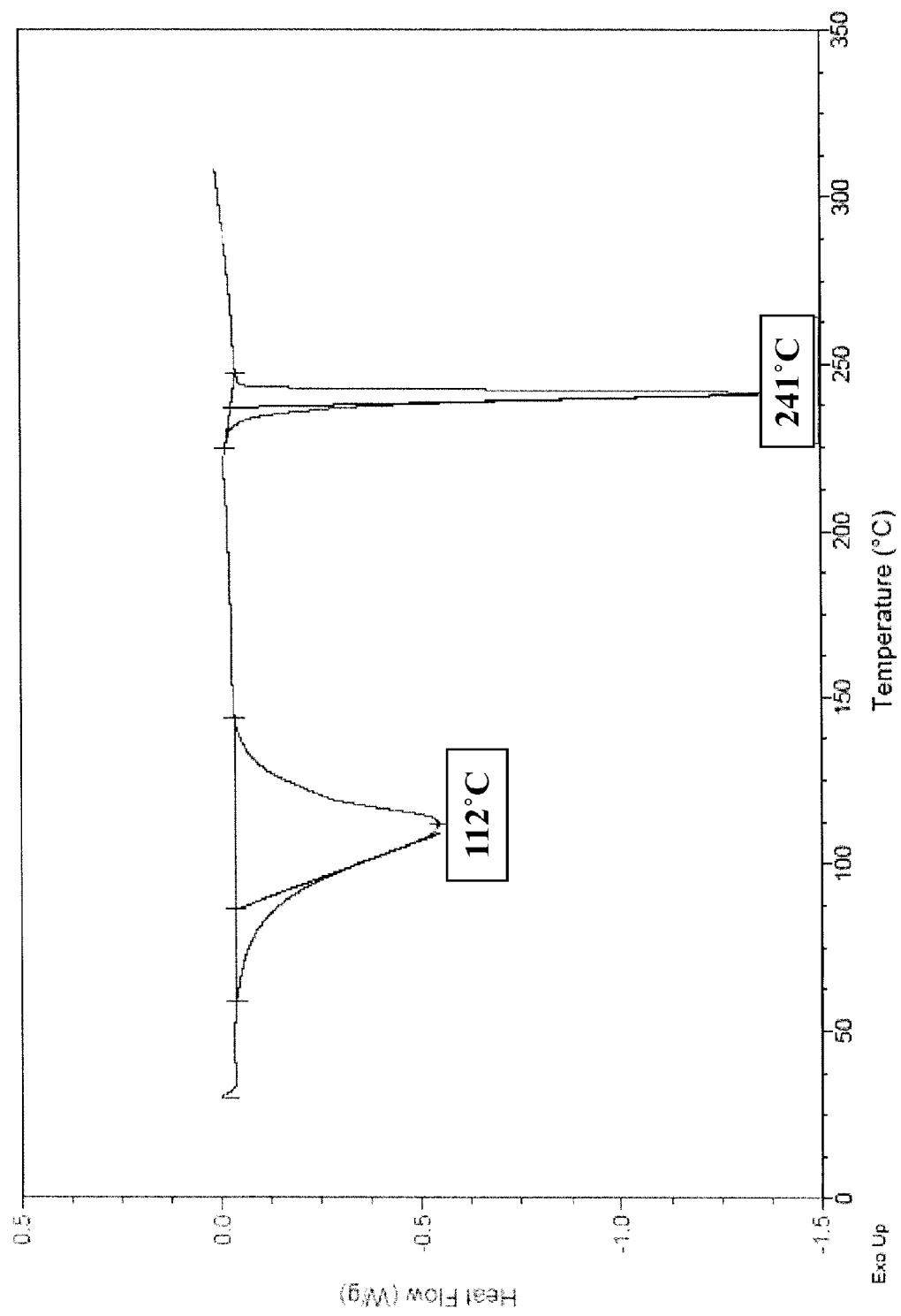
FIG. 18 shows a Differential Scanning calorimetry (DSC) trace of Form I of Compound 2.

In certain embodiments, "Form I" Compound 2 has at least one of the following characteristics:
(i) one or more transition temperatures selected from about 112±5° C. and about 241±2° C. as determined by differential scanning calorimetry (DSC);
(ii) one or more peaks in an X-ray powder diffraction (XRPD) pattern selected from 6.32±0.10, 12.69±0.10, 17.69±0.10, and 26.77±0.10;
(iii) an X-ray powder diffraction (XRPD) pattern substantially similar to that depicted in FIG. 8, 29 or 29; and/or
(iv) a diffraction scanning calorimetry (DSC) scan substantially similar to that depicted in FIG. 18.

In some embodiments, the Form I crystal form of Compound 2 is isolated.

In certain embodiments, "Form I" is characterized by peaks in an XRPD pattern located at 1, 2, 3, or all of the following approximate peak positions: 6.32±0.10, 12.69±0.10, 17.69±0.10, and 26.77±0.10 θ-2θ (degrees). In certain embodiments, "Form I" is defined by two or more peaks 6.32±0.10, 12.69±0.10, 17.69±0.10, and 26.77±0.10. In certain embodiments, "Form I" is defined by three or more peaks 6.32±0.10, 12.69±0.10, 17.69±0.10, and 26.77±0.10. In certain embodiments, "Form I" is defined by the X-ray powder diffraction pattern substantially similar to that depicted in FIG. 8.

In certain embodiments, provided herein is a crystalline form of Compound 2 having an XRPD pattern comprising peaks at approximately 6.32, 12.69, and 26.77 degrees 2θ. In further embodiments, the XRPD pattern further comprises peaks at approximately 17.69 degrees 2θ.

In some embodiments, provided herein is a crystal form having at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, or all of the following approximate XRPD pattern peaks: 6.3, 9.6, 11.2, 11.5, 12.7, 13.1, 14.7, 15.2, 16.9, 17.3, 17.4, 17.7, 18.0, 18.6, 19.0, 19.4, 20.4, 20.8, 21.6, 22.5, 22.7, 23.0, 23.4, 24.5, 24.7, 25.1, 25.5, 26.8, 27.7, 28.3, 29.0 degrees 2θ. In some embodiments, the crystal form has at least 8, at least 9, or at least 10 of the peaks. In some embodiments, the crystal form has at least 10 of the peaks. In certain embodiments, provided herein is a crystal form having an XRPD pattern comprising peaks at the following approximate positions: 6.3, 12.7, 17.7, 18.6, 19.4, 21.6, 23.4, 24.5, 26.8, and 27.7 degrees 2θ.

In some embodiments, provided herein is a crystal form having at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, or all of the following approximate XRPD pattern peaks: 6.3, 11.2, 11.5, 12.7, 13.1, 14.7, 16.9, 17.3, 17.4, 17.7, 18.0, 18.6, 19.0, 19.4, 20.4, 20.8, 21.6, 22.5, 22.7, 23.0, 23.4, 24.5, 24.7, 25.1, 25.5, 26.8, 27.7, 28.3, 29.0 degrees 2θ.

In certain embodiments, the XRPD peaks above (degrees 2θ peaks) are when analyzed using copper Kα radiation.

In some embodiments, provided herein is an isolated Form I crystal form of Compound 2. In certain embodiments, the Form I crystal form of Compound 2 has an XRPD pattern, which is substantially similar to the pattern exhibited in FIG. 8. In some embodiments, provided herein is an isolated Form I crystal form of Compound 2, which has an XRPD pattern comprising peaks at approximately 6.32, 12.69, and 26.77 degrees 2θ when analyzed using copper Kα radiation.

In certain embodiments, "Form I" is characterized by one or more transition temperatures selected from about 112±5° C. and about 241±2° C. as determined by differential scanning calorimetry (DSC). In certain embodiments, "Form I" is characterized by a transition temperature of about 241±2° C. as determined by differential scanning calorimetry (DSC). In certain embodiments, "Form I" is characterized by a transition temperature of about 112±5° C. as determined by differential scanning calorimetry (DSC). In certain embodiments, "Form I" is characterized by two transition temperatures selected from about 112±5° C. and about 241±2° C. as determined by differential scanning calorimetry (DSC). In certain embodiments, "Form I" is characterized by a differential scanning calorimetry (DSC) scan substantially similar to that depicted in FIG. 18.

In some embodiments, Form I is chemically stable. In some embodiments, Form I is physically stable.

In some embodiments, the Form I crystal form of Compound 2 is substantially free of other crystalline forms of Compound 2.

The term "substantially similar," when used herein in the context of comparing X-ray powder diffraction pattern or differential scanning calorimetry scan obtained for a solid form of Compound 2, means that two spectra share defining characteristics sufficient to differentiate them from a spectrum obtained for a different form of Compound 2. In certain embodiments, the term "substantially similar" means that two spectra are the same, i.e., visibly overlap.

In certain embodiments, "Form I" refers to a specific crystalline form of Compound 2 having at least two of the above listed (i) to (iv) characteristics. In certain embodiments, "Form I" refers to a specific crystalline form of Compound 2 having at least three of the above listed (i) to (iv) characteristics. In certain embodiments, "Form I" refers to a specific crystalline form of Compound 2 having all four of the above listed (i) to (iv) characteristics.

It is also contemplated that Compound 2 can exist in a variety of solid forms. Such solid forms include crystalline solids, such as polymorphs, solvates and hydrates of crystalline Compound 2, as well as amorphous solids. All such solid forms of Compound 2 are contemplated under the present invention.

Pharmaceutical Compositions

The terms "pharmaceutical composition" and "formulation" refer to a composition comprising at least one pharmaceutically active compound as described herein (e.g., crystalline Compound 1 or anhydride thereof) and a pharmaceutically acceptable excipient.

In some embodiments, the present invention provides a pharmaceutical composition comprising Compound 1 and a Compound 1 anhydride and a pharmaceutically acceptable excipient.

In some embodiments, the present invention provides a pharmaceutical composition comprising a mixture of Compound 1 and Compound 2, and a pharmaceutically acceptable excipient.

In some embodiments, the present invention provides a pharmaceutical composition comprising a mixture of Compound 1, Compound 2, and at least one other Compound 1 anhydride (e.g., a dimer, a linear trimer, an oligomer), and a pharmaceutically acceptable excipient.

In some embodiments, provided herein are pharmaceutical compositions comprising any of the compounds, crystal forms, materials, or mixtures described herein. In certain embodiments, provided herein are pharmaceutical compositions comprising crystalline Compound 1 that is substantially free of IMP-1, IMP-2, IMP-3, or IMP-4. In certain embodiments, provided herein are pharmaceutical compositions comprising Form A, Material B, or Form A1 of Compound 1, or comprising a mixture of Form A and Material B of Compound 1. In one embodiment, the pharmaceutical composition comprising Form A is substantially free of other crystal forms of Compound 1. In one embodiment, the pharmaceutical composition comprising Material B is substantially free of other crystal forms of Compound 1. In one embodiment, the pharmaceutical composition comprising Form A1 is substantially free of other crystal forms of Compound 1. In some embodiments, provided herein are pharmaceutical compositions comprising Compound 2. In some embodiments, provided herein are pharmaceutical compositions comprising Form I of Compound 2. In certain embodiments, the pharmaceutical compositions comprising Form I of Compound 2 are substantially free of other crystal forms of Compound 2.

In some embodiments, the present invention provides a pharmaceutical composition comprising Compound 1 substantially free of Compound 1 anhydride and a pharmaceutically acceptable excipient. In some embodiments, the present invention provides a pharmaceutical composition comprising Compound 1 substantially free of Compound 2 and a pharmaceutically acceptable excipient.

The phrases "a pharmaceutical composition comprising Compound 1 substantially free of Compound 1 anhydride" or "a pharmaceutical composition comprising Compound 1 substantially free of Compound 2" means that about 90% to about 100% by weight, about 95% to about 100% by weight, about 98% to about 100% by weight, or about 99% to about 100% by weight of the compound provided in the composition is the monomer Compound 1.

In some embodiments, the present invention provides a pharmaceutical composition comprising a mixture of Compound 2 and at least one other Compound 1 anhydride and one or more pharmaceutically acceptable excipients.

The present invention also provides methods for administering pharmaceutical compositions. In certain embodiments, the present invention provides pharmaceutical compositions that are suitable for oral, topical, and/or parenteral administration of Compound 1. In some embodiments, the present invention provides pharmaceutical compositions for oral administration. For example, in certain embodiments, Compound 1 is provided as a powder in a pharmaceutical composition, e.g., for an oral suspension (e.g., wherein the powder is suspended in a vehicle comprising components which will allow for consistent oral dosing, e.g., commercially available USP carboxymethylcellulose sodium (CMC) in sterile Water for Injection (sWFI)), for encapsulation in a capsule or for compressing into a tablet. In certain embodiments, the powder optionally comprises a mixture of crystalline Compound 1 and a pharmaceutically acceptable excipient.

For example, in some embodiments, the powder comprising crystalline Compound 1 and optionally containing one or more excipients is processed to generate particles of a consistent size. In certain embodiments, processing the powder (i.e., crystalline Compound 1) comprises milling the powder for an amount of time suitable to bring about a desired particle size ("milled powder").

In some embodiments, the particle size of the milled powder is less than about 400 µm. In some embodiments, the particle size of the milled powder is less than about 350 µm. In some embodiments, the particle size of the milled powder is less than about 300 µm. In some embodiments, the particle size of the milled powder is less than about 275 µm. In some embodiments, the particle size of the milled powder is less than about 250 µm. In some embodiments, the particle size of the milled powder ranges from about 50 µm to about 500 µm. In some embodiments, the particle size of the milled powder ranges from about 50 µm to about 400 µm. In some embodiments, the particle size of the milled powder ranges from about 50 µm to about 350 µm. In some embodiments, the particle size of the milled powder ranges from about 75 µm to about 350 µm. In some embodiments, the particle size of the milled powder ranges from about 100 µm to about 300 µm. In some embodiments, the particle size of the milled powder ranges from about 100 µm to about 275 µm. In some embodiments, the particle size of the milled powder ranges from about 100 µm to about 250 µm. In some embodiments, the particle size of the milled powder ranges from about 50 µm to about 500 µm. The term "about," as used herein with respect to particle size, means +/−5 µm.

In some embodiments, at least 90% of a representative sample of the milled powder has a particle size of less than about 400, about 375, about 350, about 300, about 290, about 280, about 270, about 260, or about 250 µm. In some embodiments, at least about 90% of a representative sample of the milled powder has a particle size of less than about 244 µm.

In some embodiments, at least 50% of a representative sample of the milled powder has a particle size of less than about 200, about 175, about 150, about 140, about 130, about 120, about 115, about 110, or about 105 µm. In some embodiments, at least about 50% of a representative sample of the milled powder has a particle size of less than about 105 µm.

In certain embodiments, the milled powder optionally contains excipients and is formulated as a powder for oral suspension, a capsule, or a tablet.

In some embodiments, crystalline Compound 1 is present in a pharmaceutical composition in an amount ranging from about 10 mg per unit dose to about 4000 mg per unit dose. In some embodiments, Compound 1 is present in a formulation in an amount ranging from about 10 mg per unit dose to about 2000 mg per unit dose. In some embodiments, Compound 1 is present in a pharmaceutical composition in an amount ranging from about 10 mg per unit dose to about 1500 mg per unit dose. In some embodiments, Compound 1 is present in a pharmaceutical composition in an amount ranging from about 25 mg per unit dose to about 1500 mg per unit dose. In some embodiments, Compound 1 is present in a pharmaceutical composition in an amount ranging from about 50 mg per unit dose to about 1500 mg per unit dose. In some embodiments, Compound 1 is present in a pharmaceutical composition in an amount ranging from about 75 mg per unit dose to about 1500 mg per unit dose. In some embodiments, Compound 1 is present in a pharmaceutical composition in an amount ranging from about 100 mg per unit dose to about 1500 mg per unit dose. In some embodiments, Compound 1 is present in a pharmaceutical composition in an amount ranging from about 100 mg per unit dose to about 1000 mg per unit dose. In some embodiments, Compound 1 is present in a pharmaceutical composition in an amount ranging from about 500 mg per unit dose to about 1000 mg per unit dose. In some embodiments, Compound 1 is present in a pharmaceutical composition in an amount of about 10, about 25, about 50, about 100, about 250, about 500, about 750, about 1000, or about 2000 mg per unit dose. In certain embodiments, Compound 1 is present in a suspension for oral administration in an amount of about 10, about 25, about 50, about 100, about 250, about 500, about 750, about 1000, or about 2000 mg per unit dose.

The expression "unit dose," as used herein, refers to a physically discrete unit of a pharmaceutical composition appropriate for a subject to be treated. It will be understood, however, that the total daily usage of a pharmaceutical composition of the present invention will be decided by the attending physician within the scope of sound medical judgment. The specific effective dose level for any particular subject or organism will depend upon a variety of factors including the condition being treated and the severity of the condition; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

In some embodiments, Compound 1 is present in a pharmaceutical composition in an effective amount to provide to a subject an exposure of about 2 to about 100 ng-h/mL per unit dose. In some embodiments, Compound 1 is present in a pharmaceutical composition in an effective amount to provide to a subject an exposure of about 5 to about 75 ng-h/mL per unit dose. In some embodiments, Compound 1 is present in a pharmaceutical composition in an effective amount to provide to a subject an exposure of about 10 to about 50 ng-h/mL per unit dose. In certain embodiments, Compound 1 is present in a pharmaceutical composition in an effective amount to provide to a subject an exposure of about 23 to about 43 ng-h/mL per unit dose.

In some embodiments, the present invention provides dosage forms suitable for administration of one or more unit dosages. For example, the present invention provides dosage forms for the administration of 2, 3, 4, 5, 6, 7, 8, 9, or 10 unit dosages (i.e., multiple unit dosages for administration are contained within a single container). The expression "dosage form" refers to means by which a pharmaceutical composition is stored and/or administered to a subject. For example, the pharmaceutical composition may be stored in a vial or syringe. The pharmaceutical composition may also be stored in a container, which protects the pharmaceutical composition from light (e.g., UV light). Alternatively, a container or vial, which itself is not necessarily protective from light, may be stored in a secondary storage container (e.g., an outer box, bag, etc.), which protects the pharmaceutical composition from light.

In certain embodiments, the solubility of Compound 1 in a pharmaceutical composition can be improved by the addition of one or more solubilizing agents. Solubilizing agents are known to one skilled in the art and include any of those described below and herein.

In some embodiments, Compound 1 is suspended in a suspension vehicle comprising a solubilizing agent prior to administration to a subject. In certain embodiments, the suspension vehicle comprises 0.5% medium viscosity carboxymethylcellulose sodium (CMC) dissolved in sterile water for injection (sWFI) and is administered orally.

As described above, the pharmaceutical compositions of the present invention may optionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980) discloses various carriers used in pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials that can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient, which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive compositions. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and Veegum [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [TWEEN® 20], polyoxyethylene sorbitan [TWEEN® 60], polyoxyethylene sorbitan monooleate [TWEEN® 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc., and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol, etc.); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable pharmaceutical compositions can be sterilized, for example, by filtration through a bacterial-retaining filter, or by incorporating sterilizing agents in the form of sterile solid compositions, which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Solid dosage forms for oral administration include capsules, tablets, pills, powders, and granules. In such solid dosage forms, the active ingredient may optionally be mixed with one or more inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions that can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form and may optionally contain one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such as magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions that can be used include polymeric substances and waxes.

General considerations in the pharmaceutical composition and/or manufacture of pharmaceutical agents may be found, for example, in *Remington: The Science and Practice of Pharmacy* 21st ed., Lippincott Williams & Wilkins, 2005.

Although the descriptions of pharmaceutical compositions provided herein are principally directed to pharmaceutical compositions, which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Still further encompassed by the invention are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of the provided formulation container and solvent container combine to form at least one unit dosage form.

In some embodiments, a provided composition of the invention may be useful in conjunction with patient controlled analgesia (PCA) devices, wherein a patient can administer, for example, opioid analgesia as required for pain management.

Optionally, a single container may comprise one or more compartments for containing a provided composition, and/or appropriate aqueous carrier for suspension or dilution. In some embodiments, a single container may be appropriate for modification such that the container may receive a physical modification so as to allow combination of compartments and/or components of individual compartments. For example, a foil or plastic bag may comprise two or more compartments separated by a perforated seal, which may be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension. Optionally, instructions for use are additionally provided in such kits.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy. In one non-limiting example, the pharmaceutical compositions of the invention may be used in conjunction with opioid analgesia administration, which may, optionally, comprise use of a patient controlled analgesia (PCA) device. Thus, instructions for use of provided pharmaceutical compositions may comprise instructions for use in conjunction with PCA administration devices.

Methods of Use and Administration

As described above, Compound 1 is an inhibitor of FAAH. As such, it is useful for treating conditions mediated by FAAH.

The present invention provides methods for treating a FAAH-mediated condition comprising administering to a subject in need thereof a therapeutically effective amount of Compound 1, as described herein.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition.

As used herein, unless otherwise specified, the terms "prevent," "preventing" and "prevention" contemplate an action that occurs before a subject begins to suffer from the specified disease, disorder or condition, which inhibits or reduces the severity of the disease, disorder or condition.

As used herein, and unless otherwise specified, the terms "manage," "managing" and "management" encompass preventing the recurrence of the specified disease, disorder or condition in a subject who has already suffered from the disease, disorder or condition, and/or lengthening the time that a subject who has suffered from the disease, disorder or condition remains in remission. The terms encompass modulating the threshold, development and/or duration of the disease, disorder or condition, or changing the way that a subject responds to the disease, disorder or condition.

As used herein, and unless otherwise specified, a "therapeutically effective amount" of a compound is an amount sufficient to provide a therapeutic benefit in the treatment or management of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment or management of the disease, disorder or condition. The term "therapeutically effective amount" can encompass an amount that improves overall therapy, reduces or avoids symptoms or causes of the disease, disorder, or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein "inhibition," "inhibiting," "inhibit," and "inhibitor," and the like, refer to the ability of a compound to reduce, slow, halt or prevent activity of a particular biological process (e.g., FAAH activity) in a cell relative to vehicle.

"FAAH-mediated condition" as used herein, refers to a disease, disorder or condition, which is treatable by inhibition of FAAH activity. "Disease," "disorder" or "condition" are terms used interchangeably herein. FAAH-mediated conditions include, but are not limited to, painful conditions, inflammatory conditions, immune disorders, disorders of the central nervous system, metabolic disorders, cardiac disorders and glaucoma.

In certain embodiments, the FAAH-mediated condition is a painful condition. As used herein, a "painful condition" includes, but is not limited to, neuropathic pain (e.g., peripheral neuropathic pain), central pain, deafferentation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), non-inflammatory pain, inflammatory pain, pain associated with cancer, wound pain, burn pain, post-operative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like.

One or more of the painful conditions contemplated herein can comprise mixtures of various types of pain provided above and herein (e.g., nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the painful condition is neuropathic pain. The term "neuropathic pain" refers to pain resulting from injury to a nerve. Neuropathic pain is distinguished from nociceptive pain, which is the pain caused by acute tissue injury involving small cutaneous nerves or small nerves in muscle or connective tissue. Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Neuropathic pain conditions can develop following neuronal injury and the resulting pain may persist for months or years, even after the original injury has healed. Neuronal injury may occur in the peripheral nerves, dorsal roots, spinal cord or certain regions in the brain. Neuropathic pain conditions include, but are not limited to, diabetic neuropathy (e.g., peripheral diabetic neuropathy); sciatica; non-specific lower back pain; multiple sclerosis pain; carpal tunnel syndrome, fibromyalgia; HIV-related neuropathy; neuralgia (e.g., post-herpetic neuralgia, trigeminal neuralgia); pain resulting from physical trauma (e.g., amputation, surgery, invasive medical procedures, toxins, burns, infection); pain resulting from cancer or chemotherapy (e.g., chemotherapy-induced pain such as chemotherapy-induced peripheral neuropathy); and pain resulting from an inflammatory condition (e.g., a chronic inflammatory condition). Neuropathic pain can result from a peripheral nerve disorder such as neuroma; nerve compression; nerve crush, nerve stretch or incomplete nerve transsection; mononeuropathy or polyneuropathy. Neuropathic pain can also result from a disorder such as dorsal root ganglion compression; inflammation of the spinal cord; contusion, tumor or hemisection of the spinal cord; tumors of the brainstem, thalamus or cortex; or trauma to the brainstem, thalamus or cortex.

The symptoms of neuropathic pain are heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

In certain embodiments, the painful condition is non-inflammatory pain. The types of non-inflammatory pain include, without limitation, peripheral neuropathic pain (e.g., pain caused by a lesion or dysfunction in the peripheral nervous system), central pain (e.g., pain caused by a lesion or dysfunction of the central nervous system), deafferentation pain (e.g., pain due to loss of sensory input to the central nervous system), chronic nociceptive pain (e.g., certain types of cancer pain), noxious stimulus of nociceptive receptors (e.g., pain felt in response to tissue damage or impending tissue damage), phantom pain (e.g., pain felt in a part of the body that no longer exists, such as a limb that has been amputated), pain felt by psychiatric subjects (e.g., pain where no physical cause may exist), and wandering pain (e.g., wherein the pain repeatedly changes location in the body).

In certain embodiments, the painful condition is inflammatory pain. In certain embodiments, the painful condition (e.g., inflammatory pain) is associated with an inflammatory condition and/or an immune disorder.

In certain embodiments, the FAAH-mediated condition is an inflammatory condition. The term "inflammatory condition" refers to those diseases, disorders or conditions that are characterized by signs of pain (e.g., dolor, from the generation of noxious substances and the stimulation of nerves), heat (e.g., calor, from vasodilatation), redness (e.g., rubor, from vasodilatation and increased blood flow), swelling (e.g., tumor, from excessive inflow or restricted outflow of fluid), and/or loss of function (e.g., functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

In certain embodiments, the FAAH-mediated condition is an immune disorder. Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin conditions (e.g., psoriasis, eczema, burns, dermatitis, pruritus (itch)), enuresis, eosinophilic disease, gastrointestinal disorders (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the inflammatory disorder and/or the immune disorder is a gastrointestinal disorder. In some embodiments, the gastrointestinal disorder is selected from gastrointestinal disorders (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)). In certain embodiments, the gastrointestinal disorder is inflammatory bowel disease (IBD).

In certain embodiments, the inflammatory condition and/or immune disorder is a skin condition. In some embodiments, the skin condition is pruritus (itch), psoriasis, eczema, burns or dermatitis. In certain embodiments, the skin condition is psoriasis. In certain embodiments, the skin condition is pruritus.

In certain embodiments, the FAAH-mediated condition is a disorder of the central nervous system (CNS) ("CNS disorder"). Exemplary CNS disorders include, but are not limited to, neurotoxicity and/or neurotrauma, stroke, multiple sclerosis, spinal cord injury, epilepsy, a mental disorder, a sleep condition, a movement disorder, nausea and/or emesis, amyotrophic lateral sclerosis, Alzheimer's disease and drug addiction.

In certain embodiments, the CNS disorder is neurotoxicity and/or neurotrauma, e.g., for example, as a result of acute neuronal injury (e.g., traumatic brain injury (TBI), stroke, epilepsy) or a chronic neurodegenerative disorder (e.g., multiple sclerosis, Parkinson's disease, Huntington's disease, amyotrophic lateral sclerosis, Alzheimer's disease). In certain embodiments, the compound of the present invention provides a neuroprotective effect, e.g., against an acute neuronal injury or a chronic neurodegenerative disorder.

In certain embodiments, the CNS disorder is stroke (e.g., ischemic stroke).

In certain embodiments, the CNS disorder is multiple sclerosis.

In certain embodiments, the CNS disorder is spinal cord injury.

In certain embodiments, the CNS disorder is epilepsy.

In certain embodiments, the CNS disorder is a mental disorder, e.g., for example, depression, anxiety or anxiety-related conditions, a learning disability or schizophrenia.

In certain embodiments, the CNS disorder is depression. "Depression," as used herein, includes, but is not limited to, depressive disorders or conditions, such as, for example, major depressive disorders (e.g., unipolar depression), dysthymic disorders (e.g., chronic, mild depression), bipolar disorders (e.g., manic-depression), seasonal affective disorder, and/or depression associated with drug addiction (e.g., withdrawal). The depression can be clinical or subclinical depression. The depression can be associated with premenstrual syndrome and/or premenstrual dysphoric disorder.

In certain embodiments, the CNS disorder is anxiety. "Anxiety," as used herein, includes, but is not limited to, anxiety and anxiety-related conditions, such as, for example, clinical anxiety, panic disorder, agoraphobia, generalized anxiety disorder, specific phobia, social phobia, obsessive-compulsive disorder, acute stress disorder, post-traumatic stress disorder, adjustment disorders with anxious features, anxiety disorder associated with depression, anxiety disorder due to general medical conditions, and substance-induced anxiety disorders, anxiety associated with drug addiction (e.g., withdrawal, dependence, reinstatement) and anxiety associated with nausea and/or emesis. This treatment may also be to induce or promote sleep in a subject (e.g., for example, a subject with anxiety).

In certain embodiments, the CNS disorder is a learning disorder (e.g., attention deficit disorder (ADD)).

In certain embodiments, the CNS disorder is Schizophrenia.

In certain embodiments, the CNS disorder is a sleep condition. "Sleep conditions" include, but are not limited to, insomnia, narcolepsy, sleep apnea, restless legs syndrome (RLS), delayed sleep phase syndrome (DSPS), periodic limb movement disorder (PLMD), hypopnea syndrome, rapid eye movement behavior disorder (RBD), shift work sleep condition (SWSD), and sleep problems (e.g., parasomnias) such as nightmares, night terrors, sleep talking, head banging, snoring, and clenched jaw and/or grinding of teeth (bruxism).

In certain embodiments, the CNS disorder is a movement disorder, e.g., basal ganglia disorders, such as, for example, Parkinson's disease, levodopa-induced dyskinesia, Huntington's disease, Gilles de la Tourette's syndrome, tardive diskinesia and dystonia.

In certain embodiments, the CNS disorder is Alzheimer's disease.

In certain embodiments, the CNS disorder is amyotrophic lateral sclerosis (ALS).

In certain embodiments, the CNS disorder is nausea and/or emesis.

In certain embodiments, the CNS disorder is drug addiction (e.g., for instance, addiction to opiates, nicotine, cocaine, psychostimulants or alcohol).

In still yet other embodiments, the FAAH-mediated condition is a cardiac disorder, e.g., for example, selected from hypertension, circulatory shock, myocardial reperfusion injury and atherosclerosis.

In certain embodiments, the FAAH-mediated condition is a metabolic disorder (e.g., a wasting condition, an obesity-related condition or complication thereof).

In certain embodiments, the metabolic disorder is a wasting condition. A "wasting condition," as used herein, includes, but is not limited to, anorexia and cachexias of various natures (e.g., weight loss associated with cancer, weight loss associated with other general medical conditions, weight loss associated with failure to thrive, and the like).

In certain embodiments, the metabolic disorder is an obesity-related condition or a complication thereof. An "obesity-related condition" as used herein, includes, but is not limited to, obesity, undesired weight gain (e.g., from medication-induced weight gain, from cessation of smoking) and an over-eating disorder (e.g., binge eating, bulimia, compulsive eating, or a lack of appetite control each of which can optionally lead to undesired weight gain or obesity). "Obesity" and "obese" as used herein, refers to class I obesity, class II obesity, class III obesity and pre-obesity (e.g., being "over-weight") as defined by the World Health Organization.

Reduction of storage fat is expected to provide various primary and/or secondary benefits in a subject (e.g., in a subject diagnosed with a complication associated with obesity) such as, for example, an increased insulin responsiveness (e.g., in a subject diagnosed with Type II diabetes mellitus); a reduction in elevated blood pressure; a reduction in elevated cholesterol levels; and/or a reduction (or a reduced risk or progression) of ischemic heart disease, arterial vascular disease, angina, myocardial infarction, stroke, migraines, congestive heart failure, deep vein thrombosis, pulmonary embolism, gall stones, gastroesophagael reflux disease, obstructive sleep apnea, obesity hypoventilation syndrome, asthma, gout, poor mobility, back pain, erectile dysfunction, urinary incontinence, liver injury (e.g., fatty liver disease, liver cirrhosis, alcoholic cirrhosis, endotoxin-mediated liver injury) or chronic renal failure. Thus, the method of this invention is applicable to obese subjects, diabetic subjects, and alcoholic subjects.

In some embodiments, treatment of an obesity-related condition or complication thereof involves reduction of body weight in the subject. In some embodiments, treatment of an obesity-related condition or complication thereof involves appetite control in the subject.

In other embodiments, the FAAH-mediated condition is glaucoma. The exact amount of Compound 1 and/or compositions comprising Compound 1 required to achieve a therapeutically effective amount will vary from subject to subject, depending on species, age, and general condition of a subject, severity of the side effects or disorder, mode of administration, and the like. The desired dosage may be delivered three times a day, two times a day, once a day, every other day, every third day, every week, twice weekly, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In certain embodiments of the present invention, a therapeutically effective amount of Compound 1 and/or compositions comprising Compound 1 for administration one or more times a day to a 70 kg adult human may comprise about 1 mg, about 5 mg, about 10 mg, about 25 mg, about 50 mg, about 100 mg, about 250 mg, about 500 mg, about 750 mg, about 1000 mg, about 2000 mg, about 2200 mg, about 2400 mg, about 2500 mg, about 2600 mg, about 2700 mg, about 2800 mg, about 2900 mg or about 3000 mg of Compound 1 per dose. In certain embodiments of the present invention, a therapeutically effective amount of Compound 1 and/or compositions comprising Compound 1 for administration one or more times a day to a 70 kg adult human may comprise from about 1 mg to about 3000 mg, from about 1 mg to about 2900 mg, from about 1 mg to about 2800 mg, from about 1 mg to about 2700 mg, from about 1 mg to about 2600 mg, from about 1 mg to about 2500 mg, from about 1 mg to about 2400 mg, from about 1 mg to about 2300 mg, from about 1 mg to about 2200 mg, from about 1 mg to about 2100 mg, from about 1 mg to about 2000 mg, from about 1 mg to about 1000 mg, from about 1 mg to about 900 mg, from about 1 mg to about 800 mg, from about 1 mg to about 700 mg, from about 1 mg to about 600 mg, from about 1 mg to about 500 mg, from about 1 mg to about 400 mg, from about 1 mg to about 300 mg, from about 1 mg to about 200 mg, from about 1 mg to about 100 mg, from about 1 mg to about 75 mg, from about 1 mg to about 50 mg, from about 1 mg to about 25 mg, from about 1 mg to about 10 mg, and from about 10 mg to about 800 mg of Compound 1 per dose. It will be appreciated that dose ranges as described herein provide guidance for the administration of inventive pharmaceutical compositions to an adult. The amount to be administered to, for example, a child or an adolescent can be determined by a medical practitioner or person skilled in the art and can be lower or the same as that administered to an adult.

The invention is also directed to methods of treating an FAAH-mediated disease comprising administering specific doses of Compound 1. Such doses may be administered once or more than once. In one embodiment, such dose or doses are administered according to schedules described herein. Compositions of Compound 1 formulated to contain the appropriate amount of Compound 1 so that the dose is readily administered are also envisaged.

In another aspect, the invention is directed to a method for treating an FAAH-mediated disease in a patient, comprising administering to a patient having an FAAH-mediated disease an effective amount of Compound 1.

In another aspect, the invention is directed to a method for treating an FAAH-mediated disease in a patient comprising administering to the patient an amount of about 10 mg/m$^2$ to about 3000 mg/m$^2$ of Compound 1 at least once a week. In some embodiments, the method comprises administering to the patient an amount of about 50 mg/m$^2$ to about 2000 mg/m$^2$ of Compound 1 at least once a week. In some embodiments, the method comprises administering to the patient an amount of about 100 mg/m$^2$ to about 1500 mg/m$^2$ of Compound 1 at least once a week. In some embodiments, the method comprises administering to the patient an amount of about 200 mg/m$^2$ to about 1000 mg/m$^2$ of Compound 1 at least once a week. In some embodiments, the method comprises administering to the patient an amount of about 400 mg/m$^2$ to about 800 mg/m$^2$ of Compound 1 at least once a week. In some embodiments, the method comprises administering to the patient an amount of about 600 mg/m$^2$ of Compound 1 at least once a week. The amount may be administered as a composition comprising Compound 1 and one or more pharmaceutically acceptable carriers, diluents, or excipients. The frequency and duration of the dosing can be determined by a medical practitioner or person skilled in the art.

Dosages of Compound 1 utilized in accordance with the present invention may vary with the form of administration and/or with the particular subject being treated. In general, Compound 1 is most desirably administered at a concentration level that will afford effective results without causing any harmful or deleterious side-effects. In some embodiments, Compound 1 is administered in doses ranging from about 0.01 to about 100 mg/kg/day. In some embodiments, Compound 1 is administered in doses ranging from about 0.05 to about 100 mg/kg/day. In some embodiments, Compound 1 is administered in doses ranging from about 0.1 to about 100 mg/kg/day. In some embodiments, Compound 1 is administered in doses ranging from about 1 to about 100 mg/kg/day. In some embodiments, Compound 1 is administered in doses ranging from about 5 to about 100 mg/kg/day. In some embodiments, Compound 1 is administered in doses ranging from about 10 to about 100 mg/kg/day. In some embodiments, Compound 1 is administered in doses ranging from about 10 to about 90 mg/kg/day. In some embodiments, Compound 1 is administered in doses ranging from about 10 to about 80 mg/kg/day. In some embodiments, Compound 1 is administered in doses ranging from about 10 to about 70 mg/kg/day. In some embodiments, Compound 1 is administered in doses ranging from about 10 to about 60 mg/kg/day. In some embodiments, Compound 1 is administered in doses ranging from about 10 to about 50 mg/kg/day. In some embodiments, Compound 1 is administered in doses ranging from about 10 mg/kg/day to about 40 mg/kg/day. In some embodiments, Compound 1 is administered in doses ranging from about 10 mg/kg/day to about 30 mg/kg/day. In some embodiments, Compound 1 is administered in doses ranging from about 10 mg/kg to about 20 mg/kg/day. In some embodiments, Compound 1 is administered in doses ranging from about 1 mg/kg/day to about 20 mg/kg/day. In some embodiments, Compound 1 is administered in doses ranging from about 1 mg/kg/day to about 10 mg/kg/day. In some embodiments, Compound 1 is administered in doses less than about 10 mg/kg/day. In some embodiments, Compound 1 is administered in doses less than about 5 mg/kg/day. In some embodiments, Compound 1 is administered in doses less than about 2 mg/kg/day. In some embodiments, Compound 1 is administered in doses less than about 1 mg/kg/day. In some embodiments, Compound 1 is administered in doses less than about 0.1 mg/kg/day. In some embodiments, Compound 1 is administered in doses less than about 0.01 mg/kg/day. In some embodiments, Compound 1 is administered in doses less than about 0.001 mg/kg/day. In some embodiments, Compound 1 is administered in doses of about 0.1, 0.2, 0.3, 0.4, 0.5, 0.6, 0.7, 0.8, 0.9, or 1.0 mg/kg/day. In some embodiments, Compound 1 is administered in doses of about 0.01, 0.02, 0.03, 0.04, 0.05, 0.06, 0.07, 0.08, or 0.09 mg/kg/day. In some embodiments, Compound 1 is administered in doses ranging from about 0.1 mg/kg/day to about 1 mg/kg/day. In some embodiments, Compound 1 is administered in doses ranging from about 0.01 mg/kg/day to about 0.1 mg/kg/day. In some embodiments, Compound 1 is administered in doses ranging from about 0.001 mg/kg/day to about 0.01 mg/kg/day.

In some embodiments, the dose is as described above and is administered 1, 2, 3, 4, 5, 6, 7, 8, 9, or 10 times a day. In some embodiments, the dose is as described above and is administered 1, 2, 3, or 4 times a day. In some embodiments, the dose is as described above and is administered every other day. In some embodiments, the dose is as described above and is administered every two days. In some embodiments, the dose is as described above and is administered every three days. In some embodiments, the dose is as described above and is administered every four days. In some embodiments, the dose is as described above and is administered every five days. In some embodiments, the dose is as described above and is administered every six days. In some embodiments, the dose is as described above and is administered once a week. In some embodiments, the dose is as described above and is administered once every two, three, four, five, six, seven, eight, nine, or ten weeks.

In some embodiments, Compound 1 and/or compositions comprising Compound 1 can be administered with food. "Food" typically means a solid food or mixed solid/liquid food with sufficient bulk and fat content that it is not rapidly dissolved and absorbed in the stomach. In one embodiment, food means a meal, such as breakfast, lunch or dinner. The terms "taken with food," "fed" and "non-fasted" are equivalent and are as given by FDA guidelines and criteria. In one embodiment, "with food" means that the administration occurs between about 30 minutes prior to about 2 hours after eating a meal. In another embodiment, —"with food" means that administration occurs at substantially the same time as eating the meal.

In some embodiments, Compound 1 can be administered under fasted conditions. The terms "without food," "fasted" and "an empty stomach" are equivalent and are as given by FDA guidelines and criteria. In one embodiment, "fasted conditions" means the condition wherein no food is consumed within 1 hour prior to administration or 2 hours after administration. In another embodiment, "fasted conditions"

means the condition wherein no food is consumed within 1 hour prior to administration to 2 hours after administration.

The efficacy of Compound 1 in the treatment of an FAAH-mediated disease, disorder, or condition according to the present invention may be evaluated and followed using any method known in the medical arts. Exemplary such methods include physical examination, laboratory testing, imaging studies, etc. In some embodiments, the treatment of an FAAH-mediated disease, disorder, or condition may be evaluated by monitoring the subject being treated. In some embodiments, the subject is monitored one, two, three, four, or five times a day. In some embodiments, the subject is monitored one, two, three, four or five times a week. In some embodiments, the subject is monitored twice a week. In some embodiments, monitoring is continuous. In some embodiments, monitoring occurs for the duration of the time a subject is being treated for an FAAH-mediated disease, disorder, or condition. In some embodiments, monitoring occurs for the duration of the subject's life. In some embodiments, the subject is a human and is monitored using any of the methods known in the medical arts suitable for monitoring humans undergoing treatment for an FAAH-mediated disease, disorder, or condition.

Combination Therapy

It will be also appreciated that Compound 1, or a composition thereof, as described above and herein, can be administered in combination with one or more additional therapeutically active agents.

By "in combination with," it is not intended to imply that the agents must be administered at the same time and/or formulated for delivery together, although these methods of delivery are certainly within the scope of the invention. The compositions can be administered concurrently with, prior to, or subsequent to, one or more other additional therapeutically active agents. In general, each agent will be administered at a dose and/or on a time schedule determined for that agent. In will further be appreciated that the additional therapeutically active agent utilized in this combination may be administered together in a single composition or administered separately in different compositions. The particular combination to employ in a regimen will take into account compatibility of the inventive compound with the additional therapeutically active agent and/or the desired therapeutic effect to be achieved.

In general, it is expected that additional therapeutically active agents utilized in combination be utilized at levels that do not exceed the levels at which they are utilized individually. In some embodiments, the levels utilized in combination will be lower than those utilized individually.

By a "therapeutically active agent" or "active agent" refers to any substance that is useful for therapy, including prophylactic and therapeutic treatment.

The invention encompasses the delivery of Compound 1 and/or compositions comprising Compound 1 in combination with agents that may improve the bioavailability, reduce and/or modify the metabolism, inhibit the excretion, and/or modify the distribution within the body of Compound 1. It will also be appreciated that the therapy employed may achieve a desired effect for the same disorder (for example, Compound 1 may be administered in combination with an anti-inflammatory, anti-anxiety and/or anti-depressive agent, etc.), and/or may achieve different effects (e.g., control of any adverse side-effects).

Exemplary active agents include, but are not limited to, anti-cancer agents, antibiotics, anti-viral agents, anesthetics, anti-coagulants, inhibitors of an enzyme, steroidal agents, steroidal or non-steroidal anti-inflammatory agents, antihistamines, immunosuppressant agents, anti-neoplastic agents, antigens, vaccines, antibodies, decongestants, sedatives, opioids, pain-relieving agents, analgesics, anti-pyretics, hormones, prostaglandins, progestational agents, anti-glaucoma agents, ophthalmic agents, anti-cholinergics, anti-depressants, anti-psychotics, hypnotics, tranquilizers, anti-convulsants, muscle relaxants, anti-spasmodics, muscle contractants, channel blockers, miotic agents, anti-secretory agents, anti-thrombotic agents, anticoagulants, anti-cholinergics, β-adrenergic blocking agents, diuretics, cardiovascular active agents, vasoactive agents, vasodilating agents, anti-hypertensive agents, angiogenic agents, modulators of cell-extracellular matrix interactions (e.g., cell growth inhibitors and anti-adhesion molecules), or inhibitors/intercalators of DNA, RNA, protein-protein interactions, protein-receptor interactions, etc. Active agents include small organic molecules such as drug compounds (e.g., compounds approved by the Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically active agent is a pain-relieving agent. Exemplary pain relieving agents include, but are not limited to, analgesics such as non-narcotic analgesics [e.g., salicylates such as aspirin, ibuprofen (MOTRIN®, ADVIL®), ketoprofen (ORUDIS®), naproxen (NAPROSYN®), acetaminophen, indomethacin] or narcotic analgesics [e.g., opioid analgesics such as tramadol, fentenyl, sufentanil, morphine, hydromorphone, codeine, oxycodone, and buprenorphine]; non-steroidal anti-inflammatory agents (NSAIDs) [e.g., aspirin, acetaminophen, COX-2 inhibitors]; steroids or anti-rheumatic agents; migraine preparations such as beta adrenergic blocking agents, ergot derivatives; tricyclic antidepressants (e.g., amitryptyline, desipramine, imipramine); anti-epileptics (e.g., clonazepam, valproic acid, phenobarbital, phenytoin, tiagaine, gabapentin, carbamazepine, topiramate, sodium valproate); $\alpha_2$ agonists; selective serotonin reuptake inhibitors (SSRIs), selective norepinephrine uptake inhibitors; benzodiazepines; mexiletine (MEXITIL®); flecainide (TAMBOCOR®); NMDA receptor antagonists [e.g., ketamine, detromethorphan, methadone]; and topical agents [e.g., capsaicin (Zostrix), EMLA cream, lidocaine, prilocaine].

In other embodiments, the additional therapeutically active agent is an anti-inflammatory agent. Exemplary anti-inflammatory agents include, but are not limited to, aspirin; ibuprofen; ketoprofen; naproxen; etodolac (LODINE®); COX-2 inhibitors such as celecoxib (CELEBREX®), rofecoxib (VIOXX™) valdecoxib (BEXTRA®), parecoxib, etoricoxib (MK663), deracoxib, 2-(4-ethoxy-phenyl)-3-(4-methanesulfonyl-phenyl)-pyrazolo[1,5-b]pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl) cyclopenta-2,4-dien-3-yl)benzene, 4-(1,5-Dihydro-6-fluoro-7-methoxy-3-(trifluoromethyl)-(2)-benzothiopyrano(4,3-c) pyrazol-1-yl)benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzofuranyl)-4-cyclopropyl butan-1-one, or their physiologically acceptable salts, esters or solvates; sulindac (CLINORIL®); diclofenac (VOLTAREN®); piroxicam (FELDENE®); diflunisal (DOLOBID®), nabumetone (RELAFEN®), oxaprozin (DAYPRO®), indomethacin (INDOCIN®); or steroids such as PEDIPRED® prednisolone sodium phosphate oral solution, SOLU-MEDROL® methylprednisolone sodium succinate for injection, PRELONE® brand prednisolone syrup.

Further examples of anti-inflammatory agents include naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX™ brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDINE EN-TABS® brand of sulfasalazine delayed release tablets, FELDENE® brand piroxicam capsules, CATAFLAM® diclofenac potassium tablets, VOLTAREN® diclofenac sodium delayed release tablets, VOLTARENe-XR diclofenac sodium extended release tablets, or ENBREL® etanerecept products.

IMP-4 as an FAAH Inhibitor

It has also been discovered that IMP-4 is also an inhibitor of FAAH.

Accordingly, in some embodiments, the present invention provides a composition comprising IMP-4 and a pharmaceutically acceptable carrier, adjuvant, or vehicle.

In certain embodiments, the present invention provides a method for inhibiting FAAH in a patient, comprising administering to the patient IMP-4, or a pharmaceutically acceptable composition thereof. In some embodiments, the present invention provides a method for treating an FAAH-mediated disorder in a patient, comprising administering to the patient IMP-4, or a pharmaceutically acceptable composition thereof. Such disorders include pain and those described in detail herein, infra.

The present disclosure now being generally described, it will be more readily understood by reference to the following examples, which are included merely for purposes of illustration of certain aspects and embodiments of the present invention, and are not intended to limit the disclosure herein.

EXEMPLIFICATION

The original procedure for the synthesis of Compound 1 as disclosed in PCT publication number WO 2008/63300, incorporated herein by reference, is depicted in Scheme 4. The first step of the published synthesis involved a Suzuki coupling of 1,4-dibromo-2-fluoro-benzene E-1a and 3-fluorophenylboronic acid E-2a, followed by concentration and chromatographic purification to provide E-3a. A Suzuki coupling of E-3a and bis(pinacolato)diboron followed by workup and chromatographic purification provided boronate ester E-4a. Hydrolysis of ester E-4a under oxidative conditions followed by workup and trituration with hexanes provided the boronic acid, Compound 1, as a white solid.

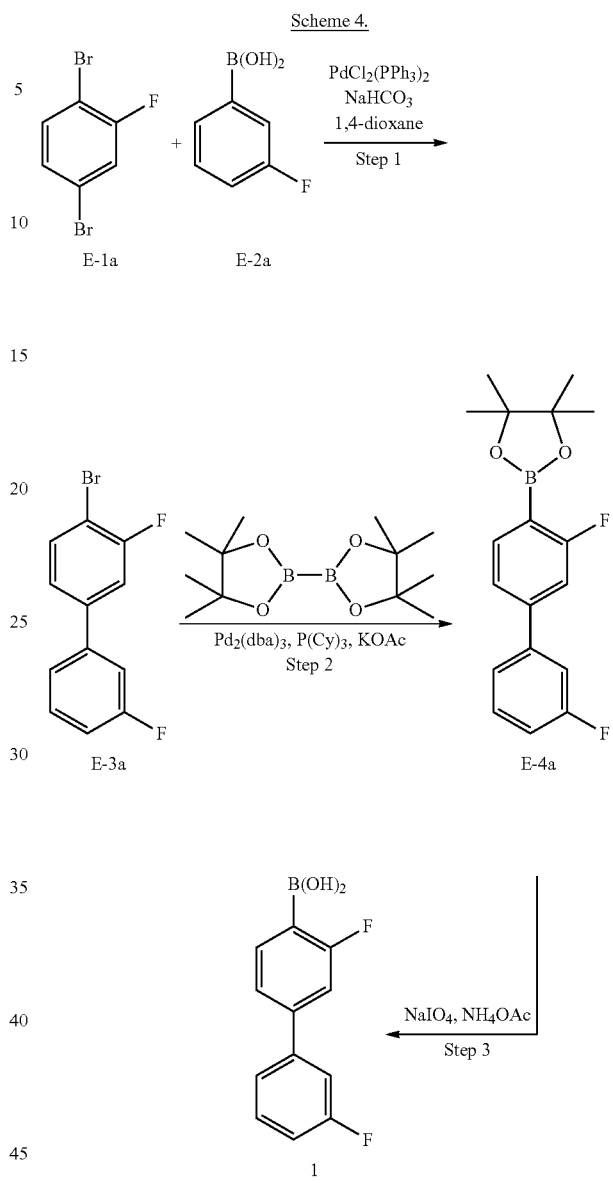

Example 1. Optimization of the Synthesis of Compound 1

Step 1: Suzuki Coupling

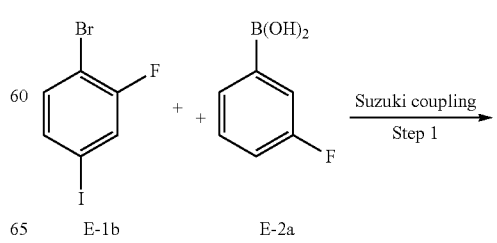

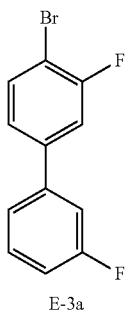

E-3a

Suzuki Coupling Starting Material:

Given the improved reactivity of aryl halides in the order Cl<Br<I (with aryl iodides reacting with Pd the most effectively), the Suzuki coupling to generate E-3a was subsequently improved to use starting material E-1b (X=I) instead. This provided a significantly improved yield for the reaction.

Generation of Impurities:

The two most common impurities for the Suzuki coupling were 3,3'-difluorobiphenyl IMP-1 and triphenyl IMP-2 resulting from the Suzuki coupling on both iodine and bromine in the starting material (FIG. 7). Interestingly, 3,3'-difluorobiphenyl IMP-1 could be generated from either homocoupling of E-2a or protodebromination of E-3a. Whereas some literature suggests that oxidation of Pd(O) to Pd(II) by dissolved oxygen is the reason behind homocoupling, no change in reaction profile was observed when the reaction was degassed and kept under an inert atmosphere compared with when it was run under ambient conditions. In the presence of excess catalyst and absence of halide coupling partner it was demonstrated that E-2a will produce IMP-1 in small amounts. However, it was also found that at elevated temperatures, and extensive reaction times, E-3a will also convert to IMP-1 independently. Without being bound to any theory, this reason supports that the formation of IMP-1 may not be attributed to one or the other mechanism, and it is believed that both are contributors to this process impurity.

Also formed in the Suzuki coupling was the dibromide IMP-3 (FIG. 7). The possibility of contamination of 3-fluorophenylboronic acid E-2a with 4-bromo-3-fluorobenzeneboronic acid was investigated, but no bromide was detected in the lots tested. Instead, without being bound to any theory, it was reasoned that IMP-3 formed through a homocoupling of E-1a in a copper-free Ullmann reaction. Without being bound to any theory, the presence of IMP-4 is attributed, in part, IMP-3 reacting in the metallation/boronation step (FIG. 7). Additional discussion of IMP-4 is provided in Example 3.

Figure 3:
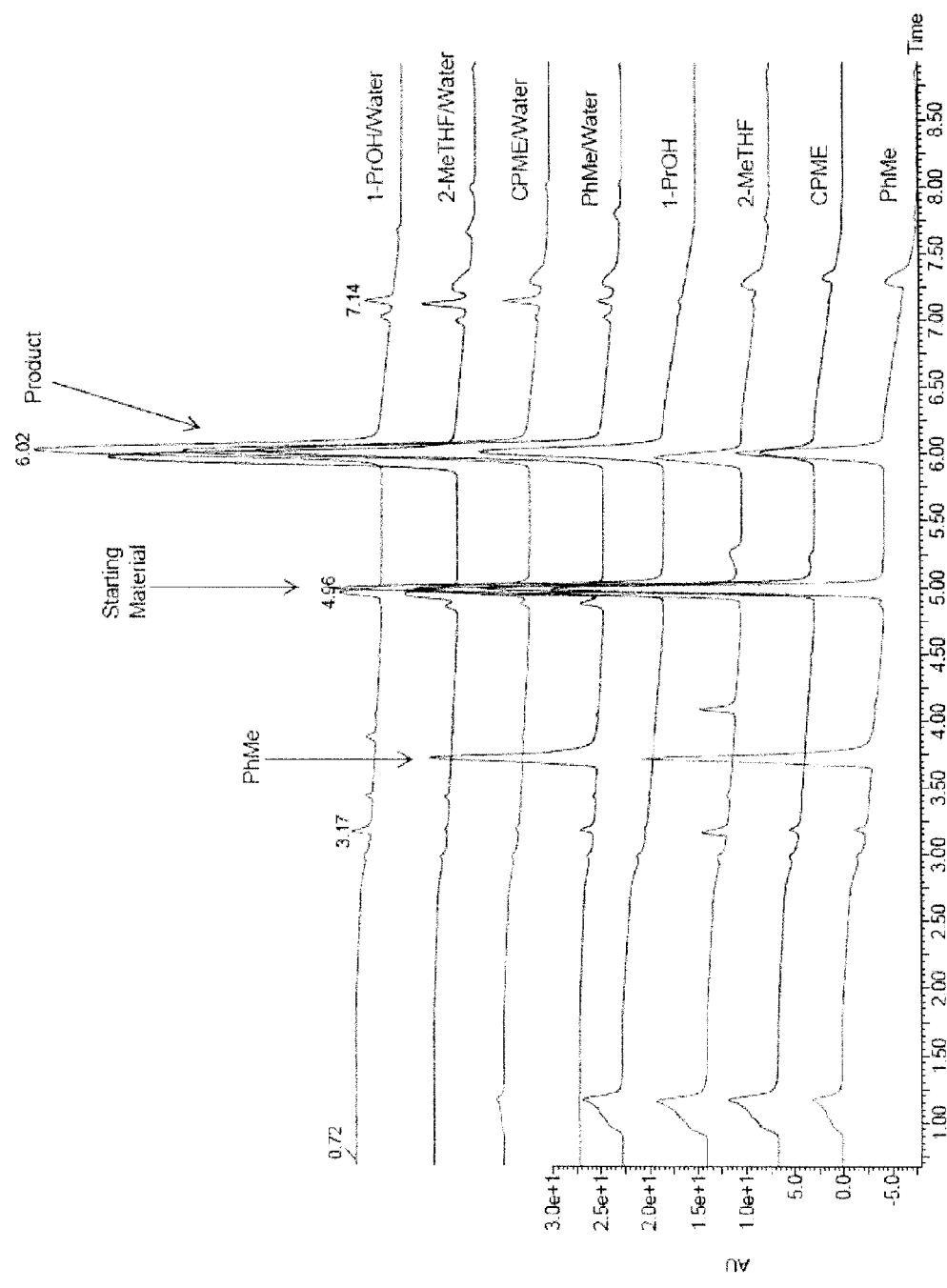
FIG. 3 shows a multiple chromatogram overlay of the Suzuki cross-coupling reaction in eight different solvents. The peak at 5 minutes is the starting material. The peak at 6 minutes is the product.

Suzuki Coupling Solvent Screens:

The Suzuki coupling to make biphenyl E-3a was optimized in stages. Solvents were first screened among a limited number of process-friendly solvents for the reaction using $PdCl_2(PPh_3)_2$ as the catalyst and $NaHCO_3$ as the base. A sample overlay chromatogram of eight of the solvent mixtures is presented in FIG. 3. From this sample overlay, it was surprisingly found that 1-PrOH produced significantly fewer impurities than the other solvents (e.g., 1-PrOH:water in approximately an 8:3 ratio).

Figure 4:
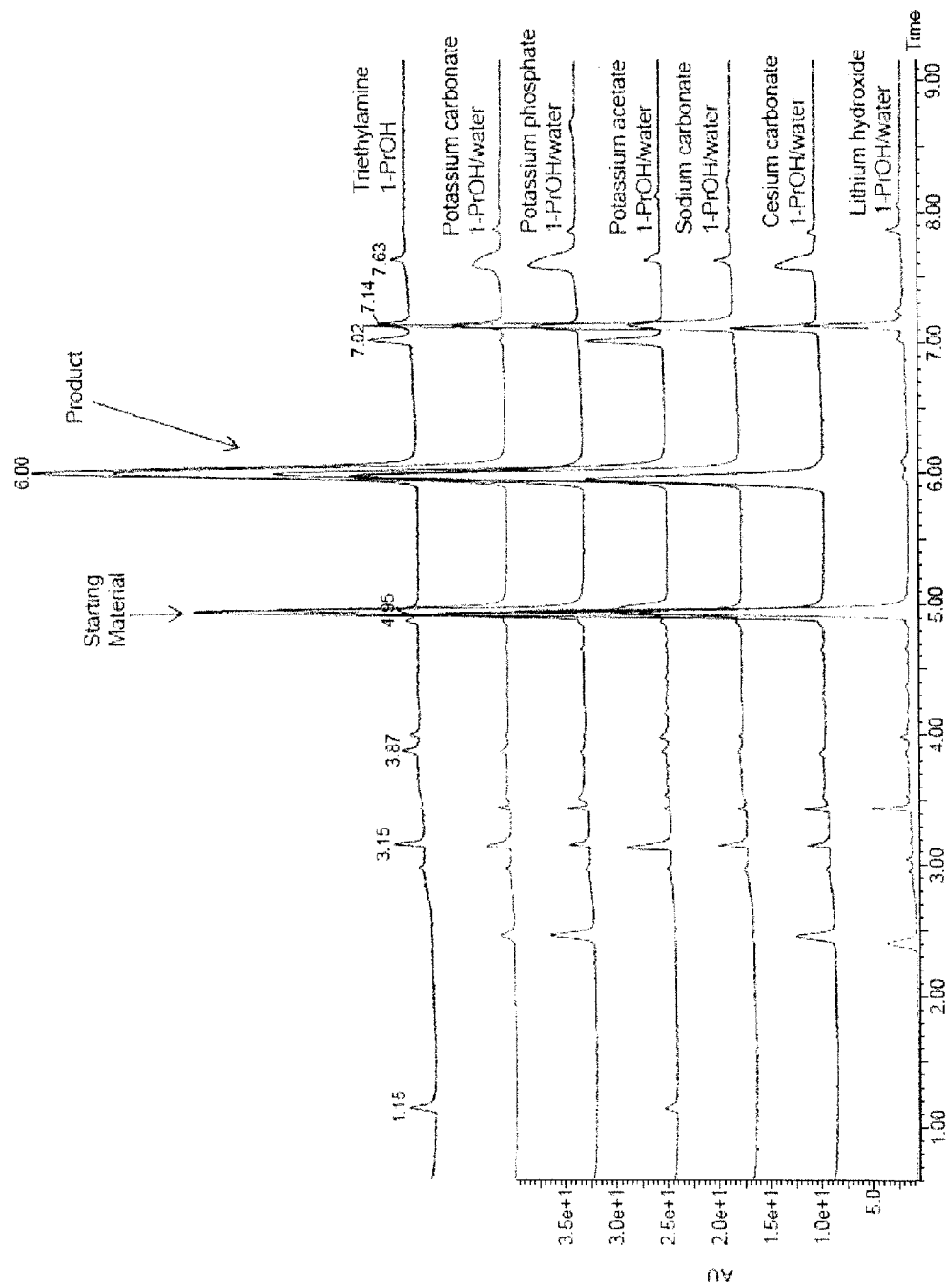
FIG. 4 shows a multiple chromatogram overlay of the initial base screen for the Suzuki cross-coupling. For all experiments, three equivalents of base were added relative to the limiting trihalide starting material.
Figure 5:
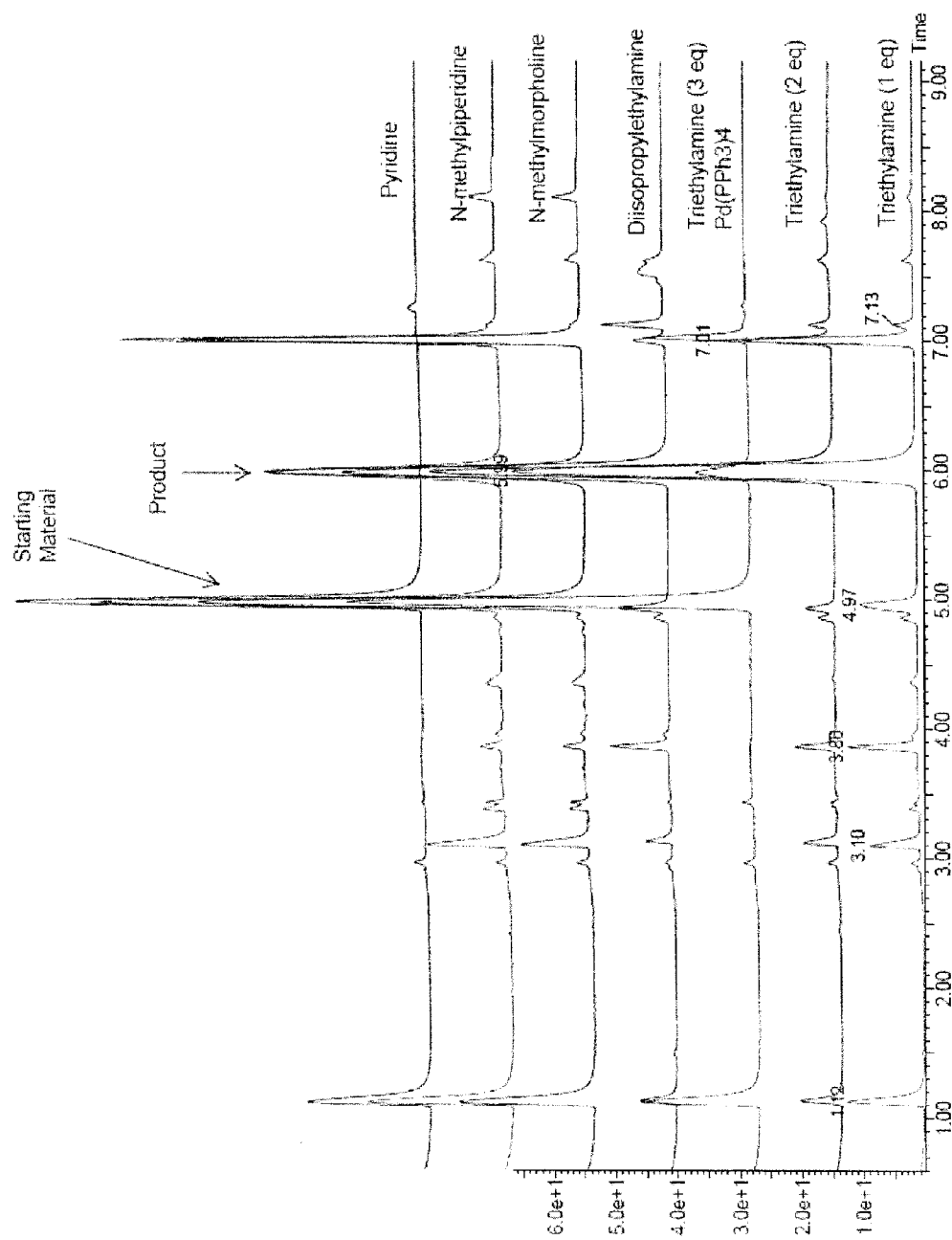
FIG. 5 shows a multiple chromatogram overlay of the organic base screen for the Suzuki cross-coupling. All reactions were performed using 1-PrOH as the only solvent. The catalyst, unless otherwise noted, was $PdCl_2(PPh_3)_2$. Unless otherwise noted, 3 equivalents of base were used in each experiment.

Suzuki Coupling Base Screens: Organic and inorganic bases (FIGS. 4 and 5) were then screened using 1-PrOH or a mixture of 1-PrOH and water as the solvent and $PdCl_2$ $(PPh_3)_2$ as the catalyst. From this base screen, $NaHCO_3$ was chosen for further development based on its superior conversion.

Figure 6:
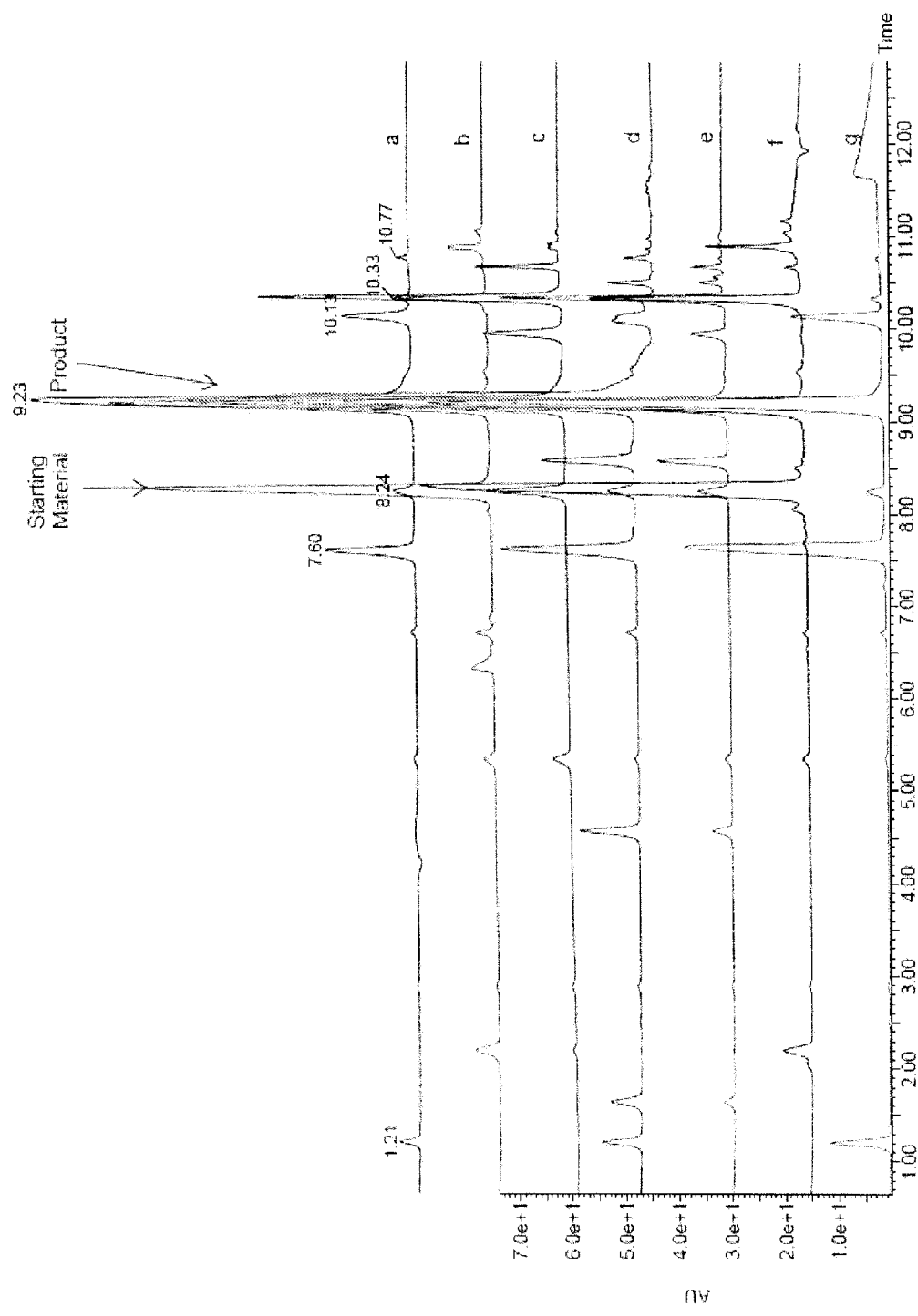
FIG. 6 shows the multiple chromatogram overlay of the catalyst screen for the Suzuki cross-coupling. (a) $Pd(PPh_3)_4/K_2CO_3$; (b) $Pd(OAc)_2/PPh_3$; (c) $Pd(OAc)_2$; (d) $Pd_2(dba)_3/PPh_3$; (e) $Pd_2(dba)_3$; (f) $Pd(dppf)_2Cl_2$; (g) $Pd(PPh_3)_4$. (dba=dibenzylideneacetone; dppf=(diphenylphosphoryl)ferrocene). All reactions, except for (a), used $NaHCO_3$ as the base. The solvent for all reactions was 1-PrOH/water. 3 Mol % of Pd was used for all reactions except (b) and (d).

Suzuki Coupling Catalyst Screens:

A number of palladium catalysts were screened at loadings of 3 mol % relative to substrate. FIG. 6 shows the multiple chromatogram overlay of an exemplary catalyst screen for the Suzuki cross-coupling: (a) $Pd(PPh_3)_4/K_2CO_3$; (b) $Pd(OAc)_2/PPh_3$; (c) $Pd(OAc)_2$; (d) $Pd_2(dba)_3/PPh_3$; (e) $Pd_2(dba)_3$; (f) $Pd(dppf)_2Cl_2$; (g) $Pd(PPh_3)_4$. (dba=dibenzylideneacetone; dppf-=(diphenylphosphoryl)ferrocene). All reactions, except for (a), used $NaHCO_3$ as the base. The solvent for all reactions was 1-PrOH/water. 3 mol % of Pd was used for all reactions except (b) and (d).

Suzuki Coupling Temperature Screens:

The effect of temperature and $PdCl_2(PPh_3)_2$ catalyst loading were studied by varying both reaction temperature and $PdCl_2(PPh_3)_2$ catalyst loading (e.g., about 50 to about 85° C. and about 0.5 to about 5.0 mol %, respectively), and monitoring conversion after 14 hrs, reaction purity as determined by HPLC, percent yield of E-3a (e.g., using weight/weight assay) and by-product formation (e.g., formation of IMP-1). From these experiments, a catalyst load from about 0.3 to about 0.5 mol % of $PdCl_2(PPh_3)_2$ and a reflux temperature of about 83±5° C. was employed and demonstrated to work on 100 g to 2 kg scaled reactions.

Suzuki Coupling Reaction Workup:

The work-up procedure was optimized in order to remove the 1-PrOH and trace palladium from the reaction mixture. It was found that n-heptane worked well as the extraction solvent for this reaction. Workup involved an initial quench with aqueous 1 M NaOH followed by extraction of the product E3a into the organic (n-heptane) phase. The aqueous quench helped dissolve inorganic solids and produced a clean phase separation with a slight rag layer emulsion at the interphase. After elimination of that first aqueous phase and its rag layer emulsion, the organic phase was again washed with aqueous 1 M NaOH. In order to mitigate emulsions observed during the final water rinse of an initial scale-up, the final (third) wash was performed with 2% (w/w) aqueous NaCl. A reduction in the volume of the organic phase indicated that the washes were very efficient at removing l—PrOH from the organic phase as determined by GC. Subsequent concentration of the n-heptane layer allowed for nearly complete removal of 1-PrOH (typically <200 ppm of 1-PrOH remains after distillation). Pd levels of the concentrated n-heptane layer were found to be >2000 ppm. Silica gel slurry in n-heptane followed by filtration provided the product E-3a with Pd levels of less than 16 ppm. In order to further facilitate the manufacturing of intermediate E-3a and generate a process that was more seamlessly integrated into the synthesis of Compound 1 as a whole, the following two improvements were made in the synthesis: 1) the silica gel treatment to remove trace Pd was optimized to be performed as an in-line filtration operation (previously, this was performed as a fed-batch operation); and 2) the yield of E-3a was determined using a weight/weight assay to better estimate the charge of the reagents for the subsequent step.

In order to clean the reactor of starting materials, products, and palladium impurities, a combination of rinses were used. The reactor was sequentially rinsed with dichloromethane, acetone, water, and dilute nitric acid/hydrochloric acid solutions. The latter allowed for complete removal of the palladium that adhered onto the reactor walls and eliminated the need for hand washing of the systems. Final polish rinses and commissioning as usual were then used to remove trace acids and water from the reactor.

Step 2: Metallation/Boronation

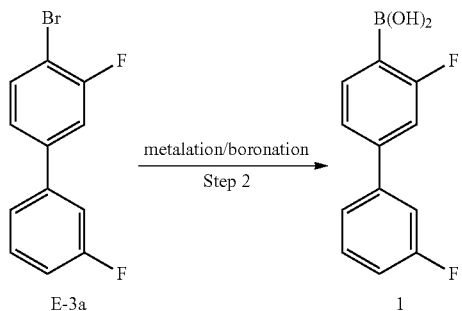 [SMILES: Fc1cccc(-c2ccc(Br)c(F)c2)c1 ; OB(O)c1ccc(-c2cccc(F)c2)cc1F]

New Metallation/Boronation Step:

In scaling up the synthesis of Compound 1, the two-step palladium-mediated formation of the pinacolboronate intermediate E-4a followed by oxidative hydrolysis (as depicted in Scheme 3) became less efficient than on a small scale. As well, a second Pd-mediated synthesis in the final step of the synthesis involves additional steps to scavenge the Pd from the drug product. A one pot lithium-halogen exchange followed by boronation and hydrolysis from E-3a was considered (e.g., see W. Li et al., *J. Org. Chem.* 2002, 67:5394-5397). Additional studies further improved the stoichiometry of the reagents in the reaction, the reaction solvent, the reaction temperature, and the workup conditions to the procedure described below.

Metallation/Boronation Solvent Conditions:

Initial conditions called for the use of toluene and THF as the reaction solvents, followed by MTBE as the workup solvent. This solvent combination required extensive concentration in addition to a solvent exchange and thus alternative solvent systems were considered in order to streamline the process to better flow from step one to the isolation of Compound 1.

Since bromide E-3a would ideally be telescoped from the first step as a solution in n-heptane, experiments were performed to demonstrate that it would be a suitable solvent for use with MTBE and THF as the workup and reaction co-solvent, respectively. In order to further simplify the reaction workup transition, water-miscible THF was replaced with water immiscible 2-MeTHF as the reaction co-solvent with n-heptane, thus eliminating the need for MTBE in the workup. A solubility plot indicated that a solubility of >100 mg/mL of Compound 1 could be obtained in at least a 2:1 ratio of a mixture of 2-MeTHF:n-heptane. This afforded a relatively wide solubility range for both the reaction and the workup while still keeping the solvent volumes at reasonable levels for the telescoped steps.

Stoichiometry of the Lithiating Agent and Boronating Agent B(OiPr)$_3$:

Several experiments were designed to test whether a local excess of alkyllithium would play an important role in this reaction. Of course, low amounts (undercharge) of triisopropyl borate (B(OiPr)$_3$) and n-butyllithium led to incomplete conversion. A reverse addition approach was also employed wherein the starting material and borate were added to the n-butyllithium solution at −45° C. When compared to a control reaction (slow n-butyllithium addition), the reverse addition approach resulted in excess unreacted starting material (7% a/a of E-3a (control) versus 45% a/a of E-3a, respectively). Addition of more n-butyllithium led to increased formation of IMP-1 and a lower overall yield. A Design of Experiment (DoE) approach model suggested that approximately 1.0 equivalent or less of alkyllithium would be optimal for this reaction. It was further reasoned that an excess of borate added to the reaction would effectively "protect" the formed product Compound 1 from adverse reactions in situ with the alkyllithium.

It was found that careful addition of the correct amount of alkyllithium based on the titration of the solution and assay of the starting material allowed for more controlled use of the reagent. An initial undercharge of the alkyllithium followed by In-Process Control (IPC) by HPLC (with microworkup using 1 M HCl) allowed for an estimation of the amount of starting material remaining relative to the product, as well as a calculation of the necessary n-butyllithium needed to get complete conversion without any adverse reaction.

Metallation/Boronation Temperature Screen:

While the lithiation/boronation reaction was initially run at −78° C., in order to facilitate scale-up, the temperature was increased to −40° C. No difference was observed when the reactions were run at these two temperatures. Additional experiments run at higher temperatures (e.g., −20° C., −10° C. and 0° C.) afforded more late-eluting impurities as observed by HPLC.

Choice of Alkyllithium Reagent:

Initial work used n-butyllithium as the reagent for this reaction. It was thought that the pyrophoric nature of n-butyllithium would not make it a desired reagent for scale-up beyond the 2 kg mark (scale-up that would require fixed equipment). Instead, hexyllithium was suggested as a more suitable reagent for scale-up for safety reasons, as it exhibits two safety advantages over n-butyllithium: (1) when formulated in hexanes it is non-pyrophoric, even at concentrations up to 85%; and (2) the byproduct of the reaction (in this case, 1-bromohexane) has a significantly higher boiling point than its butyl counterpart. Both lab scale and kilo scale experiments confirmed that hexyllithium was a good substitute for this reaction, and in many ways surpassed n-butyllithium for ease of use.

Water Tolerability of the Lithiation:

Although the amount of water in the reaction mixture prior to addition of the alkyllithium reagent had been reliably low (<500 ppm; all reagents except for hexyllithium/n-butyllithium), it was of interest to determine the "breaking point" of this reaction and the consequence of excess water in the reaction mixture. An experiment was designed to artificially contaminate the reaction mixture with up to ~1 eq. of water, monitor the water content (ppm), and monitor the effect on the reaction progress using hexyllithium as the base. It was found that greater than 1000 ppm of water (approx. 0.15 eq.), impaired the purity of the reaction. The most significant impurity identified from this reaction was IMP-1 formed from lithiation and protonation of intermediate E-3a.

Rate of Addition of Alkyllithium:

In addition to the alkyllithium amount and water content of the reaction mixture, it was also found that slower addition rates allowed for the use of less alkyllithium. Typical addition time, regardless of scale, was set to be no less than about 1 hour, with proper mixing and heat exchange being important parameters.

Isolation and Purification of Compound 1:

As described in Scheme 3, initial discovery efforts provided a reaction mixture containing Compound 1 which, after workup, were triturated with hexanes to provide a white solid. Chromatographic purification was attempted but failed due to Compound 1 precipitating on the column, presumably due to poor solubility in the eluant and high affinity to silica gel.

A number of solvent combinations were tried (2-propanol/water, acetonitrile/water, ethanol/water, acetone/water, hexanes, cyclohexane, toluene, ethyl acetate/hexanes, etc.) for the crystallization of Compound 1. It was found that all alcoholic solvents formed the corresponding boronate esters in varying amounts. In later attempts, Compound 1 was recrystallized from acetone/water, and then washed with n-heptane, to eliminate the non-polar impurities (e.g., IMP-1, IMP-2 and IMP-3) and to provide crystalline Compound 1. Certain lots of crystalline Compound 1 contained minor amounts of IMP-4; for example, compare Ex. A and Ex. B below (LOQ=0.13% a/a; LOD=0.05% a/a), as determined by HPLC (Table 1). Without being bound to any theory, the poor solubility of IMP-4 in acetone (resulting in the removal of the impurity during the clarification step) and better control of the crystallization are contributing factors to the low levels of the impurity observed in manufacturing lots.

TABLE 1

| IMP-4 (% aa) before cryst. | IMP-4 (% a/a) after cryst. |
|---|---|
| 0.35 (Ex. A) | 0.18 (Ex. B) |

In order to take advantage of the poor solubility of Compound 1 and the high solubility of the reaction impurities in n-heptane, a direct isolation was designed via solvent exchange from the reaction solution. For example, after workup of the lithiation/boronation step, the organic solution was concentrated to small bulk (2.5 vol total), and n-heptane was added to the suspension that was produced. Distillation was repeated to ensure complete solvent exchange (i.e., to minimize the amount of 2-MeTHF in the solution). The material was finally slurried in n-heptane and filtered. This distillation was performed using the rotovap (20 L). However, in order to accommodate larger scale-up (particularly in fixed equipment), a more direct isolation would be beneficial.

In an effort to eliminate the rotovap and establish a better understanding of Compound 1, atmospheric distillation and solvent exchange were attempted. It was found that the elevated temperature and more efficient azeotrope formed in the absence of reduced pressure and quantitatively dehydrated Compound 1 to an anhydride (e.g., structure assigned to Compound 2) (Scheme 5).

Scheme 5.

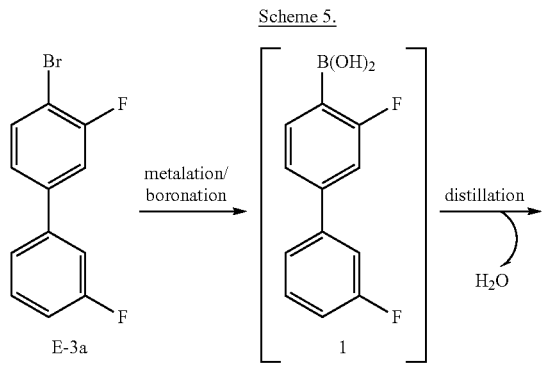

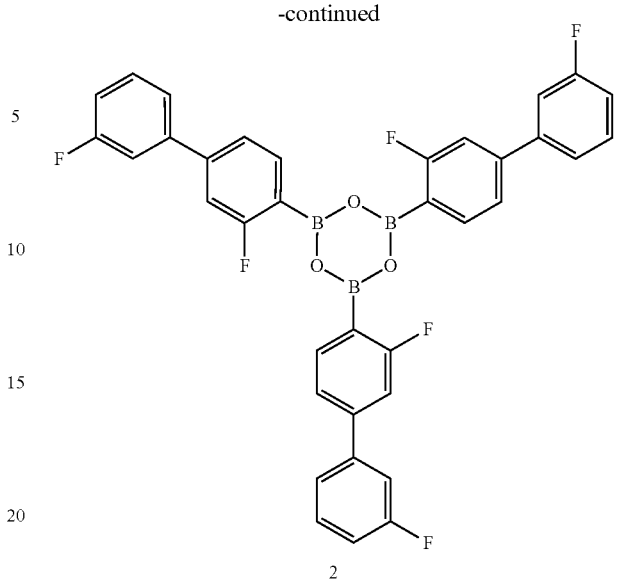

Formation of the anhydride allowed for straight-forward distillation of volatile reaction components directly from the reaction vessel (typically, a reactor). No degradation of Compound 1 or the anhydride thereof was observed during this atmospheric distillation, which can reach pot temperatures of approximately 100° C. The polar impurity IMP-4 is completely removed from Compound 1 using this procedure as determined by HPLC, see, e.g., for example, Ex. C and D below (LOQ=0.13% a/a; LOD=0.05% a/a) (Table 2).

Conversion of the anhydride (e.g., structure assigned to Compound 2) back to Compound 1 required addition of an aqueous solvent to enable hydrolysis of the oligomer. Acetone in combination with water gave the best results. It was surprisingly found that crystallization from acetone/water generated only the monomer form of Compound 1 as confirmed by evaporative Karl-Fischer titration A careful addition of water and heating/cooling profile produced a solid that had high purity (most impurities were rejected), gave consistent particle size, and would filter easily for the final isolation. Drying was performed in a vacuum oven set to 40±5° C. to avoid reformation of the anhydride.

TABLE 2

| | IMP-4 (% a/a) before cryst. | IMP-4 (% a/a) after cryst. | |
|---|---|---|---|
| Ex. C | 0.94 | < limits of detection | New process isolating |
| Ex. D | 0.31 | < limits of detection | Compound 2 as an intermediate |

Figure 9:
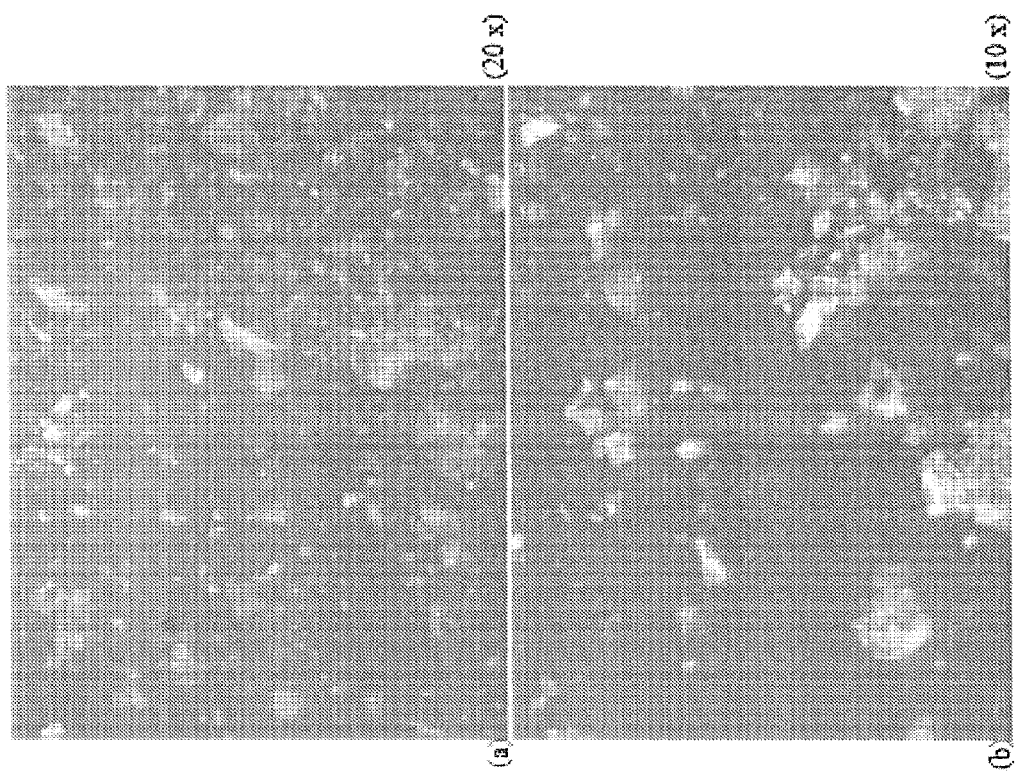
FIG. 9 shows a comparison of Compound 1 isolated from 1) n-heptane (a; 20× magnification); and 2) acetone/water (b; 10× magnification) with a pause after nucleation to allow for crystal growth.

Depending on the purification protocol used for Compound 1, different particle sizes will be observed. It is, however, noted that regardless of the procedure (e.g., organic or aqueous crystallization), the same crystal form (Form A, evidenced by identical XRPD patterns) has been isolated. A visual comparison of crystal shape and size by polarized light microscopy is provided in FIG. 9. Overall, the crystals isolated from a more controlled growth in acetone/water are much larger than those from an uncontrolled growth.

An overall scheme summarizing the improved processing and synthesis of Compound 1 is presented in Scheme 6.

Scheme 6.

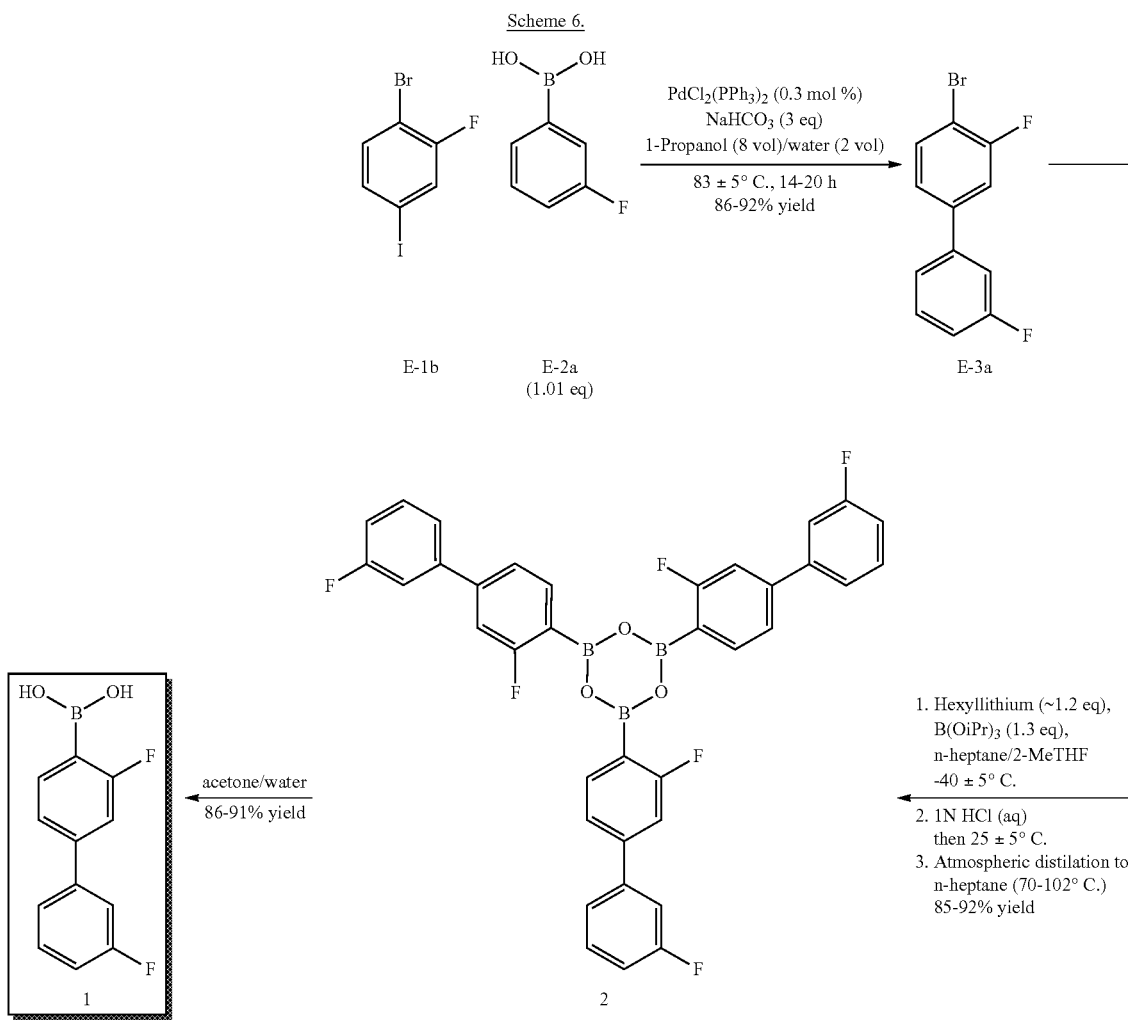

Experimental Section

HPLC Method Used:

Column Information: YMC-Pack Ph, 50×2.0 mm, PHI2S05-0502WT; Solvent A: Water with 0.1% (v/v) formic acid; Solvent B: Acetonitrile with 0.1% (v/v) formic acid; Flow rate: 1.5 mL/min; Column Temperature: 50° C.; Wavelength: 220 nm; Gradient: 95% A for 1 min., then 95 to 50% A over 8 min., 50 to 20% A over 1 min., hold for 1 min., and return to 95% A over 0.5 min. Stop time: 14 min. Relative purity (% a/a) was determined by reverse phase high-pressure liquid chromatography with UV detection (254 nm) using a C18-4.6×30 mm, 1.8 µm column with gradient elution (Solvent A: 0.1 formic acid (FA) in HPLC grade water Solvent B: 0.1 FA in HPLC grade acetonitrile (CAN)). Test samples are dissolved in 100% demethylsulfoxide (DMSO) to an approximate concentration of 0.4 mg/mL. The Limit of Quantitation (LOQ) for this method is currently ≤0.13% a/a.

The experimental details below provide exemplary procedures to obtain Compound 1. The scale provided is merely exemplary, and these procedures have been successfully adapted to be performed on a kilogram scale to provide kilogram quantities of Compound 1.

Preparation of 4-bromo-3,3'-difluorobiphenyl E-3a

To an appropriately sized reactor was charged 1-bromo-2-fluoro-4-iodobenzene (600.55 g, 1.996 mol, 1.0 eq.), 3-fluorophenylboronic acid (282.60 g, 2.020 mol, 1.01 eq.), sodium bicarbonate (503.91 g, 5.998 mol, 3.0 eq.), trans-dichlorobis(triphenylphosphine)palladium(II) (4.1947 g, 5.98 mmol, 0.003 eq.), n-propanol (4.8 L, 8 vol. relative to trihalide amount), and water (2 vol. relative to trihalide amount). The mixture was stirred at a speed adequate to produce an evenly dispersed suspension. The reaction solution was evacuated and degassed, backfilling with nitrogen or argon. The reaction mixture was heated to a target of 83±5° C. Once the target temperature was reached, the temperature was maintained for 14-20 hours. Reaction completion was determined using HPLC (trihalide RT: 5.9 min; product RT: 7.6 min), with <1% remaining starting material being the target for completion. Upon complete reaction, the mixture was cooled to 25±5° C. The mixture was then quenched with 1 M NaOH (aq) (6 L, 10 vol) and stirred to mix phases thoroughly. n-Heptane was added (6 L, 10 vol) and stirred to mix phases thoroughly. Stirring was stopped and the phases were allowed to separate. The aqueous phase was drained and discarded. The organic phase (top) was washed with 1 M NaOH (aq) (6 L, 10 vol)

and 2% (w/w) NaCl (aq) (6 L, 0 vol) successively, discarding the aqueous phase. The organic phase was concentrated in the reaction vessel using reduced pressure to approximately 2 volumes; the vessel did not exceed 45° C. for the pot temperature; the typical vacuum for the distillation was 70-110 torr. n-Heptane (3 L, 5 vol) was added to the mixture and stirred to cool to 25±5° C. The solution was filtered through a column packed with silica gel (8.5 cm tall×5.5 cm diameter pad of silica gel made using 72 g; loading: 120 g of silica gel per kg of trihalide added). The reaction flask was rinsed with n-heptane (0.6 L, 1 vol) and the solution was filtered through the silica gel column. The rinse was repeated once. The solution of crude E-3a in n-heptane was transferred to the distillation flask. The solution was distilled to a total of approximately 2 (~1.2 L) volumes relative to the trihalide amount. The pot temperature did not exceed 45° C. The typical vacuum for the distillation was 70-110 torr. The concentration of the solution was determined using weight/weight assay. For preparation of a reference marker (high purity E-3a), the crude solution after workup and filtration was purified using vacuum distillation and the product was boiled at approx. 180° C., with 21 mmHg. This reaction may be performed on a kilogram scale. For example, this reaction has been successfully performed to obtain approximately 20 kg of product.

Characterization:
$^1$H NMR (400 MHz, acetone-d6) δ 7.71 (t, J=8.4 Hz, 1H), 7.58 (dd, J=1.8, 10.2 Hz, 1H), 7.52-7.44 (m, 4H), 7.17 (m, 1H) ppm. $^{13}$C NMR (100 MHz, acetone-d6) δ 165.4, 162.9, 161.4, 159.0, 142.0 (ddd), 134.9, 131.8 (d), 125.1 (d), 123.7 (d), 115.9 (dd), 114.5 (d), 108.8 (d) ppm. mp (by DSC) 35-38° C. Anal. Calcd. for $C_{12}H_7BrF_2$: C, 53.56; H, 2.62. Found: C, 53.62; H, 2.63.

Preparation of 2,4,6-tris(3,3'-difluorobiphenyl-4-yl)-1,3,5,2,4,6-trioxatriborinane (2)

An inert reactor was charged with solution of E-3a (1.5 L/1.32307 kg of a 37.0 wt % solution, 1.819 mol; 1.0 eq.) in n-heptane. Triisopropyl borate (0.55 L, 2.369 mol, 1.3 eq. relative to E-3a from w/w assay) and 2-MeTHF (3 L) were then added to the reactor. The mixture was stirred at speed adequate to produce a homogeneous solution. The solution was then evacuated and degassed, backfilling with nitrogen or argon. The reaction mixture was cooled to about −45±5° C. A solution of hexyllithium (33 wt % solution in hexanes) was titrated just prior to reaction and added to the reaction (0.820 L of a 2.44 M solution in hexane; 1.1 eq. relative to IPI-487552 from w/w assay) at a rate such that (a) TRXN<−35° C. and (b) total addition time >1 hour, but preferably no more than 3 hours. After the addition was complete, the reaction was stirred for 5 minutes while maintaining cooling. The reaction mixture was sampled to determine conversion. A reaction aliquot (1-2 mL) was taken from the reaction mixture and quenched with 1 M HCl (aq) (2 mL). The phases were mixed and then allowed to settle. From the (top) organic phase, 10 μL was diluted with 1 mL MeCN. The sample was analyzed by HPLC. Only the starting material and products peaks were integrated to determine conversion. The reaction was complete when the starting material peak was <1% relative to the product peak. If the reaction was found to be incomplete, the amount of additional hexyllithium necessary to push conversion to completion was determined using direct approximation from the HPLC data: The % a/a of the starting material was nearly identical to the relative stoichiometry in the reaction mixture. Additional hexyllithium (40 mL of a 2.44 M solution in hexane; 0.05 eq.) was added to the reaction at a rate (mL/min) similar to the rate of addition used for the bulk solution. After the addition was complete, the reaction was stirred for 5 minutes and analyzed to confirm the reaction was complete. The mixture was then quenched by adding 1 M HCl (aq) (3 L). During the quench, the temperature of the reaction was maintained at <0° C. The biphasic reaction mixture was then warmed to 25±5° C. and stirring was terminated. The layers were allowed to separate and the aqueous phase was then discarded. The organic phase was washed with water (3 L) and kept in the reactor to start distillation under nitrogen (atmospheric pressure) in order to concentrate mixture. About 3 L of distillate were collected. n-Heptane (3 L) was added and the distillation was continued until approximately 3 L of distillate were collected. This step was repeated once more, after which one last portion n-heptane (3 L) was added and the distillation was stopped. The resulting suspension was cooled to RT as a slurry and the solids were filtered, wash with n-heptane (1.5 L in three portions), and dried in a vacuum oven at 40±5° C. and 25-30 in Hg until constant weight. The resulting dry solids were taken on to the crystallization step.

Characterization:
$^1$H NMR (400 MHz, acetone-d6) δ 8.28 (t, J=7.2 Hz, 1H), 7.87 (t, J=7.2 Hz, 1H), 7.69 (d, J=7.6 Hz, 1H), 7.64 (d, J=7.6 Hz, 1H), 7.60-7.45 (m, 7H), 7.42 (d, J=1.2, 10.8 Hz, 1H), 7.28 (bs, 1H), 7.20 (m, 2H) ppm. mp (by DSC) 238-241° C. Anal. Calcd. for $C_{36}H_{21}B_3F_6O_3$: C, 66.73; H, 3.27. Found: C, 65.88; H, 3.32. A careful data analysis indicates that Compound 2 is being partially hydrolyzed in the process of performing the analysis (NMR, elemental), to provide a mixture of the linear timer and Compound 2 (the cyclic trimer), giving varying results. Anal. Calcd. for $C_{36}H_{23}B_3F_6O_4$ (linear trimer of Compound 2): C, 64.92; H, 3.48. Found: C, 65.88; H, 3.32. Evaporative Karl-Fischer titration: 0.8% water.

Without being bound to any theory, the found elemental analysis for both Compound 2 suggests that Compound 2 may be provided as a 1:1 mixture of linear and cyclic trimers, i.e., for carbon: Calcl: (66.73+64.82)/2=65.82 Found: 65.88, and for hydrogen: Calcd: (3.27+3.48)/2=3.375. Found: 3.32.

Compound 2 XRPD Parameters:
INEL XRG-3000; X-ray tube: 1.54187000 Å; voltage: 40 (kV); amperage: 30 (mA); acquisition time: 300 sec; Spinning Capillary. Step size: approx. 0.03° 2Θ. Referred to herein as "Form I." The XRPD pattern of Compound 2, Form I, is notably different from that of Compound 1 (compare FIG. 8 to FIG. 1).

Figure 8:
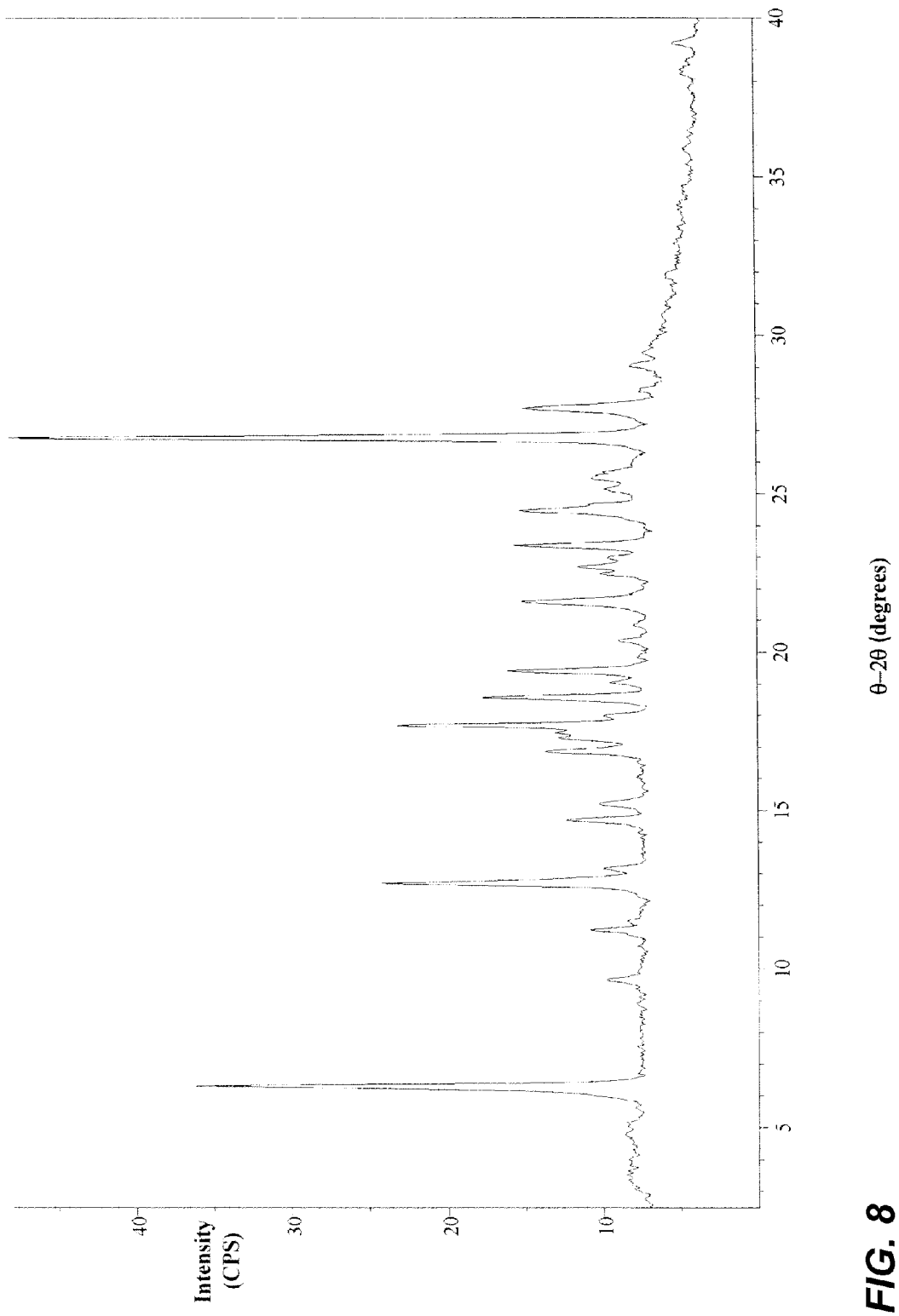
FIG. 8 depicts an XRPD pattern of a representative lot of Form I of the Compound 1 anhydride (e.g., Form I of Compound 2).

| Observed peaks for XRPD of Compound 2, FIG. 8 | | |
|---|---|---|
| | Intensity (%) | θ-2θ (degrees) |
| 1 | 75 | 6.32 ± 0.10 |
| 2 | 20 | 9.64 ± 0.10 |
| 3 | 22 | 11.20 ± 0.10 |
| 4 | 17 | 11.51 ± 0.10 |
| 5 | 50 | 12.69 ± 0.10 |
| 6 | 20 | 13.14 ± 0.10 |
| 7 | 25 | 14.67 ± 0.10 |
| 8 | 21 | 15.19 ± 0.10 |
| 9 | 28 | 16.85 ± 0.10 |
| 10 | 26 | 17.27 ± 0.10 |
| 11 | 27 | 17.44 ± 0.10 |
| 12 | 49 | 17.69 ± 0.10 |
| 13 | 20 | 17.96 ± 0.10 |
| 14 | 37 | 18.55 ± 0.10 |

Observed peaks for XRPD of Compound 2, FIG. 8

| Intensity (%) | θ-2θ (degrees) |
|---|---|
| 15 | 20 | 19.04 ± 0.10 |
| 16 | 33 | 19.42 ± 0.10 |
| 17 | 18 | 20.36 ± 0.10 |
| 18 | 16 | 20.84 ± 0.10 |
| 19 | 31 | 21.57 ± 0.10 |
| 20 | 21 | 22.47 ± 0.10 |
| 21 | 24 | 22.68 ± 0.10 |
| 22 | 19 | 22.99 ± 0.10 |
| 23 | 33 | 23.37 ± 0.10 |
| 24 | 31 | 24.45 ± 0.10 |
| 25 | 22 | 24.66 ± 0.10 |
| 26 | 20 | 25.14 ± 0.10 |
| 27 | 22 | 25.49 ± 0.10 |
| 28 | 100 | 26.77 ± 0.10 |
| 29 | 31 | 27.71 ± 0.10 |
| 30 | 15 | 28.26 ± 0.10 |
| 31 | 17 | 29.03 ± 0.10 |

Preparation of 3,3'-difluorobiphenyl-4-ylboronic acid (Compound 1) from Compound 2

Compound 2 (333.73 g, 515 mmol, 1 eq.) was charged into a suitable reactor/flask equipped with an overhead stirrer, thermocouple, reflux condenser, and heating mantle. Acetone (2.34 L, 7 vol) was then added and stirring was initiated to produce a suspension. The reactor was evacuated and the reactor inerted. The solution/suspension was degassed, stirred, and heated to a target of 50±5° C. Water (30 mL, 1.665 mol, 3.2 eq. relative to Compound 2) was then added to produce a clear solution. The temperature was maintained for 20-60 min. The solution was then clarified through a 1.0 µm PTFE filter into the crystallization reactor and heated to reflux (55-60° C.). Water was charged (3 L, 9 vol.) in portions and heating was increased to maintain temperature (i.e., to resume reflux (65-70° C.)). Acetone was then added (0.33 L, 1 vol.) followed by continued heating to resume reflux (65-70° C.), then an additional portion of water (0.33 L, 1 vol.) to produce a clear solution. Reflux was maintained for 15-30 minutes and then terminated to allow the mixture to slowly cool (i.e., for at least 8 hours) to 25±5° C. At 62° C., the mixture began to nucleate (haze). The mixture was filtered to collect the crystalline solid, and the filter cake was washed with 6:4 water:acetone (0.33 L, 1 vol.) three times. The resulting material were then dried to constant weight in a vacuum oven equilibrated at 40±5° C. and 25-30 in. Hg with a nitrogen bleed. This procedure may be adapted to a kilogram scale.

Preparation of 3,3'-difluorobiphenyl-4-ylboronic acid (Compound 1) from Preparation of 4-bromo-3,3'-difluorobiphenyl E-3a An inert reactor was charged with solution of E-3a (4.610 kg of a 33.7 wt % solution in n-heptane; 5 L; 5.77 mol, 1.0 eq.) in n-heptane. Triisopropyl borate (1.412 kg, 7.51 mol, 1.3 eq. relative to E-3a from w/w assay) and 2-MeTHF (5.3 weights) were then added to the reactor. The mixture was stirred at speed adequate to produce a homogeneous solution. The solution was then evacuated and degassed, back-filling with nitrogen or argon. The reaction mixture was cooled to about −45±5° C. A solution of n-butyllithium (2.5 M solution in hexanes) was titrated just prior to reaction and added to the reaction (1.735 kg of a 24.7 wt % solution in hexanes, 6.69 mol, 1.16 eq.) at a rate such that (a) TRXN<−35° C. and (b) total addition time>1 hour, but preferably no more than 3 hours. After the addition was complete, the reaction was stirred for 5 minutes while maintaining cooling. The reaction mixture was sampled to determine conversion. A reaction aliquot (1-2 mL) was taken from the reaction mixture and quenched with 1 M HCl (aq) (2 mL). The phases were mixed and then allowed to settle. From the (top) organic phase, 10 µL was diluted with 1 mL MeCN. The sample was analyzed by HPLC. Only the starting material and products peaks were integrated to determine conversion. The reaction was determined to be complete as the starting material peak was <1% relative to the product peak. The mixture was then quenched by adding 1 M HCl (aq) (10 L). During the quench, the temperature of the reaction was maintained at <0° C. The biphasic reaction mixture was then warmed to 25±5° C. and stirring was terminated. The layers were allowed to separate and the aqueous phase was then discarded. The organic phase was washed with water (6.3 weights), then concentrated under vacuum (on the rotovap or in a suitable reactor) at reduced pressure (<100 torr) and at a temperature less than about 45° C. to a total volume of approximately 5 L. n-Heptane (10 L) was added and the distillation was continued until approximately 10 L of distillate were collected. This step was repeated once more, after which one last portion n-heptane (10 L) was added and the distillation was stopped. The resulting suspension was cooled to RT and the slurry and the solids were filtered, washed with n-heptane (5 L), and dried in a vacuum oven at 40±5° C. and 25-30 in. Hg until constant weight.

Characterization:

$^1$H NMR (400 MHz, acetone-d6) δ 7.85 (dd, J=6.9, 7.5 Hz, 1H), 7.56 (m, 1H), 7.54 (m, 2H), 7.50 (m, 1H), 7.41 (dd, J=1.7, 11.1 Hz, 1H), 7.25 (d, J=2.1 Hz, 2H—B(OH)$_2$), 7.18 (dddd, J=1.5, 2.6, 7.8, 8.8 Hz, 1H) ppm. $^{13}$C NMR (100 MHz, acetone-d6) δ 167.5 (d), 163.3 (d), 143.8 (dd), 141.8 (dd), 136.9 (d), 130.8 (d), 122.9 (d), 122.3 (d), 119.7 (br), 114.8 (d), 113.6 (d), 113.2 (d) ppm. Anal. Calcd. for C$_{12}$H$_9$BF$_2$O$_2$: C, 61.59; H, 3.88. Found: C, 61.60; H, 3.73. Karl Fischer water (evaporative Karl Fischer): 7.88% (Theoretical: 7.7%). Metal content of final isolated product is typically <1 ppm Pd.

$^1$H and $^{13}$C Chemical Shifts and Assignment for Compound 1:

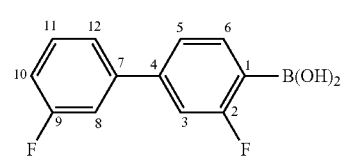

Compound 1

TABLE 3

| | $^{13}$C NMR (acetone-d6) | | $^1$H NMR (acetone-d6) | |
|---|---|---|---|---|
| Label | Chemical Shift (ppm) | $^{13}$C—$^{19}$F Mult.$^a$, Splitting$^b$ (Hz) | Chemical Shift (ppm) | Mult.$^a$, Splitting$^b$ (Hz) |
| 1 | 119.7 | br | — | — |
| 2 | 167.5 | d (244.7) | — | — |
| 3 | 113.2 | d (26.5) | 7.41 | dd (11.1, 1.7) |
| 4 | 143.8 | dd (8.9, 1.8) | — | — |

TABLE 3-continued

| | $^{13}$C NMR (acetone-d6) | | $^1$H NMR (acetone-d6) | |
|---|---|---|---|---|
| Label | Chemical Shift (ppm) | $^{13}$C—$^{19}$F Mult.[a], Splitting[b] (Hz) | Chemical Shift (ppm) | Mult.[a], Splitting[b] (Hz) |
| 5 | 122.3 | d (2.4) | 7.54 | m |
| 6 | 136.9 | d (9.3) | 7.85 | dd (6.9, 7.5) |
| 7 | 141.8 | dd (7.7, 1.8) | — | — |
| 8 | 113.6 | d (22.6) | 7.50 | m |
| 9 | 163.3 | d (244.7) | — | — |
| 10 | 114.8 | d (21.4) | 7.18 | dddd (1.5, 2.6, 7.8, 8.8) |
| 11 | 130.8 | d (8.6) | 7.54 | m |
| 12 | 122.9 | d (2.4) | 7.56 | m |
| OH | — | — | 7.25 | d (2.1) |

[a]Multiplicity: d = doublet; t = triplet; m = multiplet; br = broad
[b]$^1$H multiplicity were obtained from HSQC spectrum for H-11, H-12, H-5, and H-8 due to overlap in the $^1$H spectrum.

Elemental Analysis:

Compound 1 was analyzed for C, H, and F content (Table 4). The percent carbon, hydrogen, and fluorine found corresponded to the proposed structure for Compound 1 (i.e., $C_{12}H_9BF_2O_2$). Elemental analysis was performed using standard combustion analysis (for carbon and hydrogen). The amount of fluorine was calculated by a nitric acid digestion followed by ion chromatography analysis.

TABLE 4

| | Found (%) | | |
|---|---|---|---|
| Element | Theoretical Compound 1 monomer | Actual Compound 1 monomer | Theoretical Compound 2 |
| carbon | 61.59 | 61.69 | 66.73 |
| hydrogen | 3.88 | 3.76 | 3.27 |
| fluorine | 16.24 | 16.00 | 17.59 |

Compound 1 XRPD Parameters:

INEL XRG-3000; X-ray tube: 1.54187000 Å; voltage: 40 (kV); amperage: 30 (mA); acquisition time: 300 sec; Spinning Capillary. Step size: approx. 0.03° 2Θ. Referred to herein as "Form A." The XRPD pattern of Compound 1, Form A, has been reproduced for all crystalline lots, regardless of isolation (from heptane/2-MeTHF or acetone/water) and particle size (see FIG. 1).

| Observed peaks for XRPD of Compound 1, Form A, FIG. 1 | | |
|---|---|---|
| | Intensity (%) | θ-2θ (degrees) |
| 1 | 13 | 4.83 ± 0.10 |
| 2 | 19 | 9.68 ± 0.10 |
| 3 | 15 | 16.12 ± 0.10 |
| 4 | 16 | 16.92 ± 0.10 |
| 5 | 100 | 17.26 ± 0.10 |
| 6 | 13 | 17.75 ± 0.10 |
| 7 | 17 | 18.58 ± 0.10 |
| 8 | 10 | 18.89 ± 0.10 |
| 9 | 10 | 19.34 ± 0.10 |
| 10 | 10 | 19.69 ± 0.10 |
| 11 | 10 | 21.01 ± 0.10 |
| 12 | 92 | 21.60 ± 0.10 |
| 13 | 11 | 22.46 ± 0.10 |
| 14 | 10 | 23.67 ± 0.10 |
| 15 | 14 | 24.33 ± 0.10 |
| 16 | 48 | 24.68 ± 0.10 |
| 17 | 17 | 25.16 ± 0.10 |
| 18 | 38 | 25.48 ± 0.10 |
| 19 | 12 | 25.96 ± 0.10 |
| 20 | 10 | 26.48 ± 0.10 |
| 21 | 94 | 27.73 ± 0.10 |
| 22 | 27 | 29.08 ± 0.10 |
| 23 | 17 | 29.43 ± 0.10 |
| 24 | 13 | 29.84 ± 0.10 |

Example 2. Exemplary Pharmaceutical Compositions of Compound 1

(i) Oral Suspensions

Compound 1 ("drug product") is supplied as a powder for oral suspension in USP Type III amber glass bottles. In the clinical setting, a protocol-specified portion of powder is weighed into an appropriate container and suspended with freshly prepared vehicle. The drug product is a single-use vial containing 1.00+/−0.05 g of the active ingredient, which may be used to prepare doses for multiple patients on the same day. The remaining unused portion of the drug product vial is then discarded. The container closure for the drug product consists of 1-oz. USP Type III glass bottles with TEFLON®-lined polypropylene caps.

The drug product is a crystalline solid that is sparingly soluble in water. The drug product does not contain excipients. In the clinic, protocol-specified portions of drug product are suspended in a vehicle consisting of commercially available medium viscosity USP carboxymethylcellulose sodium (CMC) in Sterile Water for Injection (SWFI). CMC is a chemically stable compound that is commonly used in oral pharmaceutical formulations and appears on the FDA list of substances that are Generally Recognized As Safe (GRAS). A recent compatibility study showed that the stability of the drug product suspended in CMC is at least 48 hours, which exceeds the clinical dosing window (12 hours).

The drug product formulation was chosen for its ability to wet the powder and form a suspension with CMC in SWFI, allowing for consistent oral dosing. No overages are used in the manufacture of the drug product. During the drug product manufacturing process, the drug product is milled prior to filling to generate particles of consistent size. The drug product undergoes microbial limits testing as part of release testing.

Manufacturing of the drug product was performed in accordance with current Good Manufacturing Practices (cGMP). The manufacturing process involved milling of drug product, passing the milled drug product through a 500 μm screen, followed by weighing 1.00±0.05 g into 1-oz. USP Type III amber glass jars and capping. Upon labeling and packaging, the drug product was stored at −20° C.±5° C. at the manufacturer and the clinical site. Material was shipped in an appropriate container on dry ice.

(ii) Capsules

The drug product (Compound 1) has been formulated into a capsule as a direct blend powder fill, using excipients that consist of the different components such as a filler, disintegrant and glidant/lubricant, e.g.:

Compound 1: about 25 to about 45% w/w
Filler: AVICEL® (Microcrystalline Cellulose) (about 49 to about 75% w/w)
Disintegrant: AcDiSol (Croscarmellose Sodium) (0% to about 6% w/w)

Glidant: PRUV® (Sodium stearyl fumarate) (0% to about 2% w/w)

Other excipients envisioned being used include, but are not limited to, fillers such as lactose, mannitol, starch, sorbitol, sucrose, dicalcium phosphate; disintegrants such as copovidone, and sodium starch glycolate; glidants such as colloidal silicon dioxide, silicon dioxide, magnesium silicate, talc; lubricants such as magnesium stearate and stearic acid; and surfactants such as sodium lauryl sulphate, sodium dodecyl sulphate, TWEEN® 80, LUTROL®. The choice of the excipients is based on an excipient compatibility study done under accelerated conditions. The choice and the percentage of the filler was based on the flowability of the blend. The choice and the percentage of the superdisintegrant was based on release profile of the capsule in 0.1 N hydrochloric acid with 0.8% (lower strength capsules)/1.5% (higher strength capsules) TWEEN® 80 media. The particular ratios of API to filler/disintegrant/lubricant have been chosen to enhance the powder flowability, blending process and capsule filling process.

The current particle size D (0.5) is targeted at about 40 to about 80 microns.

Direct blend formulations have been prepared in dosage strengths of between about 25 mg to about 200 mg of Compound 1 per unit dosage form.

|  | mg per capsule | mg per capsule | Percentage per capsule |
|---|---|---|---|
| Compound 1 | 100.0 | 25 | 27.0 |
| AVICEL ® pH 200 (Microcrystalline Cellulose NF., Ph. Eur., JP) | 246.0 | 61.5 | 66.5 |
| AcDiSol SD-711 (Croscarmellose Sodium NF., Ph. Eur., JP) | 22.2 | 5.6 | 6.0 |
| PRUV ®(Sodium Stearyl | 1.9 | 0.5 | 0.5 |
| Fumarate Ph. Eur., NF, JPE) |  |  |  |
| Total | 370.0 | 92.5 | 100.0 |
| HPMC Capsule Size | 0EL | 4 | na |

|  | mg per capsule | Percentage per capsule |
|---|---|---|
| Compound 1 | 200.0 | 42.6 |
| AVICEL ® pH 112 (Microcrystalline Cellulose NF., Ph. Eur., JP) | 23.5 | 5.0 |
| AVICEL ® pH 200 (Microcrystalline Cellulose NF., Ph. Eur., JP) | 208.9 | 44.4 |
| AcDiSol SD-711 (Croscarmellose Sodium NF., Ph. Eur., JP) | 28.2 | 6.0 |
| PRUV ® (Sodium Stearyl Fumarate | 9.4 | 2.0 |
| Ph. Eur., NF, JPE) |  |  |
| Total | 470.0 | 100.0 |
| HPMC capsule Size | 00 | na |

(iii) Tablets

The drug product can be translated over to a tablet form, either through direct compression of the direct blend formulation or via a dry granulation or wet granulation process. Other excipients can be added, such as binders, and/or surfactants, and coating films to aid in tablet integrity, taste masking and aesthetics.

Example 3. Identification and Biological Activity of IMP-4

Lots containing high levels of impurities were analyzed using LCMS with ESI-mode, and a parent peak of m/z 277.1 [M-H]$^-$ was identified for this material.

The impurity was isolated using preparative liquid chromatography. After confirming that the isolated impurity matched the retention time of the target impurity, the isolated solids were analyzed by Liquid Chromatography-Mass Spectrometry (LC-MS) and Nuclear Magnetic Resonance (NMR).

The ion mass of the isolated impurity matched the ion mass impurity present in the Compound 1 DS lots by LC-MS using Electrospray Ionization in negative mode (ESI-MS). The impurity had a parent/base peak at m/z 277 and an apparent dimer peak at m/z 536.

By NMR (400 MHz in acetone-$d_6$), only three resonances were observed in the proton spectrum. All three integrated equally and were in the aromatic region. Of the three resonances, one was a singlet, indicating an isolated proton (no coupling). Based on the NMR data, the early retention time of the impurity, and the mass spectrometry data of the isolated impurity, a symmetrical diboronic acid derivative of Compound 1 was proposed as a structure for this impurity.

Synthesis of the proposed impurity is provided below in Scheme 7. Suzuki coupling with E1b and E2a produced the symmetrical 4,4'-dibromo-3,3'-difluorobiphenyl, IMP-3, followed by double lithiation and boronation to produce the desired diboronic acid IMP-4. The largest impurity in this second boronation reaction was Compound 1, which is formed as a result of rapid addition of hexyllithium to the starting material.

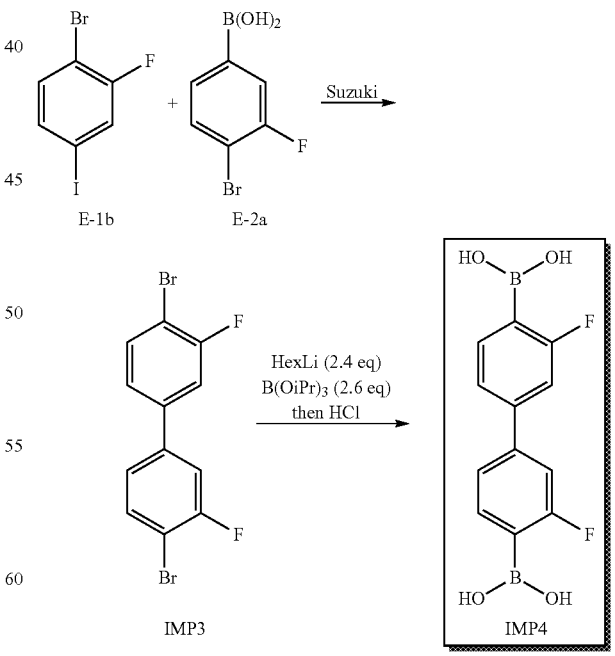

Scheme 7.

Figure 10:
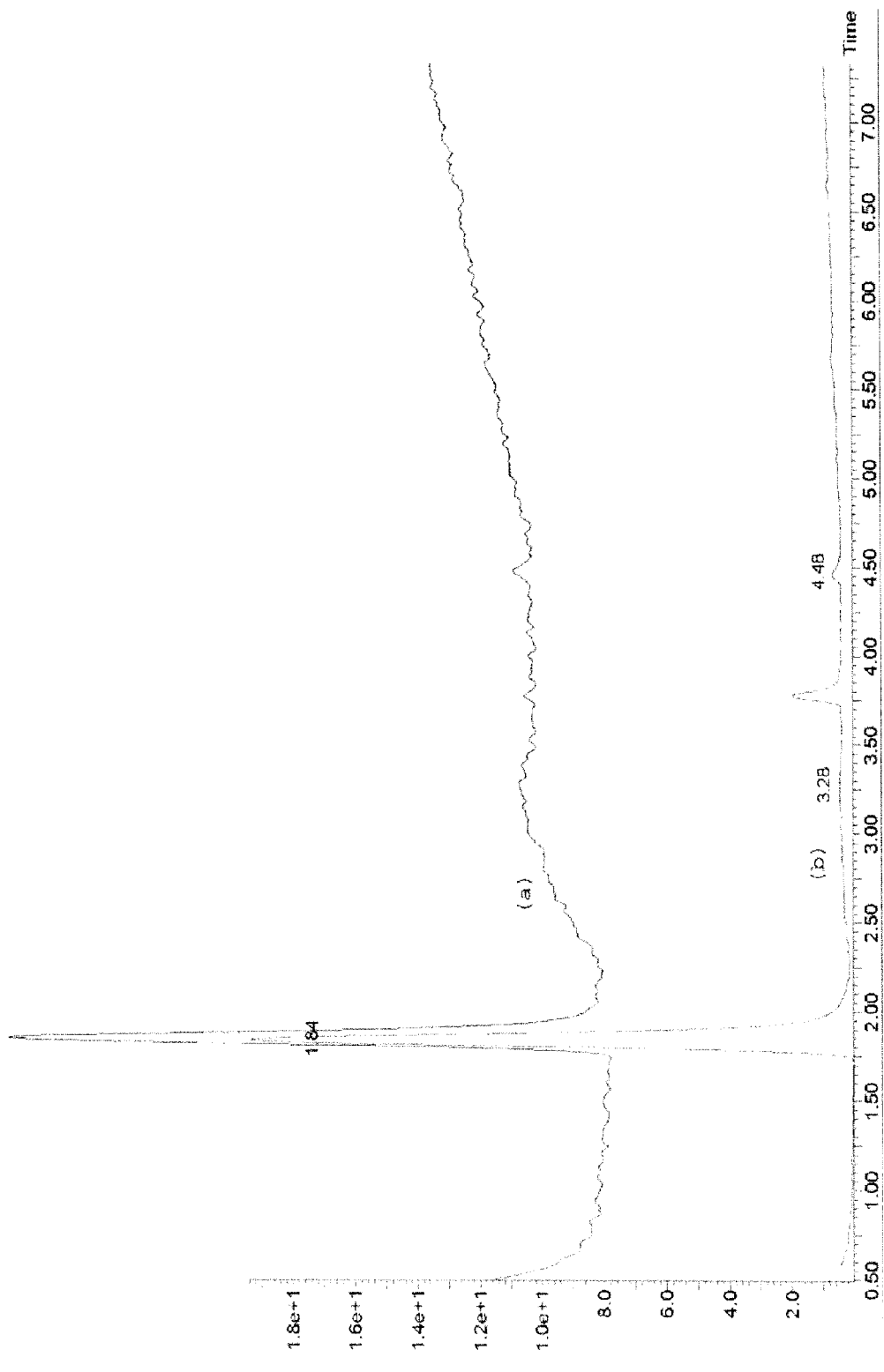
FIG. 10 shows a comparison of HPLC retention times for (a) the synthesized impurity versus (b) the isolated impurity IMP-4.
Figure 11:
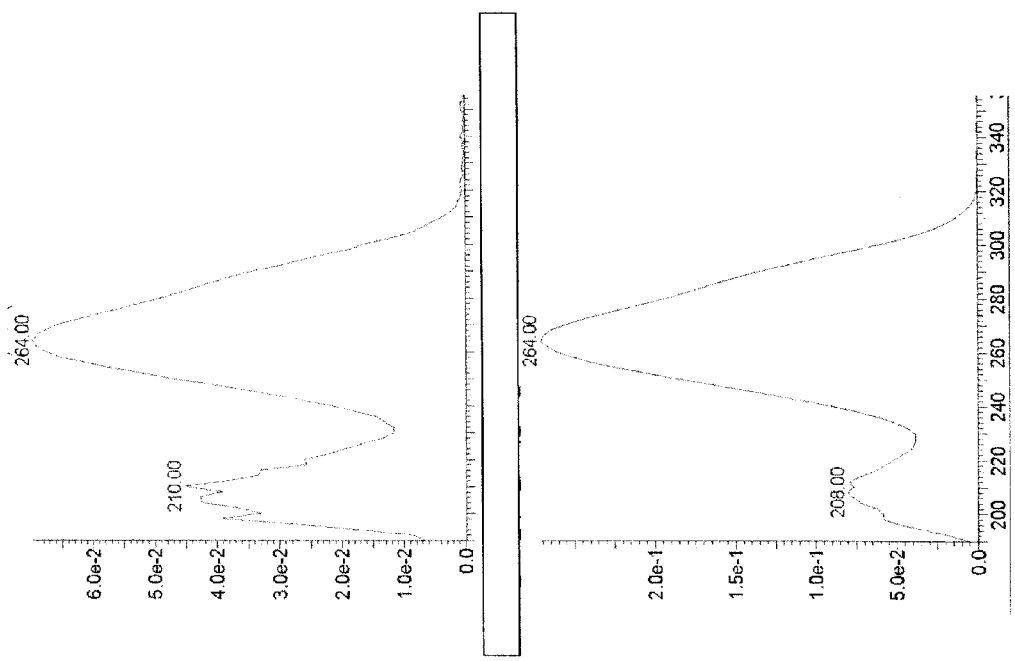
FIG. 11 shows a comparison of the UV spectra of the isolated (bottom) and synthetic (top) IMP-4.
Figure 12:
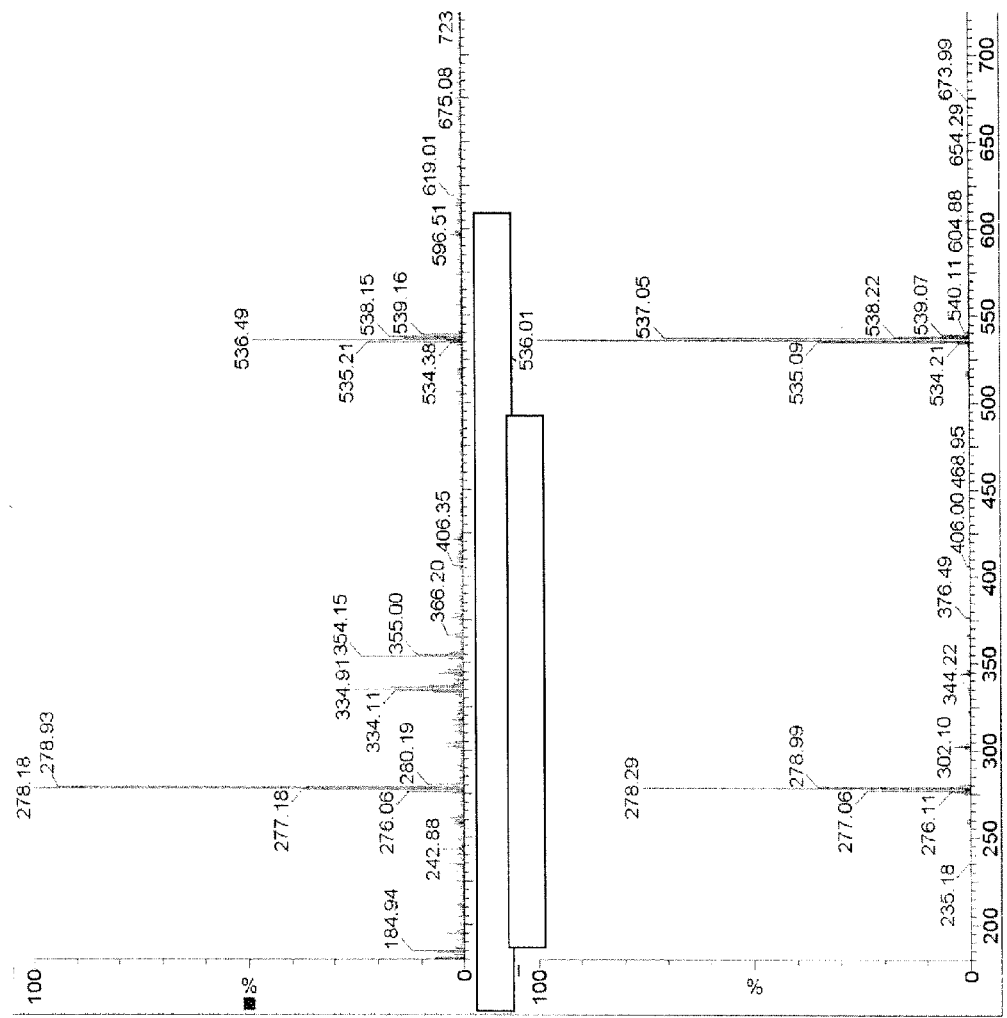
FIG. 12 shows a comparison of mass spectra of the isolated (bottom) and synthetic (top) IMP-4.
Figure 13:
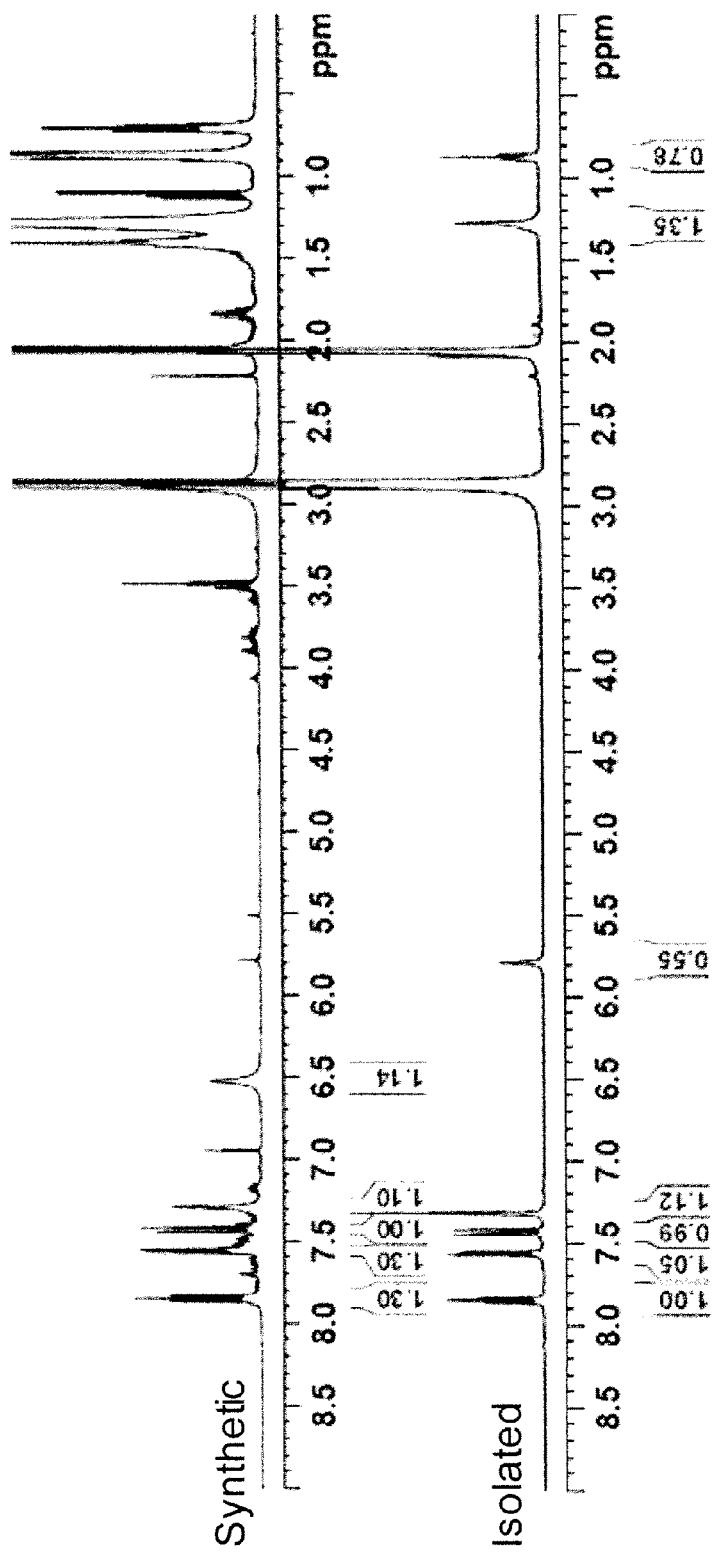
FIG. 13 shows a comparison of full NMR spectra of the isolated (bottom) and synthetic (top) IMP-4 (400 MHz in acetone-$d_6$).
Figure 14:
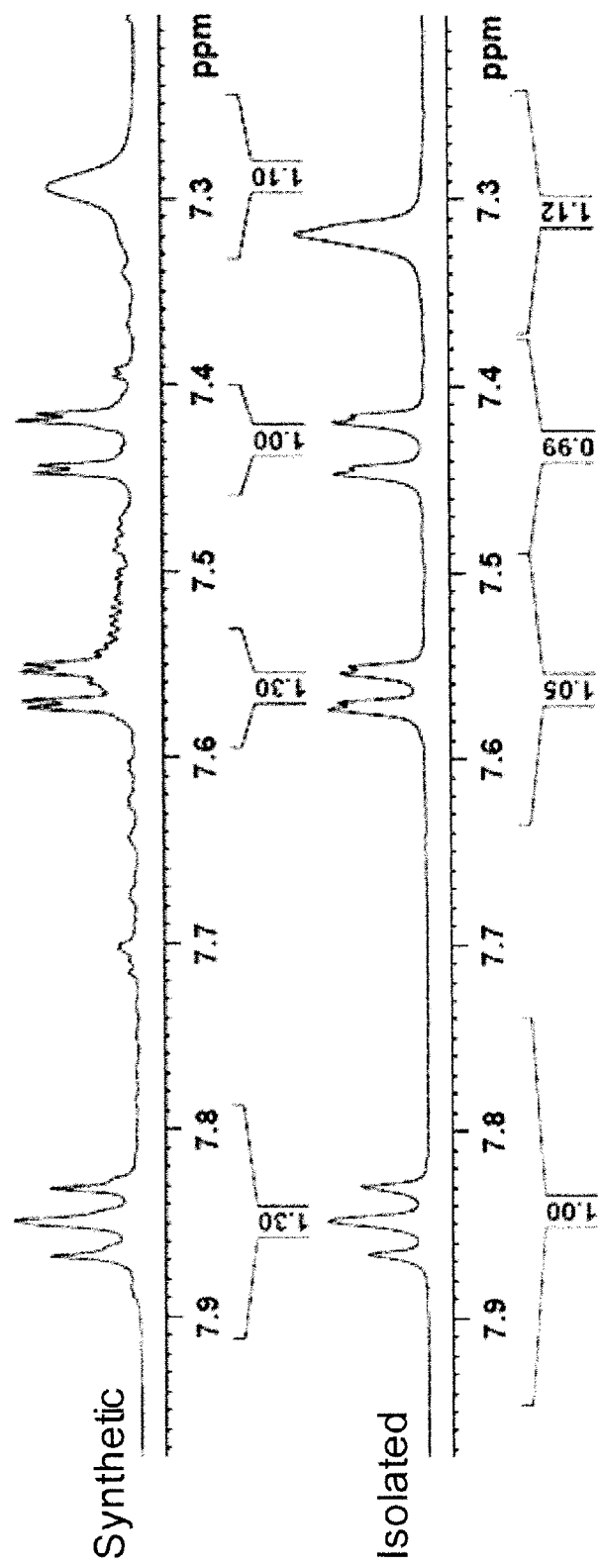
FIG. 14 shows a comparison of the aromatic region of NMR spectra of the isolated (bottom) and synthetic (top) IMP-4 (400 MHz in acetone-$d_6$).
Figure 15:
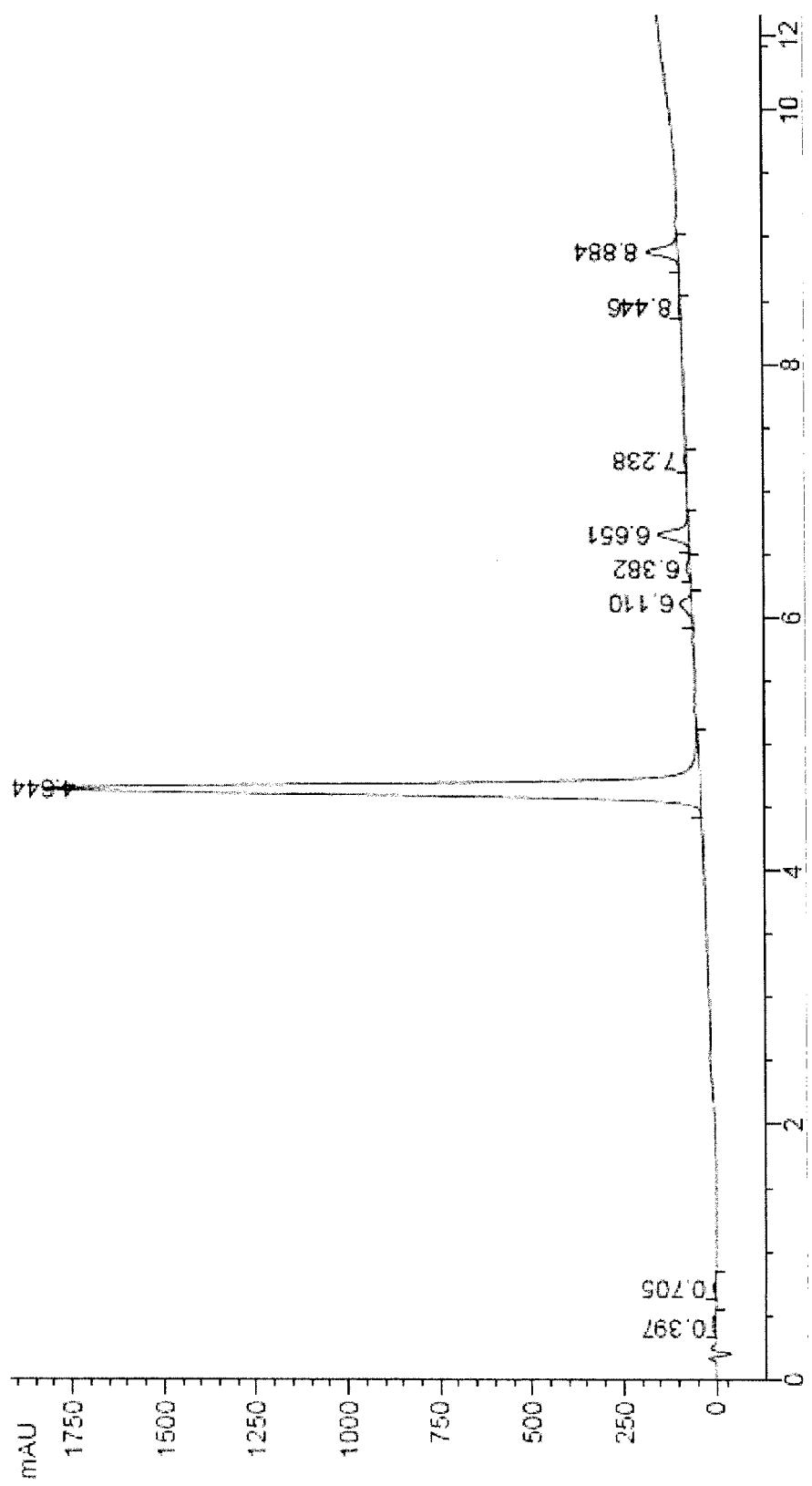
FIG. 15 shows a typical reaction IPC for the conversion of E-3a to Compound 1 (complete reaction).
Figure 16:
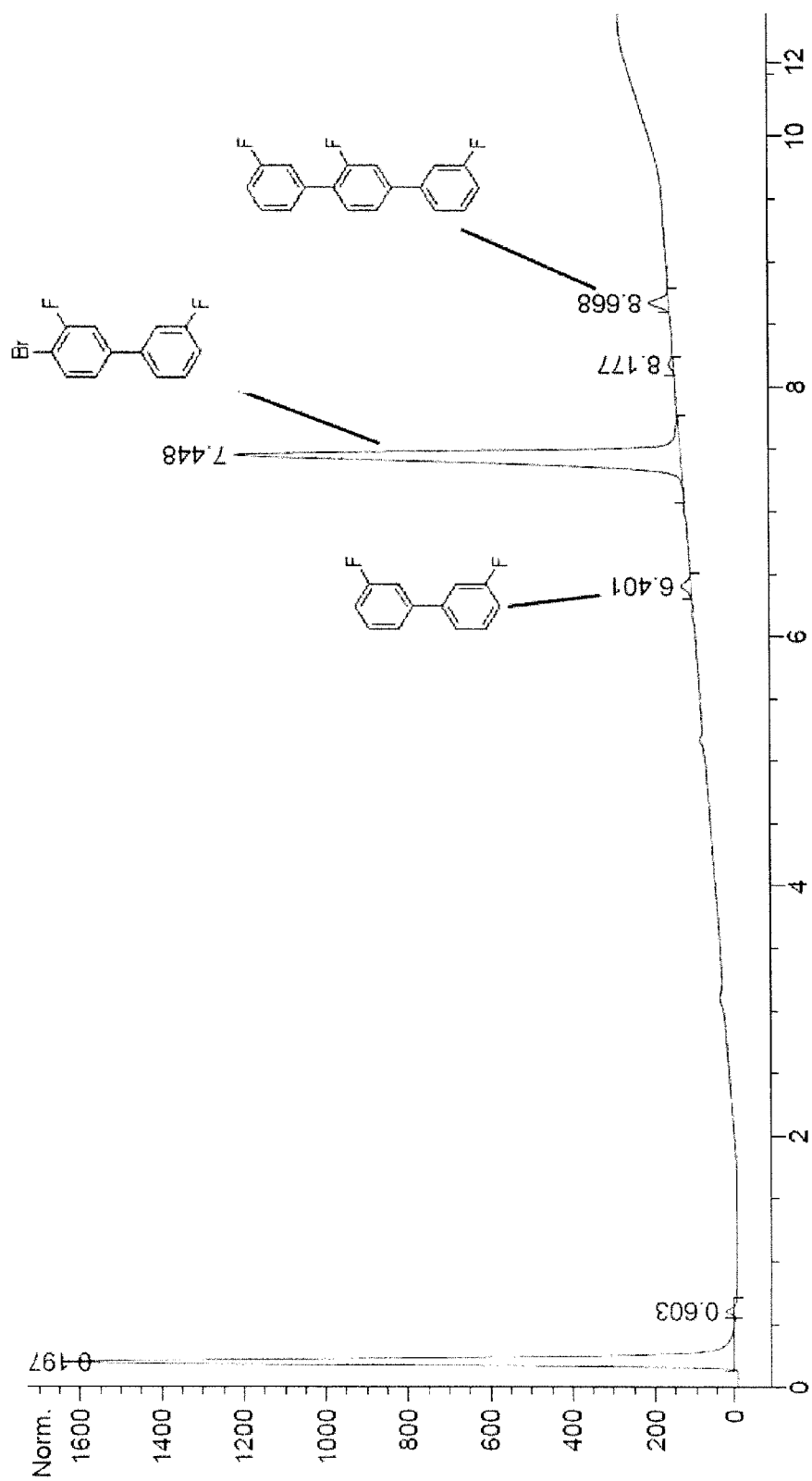
FIG. 16 shows a typical reaction IPC (14 hours) for the formation of E-3a (complete reaction).
Figure 17:
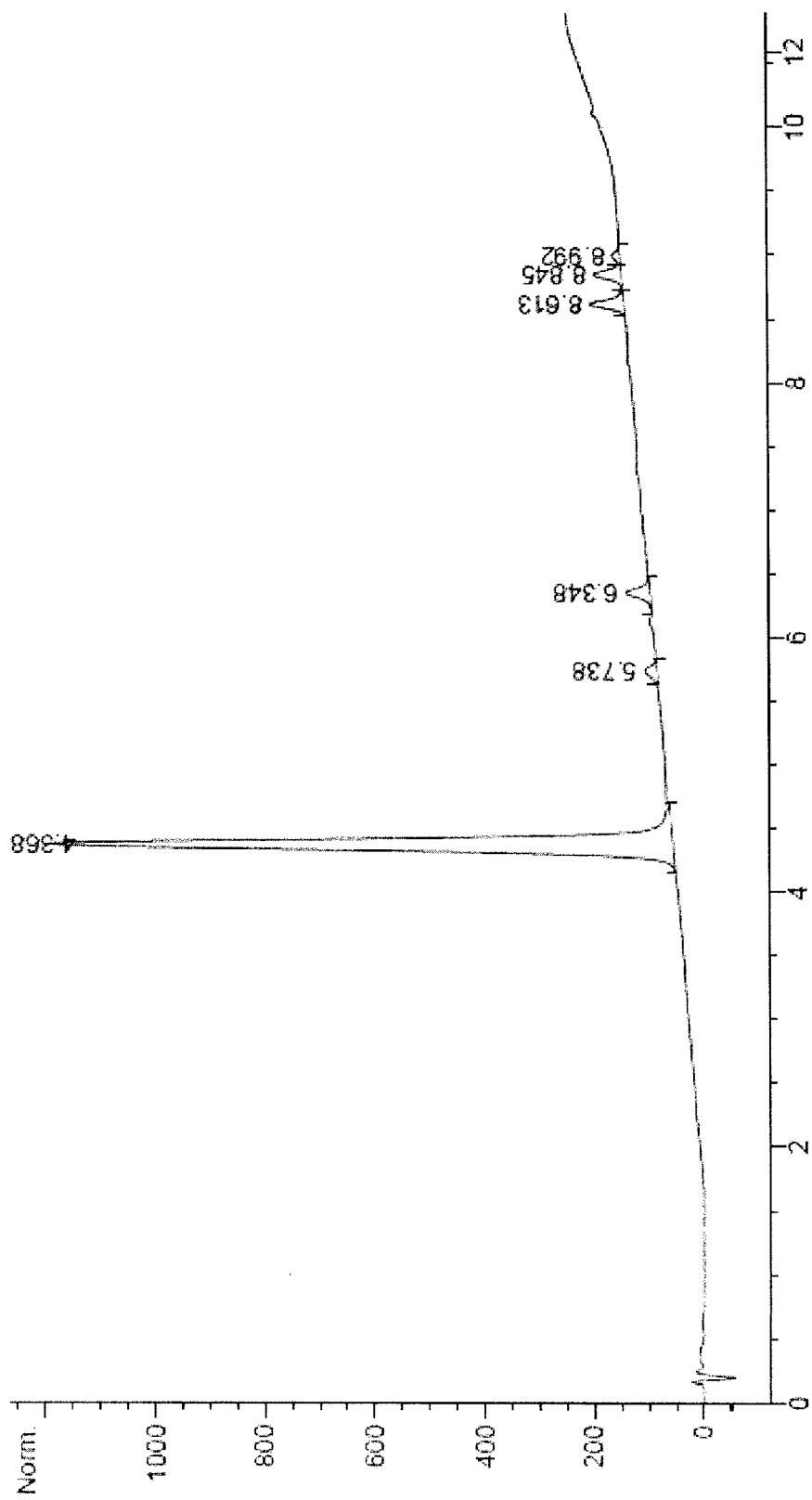
FIG. 17 shows a typical IPC for the conversion of E-3a to Compound 1/Compound 1 anhydride (e.g., Compound 2) (complete reaction).

The synthesized impurity matched the isolated impurity by HPLC retention time (FIG. 10), UV absorption (FIG. 11), LCMS (FIG. 12), and $^1$H-NMR (FIG. 13, FIG. 14).

The origin of IMP-4 was determined to be from IMP-3, and it was reasoned that IMP-3 was generated either: (1) as a homocoupling product of 1-bromo-2-fluoro-4-iodobenzene (e.g., an Ullmann coupling, which normally requires stoichiometric amounts of copper), or (2) from contamination with 4-bromo-3-fluorobenzeneboronic acid in the 3-fluorophenylboronic acid starting material (Scheme 8).

Scheme 8.

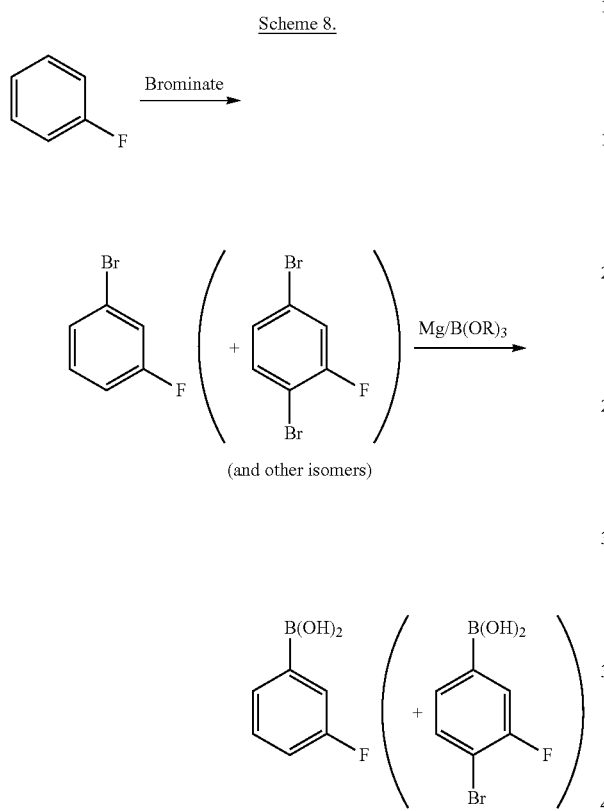

When 1-bromo-2-fluoro-4-iodobenzene was treated with PdCl$_2$(PPh$_3$)$_2$ and NaHCO$_3$ at reflux in I—PrOH and water but in the absence of 3-fluorophenylboronic acid (the Suzuki coupling partner for making E-3a), IMP-3 was formed with high conversion, but the product was not isolated to confirm isolated yield (Scheme 9).

Scheme 9.

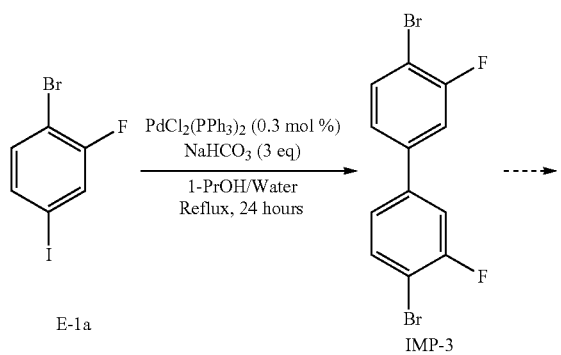

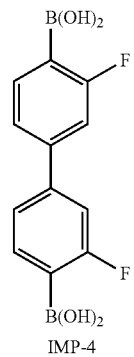

IMP-4

Qualitatively, the Ullmann coupling that generates IMP-3 was observed to proceed more slowly than the corresponding Suzuki coupling used to make E-3a. It is believed that the lower catalyst used for the Suzuki coupling (from 5 mol % for the early development batches to 0.3 mol % for the current synthesis) combined with the different reaction rates for the Suzuki and Ullmann couplings in this synthetic operation are significant contributors to the low levels of IMP-3, and subsequently IMP-4, observed in recent lots.

IMP-4 was tested for FAAH inhibitory activity. Using the FAAH assay as described below the K$_i$ for IMP-4 was measured to be as follows: K$_i$ (human): 14.1 nm; K$_i$ (rat): 5.1 nM.

Human FAAH Expression and Isolation.

A human FAAH (hFAAH) cDNA clone was purchased from Origen (Catalog #TC 119221, Accession #NM_001441.1). The clone was in an ORIGENE® pCMV6-XL5 with an insert size of ~2.2 kb. Sequencing of the clone indicated a conservative mutation of K48R. This point mutation is possibly an allelic difference, and is far from the active site and unlikely to effect the activity. This plasmid was amplified in *E. coli* and isolated by precipitation.

Transfection and purification of hFAAH was modified from published procedures (see Patricelli et al., *Biochemistry* (1998) 37:15177-15187; Maurelli et al., *FEBS Letters* (1995) 377:82-86; Hillard et al., *Biochim Biophy Acta.* (1995) 1257(3):249-256; and Giang et al., *Proc. Natl. Acad. Aci. USA* (1997) 94:2238-2242) and was adapted to 293 suspension cells (Invitrogen, cat#R790-07) for scale-up. Briefly, 60 mL of 293 cells were cultured to a density of 1×10$^6$ cells/mL in FreeStyle 293 expression media (Invitrogen, Gibco Catalogue #12338026) [no penicillin/streptomycin or fetal bovine serum (FBS)] at 37° C. with 8% CO$_2$. The transfection DNA was prepared by premixing 75 μg of hFAAH 1.2 mL OptiPro SFM (serum free medium) to 75 μL of FreeStyle Max transfection reagent in 1.2 mL OptiPro SFM. The final 2.4 mL OptiPro mixture, with 75 μg of hFAAH cDNA, and 75 μL of FreeStyle Max transfection reagent was incubated for 20 minutes, and then added slowly with mixing to 60 mL of 293 cell culture. The 293 cells were cultured for 2.5 days post-transfection, harvested via centrifugation at 5000×g, and the resultant cell pellet snap frozen with liquid nitrogen and stored at −80° C.

Frozen cell pellets were thawed on ice and resuspended in: 12.5 mM HEPES (pH 8.0), 100 mM NaCl, and 1 mM EDTA at a ratio of 25 mL per gram of cells. All subsequent steps were performed on ice. The cell suspension was homogenized with a dounce homogenizer for 30 strokes and sonicated to generate cell lysate. The resultant cell lysate was centrifuged at 1000×g to pellet cell debris. The supernatant was removed and centrifuged at 13,000×g to generate a microsomal membrane pellet. The supernatant was discarded and the microsomal pellet resuspended in 20 mM HEPES (pH 7.8), 10% vol/vol glycerol, 1 mM EDTA and 1% TRITON® X-100, for 1 hour to solubilize the membrane bound hFAAH. The enriched hFAAH preparation was clarified by a further centrifugation step at 13,000×g to pellet any membrane components. The supernatant contained solubilized enriched hFAAH. Total protein concentrations were determined using a Bio-Rad Protein Assay (Protein Assay Dye Reagent Concentrate, cat#500-0006) ref. 5. The samples were aliquotted and snap frozen with liquid nitrogen for storage until later use.

Rat FAAH Expression and Purification.

An N-terminal transmembrane domain deleted rat FAAH (rFAAH) was cloned as described in Patricelli et al., Biochemistry (1998) 37:15177-15187, encoding for amino acids 32-579 and an N-terminal His-tag, herein referred to as rFAAH. E. coli BL21 (DE3) were transformed according to manufacturer protocols (Invitrogen) and rFAAH was expressed and purified from a modified procedure described in Patricelli et al., 1998.

Briefly, 8 L of cells were cultured to an $OD_{600nm}$ of 0.6 at 37° C., and FAAH expression induced by 1 mM IPTG, followed by 4 hours of growth. Cells were pelleted by centrifugation at 5000×g to generate the cell paste. The cell paste was resuspended at a ratio of 32 g per 65 mL of lysis buffer [50 mM Tris pH 8.0, 200 mM NaCl and 1% n-octyl-β-D-glucopyranoside (LDAO)] plus 10 mM imidazole. Lysozyme was added to a final concentration of 1 mg/mL and the sample incubated in ice for 30 minutes. Cell lysate was generated by sonication followed by centrifugation at 17,000×g to pellet cell debris.

Soluble rFAAH was purified from the supernatant using nickel (Ni), heparin and size exclusion chromatography (SEC) columns. First, the supernatant was added to 10 mL of Ni resin that had been pre-equilibrated with lysis buffer. The supernatant was incubated with the resin for 30 minutes with constant stirring. The resin was poured into a 20 mL column, and non-specifically bound proteins were removed by washing with lysis buffer plus 20 mM imidazole. rFAAH was eluted in a batch mode with lysis buffer plus 500 mM imidazole. Peak fractions were pooled and loaded onto a 20 mL heparin column that had been pre-equilibrated in heparin buffer [20 mM HEPES (pH 7.5), 1 mM EDTA, 10% glycerol, and 0.015% LDAO]. The heparin column was washed to baseline with the heparin buffer plus 150 mM NaCl, and rFAAH (32-579aa) was eluted by running a linear gradient to from 150 mM NaCl to 1M NaCl in heparin buffer. Pooled rFAAH (32-579aa) samples were dialyzed against SEC buffer (20 mM EDTA, 1 mM EDTA, 150 mM NaCl, 0.015% LDAO, 1 mM DTT). Following dialysis, rFAAH was concentrated to 10 mg/mL via an amicon ultrafiltration unit with a 30 kDa molecular weight cut off. The concentrated samples were loaded onto a SUPERDEX® 200 16/60 SEC column (GE catalogue #17-1069-01), pre-equilibrated with SEC buffer. The column was run isocratically in SEC buffer, with rFAAH eluting as a 600 kDa oligomer. Eluted samples were pooled, concentrated to ~5 mg/mL and final rFAAH concentrations determined by measuring the absorbance at 280 nm, using an extinction coefficient of $\epsilon$=60850 $M^{-1}$ $cm^{-1}$. The pooled fractions containing rFAAH were aliquotted and snap frozen with liquid nitrogen for storage until later use.

$K_i$ Determination.

The $K_i$ of a test compound was determined for rat and human FAAH by measuring the dose dependent inhibition of AMC-Arachidonoyl amide hydrolysis as an end point read. Assays were carried out in Corning COSTAR® 384 well flat black bottom microtiter plates (Catalog #3654) and monitored in an Envision 2100 multilabel plate reader (Perkin Elmer-Wallac), with a 355 nm (40 nm band pass) excitation filter and 460 nm (25 nm bandpass) emission filter. The test compound was serially diluted three-fold in DMSO, from which 1 µL was added to 24 µL of a 2x stock solution of rat or human FAAH, and the resulting enzyme inhibitor mixture incubated for 30 minutes at room temperature. An enzymatic reaction was initiated by the addition of 25 µL of AMC-arachidonoyl amide, yielding final rFAAH, hFAAH, and substrate concentrations of 6 nM, 108 µg/mL and 20 µM, respectively. The final DMSO concentration was 2% and the concentration of the test compound varied three-fold from 12.5 µM to 0.21 nM. The final reaction mixture was incubated for 4 hours at room temperature after substrate addition, and then terminated by the addition of 25 µL of the FAAH inhibitor CAY10435 (Cayman Chemical Company, catalog #10005102) to achieve a final concentration of 4 µM. The assay plates were centrifuged and then read on the Envision plate reader. The dose dependent decrease in fluorescence intensity with respect to test compound concentration was fitted to Equation 1 to yield the $K_i$ where: $F_i$ is the experimentally determined fluorescence intensity at a given test compound concentration; $F_{max}$ represents the theoretical maximum fluorescence intensity in the absence of the test compound and at saturating substrate concentration determined from the non-linear regression analysis; and B is the baseline fluorescence of 100% inhibition. The substrate concentration (S) was constrained to 20 µM and the $K_m$ constrained an experimentally determined value of to 9 µM for both the rat and human FAAH. The inhibition constant $K_i$ was floated and determined via the non-linear regression fit.

$$F_i = \frac{F_{max} * S}{S + Km\left(1 + \frac{[IPI - 940]}{K_i}\right)} + B \qquad (1)$$

Example 4. Characterization and Properties of Solid Forms

A. General

XRPD

Unless indicated otherwise, the X-Ray Powder Diffraction patterns provided in the figures and in the examples were performed based on one of the following procedures.

1: Inel XRG-3000 Diffractometer

XRPD patterns were collected with an Inel XRG-3000 diffractometer. An incident beam of Cu Kα radiation was produced using a fine-focus tube and a parabolically graded multilayer mirror. Prior to the analysis, a silicon standard (NIST SRM 640c) was analyzed to verify the Si 111 peak position. A specimen of the sample was packed into a thin-walled glass capillary, and a beam-stop was used to minimize the background from air. Diffraction patterns were collected in transmission geometry using Windif v. 6.6 software and a curved position-sensitive Equinox detector with a 2θ range of 120°.

2: PANALYTICAL® EXPERT Pro MPD Diffractometer

XRPD patterns were collected with a PANALYTICAL® X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640c) was analyzed to verify the Si 111 peak position. A specimen of the sample was sandwiched between 3 μm-thick films and analyzed in transmission geometry. A beam-stop and short antiscatter extension were used to minimize the background generated by air. Soller slits for the incident and diffracted beams were used to minimize broadening from axial divergence. Diffraction patterns were collected using a scanning position-sensitive detector (X'CELERATOR®) located 240 mm from the specimen and Data Collector software v. 2.2b.

For samples with limited material, the XRPD pattern was collected with a PANALYTICAL® X'Pert PRO MPD diffractometer using an incident beam of Cu Kα radiation produced using a long, fine-focus source and a nickel filter. The diffractometer was configured using the symmetric Bragg-Brentano. Prior to the analysis, a silicon specimen (NIST SRM 640c) was analyzed to verify the Si 111 peak position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'CELERATOR®) located 240 mm from the sample and Data Collector software v. 2.2b.

3: PANALYTICAL® EXPERT Pro MPD Diffractometer (Variable Temperature/Humidity Analysis)

The XRPD pattern was collected with a PANALYTICAL® X'Pert PRO MPD diffractometer using an incident beam of Cu Kα radiation produced using a long, fine-focus source and a nickel filter. The diffractometer was configured using the symmetric Bragg-Brentano. Data were collected and analyzed using Prior to the analysis, a silicon specimen (NIST SRM 640c) was analyzed to verify the Si 111 peak position. A specimen of the sample was packing into a nickel-coated copper well. Antiscatter slits (SS) were used to minimize the background generated by air. Soller slits for the incident and diffracted beams were used to minimize broadening from axial divergence. Diffraction patterns were collected using a scanning position-sensitive detector (X'CELERATOR®) located 240 mm from the sample and Data Collector software v. 2.2b. An Anton Paar temperature-humidity chamber (THC) was used to collect in-situ XRPD patterns as a function of humidity and temperature. The specimen was heated with a Peltier thermoelectric device located directly under the specimen holder, and the temperature was monitored with a platinum 100 resistance sensor located directly under the specimen. Power to the heater was supplied and controlled by an Anton Paar TCU 50 interfaced with Data Collector. The humidity was generated with an RH-200 manufactured by VTI Inc. and carried by a flow of nitrogen gas. The humidity and temperature was monitored by a HYGROCLIP® sensor manufactured by Rotronic located next to the specimen inside the THC.

Differential Scanning Calorimetry (DSC)

Unless indicated otherwise, the DSC patterns provided in the figures and in the examples were performed based on the following procedure.

DSC was performed using a TA Instruments Q2000 differential scanning calorimeter. Temperature calibration was performed using NIST traceable indium metal. The sample was placed into an aluminum DSC pan, covered with a lid, and the weight was accurately recorded. A weighed aluminum pan configured as the sample pan was placed on the reference side of the cell.

Solution 1D $^1$H NMR Spectroscopy

Unless indicated otherwise, the solution NMR spectra provided in the figures and in the examples were acquired based on the following procedure. Samples were prepared by dissolving approximately 4-10 mg of sample in CDCl$_3$ containing TMS. Spectra were then obtained with a Varian$^{UNITY}$ INOVA-400 spectrometer.

Thermogravimetry (TGA)

Unless indicated otherwise, the TGA thermograms provided in the figures and in the examples were acquired based on the following procedure. TG analyses were performed using a TA Instruments Q5000 IR thermogravimetric analyzer. Temperature calibration was performed using nickel and ALUMEL®. Each sample was placed in an aluminum pan. The sample was hermetically sealed, the lid pierced, then inserted into the TG furnace. The furnace was heated under nitrogen.

B. Polymorph Screen of Compound 1

Compound 1 was subjected various crystallization conditions. The following procedures were utilized.

Crash Precipitation

Solutions of Compound 1 were prepared in various solvents and filtered through a 0.2-μm nylon filter. Aliquots of various antisolvents were dispensed with stirring until precipitation occurred. Solids were collected by vacuum filtration or by decanting the liquid phase and allowing the solids to dry at ambient conditions or under nitrogen gas.

Fast Evaporation

Solutions of Compound 1 were prepared in various solvents in which samples were sonicated with solvent addition. Once a mixture reached complete dissolution, as judged by visual observation, the solution was filtered through a 0.2-μm nylon filter. The solution was allowed to evaporate from an open vial at ambient conditions. Solutions were allowed to evaporate to dryness unless designated as partial evaporations (solid present with a small amount of solvent remaining), in which case solids were isolated by vacuum filtration or by decanting the liquid phase and allowing the solids to dry at ambient conditions or under nitrogen gas.

Slow Cool

Saturated solutions of Compound 1 were prepared in various solvents at an elevated temperature and filtered warm through a 0.2-μm nylon filter into a warm vial. The vial was capped and left on the hot plate, and the hot plate was turned off to allow the sample to slowly cool to ambient temperature. If little or no solids were present after cooling to ambient temperature, the sample was placed in the refrigerator (approximately 2 to 8° C.) for further cooling. Solids were collected by vacuum filtration or by decanting the liquid phase and allowing the solids to dry at ambient conditions or under nitrogen gas.

Slow Evaporation

Solutions of Compound 1. Once a mixture reached complete dissolution, as judged by visual observation, the solution was filtered through a 0.2-μm nylon filter. The solution was allowed to evaporate at ambient conditions from a vial covered with aluminum foil perforated with pinholes (or a loosely capped vial in some cases). Solutions were allowed to evaporate to dryness unless designated as partial slow evaporations (solid present with a small amount of solvent remaining), in which case solids were isolated by vacuum filtration or by decanting the liquid phase and allowing the solids to dry at ambient conditions or under nitrogen gas.

Slurry

Solutions of Compound 1 were prepared by adding enough solids to a given solvent at ambient conditions so that undissolved solids were present. The mixture was then loaded onto an orbit shaker in a sealed vial at ambient temperature for an extended period of time, typically approximately 1 week. The solids were isolated by vacuum filtration or by decanting the liquid phase and allowing the solids to dry at ambient conditions or under nitrogen gas.

Vapor Diffusion

Concentrated solutions of Compound 1 were prepared in various solvents and filtered through a 0.2-μm nylon filter. The filtered solution was dispensed into a 1-dram vial, which was then placed inside a 20-mL vial containing antisolvent. The 1-dram vial was left uncapped and the 20-mL vial was capped to allow vapor diffusion to occur. The solids were isolated by vacuum filtration or by decanting the liquid phase and allowing the solids to dry at ambient conditions or under nitrogen gas.

| Solvent/Solvent System | Conditions | Habit/Description | XRPD Result | Example |
|---|---|---|---|---|
| acetone | SE | white, agglomerated plates, birefringent; possible single crystals (PS) | Form A | 1 |
| | CP w/heptane | white solid in clear solution; white, tiny plates and morphology unknown, birefringent (PS) | Form A | 2 |
| ACN | SE | white, agglomerated and irregular plates, birefringent (PS) | Form A | 3 |
| | SC, ~51° C. to RT, stand at RT 1 day | solids present, clear solution; white, irregular and rectangular plates, morphology unknown, and aggregates, birefringent (PS) | Form A + minor material B | 4 |
| | VD w/water, 8 days | white, agglomerated plates and few needles, birefringent (PS) | Form A | 5 |
| chloroform | SE | white, aggregates of plates and irregular particles, birefringent (PS) | Form A1 | 6 |
| | SC, ~51° C. to RT, stand at RT 1 day | small amount solids on walls and in suspension | — | 7 |
| | refrigerator, 11 days | white solid on bottom and in suspension; morphology unknown and plates, birefringent (PS) | Form A | |
| | VD w/heptane, 13 days | white, agglomerated plates, birefringent (PS) | Form A | 8 |
| DCM | SE | white, rectangular plates and morphology unknown, birefringent (PS) | Form A1 | 9 |
| | CP w/heptane | white precipitate in clear solution; white, tiny needles and aggregates, birefringent (PS) | Form A1 | 10 |
| diethyl ether | SE | white, rectangular plates and aggregates, birefringent (PS) | Form A | 11 |
| DMF | FE | white, agglomerates and morphology unknown, birefringent | Form A | 12 |
| p-dioxane | SE | white, aggregates of plates, needles, and morphology unknown, birefringent (PS) | Form A | 13 |
| EtOAc | SE | white, small, irregular particles and rectangular plates, birefringent (PS) | Form A | 14 |
| | CP w/heptane | white solid in clear solution; white, tiny rectangular plates and morphology unknown, birefringent (PS) | Form A | 15 |
| heptane | slurry, RT, 14 days | clear solution, white solid; tiny plates and specks, birefringent | Form A | 16 |

-continued

| Solvent/Solvent System | Conditions | Habit/Description | XRPD Result | Example |
|---|---|---|---|---|
| heptane:chloroform 2:1 | SE | white, rectangular plates, needles, and morphology unknown, birefringent (PS) | Form A | 17 |
| heptane:THF 2:1 | SE | white, needles, rectangular plates, and agglomerates, birefringent (PS) | Form A | 18 |
| IPE | SE | white, agglomerated, irregular plates, tiny particles, and rectangular plates, birefringent (PS) | Form A | 19 |
| | slurry, RT, 14 days | clear solution, white solid; specks and morphology unknown, birefringent | Form A1 | 20 |
| | SC, ~51° C. to RT, stand at RT 1 day | solids present, clear solution; white, aggregates of rectangular plates and morphology unknown, birefringent (PS) | Form A | 21 |
| | CP w/heptane | white solid in hazy solution; white, morphology unknown, few tiny needles and plates, birefringent (PS) | Form A | 22 |
| MEK | SE | white, aggregates of irregular plates and morphology unknown, birefringent (PS) | Form A | 23 |
| | CP w/heptane | white solid in clear solution; white, aggregates, morphology unknown, and few tiny plates, birefringent (PS) | Form A | 24 |
| 2-Me THF | SE | white, aggregates, morphology unknown, birefringent | Form A | 25 |
| MIBK | SE | white, irregular and rectangular plates, morphology unknown, and dendridic formations, birefringent (PS) | Form A1 | 26 |
| MTBE | SE | white, tiny particles, irregular and rectangular plates, birefringent (PS) | Form A | 27 |
| | CP w/heptane | white solid in clear solution; white, aggregates, morphology unknown, and few tiny plates, birefringent (PS) | Form A + minor material B | 28 |
| nitromethane | SE | white, agglomerated plates, birefringent (PS) | Form A | 29 |
| | slurry, RT, 14 days | clear solution, white solid; aggregates and morphology unknown, birefringent | Form A | 30 |
| | SC, ~51° C. to RT, stand at RT 1 day | clear solution, very small amount solids in suspension | — | 31 |
| | refrigerator, 11 days | white solid on bottom and in suspension; square plates and agglomerates, birefringent (PS) | Form A | |
| THF | SE | white, aggregates of fine needles and morphology unknown, birefringent | material B | 32 |
| | VD w/heptane, 1 day | white, needles, specks, and aggregates, birefringent (PS) | material B | 33 |
| | VD w/water, 1 day | white, aggregates of irregular plates and dendridic formations, birefringent (PS) | Form A; no peak at ~24° 2θ, possible PO | 34 |

-continued

| Solvent/Solvent System | Conditions | Habit/Description | XRPD Result | Example |
|---|---|---|---|---|
| toluene | FE | white, needles and rectangular plates, birefringent (PS) | Form A | 35 |
| | slurry, RT, 14 days | clear solution, white solid; aggregates and morphology unknown, birefringent | Form A | 36 |
| | SC, ~51° C. to RT, stand at RT 1 day | solids present, clear solution; white, spherulites of thick needles, birefringent (PS) | Form A | 37 |
| water | slurry, RT, 14 days | clear solution, white solid; aggregates, plates, and morphology unknown, birefringent (PS) | Form A | 38 |
| acetone:water 50:50 | partial SE | white, rectangular plates and aggregates, birefringent (PS) | Form A | 39 |
| | slurry, RT, 14 days | clear solution, white solid; aggregates and morphology unknown, birefringent | Form A | 40 |
| | SC, ~51° C. to RT, stand at RT 1 day | solids present, clear solution; white, rectangular plates and agglomerates, birefringent (PS) | Form A | 41 |
| ACN:water 50:50 | partial SE | white, rectangular plates and morphology unknown, birefringent (PS) | Form A | 42 |
| | slurry, RT, 14 days | clear solution, white solid; aggregates and morphology unknown, birefringent | Form A | 43 |
| | SC, ~51° C. to RT, stand at RT 1 day | solids present, clear solution; white, rectangular plates and agglomerates, birefringent (PS) | Form A | 44 |
| DMF:water 50:50 | FE | white, irregular plates and aggregates, birefringent (PS) | Form A | 45 |
| | slurry, RT, 14 days | clear solution, white solid; morphology unknown and a few plates, birefringent (PS) | Form A | 46 |
| | SC, ~51° C. to RT, stand at RT 1 day | solids present, clear solution; white, irregular plates, agglomerates, and morphology unknown, birefringent (PS) | Form A | 47 |
| p-dioxane:water 50:50 | SE | white, rectangular and irregular plates, birefringent (PS) | Form A | 48 |
| | SC, ~51° C. to RT, stand at RT 1 day | clear solution | — | 49 |
| | refrigerator, 11 days | clear solution, white solid; aggregates of plates, birefringent (PS) | Form A | |
| THF:water 50:50 | SE | white, spherulites of thick needles and aggregates, birefringent (PS) | material B + material C | 50 |
| | add solvent | oily solids | — | 51 |
| | slurry, RT, 14 days | cloudy solution, oily droplets present | — | |
| | add solvent at ~51° C. | solids dissolve, then immediately ppt as oil | — | 52 |
| | add solvent stir few mins. | clear solution | — | |
| | | hazy solution | — | |
| | hot filter soln. | hazy solution | — | |
| | SC, ~51° C. to RT, stand | clear solution | — | |

-continued

| Solvent/Solvent System | Conditions | Habit/Description | XRPD Result | Example |
|---|---|---|---|---|
| | at RT 1 day refrigerator, 11 days | clear solution | — | |
| | freezer, 1 day | frozen solid | — | |
| | equilibrate to RT | clear solution | — | |
| | partial FE | white, dendridic needles, specks, and aggregates, birefringent | material B + material C | |
| | | | material B + material C$^a$ | |

Abbreviations

| Type | Abbreviations/Acronyms | Full Name/Description |
|---|---|---|
| Solvent | ACN | acetonitrile |
| | DCM | dichloromethane |
| | DMF | dimethylformamide |
| | EtOAc | ethyl acetate |
| | IPE | isopropyl ether |
| | MEK | methyl ethyl ketone |
| | 2-Me THF | 2-methyltetrahydrofuran |
| | MIBK | methyl iso-butyl ketone |
| | MTBE | tert-butyl methyl ether |
| | THF | tetrahydrofuran |
| Methods | CP | crash precipitation |
| | FE | fast evaporation |
| | SC | slow cool |
| | SE | slow evaporation |
| | VD | vapor diffusion |
| Techniques | DSC | differential scanning calorimetry |
| | $^1$H NMR | proton nuclear magnetic resonance spectroscopy |
| | KF | Karl Fischer |
| | SCXRD | single crystal x-ray diffraction |
| | TG or TGA | thermogravimetric analysis |
| | VT/VRH | variable temperature/variable relative humidity |
| | XRPD | x-ray powder diffraction |
| Other | N$_2$ | nitrogen gas |
| | PO | preferred orientation |
| | PS | possible single crystals |
| | RH | relative humidity |
| | RT | room (ambient) temperature |
| Solvent | ACN | acetonitrile |
| | DCM | dichloromethane |
| | DMF | dimethylformamide |
| | EtOAc | ethyl acetate |
| | IPE | isopropyl ether |
| | MEK | methyl ethyl ketone |
| | 2-Me THF | 2-methyltetrahydrofuran |
| | MIBK | methyl iso-butyl ketone |
| | MTBE | tert-butyl methyl ether |
| | THF | tetrahydrofuran |
| Methods | CP | crash precipitation |
| | FE | fast evaporation |
| | SC | slow cool |
| | SE | slow evaporation |
| | VD | vapor diffusion |
| Techniques | DSC | differential scanning calorimetry |
| | $^1$H NMR | proton nuclear magnetic resonance spectroscopy |
| | KF | Karl Fischer |
| | SCXRD | single crystal x-ray diffraction |
| | TG or TGA | thermogravimetric analysis |
| | VT/VRH | variable temperature/variable relative humidity |
| | XRPD | x-ray powder diffraction |

-continued

Abbreviations

| Type | Abbreviations/Acronyms | Full Name/Description |
|---|---|---|
| Other | N$_2$ | nitrogen gas |
| | PO | preferred orientation |
| | PS | possible single crystals |
| | RH | relative humidity |
| | RT | room (ambient) temperature |

C. Stressing Experiments, Form A, Compound 1

Form A crystal form of Compound 1 was subjected to (1) mechanical stressing experiments and (2) relative humidity stressing experiments, where the material was subjected to different levels of relative humidity (R.H.) and temperature. Form A was found to be stable to humidity stressing at 75% and 97% R.H. at room temperature for 7 days, and 75% R.H. at about 40° C. for 7 days. The results are summarized in the tables below.

Mechanical Stressing

| Solvent/Solvent System | Conditions | Habit/Description | XRPD Result |
|---|---|---|---|
| — | mill, 30 Hz, 20 min. | white, tiny particles and aggregates, partially birefringent | Form A, low crystallinity |
| ACN | mill, 30 Hz, 20 min. | white, tiny particles and aggregates, partially birefringent | Form A |
| MEK | mill, 30 Hz, 20 min. | white, tiny particles and aggregates, partially birefringent | Form A |
| THF | mill, 30 Hz, 20 min. | white, tiny particles and aggregates, partially birefringent | Form A |
| — | compress, 10,000 lb, 5 min. | white, tiny particles and aggregates, birefringent | Form A, low crystallinity |

Relative Humidity Stressing

| Conditions | Time | Observations | XRPD Result | Example |
|---|---|---|---|---|
| 75% RH, RT | 1 day | free-flowing white powder | — | A |
| | 3 days | free-flowing white powder | — | |
| | 7 days | free-flowing white powder; tiny, | Form A | |

Relative Humidity Stressing

| Conditions | Time | Observations | XRPD Result | Example |
|---|---|---|---|---|
| 75% RH, 40° C. | 1 day | irregular particles, birefringent free-flowing white powder | — | B |
| | 4 days | free-flowing white powder | — | |
| | 7 days | free-flowing white powder; tiny, irregular particles and aggregates, birefringent | Form A | |
| 97% RH, RT | 1 day | free-flowing white powder | — | C |
| | 3 days | free-flowing white powder | — | |
| | 7 days | free-flowing white powder; tiny, irregular particles, birefringent | Form A | |

D. Single Crystal Structure Determination, Form A, Compound 1

Single crystal analysis was performed on Form A of Compound 1. The structure was determined by single crystal X-ray diffraction. In sum, the single crystal structure was determined to confirm the molecular structure. The structure was determined to be an anhydrous crystal form. The crystal structure was comprised of a single molecule in the asymmetric unit. All peaks in the experimental patterns are represented in the calculated XRPD pattern, indicating the bulk material is likely a single phase.

EXPERIMENTAL

Preparation of Sample

Compound 1 was dissolved in a 50:50 mixture of acetone and water with stirring at 51° C. The solution was then hot filtered into a warm vial, capped, and left on the hot plate, which was then turned off to allow the solution to slowly cool to ambient temperature. After standing at ambient temperature 1 day, crystals were harvested.

Data Collection

A colorless plate of $C_{12}H_9BF_2O_2$ having approximate dimensions of 0.20×0.20×0.04 mm, was mounted on a fiber in random orientation. Preliminary examination and data collection were performed with Cu $K_\alpha$ radiation ($\lambda$=1.54184 Å) on a Rigaku Rapid II diffractometer equipped with confocal optics. Refinements were performed on an LINUX PC using SHELX97. G. M. Sheldrick, *Acta Cryst.*, 2008, A64, 112.

Cell constants and an orientation matrix for data collection were obtained from least-squares refinement using the setting angles of 11613 reflections in the range 70<θ<66°. The refined mosaicity from CrystalClear is 0.72° indicating moderate crystal quality. CrystalClear: An Integrated Program for the Collection and Processing of Area Detector Data, Rigaku Corporation, © 1997-2002. The space group was determined by the program XPREP. Bruker, XPREP in SHELXTL v. 6.12., Bruker AXS Inc., Madison, Wis., USA, 2002. From the systematic presence of the following conditions: h0l l=2n; 0k0 k=2n, and from subsequent least-squares refinement, the space group was determined to be $P2_1/c$ (no. 14). The data were collected to a max 2θ value of 133.18°, at a temp of 150±1 K.

Data Reduction

Frames were integrated with CrystalClear. A total of 11613 reflections were collected, of which 1786 were unique. Lorentz and polarization corrections were applied to the data. The linear absorption coefficient is 1.041 mm$^{-1}$ for Cu $K_\alpha$ radiation. An empirical absorption correction using CrystalClear was applied. Transmission coefficients ranged from 0.743 to 0.959. A secondary extinction correction was applied. G. M. Sheldrick, *Acta Cryst.*, 2008, A64, 112. The final coefficient, refined in least-squares, was 0.0063000 (in absolute units). Intensities of equivalent reflections were averaged. The agreement factor for the averaging was 3.84% based on intensity.

Structure Solution and Refinement

The structure was solved by direct methods using SIR2004. M. C. Burla, R. Caliandro, M. Camalli, B. Carrozzini, G. L. Cascarano, L. De Caro, C. Giacovazzo, G. Polidori, and R. Spagna, *J. Appl. Cryst.* 2005, 38, 381. The remaining atoms were located in succeeding difference Fourier syntheses. Hydrogen atoms were included in the refinement but restrained to ride on the atom to which they are bonded. The structure was refined in full-matrix least-squares by minimizing the function:

$$\Sigma w(|F_o|^2-|F_c|^2)^2$$

The weight w is defined as $1/[\sigma^2(F_o^2)+(0.0702P)^2+(0.0000P)]$, where $P=(F_o^2+2F_c^2)/3$.

Scattering factors were taken from the "International Tables for Crystallography," *International Tables for Crystallography*, Vol. C, Kluwer Academic Publishers: Dordrecht, The Netherlands, 1992, Tables 4.2.6.8 and 6.1.1.4. Of the 1786 reflections used in the refinements, only the reflections with $F_o^2>2\sigma(F_o^2)$ were used in calculating R. A total of 1378 reflections were used in the calculation. The final cycle of refinement included 163 variable parameters and converged (largest parameter shift was <0.01 times its estimated standard deviation) with unweighted and weighted agreement factors of:

$$R=\Sigma|F_o-F_c|/\Sigma F_o=0.042$$

$$R_w=\sqrt{\Sigma w(F_o^2-F_c^2)^2/\Sigma w(F_o^2)^2}=0.109$$

The standard deviation of an observation of unit weight (goodness of fit) was 1.123. The highest peak in the final difference Fourier had a height of 0.23 e/Å$^3$. The minimum negative peak had a height of −0.27 e/Å$^3$.

Calculated X-ray Powder Diffraction (XRPD) Pattern

A calculated XRPD pattern was generated for Cu radiation using PowderCell 2.3 and the atomic coordinates, space group, and unit cell parameters from the single crystal data. PowderCell for Windows Version 2.3 W. Kraus; G. Nolze, Federal Institute for Materials Research and Testing, Berlin Germany, EU, 1999. Since the single crystal data are collected at low temperatures (150 K) some shifting between the calculated and experimental powder diffraction pattern is expected.

ORTEP and Packing Diagrams

The ORTEP diagram was prepared using ORTEP III (C. K. Johnson, ORTEPIII, Report ORNL-6895, Oak Ridge National Laboratory, TN, U.S.A. 1996, OPTEP-3 for Windows V1.05, L. J. Farrugia, *J. Appl. Cryst.* 1997, 30, 565) program within the PLATON (A. L. Spek, *PLATON, Molecular Graphics Program*. Utrecht University, Utrecht, The Netherlands, 2008; A. L. Spek, *J. Appl. Cryst.* 2003, 36, 7) software package. Atoms are represented by 50% probability anisotropic thermal ellipsoids. Packing diagrams were prepared using CAMERON 9 modeling software. Additional figures were generated with the PLATON software package, and with the Mercury 2.3 (C. F. Macrae, P. R. Edgington, P. McCabe, E. Pidcock, G. P. Shields, R. Taylor, M. Towler and J. van de Streek, *J. Appl. Cryst.*, 2006, 39, 453-457) visualization package. Hydrogen bonding is represented as dashed lines.

X-Ray Powder Diffraction (XRPD)

X-ray powder diffraction (XRPD) analyses were performed using an Inel XRG-3000 diffractometer equipped with a CPS (Curved Position Sensitive) detector with a 2θ range of 120°. Real time data were collected using Cu-Kα radiation starting at approximately 402θ at a resolution of 0.03° 2θ. The tube voltage and amperage were set to 40 kV and 30 mA, respectively. The monochromator slit was set at 5 mm by 160 µm. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 300 seconds. Instrument calibration was performed using a silicon reference standard. The experimental XRPD pattern was collected at SSCI, a division of Aptuit, according to cGMP specifications.

Results

The monoclinic cell parameters and calculated volume are: a=5.44850(10) Å, b=5.16460(10) Å, c=36.124(3) Å, α=90.00°, β=90.490(6)°, γ=90.00°, V=1016.48(8) Å³. The molecular weight of the asymmetric unit in the crystal structure of Compound 1 is 234.01 g mol⁻¹ with Z=4, resulting in a calculated density of 1.529 g cm⁻³. The space group was determined to be P2₁/c. A summary of the crystal data and crystallographic data collection parameters are provided in the Table below.

| Crystal Data and Data Collection Parameters | |
|---|---|
| formula | $C_{12}H_9BF_2O_2$ |
| formula weight | 234.01 |
| space group | $P2_1/c$ (No. 14) |
| a, Å | 5.44850(10) |
| b, Å | 5.16460(10) |
| c, Å | 36.124(3) |
| β, deg | 90.490(6) |
| V, Å³ | 1016.48(8) |
| Z | 4 |
| $d_{calc}$, g cm⁻³ | 1.529 |
| crystal dimensions, mm | 0.20 × 0.20 × 0.04 |
| temperature, K | 150. |
| radiation (wavelength, Å) | Cu $K_α$ (1.54184) |
| monochromator | Confocal Optics |
| linear abs coef, mm⁻¹ | 1.041 |
| absorption correction applied | empirical[a] |
| transmission factors: min, max | 0.743, 0.959 |
| diffractometer | Rigaku Rapid II |
| h, k, l range | −6 to 6 −5 to 6 −42 to 42 |
| 2θ range, deg | 14.71-133.18 |
| mosaicity, deg | 0.72 |
| programs used | SHELXTL |
| $F_{000}$ | 480.0 |
| weighting $1/[σ^2(F_o^2) + (0.0702P)^2 + 0.0000P]$ where $P = (F_o^2 + 2F_c^2)/3$ | |
| data collected | 11613 |
| unique data | 1786 |
| $R_{int}$ | 0.038 |
| data used in refinement | 1786 |
| cutoff used in R-factor calculations | $F_o^2 > 2.0σ(F_o^2)$ |
| data with I > 2.0σ(I) | 1378 |
| refined extinction coef | 0.0063 |
| number of variables | 163 |
| largest shift/esd in final cycle | 0.00 |
| $R(F_o)$ | 0.042 |
| $R_w(F_o^2)$ | 0.109 |
| goodness of fit | 1.123 |

[a]CrystalClear: *An Integrated Program for the Collection and Processing of Area Detector Data*, Rigaku Corporation, © 1997-2002.

The quality of the structure is indicated by the R-value of 0.042 (4.2%).

Figure 20:
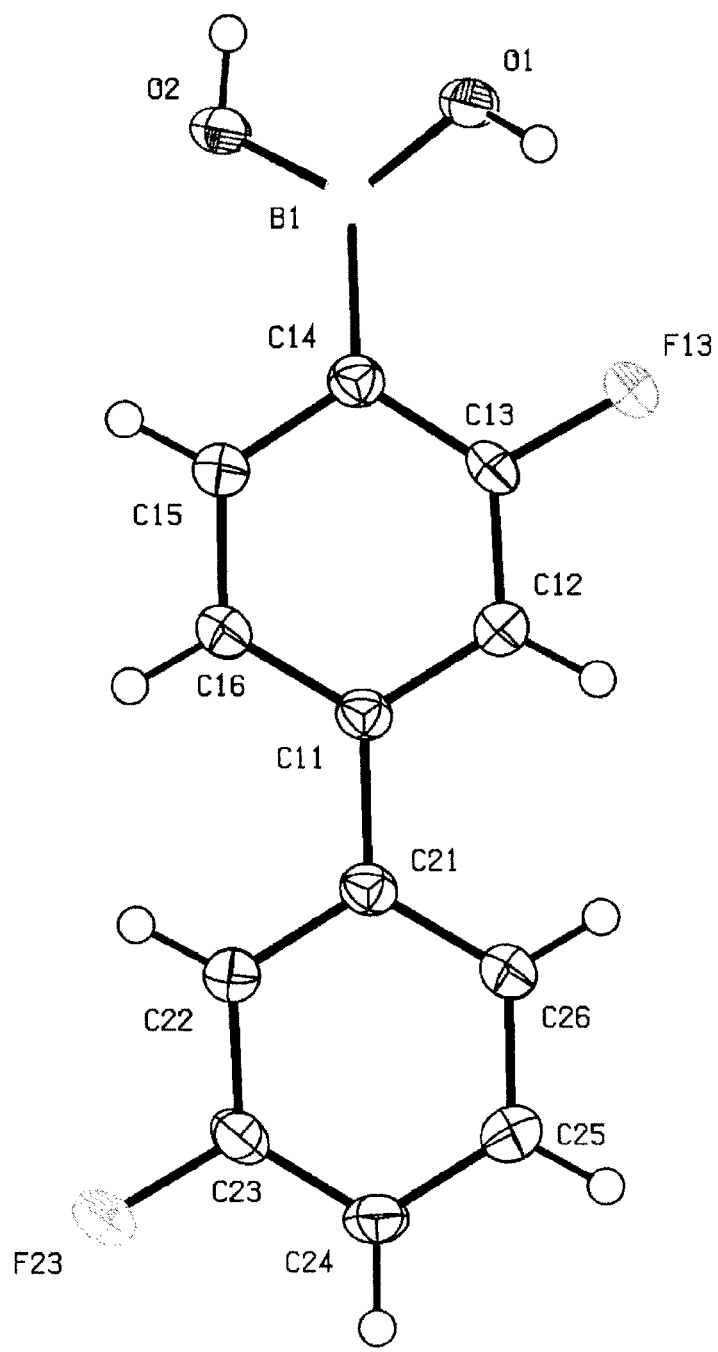
FIG. 20 shows an ORTEP drawing of Compound 1.

An ORTEP drawing is shown in FIG. 20. One of the phenyl groups is rotated 180 degrees from the as-drawn molecule. The asymmetric unit shown in FIG. 20 contains a single Compound 1 molecule.

Figure 21:
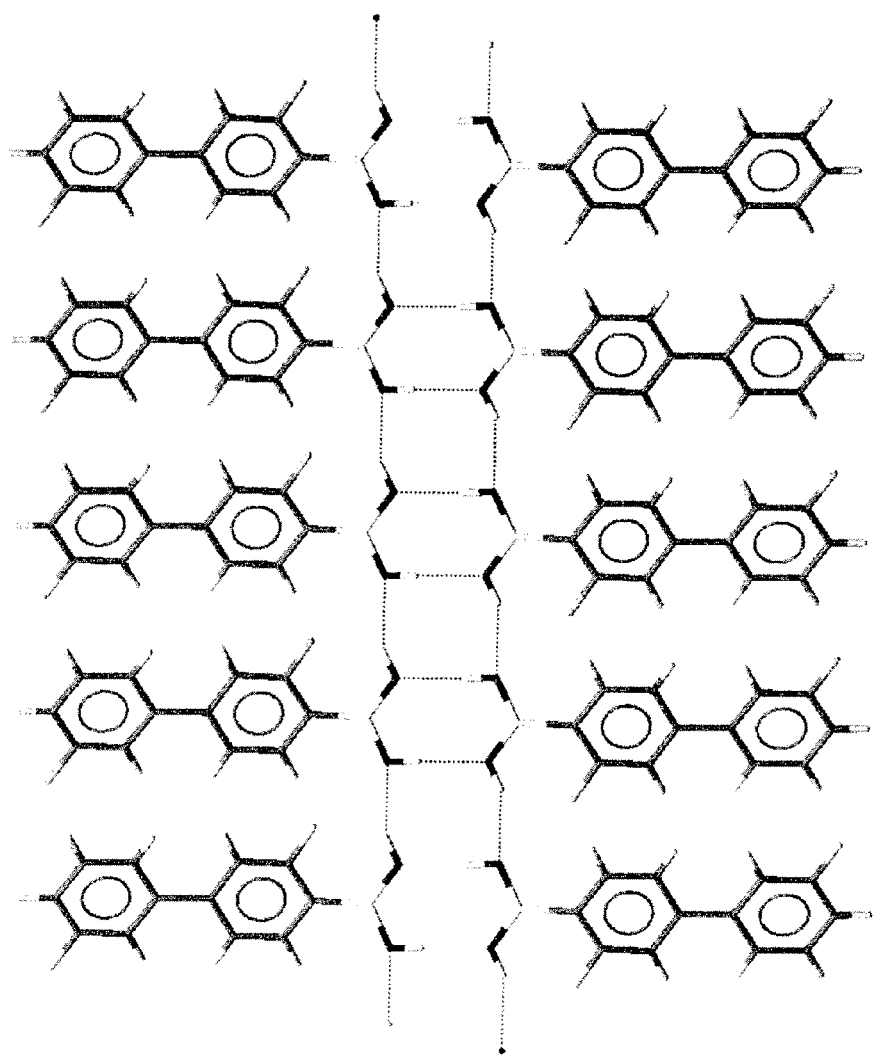
FIG. 21 shows hydrogen bonding in Compound 1.
Figure 24:
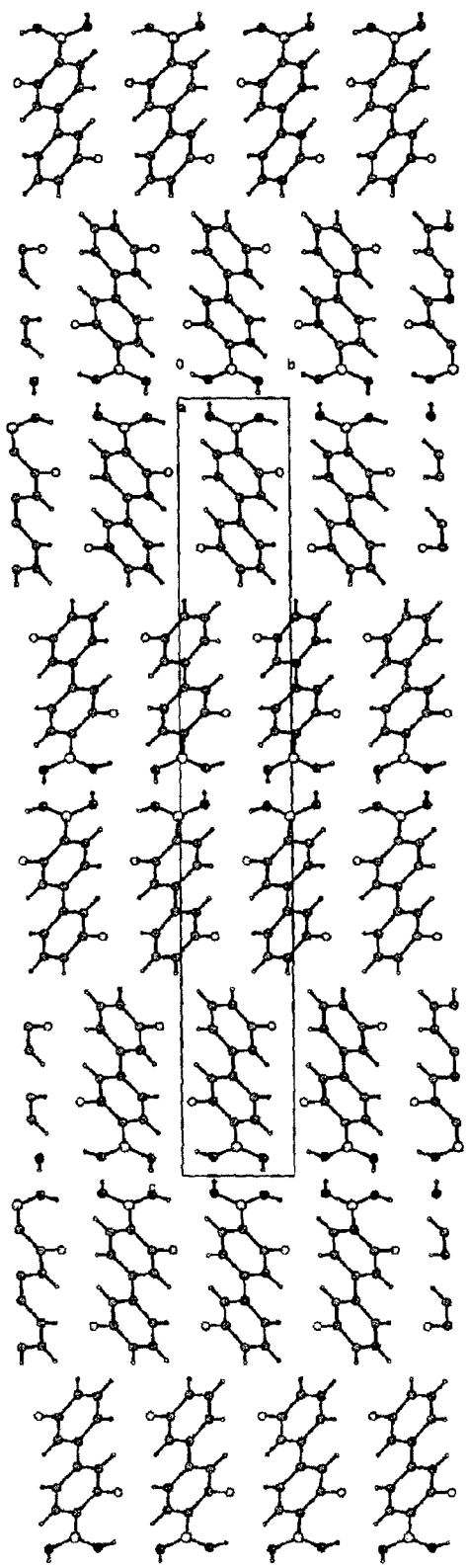
FIG. 24 shows a packing diagram of a crystalline Compound 1 viewed down the crystallographic a axis.
Figure 25:
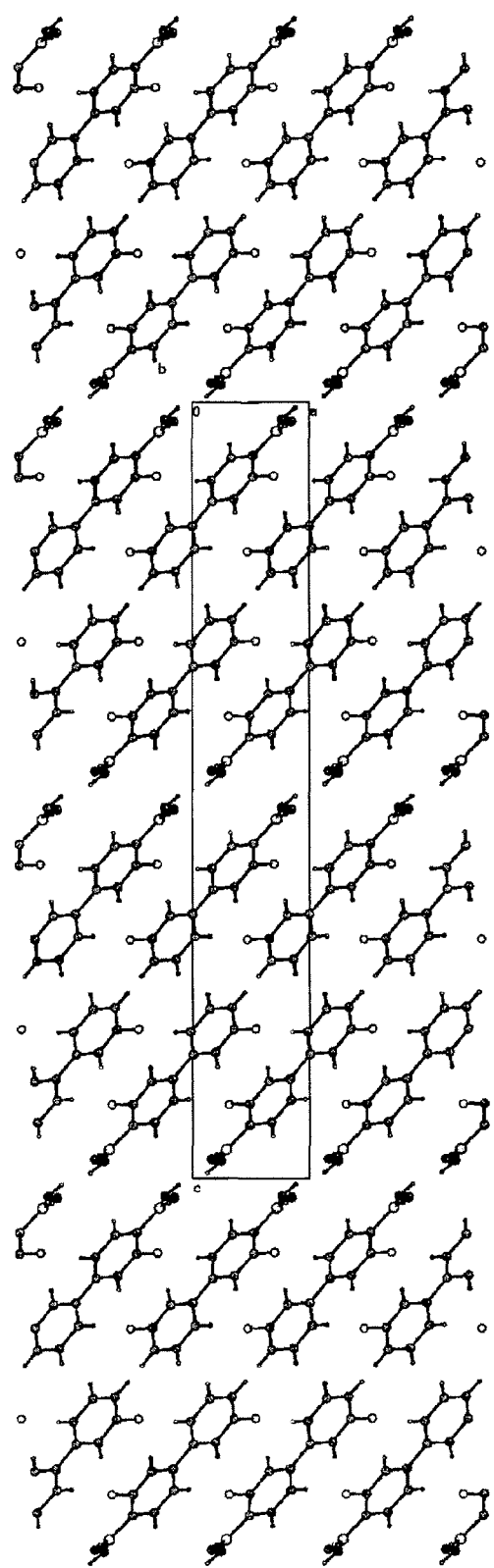
FIG. 25 shows a packing diagram of a crystalline Compound 1 viewed down the crystallographic b axis.
Figure 26:
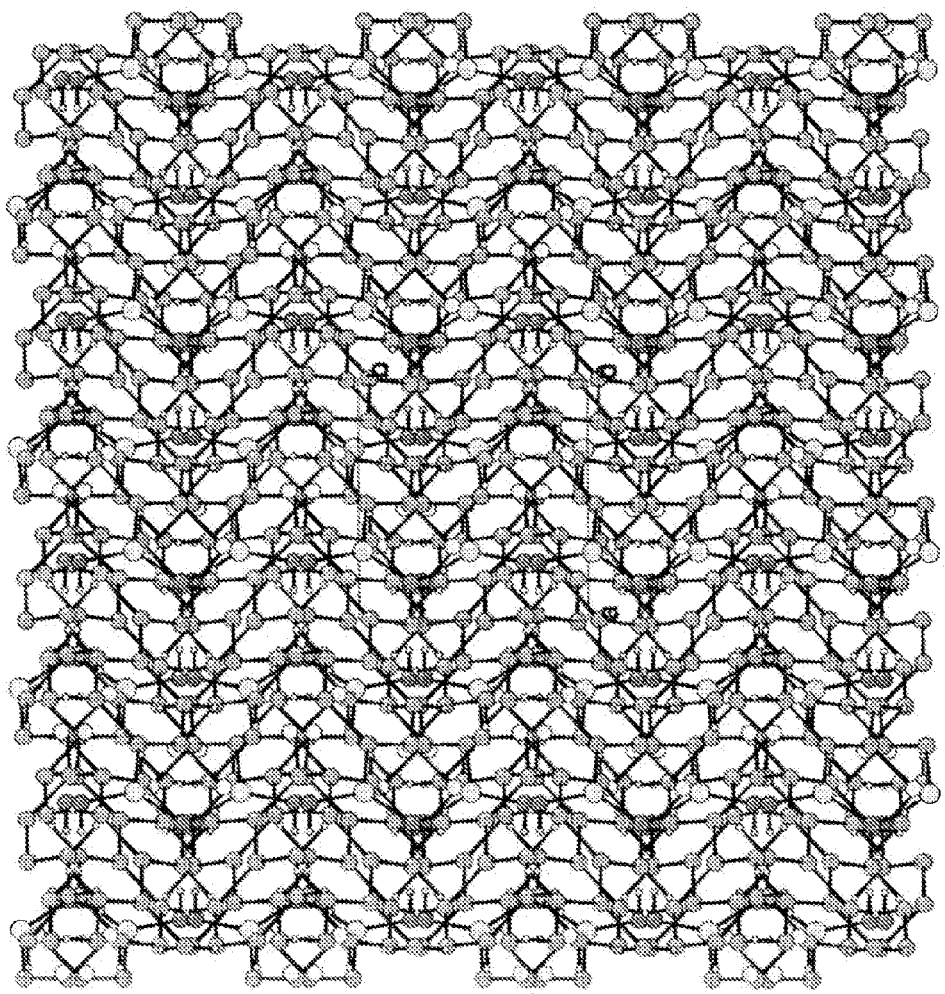
FIG. 26 shows a packing diagram of a crystalline Compound 1 viewed down the crystallographic c axis.

Packing diagrams viewed along the a, b, and c crystallographic axes are shown in FIGS. 24-26, respectively. Hydrogen bonding between adjacent boronic acid groups creates infinite one dimensional chains that run along the b axis, shown in FIG. 21. Without being limited to any theory, this is a commonly observed hydrogen bonding configuration between Ph-B—(OH)₂ groups. The chains run parallel to each other in approximately the (106) plane.

Figure 22:
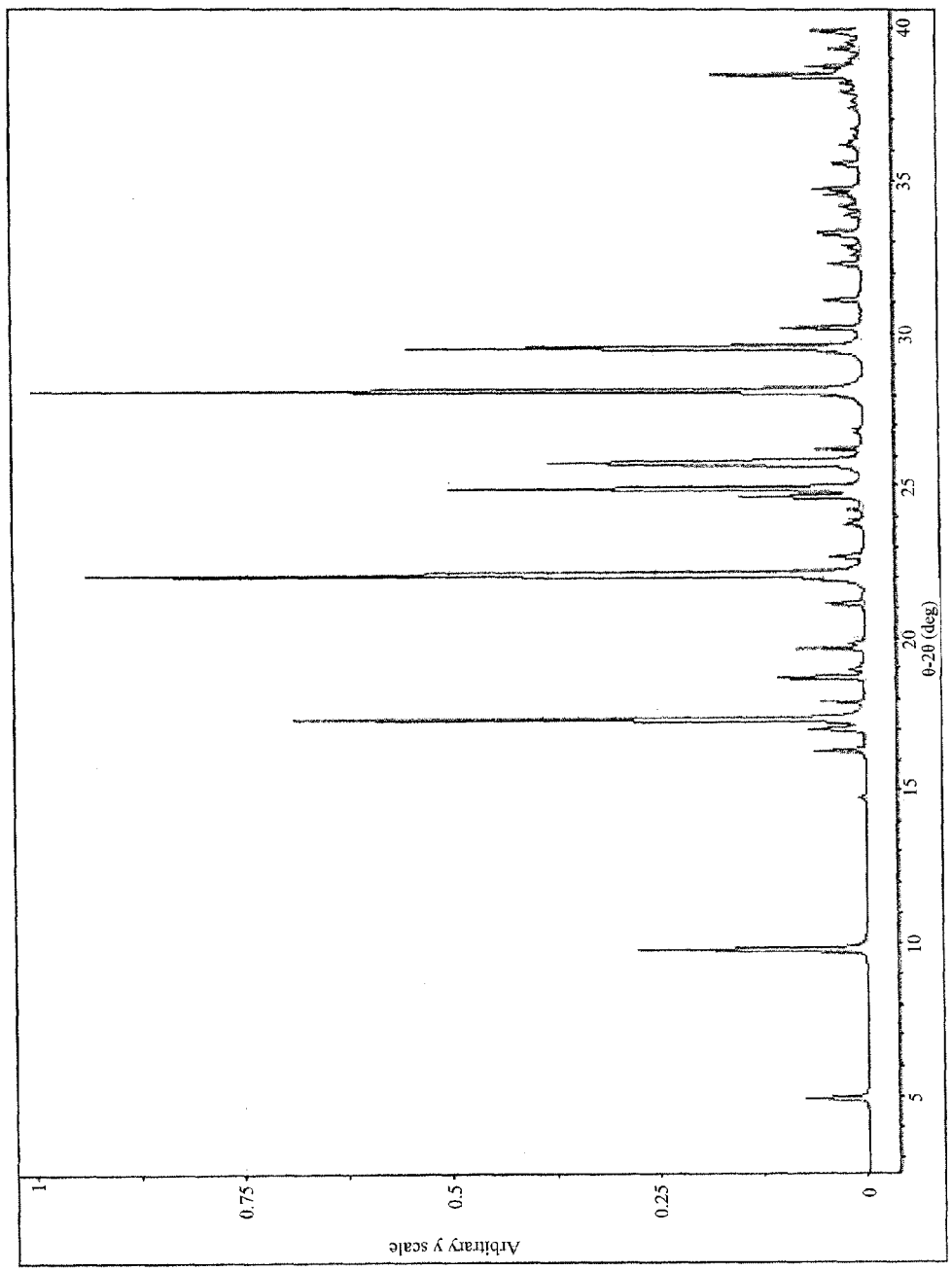
FIG. 22 shows a calculated XRPD pattern of Form A of Compound 1.
Figure 23:
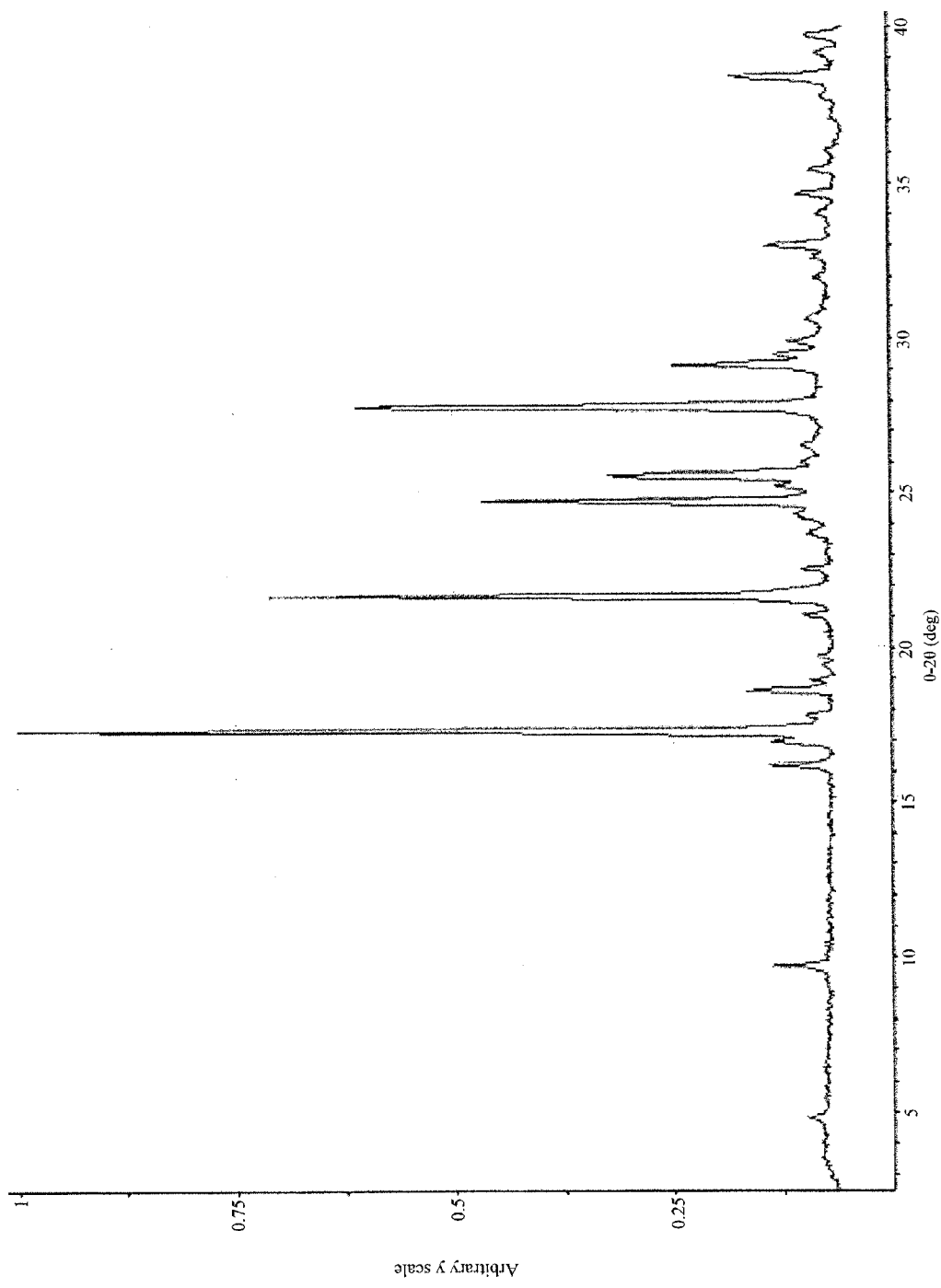
FIG. 23 shows an experimental XRPD pattern of Form A of Compound 1.
Figure 27:
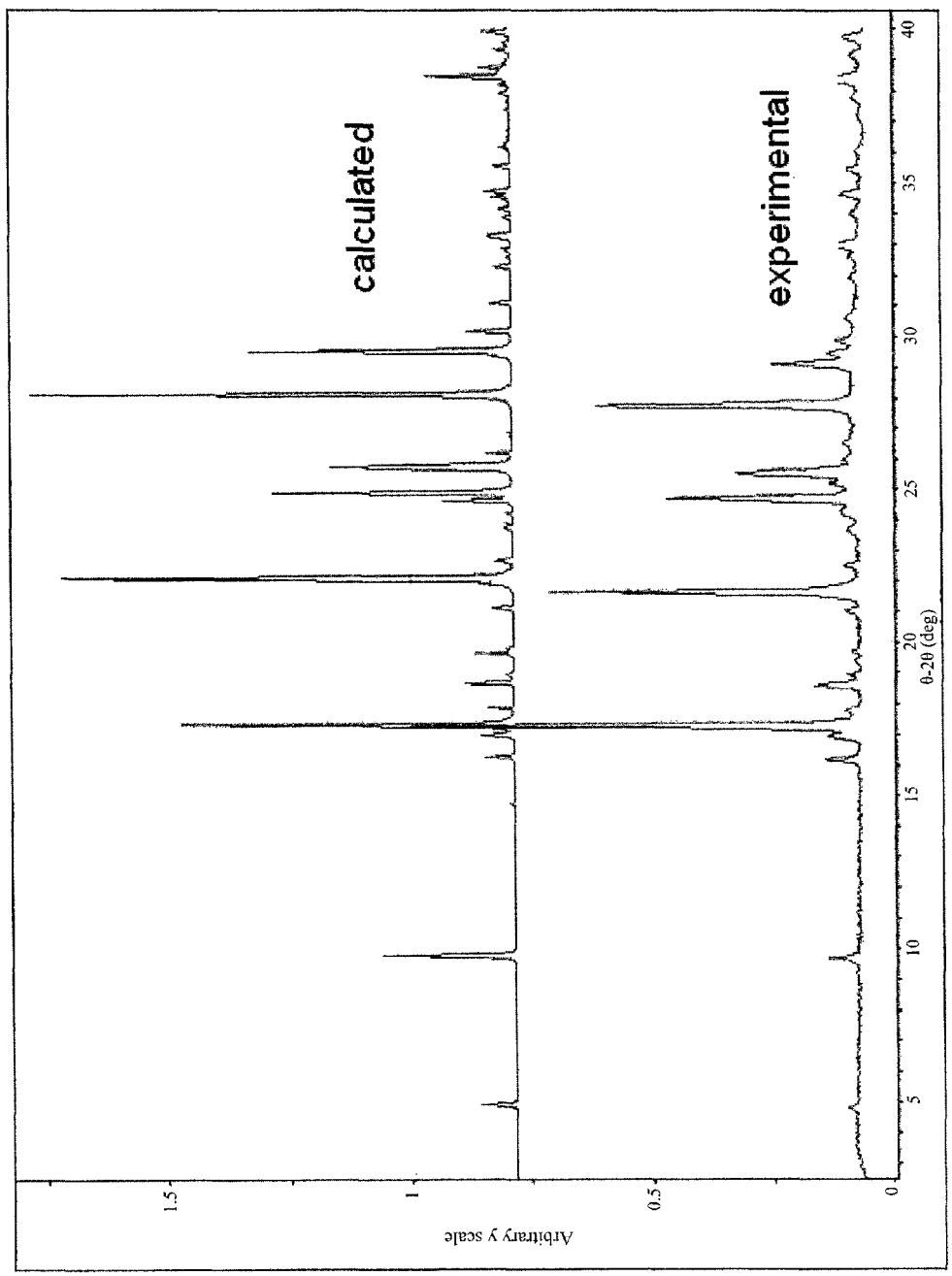
FIG. 27 shows a comparison of the calculated XRPD pattern to the experimental pattern of Form A of Compound 1.

FIG. 22 shows a calculated XRPD pattern of Compound 1, generated from the single crystal data. The experimental XRPD pattern of Compound 1 is shown in FIG. 23. FIG. 27 shows a comparison of the calculated XRPD pattern to the experimental pattern of Compound 1. All peaks in the experimental patterns are represented in the calculated XRPD pattern, supporting a single phase. Previously obtained unit cell from XRPD indexing of an experimental XRPD pattern is in agreement with the single crystal unit cell, which may indicate the same crystal form.

Differences in intensities between the calculated and experimental powder diffraction patterns may be due to preferred orientation. Preferred orientation may, in some embodiments, be defined as the tendency for crystals, in some cases plates or needles, to align themselves with some degree of order. This preferred orientation of the sample can, in some embodiments, significantly change peak intensities, but not peak positions, in the experimental powder diffraction pattern. Without being limited to any theory, there may be some slight shifting in peak location between the calculated and experimental powder diffraction patterns because the experimental powder pattern was collected at ambient temperature, and the single crystal data was collected at 150 K.

In sum, the single crystal structure was determined to be an anhydrous crystal form. The crystal structure was comprised of a single Compound 1 molecule in the asymmetric unit. All peaks in the experimental patterns are represented in the XRPD pattern, indicating the material is likely a single phase.

Tables of positional parameters and their estimated standard deviations, anisotropic temperature factor coefficients, bond distances, bond angles, hydrogen bonds and angles and torsion angles are provided below.

| Positional Parameters and Their Estimated Standard Deviations | | | | |
|---|---|---|---|---|
| Atom | x | y | z | U(Å²) |
| F13 | 0.30691(18) | 0.4093(2) | 0.40498(3) | 0.0388(3) |
| F23 | 1.53596(19) | −0.3017(2) | 0.30765(3) | 0.0419(4) |

Positional Parameters and Their Estimated Standard Deviations

| Atom | x | y | z | U(Å$^2$) |
|---|---|---|---|---|
| O1 | 0.1584(2) | 0.2260(3) | 0.47540(3) | 0.0287(4) |
| O2 | 0.2405(2) | −0.2185(2) | 0.47756(3) | 0.0298(4) |
| C11 | 0.8284(3) | 0.0464(3) | 0.37199(4) | 0.0220(5) |
| C12 | 0.6477(3) | 0.2352(3) | 0.37506(5) | 0.0272(5) |
| C13 | 0.4849(3) | 0.2227(3) | 0.40405(5) | 0.0249(5) |
| C14 | 0.4841(3) | 0.0349(3) | 0.43119(4) | 0.0229(5) |
| C15 | 0.6694(3) | −0.1498(3) | 0.42766(5) | 0.0290(5) |
| C16 | 0.8380(3) | −0.1441(3) | 0.39921(5) | 0.0281(5) |
| C21 | 1.0035(3) | 0.0486(3) | 0.34018(4) | 0.0227(5) |
| C22 | 1.1926(3) | −0.1313(3) | 0.33823(5) | 0.0278(5) |
| C23 | 1.3503(3) | −0.1249(3) | 0.30855(5) | 0.0272(5) |
| C24 | 1.3308(3) | 0.0493(3) | 0.28025(5) | 0.0282(5) |
| C25 | 1.1432(3) | 0.2263(4) | 0.28196(5) | 0.0351(5) |
| C26 | 0.9808(3) | 0.2263(3) | 0.31134(5) | 0.0317(5) |
| B1 | 0.2864(3) | 0.0187(3) | 0.46252(5) | 0.0247(5) |
| H1 | 0.207(5) | 0.370(6) | 0.4691(8) | 0.087(10)* |
| H2 | 0.124(4) | −0.217(4) | 0.4925(7) | 0.059(7)* |
| H12 | 0.637 | 0.368 | 0.358 | 0.033 |
| H15 | 0.680 | −0.282 | 0.445 | 0.035 |
| H16 | 0.960 | −0.270 | 0.398 | 0.034 |
| H22 | 1.213 | −0.255 | 0.357 | 0.033 |
| H24 | 1.440 | 0.048 | 0.261 | 0.034 |
| H25 | 1.125 | 0.348 | 0.263 | 0.042 |
| H26 | 0.854 | 0.347 | 0.312 | 0.038 |

Starred atoms were refined isotropically $U_{eq} = (1/3)\Sigma_i\Sigma_j U_{ij}a^*_i a^*_j a_i \cdot a_j$ Hydrogen atoms are included in calculation of structure factors but not refined Anisotropic Temperature Factor Coefficients - U's

| Name | U(1,1) | U(2,2) | U(3,3) | U(1,2) | U(1,3) | U(2,3) |
|---|---|---|---|---|---|---|
| F13 | 0.0412(6) | 0.0353(7) | 0.0402(6) | 0.0201(5) | 0.0171(5) | 0.0096(5) |
| F23 | 0.0416(7) | 0.0471(7) | 0.0372(7) | 0.0226(5) | 0.0161(5) | 0.0066(5) |
| O1 | 0.0317(7) | 0.0211(8) | 0.0336(7) | 0.0016(6) | 0.0146(5) | 0.0007(5) |
| O2 | 0.0308(7) | 0.0257(8) | 0.0331(7) | 0.0041(5) | 0.0156(6) | 0.0027(5) |
| C11 | 0.0197(8) | 0.0217(10) | 0.0246(9) | −0.0016(7) | 0.0027(6) | −0.0011(7) |
| C12 | 0.0308(10) | 0.0252(10) | 0.0257(9) | 0.0036(8) | 0.0055(7) | 0.0041(7) |
| C13 | 0.0232(8) | 0.0226(10) | 0.0289(9) | 0.0074(7) | 0.0052(7) | −0.0018(7) |
| C14 | 0.0223(8) | 0.0218(10) | 0.0247(9) | −0.0013(7) | 0.0028(7) | −0.0007(7) |
| C15 | 0.0271(9) | 0.0286(11) | 0.0314(10) | 0.0048(8) | 0.0079(7) | 0.0060(8) |
| C16 | 0.0236(9) | 0.0277(11) | 0.0330(10) | 0.0058(7) | 0.0075(7) | 0.0045(7) |
| C21 | 0.0203(8) | 0.0224(10) | 0.0253(9) | −0.0018(7) | 0.0029(7) | −0.0019(7) |
| C22 | 0.0318(9) | 0.0268(10) | 0.0249(9) | 0.0051(8) | 0.0060(7) | 0.0023(7) |
| C23 | 0.0236(9) | 0.0285(10) | 0.0295(9) | 0.0070(8) | 0.0039(7) | −0.0026(7) |
| C24 | 0.0268(9) | 0.0309(11) | 0.0272(9) | −0.0012(8) | 0.0093(7) | 0.0012(7) |
| C25 | 0.0342(10) | 0.0345(11) | 0.0368(11) | 0.0035(9) | 0.0114(8) | 0.0111(8) |
| C26 | 0.0273(9) | 0.0307(11) | 0.0373(11) | 0.0074(8) | 0.0102(8) | 0.0072(8) |
| B1 | 0.0227(9) | 0.0239(12) | 0.0274(10) | 0.0016(8) | 0.0026(8) | 0.0019(8) |

The form of the anisotropic temperature factor is: $\exp[-2\pi^2 h^2 a^{*2} U(1,1) + k^2 b^{*2} U(2,2) + l^2 c^{*2} U(3,3) + 2hka^* b^* U(1,2) + 2hla^* c^* U(1,3) + 2klb^* c^* U(2,3)]$ where a*, b*, and c* are reciprocal lattice constants.

Table of Bond Distances in Angstroms

| Atom 1 | Atom 2 | Distance |
|---|---|---|
| F13 | C13 | 1.3680(18) |
| F23 | C23 | 1.3634(18) |
| O1 | B1 | 1.362(2) |
| O1 | H1 | 0.82(3) |
| O2 | B1 | 1.364(2) |
| O2 | H2 | 0.84(2) |
| C11 | C12 | 1.391(2) |
| C11 | C16 | 1.392(2) |
| C11 | C21 | 1.500(2) |
| C12 | C13 | 1.380(2) |
| C12 | H12 | 0.930 |
| C13 | C14 | 1.379(2) |
| C14 | C15 | 1.395(2) |
| C14 | B1 | 1.571(2) |
| C15 | C16 | 1.385(2) |
| C15 | H15 | 0.930 |
| C16 | H16 | 0.930 |
| C21 | C22 | 1.389(2) |
| C21 | C26 | 1.393(2) |
| C22 | C23 | 1.380(2) |
| C22 | H22 | 0.930 |
| C23 | C24 | 1.365(2) |
| C24 | C25 | 1.373(2) |
| C24 | H24 | 0.930 |
| C25 | C26 | 1.388(2) |
| C25 | H25 | 0.930 |
| C26 | H26 | 0.930 |

Numbers in parentheses are estimated standard deviations in the least significant digits.

Table of Bond Angles in Degrees

| Atom 1 | Atom 2 | Atom 3 | Angle | Atom 1 | Atom 2 | Atom 3 | Angle |
|---|---|---|---|---|---|---|---|
| B1 | O1 | H1 | 116.7(18) | C22 | C21 | C11 | 120.71(15) |
| B1 | O2 | H2 | 113.0(15) | C26 | C21 | C11 | 121.65(15) |
| C12 | C11 | C16 | 117.50(14) | C23 | C22 | C21 | 119.36(16) |
| C12 | C11 | C21 | 120.74(15) | C23 | C22 | H22 | 120.30 |
| C16 | C11 | C21 | 121.76(15) | C21 | C22 | H22 | 120.30 |
| C13 | C12 | C11 | 119.18(16) | F23 | C23 | C24 | 118.48(14) |
| C13 | C12 | H12 | 120.40 | F23 | C23 | C22 | 117.99(15) |
| C11 | C12 | H12 | 120.40 | C24 | C23 | C22 | 123.53(16) |
| F13 | C13 | C14 | 118.12(14) | C23 | C24 | C25 | 117.27(15) |
| F13 | C13 | C12 | 116.49(15) | C23 | C24 | H24 | 121.40 |
| C14 | C13 | C12 | 125.37(15) | C25 | C24 | H24 | 121.40 |
| C13 | C14 | C15 | 114.13(14) | C24 | C25 | C26 | 120.96(17) |
| C13 | C14 | B1 | 123.78(15) | C24 | C25 | H25 | 119.50 |
| C15 | C14 | B1 | 122.03(15) | C26 | C25 | H25 | 119.50 |
| C16 | C15 | C14 | 122.60(16) | C25 | C26 | C21 | 121.24(16) |
| C16 | C15 | H15 | 118.70 | C25 | C26 | H26 | 119.40 |
| C14 | C15 | H15 | 118.70 | C21 | C26 | H26 | 119.40 |
| C15 | C16 | C11 | 121.20(16) | O1 | B1 | O2 | 118.28(15) |
| C15 | C16 | H16 | 119.40 | O1 | B1 | C14 | 124.09(15) |
| C11 | C16 | H16 | 119.40 | O2 | B1 | C14 | 117.64(15) |

-continued

Table of Bond Angles in Degrees

| Atom 1 | Atom 2 | Atom 3 | Angle | Atom 1 | Atom 2 | Atom 3 | Angle |
|---|---|---|---|---|---|---|---|
| C22 | C21 | C26 | 117.63 (15) | | | | |

Numbers in parentheses are estimated standard deviations in the least significant digits.

Table of Hydrogen Bond Distances in Angstroms and Angles in Degrees

| D | H | A | D-H | A-H | D-A | D-H-A |
|---|---|---|---|---|---|---|
| O1 | H1 | O2 | 0.82 (3) | 2.15 (3) | 2.905 (2) | 152 (3) |
| O2 | H2 | O1 | 0.84 (2) | 1.94 (2) | 2.7706 (18) | 176 (2) |

Numbers in parentheses are estimated standard deviations in the least significant digits.

Table of Torsion Angles in Degrees

| Atom 1 | Atom 2 | Atom 3 | Atom 4 | Angle |
|---|---|---|---|---|
| C16 | C11 | C12 | C13 | −1.36 (0.23) |
| C21 | C11 | C12 | C13 | 178.00 (0.15) |
| C12 | C11 | C16 | C15 | 1.88 (0.24) |
| C21 | C11 | C16 | C15 | −177.48 (0.15) |
| C12 | C11 | C21 | C22 | 176.35 (0.15) |
| C12 | C11 | C21 | C26 | −4.81 (0.24) |
| C16 | C11 | C21 | C22 | −4.32 (0.24) |
| C16 | C11 | C21 | C26 | 174.52 (0.16) |
| C11 | C12 | C13 | F13 | −178.12 (0.14) |
| C11 | C12 | C13 | C14 | 0.04 (0.27) |
| F13 | C13 | C14 | C15 | 178.91 (0.14) |
| F13 | C13 | C14 | B1 | 1.66 (0.24) |
| C12 | C13 | C14 | C15 | 0.77 (0.25) |
| C12 | C13 | C14 | B1 | −176.47 (0.16) |
| C13 | C14 | C15 | C16 | −0.25 (0.24) |
| B1 | C14 | C15 | C16 | 177.05 (0.15) |
| C13 | C14 | B1 | O1 | −26.38 (0.25) |
| C13 | C14 | B1 | O2 | 153.42 (0.15) |
| C15 | C14 | B1 | O1 | 156.59 (0.16) |
| C15 | C14 | B1 | O2 | −23.61 (0.23) |
| C14 | C15 | C16 | C11 | −1.09 (0.26) |
| C11 | C21 | C22 | C23 | 179.79 (0.16) |
| C26 | C21 | C22 | C23 | 0.90 (0.24) |
| C11 | C21 | C26 | C25 | −179.78 (0.15) |
| C22 | C21 | C26 | C25 | −0.90 (0.24) |
| C21 | C22 | C23 | F23 | 179.16 (0.14) |
| C21 | C22 | C23 | C24 | −0.53 (0.26) |
| F23 | C23 | C24 | C25 | −179.58 (0.15) |
| C22 | C23 | C24 | C25 | 0.11 (0.26) |
| C23 | C24 | C25 | C26 | −0.09 (0.28) |
| C24 | C25 | C26 | C21 | 0.51 (0.27) |

Numbers in parentheses are estimated standard deviations in the least significant digits.

E. Characterization of Compound 2, Form I

XRPD Analysis

XRPD patterns were collected with a PANALYTICAL® X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640c) was analyzed to verify the Si 111 peak position. A specimen of the sample was sandwiched between 3 μm-thick films and analyzed in transmission geometry. A beam-stop and short antiscatter extension were used to minimize the background generated by air. Soller slits for the incident and diffracted beams were used to minimize broadening from axial divergence. Diffraction patterns were collected using a scanning position-sensitive detector (X'CELERATOR®) located 240 mm from the specimen and Data Collector software v. 2.2b. The data-acquisition parameters for each pattern are displayed above the image in the Data section of this report including the divergence slit (DS) before the mirror and the incident-beam antiscatter slit (SS).

The XRPD was indexed using X'Pert High Score Plus 2.2a (2.2.1).

XRPD patterns were collected with an Inel XRG-3000 diffractometer. An incident beam of Cu Kα radiation was produced using a fine-focus tube and a parabolically graded multilayer mirror. Prior to the analysis, a silicon standard (NIST SRM 640c) was analyzed to verify the Si 111 peak position. A specimen of the sample was packed into a thin-walled glass capillary, and a beam-stop was used to minimize the background from air. Diffraction patterns were collected in transmission geometry using Windif v. 6.6 software and a curved position-sensitive Equinox detector with a 2θ range of 120°.

Figure 28:
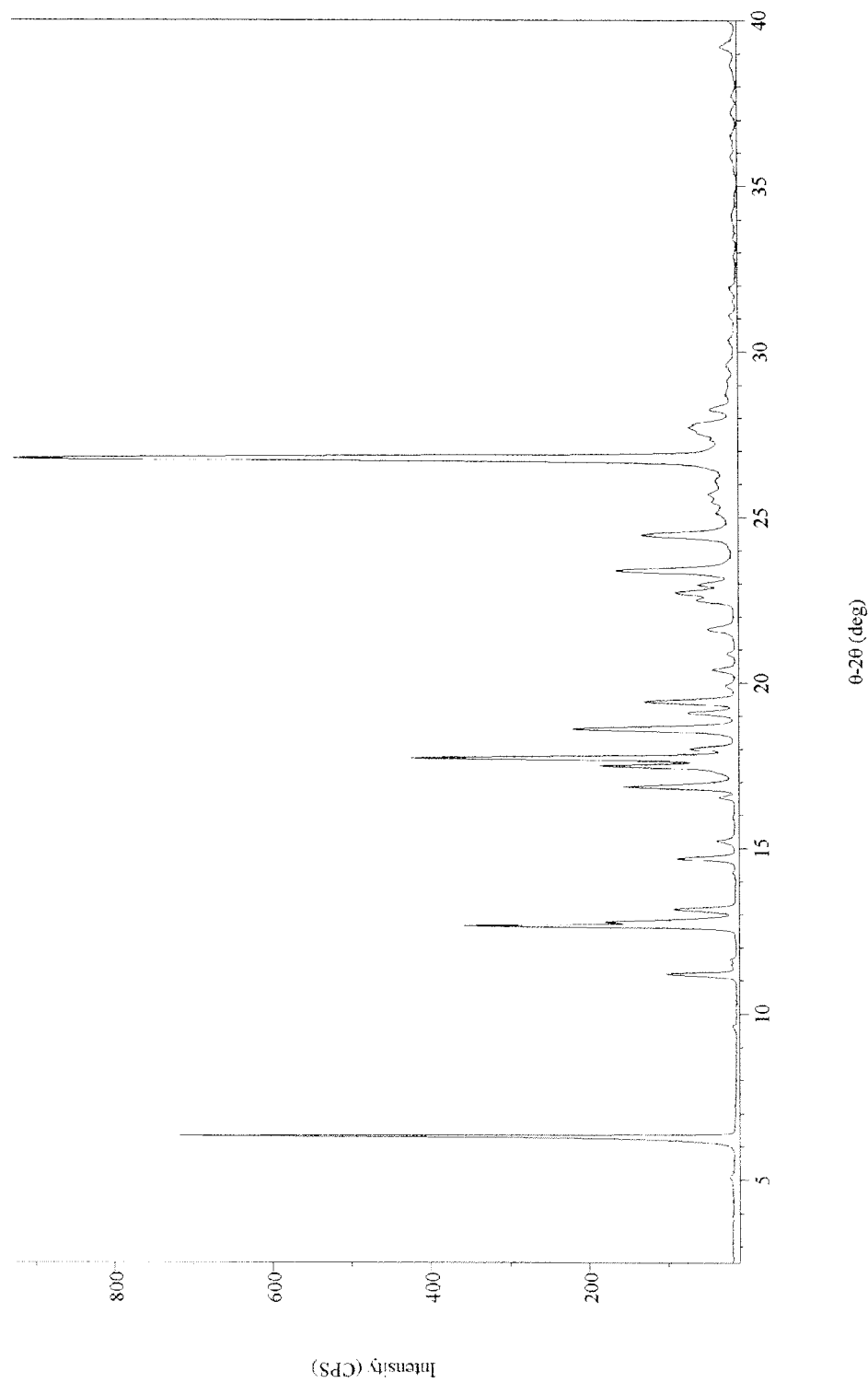
FIG. 28 shows a PANALYTICAL XRPD pattern of Form I of Compound 2.

The high-resolution (PANALYTICAL®) XRPD pattern of Compound 2 was indexed, and the solution is shown in FIG. 28. The cell volume obtained from the indexing solution is consistent with three monomers in the asymmetric unit.

Figure 29:
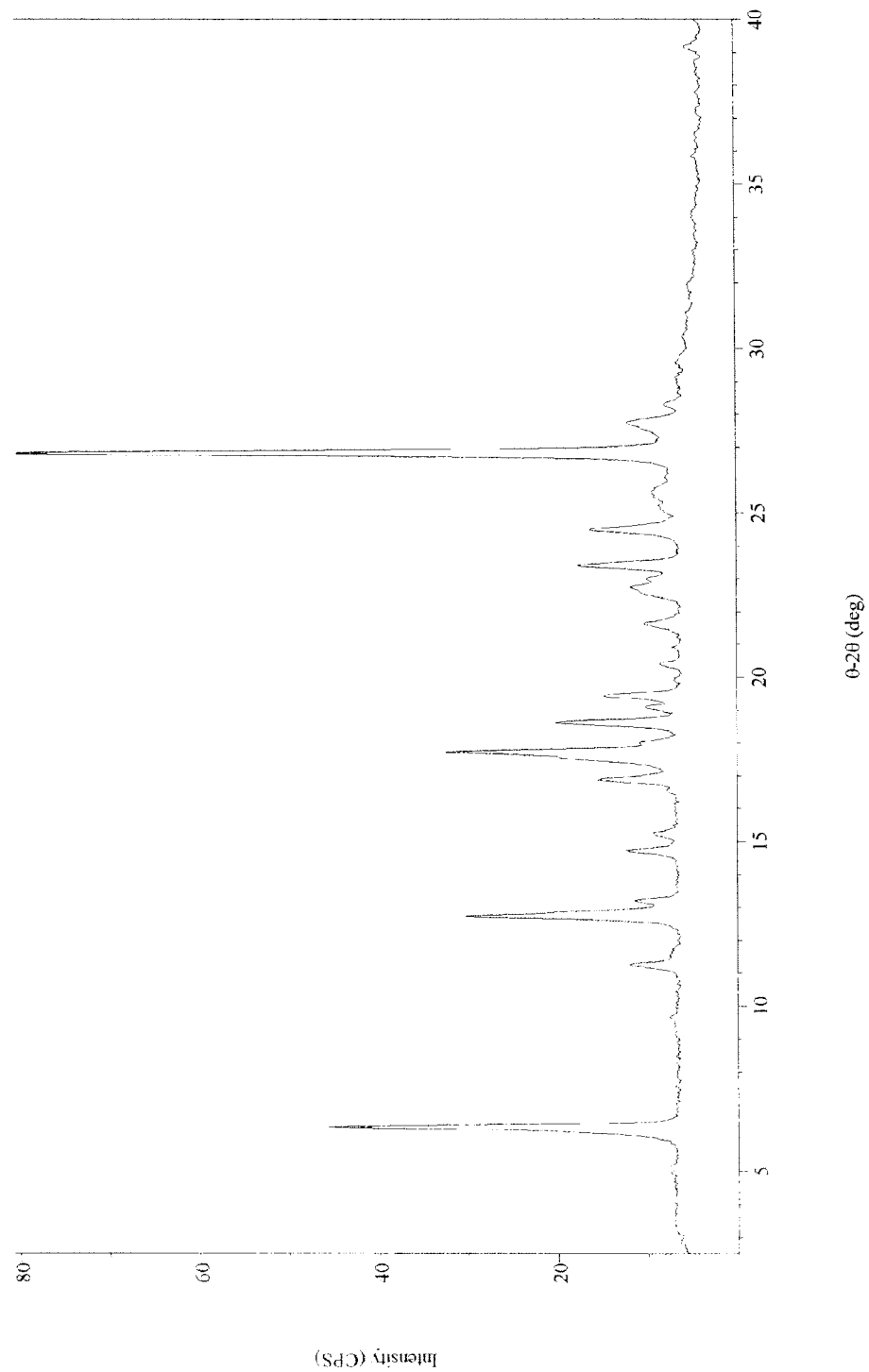
FIG. 29 shows an XRPD pattern of Form I of Compound 2.

The INEL XRPD pattern is shown in FIG. 29.

Proton NMR Analysis

The solution NMR spectra were acquired with a Varian$^{UNITY}$INOVA-400 spectrometer. The samples were prepared by dissolving approximately 4-10 mg of sample in CDCl$_3$ containing TMS.

Figure 30:
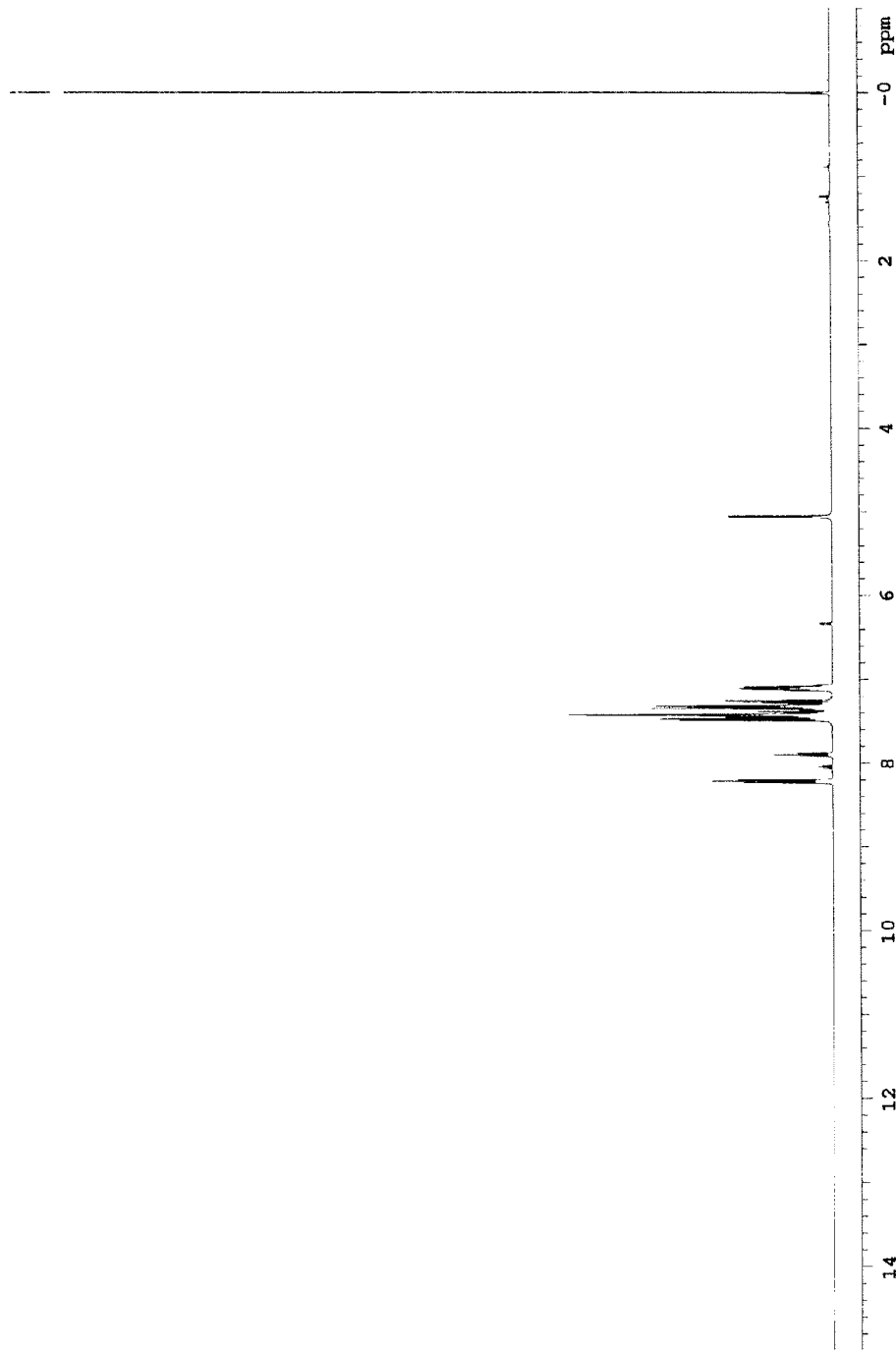
FIG. 30 shows a proton NMR of crystalline Compound 2.

The obtained spectrum was consistent with the presence of Compound 2, as well as Compound 1. Compound 1 and Compound 2 are distinguishable by proton NMR based on the presence or absence of hydroxyl protons at approximately 5.1 ppm in deuterated chloroform. Without being bound by any theory, a small amount of water may been present in the NMR solvent, and that water may have reacted with Compound 2 in the NMR sample, thereby forming Compound 1. The proton NMR spectrum is shown in FIG. 30.

F. Characterization of Compound 1 Material B

Exemplary XRPD patterns of Material B are provided in FIGS. 19 (row B), 32, and 35.

Exemplary TGA and DSC thermograms of Material B are provided in FIG. 34. TGA indicates approximately 10% weight loss from 25 to 130° C.

G. Material B/Form A (Compound 1) Conversion Studies

Relative Humidity Stressing

A mixture of Form A and Material B was subjected to approximately 97% R.H. for one week. Conversion of this mixture to Material B was observed after the one week. In another experiment, Material B was found to convert to a mixture of Material B and Form A as early as 1 day at approximately 75% R.H. and 41° C. The same mixture (with a constant ratio of Material B to Form A based on relative XRPD intensities) was observed after 4, 7, and 14 days under those conditions.

Interconversion Studies

A saturated solution of Compound 1 Form A was prepared by adding enough solids to a given solvent system at ambient conditions so that undissolved solids were present. The mixture was then allowed to stir in a sealed vial at ambient temperature for 3 days to ensure saturation. Solids from a mixture of Form A and Material B were added to aliquots of the saturated solution (filtered through a 0.2-μm nylon filter) so that undissolved solids were present. The mixture was then allowed to stir in a sealed vial at ambient temperature for an extended period of time. The solids were isolated by vacuum filtration and analyzed. Form A was observed by XRPD.

EQUIVALENTS

The specific examples presented above are merely exemplary and are non-limiting. While we have presented a number of embodiments of this invention, it is apparent that our basic teaching can be altered to provide other embodiments, which utilize the compounds and methods of this invention. Therefore, it will be appreciated that the scope of this invention is to be defined by the appended claims rather than by the specific embodiments, which have been represented by way of example.

---

We claim:

1. A method of treating an FAAH-mediated condition comprising administering to a subject in need thereof a therapeutically effective amount of a solid form of a crystalline compound of formula 1:

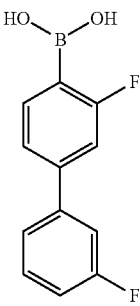

1 or a pharmaceutically acceptable salt, hydrate, or solvate thereof, or anhydride thereof, wherein the crystalline compound of formula 1 is a Form A crystal form of formula 1 having an X-ray powder diffraction pattern comprising peaks at approximate peak positions of 17.26±0.10, 21.60±0.10, and 27.73±0.10 degrees 2θ and at least one peak at an approximate peak position of 9.68±0.10, 24.68±0.10, 25.48±0.10, and 29.08±0.10 degrees 2θ, wherein the FAAH-mediated condition is a painful condition.

2. The method according to claim 1, wherein the FAAH-mediated condition is a painful condition selected from the group consisting of inflammatory pain, joint pain, arthritic pain, lumbosacral pain, musculoskeletal pain, headache, migraine, muscle ache, lower back pain, neck pain, and toothache dental/maxillofacial pain.

3. The method according to claim 1, wherein the FAAH-mediated condition comprises diabetic neuropathy, sciatica, non-specific lower back pain, multiple sclerosis pain, fibromyalgia, HIV-related neuropathy, neuralgia, post-herpetic neuralgia, trigeminal neuralgia, or pain resulting from chronic inflammatory conditions.

4. The method according to claim 1, wherein the FAAH-mediated condition comprises post-herpetic neuralgia.

5. The method according to claim 1, wherein the FAAH-mediated condition comprises arthritic pain associated with crystalline arthritis, osteoarthritis, psoriatic arthritis, gouty arthritis, reactive arthritis, rheumatoid arthritis, or Reiter's arthritis.

6. The method according to claim 1, wherein the FAAH-mediated condition comprises joint pain.

7. The method according to claim 1, wherein the FAAH-mediated condition comprises arthritic pain.

* * * * *